US007087626B2

(12) United States Patent
Beight et al.

(10) Patent No.: US 7,087,626 B2
(45) Date of Patent: Aug. 8, 2006

(54) PYRROLE DERIVATIVES AS PHARMACEUTICAL AGENTS

(75) Inventors: Douglas Wade Beight, Frankfort, IN (US); Todd Vincent DeCollo, Noblesville, IN (US); Alexander Glenn Godfrey, Greenwood, IN (US); Theodore Goodson, Jr., Indianapolis, IN (US); Hong-Yu Li, Zionsville, IN (US); William Thomas McMillen, Indianapolis, IN (US); Shawn Christopher Miller, Noblesville, IN (US); Jason Scott Sawyer, Indianapolis, IN (US); Edward C. R. Smith, Fishers, IN (US); Jonathan Michael Yingling, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 324 days.

(21) Appl. No.: 10/477,111

(22) PCT Filed: May 13, 2002

(86) PCT No.: PCT/US02/11884

§ 371 (c)(1),
(2), (4) Date: Nov. 6, 2003

(87) PCT Pub. No.: WO02/094833

PCT Pub. Date: Nov. 28, 2002

(65) Prior Publication Data

US 2004/0106604 A1 Jun. 3, 2004

Related U.S. Application Data

(60) Provisional application No. 60/293,464, filed on May 24, 2001.

(51) Int. Cl.
*A61K 31/47* (2006.01)
*C07D 205/16* (2006.01)
*C07D 307/00* (2006.01)
*C07D 405/00* (2006.01)

(52) U.S. Cl. .............. 514/338; 514/226.8; 514/230.5; 514/255.05; 514/300; 514/314; 514/368; 514/375; 514/405; 514/456; 514/434; 544/91; 544/48; 544/405; 546/275.7; 546/121; 546/167; 546/173; 546/176; 546/122; 549/360.1; 549/218; 549/154

(58) Field of Classification Search .............. 514/368, 514/226.8, 230.5, 255.05, 300, 314, 375, 514/405, 434, 456; 546/275.7, 121, 167, 546/173, 176, 122; 544/91, 48, 405; 548/360.1, 548/218, 154
See application file for complete search history.

(56) References Cited

U.S. PATENT DOCUMENTS 5,358,947 A   10/1994   Venkatesan
5,670,503 A    9/1997   Kawai et al.

FOREIGN PATENT DOCUMENTS

| EP | 0 666 079 A1 | 8/1995 |
|---|---|---|
| EP | 0 923 929 A1 | 6/1999 |
| WO | 0 531 901 A2 | 3/1993 |
| WO | WO 97 35551 | 10/1997 |
| WO | WO 98 52940 | 11/1998 |
| WO | WO 99 58128 | 11/1999 |
| WO | WO 00 61576 | 10/2000 |
| WO | WO 01 16138 A1 | 3/2001 |
| WO | WO 01 72737 | 10/2001 |
| WO | WO 00 44743 | 11/2001 |
| WO | WO 02 16359 | 2/2002 |
| WO | WO 02 066462 | 8/2002 |
| WO | WO 02/034716 * | 5/2004 |
| WO | WO 04/106604 * | 6/2004 |

OTHER PUBLICATIONS

XP-002210048; *Effect of FR167653, a Cytokine Suppressive Agent, on Endotoxin–Induced Disseminated Intravascular Coagulation*; Nobuchika Yamamotot, et al.; European Journal of Pharmacology 314; 1996; pp. 137–142.

(Continued)

*Primary Examiner*—D. Margaret Seaman
(74) *Attorney, Agent, or Firm*—Michael J. Sayles

(57) ABSTRACT

Novel pyrrazole derivative compounds and their use as pharmaceutical agents, in particular their use as TGF-beta signal transduction inhibitors. The disclosed invention relates to compounds of the structure (I) wherein (I) is a four, five, or six membered saturated ring and X is C, O or S (I)

7 Claims, No Drawings

OTHER PUBLICATIONS

XP-001096045; *Effect of FR143430, a Novel Cytokine Suppressive Agent, on Adenocarcinoma Colon–26—Induced Cachexia in Mice*; Nobuchika Yamamoto, et al; Anticancer Research 18; 1998; pp. 139–1444.

XP-001097427; *Further Investigations on the Antiinflammatory Actvity of Some2–Phenylpyrozolo[1,5–a] Pyrimidine Compounds*; R. Pirisino, et al; II Farmaco—Ed. Sci.; vol. 36, Fasc. 8; pp. 682–691.

XP-001097437; *Pharmacological Activity of Some Pyrazolo[1,5–a] Pyrimidines*; R. Pirisino; II Farmaco—Ec. Sc.; vol. 34—Fasc. 9; pp. 802–807.

*Discovery of FR166124, A Novel Water–Soluble Pyrazolo-[1,5–a] Pyridine Adenosine $A_1$ Receptor Antagonist*; Satour Kuroda, et al.; Bioorganic & Medicinal Chemistry Letters 9 (1999); pp. 1979–1984.

\* cited by examiner

PYRROLE DERIVATIVES AS PHARMACEUTICAL AGENTS

This application claims the benefit of provisional application 60/293,464 filed May 24, 2001.

The invention relates to new pyrrole derivative compounds and their use as pharmaceutical agents, in particular their use as TGF-beta signal transduction inhibitors.

BACKGROUND OF THE INVENTION

The transforming growth factor-beta (TGF-Beta) ("TGF-β") polypeptides influence growth, differentiation, and gene expression in many cell types. The first polypeptide of this family that was characterized, TGF-β1, has two identical 112 amino acid subunits that are covalently linked. TGF-β1 is a highly conserved protein with only a single amino acid difference distinguishing humans from mice. There are two other members of the TGF-β gene family that are expressed in mammals. TGF-β2 is 71% homologous to TGF-β1 (de Martin, et al., (1987) EMBO J 6:3673–3677), whereas TGF-β3 is 80% homologous to TGF-β1 (Derynck, et al. (1988) EMBO J. 7:3737–3743). The structural characteristics of TGF-β1 as determined by nuclear magnetic resonance (Archer, et al. (1993) Biochemistry 32:1164–1171) agree with the crystal structure of TGF-β2 (Daopin, et al. (1992) Science 257:369–374; Schlunegger and Grutter (1992) Nature 358:430–434).

There are at least three different extracellular TGF-β receptors, Type I, II and III that are involved in the biological functions of TGF-β1, -β2 and -β3 (For reviews, see Derynck (1994) TIBS 19:548–553 and Massague (1990) Ann. Rev. Cell Biol. 6:597–641). The Type I and Type II receptors are transmembrane serine/threonine kinases which in the presence of TGF-β form a heteromeric signaling complex (Wrana, et al (1992) Cell 71: 1003–1014).

The mechanism of activation of the heteromeric signaling complex at the cell surface has been elucidated (Wrana, et al. (1994) Nature 370: 341–347). TGF-β first binds the type II receptor that is a constitutively active transmembrane serine/threonine kinase. The type I receptor is subsequently recruited into the complex, phoshorylated at the GS domain and activated to phosphorylate downstream signaling components (e.g. Smad proteins) to initiate the intracellular signaling cascade. A constitutively active type I receptor (T204D mutant) has been shown to effectively transduce TGF-β responses, thus bypassing the requirement for TGF-β and the type II receptor (Wieser, et al. (1995) EMBO J 14: 2199–2208). Although no signaling function has been discovered for the type III receptor, it does increase TGF-β2's affinity for the type II receptor making it essentially equipotent with TGF-β1 and TGF-β3 (Lopez-Casillas, et al. (1993) Cell 73: 1435–1444).

Vascular endothelial cells lack the Type III receptor. Instead endothelial cells express a structurally related protein called endoglin (Cheifetz, et al., (1992) J. Biol. Chem. 267:19027–19030), which only binds TGF-β1 and TGF-β3 with high affinity. Thus, the relative potency of the TGF-β's reflects the type of receptors expressed in a cell and organ system. In addition to the regulation of the components in the multi-factorial signaling pathway, the distribution of the synthesis of TGF-β polypeptides also affects physiological function. The distribution of TGF-β2 and TGF-β3 is more limited (Derynck, et al. (1988) EMBO J. 7:3737–3743) than TGF-β1, e.g., TGF-β3 is limited to tissues of mesenchymal origin, whereas TGF-β1 is present in both tissues of mesenchymal and epithelial origin.

TGF-β1 is a multifunctional cytokine critical for tissue repair. High concentrations of TGF-β1 are delivered to the site of injury by platelet granules (Assoian and Sporn (1986) J. Cell Biol. 102:1217–1223). TGF-β1 initiates a series of events that promote healing including chemo taxis of cells such as leukocytes, monocytes and fibroblasts, and regulation of growth factors and cytokines involved in angiogenesis, cell division associated with tissue repair and inflammatory responses. TGF-β1 also stimulates the synthesis of extracellular matrix components (Roberts, et al. (1986) Proc. Natl. Acad. Sci. USA 83:4167–4171; Sporn, et al. (1983) Science 219:1329–1330; Massague (1987) Cell 49:437–438) and most importantly for understanding the pathophysiology of TGF-β1, TGF-β1 autoregulates its own synthesis (Kim, et al. (1989) J. Biol. Chem. 264:7041–7045).

SUMMARY OF THE INVENTION

The disclosed invention relates to compounds of the structure:

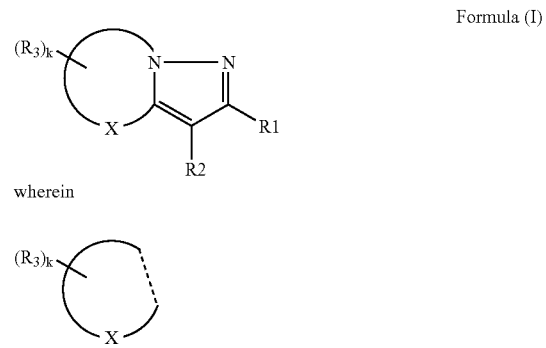

Formula (I)

wherein is a four, five, or six membered saturated ring and X is C, O or S;

R1 is unsubstituted or substituted phenyl; unsubstituted or substituted pyridine; unsubstituted or substituted pyridine N-oxide; unsubstituted or substituted quinoline; unsubstituted or substituted quinoline N-oxide; unsubstituted or substituted naphthyridine; unsubstituted or substituted pyrazine; furyl; unsubstituted or substituted thiazolyl; unsubstituted or substituted imidazolyl; unsubstituted or substituted pyrazolyl; or unsbustituted or substituted thiophenyl; wherein the substitution may be one or more of the following: (C1–C6)alkyl, (C2–C6)alkenyl, (C2–C6)alkynyl, (C1–C6)alkoxy, (C2–C6)alkenyloxy, (C2–C6)alkynyloxy, (C1–C6)alkylthio, (C1–C6)alkylsulphinyl, (C1–C6) alkylsulphonyl, (C1–C6)alkylamino, di-[(C1–C6)alkyl] amino, (C1–C6)alkoxycarbonyl, N—(C1–C6) alkylcarbamoyl, N,N-di-[(C1–C6)alkyl]carbamoyl, (C2–C6)alkanoyl, (C2–C6)alkanoyloxy, (C2–C6) alkanoylamino, N—(C1–C6)alkyl-(C2–C6)alkanoylamino, (C3–C6)alkenoylamino, N—(C1–C6)alkyl-(C3–C6) alkenoylamino, (C3–C6)alkynoylamino, N—(C1–C6)alkyl-(C3–C6)alkynoylamino, N—(C1–C6)alkylsulphamoyl, N,N-di-[(C1–C6)alkyl]sulphamoyl, (C1–C6) alkanesulphonylamino, N—(C1–C6)alkyl-(C1–C6) alkanesulphonylamino, carboxamide, ethylene, thiophenyl, aminophenyl, trifluoromethyl, halo, trifluoromethoxy, hydroxymethyl, N-pyrrolidino, N-morpholino, phenylthio, (C1–C4)dialkylaminomethyl, methoxyphenyl, amino, hydroxy, carboxyl, phenyl, arylalky;

R2 is unsubstituted or substituted quinoline; unsbustituted or substituted quinoline N-oxide; unsbustituted or substituted phenyl; unsubstituted or substituted naphthalene;

unsubstituted or substituted pyridine; unsubstituted or substituted pyridine N-oxide; unsbustituted or substituted quinazoline; unsubstituted or substituted cinnoline; unsubstituted or substituted benzodioxole; unsbustituted or substituted benzodioxane; unsubstituted or substituted pyrimidine; unsubstituted or substituted benzothiophene; or unsubstituted or substituted phenanthrolene; wherein the substitution may independently be one or more of the following: hydrogen, (C1–C6)alkyl, (C2–C6)alkenyl, (C2–C6)alkynyl, (C1–C6)alkylhalide, (C1–C6)alkoxy, (C2–C6)alkenyloxy, (C2–C6)alkynyloxy, (C1–C6) alkylthio, (C1–C6)alkylsulphinyl, (C1–C6)alkylsulphonyl, (C1–C6)alkylamino, di-[(C1–C6)alkyl]amino, (C1–C6) alkoxycarbonyl, N—(C1–C6)alkylcarbamoyl, N,N-di-[(C1–C6)alkyl]carbamoyl, aminooxy, N—(C1–C6)alkyl aminooxy, N,N-di-[(C1–C6)alkyl]aminooxy, (C2–C6) alkanoyl, (C2–C6)alkanoyloxy, (C2–C6)alkanoylamino, N—(C1–C6)alkyl-(C2–C6)alkanoylamino, (C3–C6) alkenoylamino, N—(C1–C6)alkyl-(C3–C6)alkenoylamino, (C3–C6)alkynoylamino, N—(C1–C6)alkyl-(C3–C6) alkynoylamino, sulphamoyl, N—(C1–C6)alkylsulphamoyl, N,N-di-[(C1–C6)alkyl]sulphamoyl, (C1–C6) alkanesulphonylamino, N—(C1–C6)alkyl-(C1–C6) alkanesulphonylamino, carboxamide, ethylene, phenyl, thiophenyl, aminophenyl, phenylthio, halo, cyano, pyridinyl, arylalkyl, hydroxy, N-pyrrolidino, N-morpholino, carboxyl, [5-phenyl-1,2,4-oxadiazole-3-yl]methoxy, 6-methyl-pyridazin-3-yloxy, (5-oxo-2-pyrrolidinyl) methoxy, 2-(4,5-dihydro-1H-imidazolyl), N,N-dialkylcarbamoyloxy, 1-hydroxy-1-methylethyl, 4-fluorophenyl, 3,4-methylenedioxyphenyl, trifluoromethyl, trifluoromethoxy, or a group of the formula

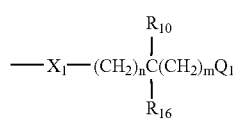

wherein: $X_1$ is O, N, S, $SO_2$, $NR_{13}$, C(O), or bond; $Q_1$ is hydrogen, phenyl, 5-(2,2-difluoro-1,3-benzodioxolyl), C(O) $Q_5$, or pyridyl when m and n are independently 0–2, except when one is 0 the other cannot be 0; $Q_1$ is $OR_{11}$, $NR_{11}R_{12}$, halo, N-morpholino, N-piperazino-N'$R_{13}$, N-imidazolyl, N-pyrazolyl, N-triazolyl, N-(4-piperidinylpiperidine), $SO_2R_{14}$, $SOR_{14}$, $NHSO_2R_{15}$, acetamido, N-phthalimido, N-oxazolidino, N-imidazolino, N-benzoxazolidino, N-pyrolidinonyl, N(N'-methylbenzimidazolino), N,N-di (C1–C4)alkylamino(C1–C4)alkoxy, N-benzimidazolino; when m and n are independently 0–2, but one or the other of m or n is not 0; $Q_5$ is hydroxy, methoxy, amino, diethylamino, dimethylamino; $R_{10}$ is hydrogen, halo, (C1–C6)alkyl; $R_{11}$ and $R_{12}$ are independently hydrogen, (C1–C6)alkyl, (C1–C6)alkoxy, arylalkyl, (C3–C8) cycloalkyl, (C3–C8)cycloalkylmethyl, 4-(N-methylpiperidinyl), pyridyl, or $R_{11}$ and $R_{10}$ can be taken together to form a 4, 5, 6, or 7 membered ring, or $R_{11}$ and $R_{12}$ can be taken together to form a 3, 4, 5, 6, or 7 membered ring; $R_{13}$ is hydrogen, (C1–C6)alkyl, 2-methoxyphenyl, 2-pyrimidinyl; $R_{14}$ is 2-pyrimidinyl, N-methyl-2-imidazolyl, 4-chlorophenyl, 2-pyridylmethyl; $R_{15}$ is (C1–C6)alkyl, N-methyl-4-imidazolyl; $R_{16}$ is hydrogen, halo, arylalkyl, aryl, or a group of the formula

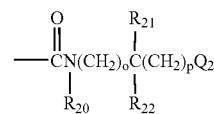

wherein: $Q_2$ is hydrogen, 4-imidazolyl, or $C(O)NR_{24}R_{25}$ when o and p are independently 0–2; $Q_2$ is $OR_{23}$, $NR_{24}R_{25}$, or N-morpholino, when o and p are independently 0–2, but one or the other of o or p is not 0; $R_{20}$ is hydrogen, or (C1–C6)alkyl; $R_{21}$ is hydrogen, (C1–C6)alkyl, or $R_2$, and $R_{20}$ can be taken together to form a 4, 5, 6, or 7 membered ring; $R_{22}$ is hydrogen, (C1–C6)alkyl, arylalkyl, aryl, or $R_2$, and $R_{22}$ can be taken together to be a 3, 4, 5, 6, 7 membered ring; $R_{23}$ is hydrogen or (C1–C6)alkyl; $R_{24}$ is hydrogen, (C1–C6)alkyl, or $R_{24}$ and $R_{25}$ can be taken together to form a 3, 4, 5, 6, or 7 membered: ring, or $R_{24}$ and $R_{20}$ can be taken together to form a 6 or 7 membered ring; $R_{25}$ is hydrogen, (C1–C6)alkyl, or acetyl, or a group of the formula

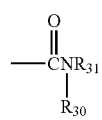

wherein: $R_{30}$ is hydrogen, or (C1–C6)alkyl; $R_{31}$ is hydrogen, (C1–C6)alkyl, 2-pyridyl, pyridylmethyl, amino, or hydroxy, or a group of the formula

wherein: $R_{32}$ and $R_{33}$ are each independently hydrogen, (C1–C6)alkyl, acetyl, (C1–C4)alkylsulphonyl, or $R_{32}$ and $R_{33}$ can be taken together to form a 4, 5, 6, or 7 membered ring, or a group of the formula

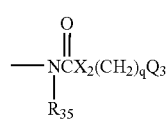

wherein: $X_2$ is $CH_2$, O, or N; q: is 2–3 except when $Q_3$ is a bond, q is 0–3; $Q_3$ is $NR_{36}R_{37}$, or $OR_{38}$, and $R_{35}$ is hydrogen, or $R_{35}$ and $Q_3$ can be taken together to form a 5 membered ring; $R_{36}$, $R_{37}$, and $R_{38}$ are each independently hydrogen, or (C1–C6)alkyl, or a group of the formula

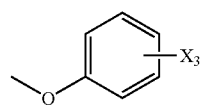

wherein: $X_3$ is cyano, carboxamide, N,N-dimethylcarboxamide, N,N-dimethylthiocarboxamide, N,N-dimethylaminomethyl, 4-methylpiperazin-1yl-methyl or carboxylate, or a group of the formula

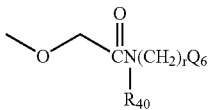

wherein: $Q_6$ is $N_1R_{41}R_{42}$; r is 2–3; $R_{40}$ is hydrogen, or (C1–C6)alkyl; $R_{41}$, and $R_{42}$ are hydrogen, (C1–C6)alkyl, or $R_{41}$, and $R_{40}$ can be taken together to form a 6 or 7 membered ring,
or a group of the formula

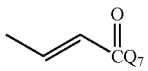

wherein: $Q_7$ is hydroxy, methoxy, dimethylamino, or N-piperidinyl;
with the proviso that when one of R1 or R2 is unsubstituted or substituted phenyl, then the other cannot be unsubstituted or substituted phenyl or thiophen-2-yl; and with the proviso that when R2 is quinolin-4-yl, substitution at the quinoline 7-position cannot include an aryl, heteroaryl, fused aryl, or fused heteroaryl;
k is 1–8; R3 is one or more of the following: hydrogen; (C1–C4)alkyl; (C1–C4)alkylhydroxy; hydroxy; N,N-di (C1–C4)alkylamino(C1–C4)alkoxy; benzyl oxymethyl; phenyloxymethyl; oxo; carboxyl; (C1–C4)alkylaryl; benzyloxy; acetoxy; amino(C1–C4)alkyl; (C2–C4)alkenyl; halo; —O—(C1–C4)alkyl; chlorophenethyl; acetonitrile; unsubsituted or substituted phenyl; wherein the substitution may be one or more of the following: (C1–C6)alkoxy, halo, carboxy, or (C1–C6)alkoxycarbonyl; and the pharmaceutically acceptable salts, esters and prodrugs thereof.

DETAILED DESCRIPTION OF THE INVENTION

The term "effective amount" as used in "an effective amount of a compound of Formula I," for example, refers to an amount of a compound of the present invention that is capable of inhibiting TGF beta.

The general chemical terms used herein have their usual meanings. For example, as used herein, the term "$C_1$–$C_4$ alkyl", alone or in combination, denotes a straight-chain or branched-chain $C_1$–$C_4$ alkyl group consisting of carbon and hydrogen atoms, examples of which are methyl, ethyl, propyl, isopropyl, butyl, sec-butyl, tert-butyl, and the like. The term "geminal dimethyl" represents two methyl groups attached at the same substitution position. The term "$C_3$–$C_6$ cycloalkyl" refers to cyclopropyl, cyclobutyl, cyclopentyl, cyclohexyl. The term "spiro-fused $C_3$–$C_6$ cycloalkyl" refers to a $C_3$–$C_6$ cycloalkyl group as defined above bonded to a carbon atom through a spiro linkage.

The term "$C_1$–$C_4$ alkoxy", alone or in combination, denotes an alkyl group as defined earlier, which is attached via an oxygen atom, such as, for example, methoxy, ethoxy, propoxy, isopropoxy, butoxy, tert-butoxy, and the like. The term "$C_1$–$C_4$ alkylthio", alone or in combination, denotes an alkyl group as defined earlier and is attached via a sulfur atom, and includes methylthio, ethylthio, isobutylthio, and the like.

As used herein, the term "halo" or "halogen" represents fluorine, chlorine, bromine, or iodine. The term "hydroxy," alone or in combination, represents an —OH moiety. The term "carboxy" or "carboxyl" refers to a carboxylic acid.

The term "carboxamide" refers to a carbonyl substituted with an —$NH_2$ moiety. The term "oxo" refers to a carbonyl group.

As used herein, the term "heteroaryl" means an aryl moiety, which contains 1–5 heteroatoms selected from O, S, and N. Examples of heteroaryl groups include pyrrolyl, pyrazolyl, pyranyl, thiopyranyl, furanyl, imidazolyl, pyridyl, thiazolyl, triazinyl, phthalimidyl, indolyl, purinyl, and benzothiazolyl.

As used herein, the term "aryl" represents a substituted or unsubstituted phenyl or naphthyl. Aryl may be optionally substituted with one or more groups independently selected from hydroxy, carboxy, $C_1$–$C_6$ alkoxy, $C_1$–$C_6$ alkyl, halogen, carboxamide, trifluoromethyl, hydroxymethyl, and hydroxy($C_1$–$C_4$)alkyl.

The term "$C_3$–$C_8$ cycloalkyl" refers to cyclopropyl, cyclobutyl, cyclopentyl, cyclohexyl, cycloheptyl, and cyclooctyl. The term "optionally substituted $C_3$–$C_8$ cycloalkyl" refers to a $C_3$–$C_8$ cycloalkyl as defined herein unsubstituted or substituted with one or more groups independently selected from hydroxy, carboxy, $C_{1-6}$ alkoxy, $C_{1-6}$ alkyl, halogen, carboxamide, trifluoromethyl, hydroxymethyl, and hydroxy($C_1$–$C_4$)alkyl.

As used herein, the term "saturated heterocycle" is taken to be a 4–9 membered ring containing nitrogen and optionally one other atom selected from oxygen, nitrogen, and sulfur. The term "optionally substituted saturated heterocycle" is taken to be a saturated heterocycle as defined herein unsubstituted or substituted with one or more groups independently selected from hydroxy, carboxy, $C_{1-6}$ alkoxy, $C_{1-6}$ alkyl, halogen, carboxamide, trifluoromethyl, hydroxymethyl, and hydroxy($C_1$–$C_4$)alkyl.

As used herein, the term "$C_1$–$C_6$ alkyl" refers to straight or branched, monovalent, saturated aliphatic chains of 1 to 6 carbon atoms and includes, but is not limited to, methyl, ethyl, propyl, isopropyl, butyl, isobutyl, t-butyl, pentyl, isopentyl, and hexyl. The term "$C_1$–$C_6$ alkyl" includes within its definition the terms "$C_1$–$C_4$ alkyl" and "$C_1$–$C_3$ alkyl."

"$C_1$–$C_6$ alkenyl" refers to a straight or branched, divalent, unsaturated aliphatic chain of 1 to 6 carbon atoms and includes, but is not limited to, methylenyl, ethylenyl, propylenyl, isopropylenyl, butylenyl, isobutylenyl, 1-butylenyl, pentylenyl, isopentylenyl, hexylenyl.

"$C_1$–$C_6$ alkoxycarbonyl" represents a straight or branched $C_1$–$C_6$ alkoxy chain, as defined above, that is attached via the oxygen atom to a carbonyl moiety. Typical $C_1$–$C_6$ alkoxycarbonyl groups include methoxycarbonyl, ethoxycarbonyl, propoxycarbonyl, isopropoxycarbonyl, butoxycarbonyl, 1-butoxycarbonyl and the like.

The term "di($C_1$–$C_6$ alkyl)amino" refers to a group of the formula:

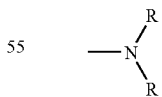

wherein each R group independently represents a "$C_1$–$C_6$ alkyl" group, as defined above.

An "optionally substituted phenyl" is a phenyl ring that is unsubstituted or substituted with 1 to 5 substituents, more preferably 1 to 3 substituents, for example: halo, $C_1$–$C_6$ alkyl, $C_1$–$C_6$ alkoxy, $C_1$–$C_6$ alkylamino, trifluoromethyl, nitro, and cyano.

An "optionally substituted benzyl" is a benzyl ring that is unsubstituted or substituted with 1 to 5 substituents, more preferably 1 to 3 substituents, for example: halo, $C_1$–$C_6$ alkyl, $C_1$–$C_6$ alkoxy, trifluoromethyl, nitro, and cyano.

"Phenoxycarbonyl" refers to the group: phenyl-O—C(O)—. "Aryl" refers to an unsaturated aromatic carbocyclic group of 6 to 14 carbon atoms having a single ring (e.g., phenyl) or multiple condensed (fused) rings (e.g., naphthyl or anthracenyl).

Unless otherwise constrained by the definition for the aryl substituent, such aryl groups can optionally be substituted with 1 to 5 substituents, more preferably 1 to 3 substituents, selected from the group consisting of halo, hydroxy, acetyl, nitro, cyano, $C_1$–$C_6$ alkyl, $C_1$–$C_6$ alkoxy, phenyl, di($C_1$–$C_6$ alkyl)amino, trifluoromethyl, trifluoromethoxy, —S(O)$_m$—($C_1$–$C_6$ alkyl), and —S(O)$_m$-(phenyl), wherein m can be 0, 1, or 2.

"Arylalkyl" refers to aryl groups attached to alkyl groups, preferably having 1 to 6 carbon atoms in the alkyl moiety and 6 to 10 carbon atoms in the aryl moiety. Such arylalkyl groups are exemplified by benzyl, phenethyl, and the like.

Unless otherwise constrained by the definition for arylalkyl, such arylalkyl groups can be optionally substituted with 1 to 5 substituents, more preferably 1 to 3 substituents, selected from the group consisting of halo, hydroxy, nitro, cyano, $C_1$–$C_6$ alkyl, $C_1$–$C_6$ alkoxy, di($C_1$–$C_6$ alkyl)amino, trifluoromethyl, trifluoromethoxy, carbamoyl, pyrrolidinyl, —S(O)$_m$—($C_1$–$C_6$ alkyl), and —S(O)$_m$-(phenyl), wherein m can be 0, 1, or 2. The arylalkyl groups may be optionally substituted on the aryl moiety, the alkyl moiety, or both the aryl moiety and the alkyl moiety.

The term "heterocycle" represents an unsubstituted or substituted 5- to 7-membered monocyclic, or 7- to 11-membered bicyclic heterocyclic ring that is saturated or unsaturated and that consists of carbon atoms and from one to five heteroatoms selected from the group consisting of nitrogen, oxygen or sulfur, and including a bicyclic group in which any of the above-defined heterocyclic rings is fused to a benzene ring to another heterocycle as defined above.

The term "heteroaryls" represents the above-defined heterocylic rings that are fused to a benzene ring to another heterocycle as defined above.

Unless otherwise constrained by the definition for the heterocyclic substituent, such heterocycles can be optionally substituted with 1 to 8 substituents selected from the group consisting of halo, nitro, cyano, hydroxy, acetyl, $C_1$–$C_6$ alkyl, $C_1$–$C_6$ alkoxy, $C_3$–$C_{10}$ cycloalkyl, optionally substituted phenyl, phenethyl, phenoxy, phenoxycarbonyl, optionally substituted benzyl, 1,1-diphenylmethyl, oxo, $C_1$–$C_6$ alkoxycarbonyl, ($C_1$–$C_6$ alkoxy)$C_1$–$C_6$ alkyl-, trifluoromethyl, pyridyl, (pyrrolidinyl)$C_1$–$C_6$ alkyl-, and (pyridyl)$C_1$–$C_6$ alkyl-, di($C_1$–$C_6$ alkyl)amino, trifluoromethyl, trifluoromethoxy, —S(O)$_m$—($C_1$–$C_6$ alkyl), and —S(O)$_m$-(phenyl), wherein m can be 0, 1, or 2.

Examples of such heterocycles include azepinyl, azetidinyl, benzazepinyl, benzimidazolyl, benzoazolyl, benzodioxolyl, benzodioxanyl, benzopyranyl, benzothiazolyl, benzothienyl, dihydropyrazolooxazinyl, dihydropyrazolooxazolyl, furyl, imidazolyl, imidazolinyl, imidazolidinyl, indolinyl, indolyl, isoindolinyl, isoquinolinyl, isothiazolidinyl, isothiazolyl, isoxazolidinyl, isoxazolyl, morpholinyl, napthyridinyl, oxadiazolyl, oxazolyl, oxazolidinyl, phthalimidyl, piperazinyl, piperidinyl, pyrazinyl, pyridyl, pyrazinyl, pyrazolidinyl, pyrazolinyl, pyrazolyl, pyridyl, pyrimidinyl, pyridazinyl, pyrrolidinyl, pyrrolopyrazolyl, pyrrolyl, quinazolinyl, quinolinyl, quinuclidinyl, tetrahydrofuryl, tetrahydropyranyl, tetrahydroisoquinolinyl, tetrahydroquinolinyl, thiazolyl, thiazolidinyl, thiadiazolyl, thienyl, thiomorpholinyl, triazolyl, and the like.

Preferred heterocycles include: benzodioxolyl, dihydropyrrolopyrazolyl, pyridyl, quinolinyl.

Preferred embodiments of the invention include the following:

One preferred embodiment of the invention are compounds of the structure:

Formula (II)

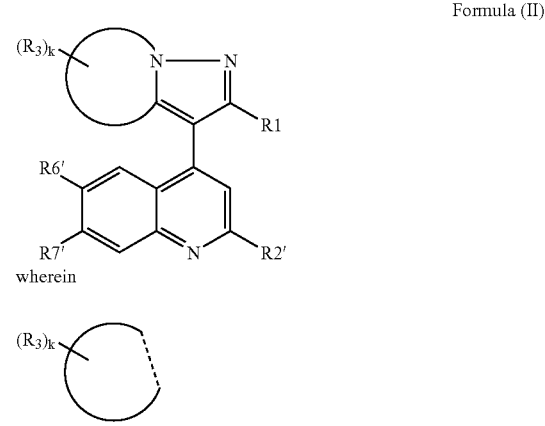

wherein

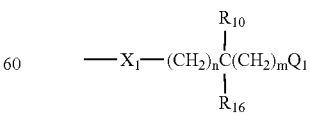

is a five or six membered saturated ring with the proviso that the ring is a fully saturated carbon ring;

R1 is defined as in claim 1;

R2' is hydrogen; (C1–C6)alkyl; (C1–C6)alkylthio; (C1–C6)alkoxy; halo; thiophenyl; aminophenyl; N-pyrrolidino; N-morpholino;

R6' and R7' are independently one or more of the following: hydrogen, (C1–C6)alkyl, (C2–C6)alkenyl, (C2–C6)alkynyl, (C1–C6)alkylhalide, (C1–C6)alkoxy, (C2–C6)alkenyloxy, (C2–C6)alkynyloxy, (C1–C6)alkylthio, (C1–C6)alkylsulphinyl, (C1–C6)alkylsulphonyl, (C1–C6)alkylamino, di-[(C1–C6)alkyl]amino, (C1–C6)alkoxycarbonyl, N—(C1–C6)alkylcarbamoyl, N,N-di-[(C1–C6)alkyl]carbamoyl, aminooxy, N—(C1–C6)alkyl aminooxy, N,N-di-[(C1–C6)alkyl]aminooxy, (C2–C6)alkanoyl, (C2–C6)alkanoyloxy, (C2–C6)alkanoylamino, N—(C1–C6)alkyl-(C2–C6)alkanoyl amino, (C3–C6)alkanoyl amino, N—(C1–C6)alkyl-(C3–C6)alkenoylamino, (C3–C6)alkynoylamino, N—(C1–C6)alkyl-(C3–C6)alkynoylamino, sulphamoyl, N—(C1–C6)alkylsulphamoyl, N,N-di-[(C1–C6)alkyl]sulphamoyl, (C1–C6)alkanesulphonylamino, N—(C1–C6)alkyl-(C1–C6)alkanesulphonylamino, carboxamide, ethylene, phenyl, thiophenyl, aminophenyl, phenylthio, halo, cyano, pyridinyl, arylalkyl, hydroxy, N-pyrrolidino, N-morpholino, carboxyl, [5-phenyl-1,2,4-oxadiazole-3-yl]methoxy, 6-methyl-pyridazin-3-yloxy, (5-oxo-2-pyrrolidinyl) methoxy, 2-(4,5-dihydro-1H-imidazolyl), N,N-dialkylcarbamoyloxy, 1-hydroxy-1-methylethyl, 4-fluorophenyl, 3,4-methylenedioxyphenyl, trifluoromethyl, trifluoromethoxy, or a group of the formula $$-X_1-(CH_2)_n\underset{\underset{R_{16}}{|}}{\overset{\overset{R_{10}}{|}}{C}}(CH_2)_mQ_1$$

wherein: $X_1$ is O, N, S, $SO_2$, $NR_{13}$, C(O), or bond, $Q_1$ is hydrogen, phenyl, 5-(2,2-difluoro-1,3-benzodioxolyl), C(O)$Q_5$, or pyridyl when m and n are independently 0–2, except when one is 0 the other cannot be 0; $Q_1$ is $OR_{11}$, $NR_{11}R_{12}$, halo, N-morpholino, N-piperazino-N'$R_{13}$, N-imidazolyl, N-pyrazolyl, N-triazolyl, N-(4-piperidinylpiperidine), $SO_2R_{14}$, $SOR_{14}$, $NHSO_2R_{15}$, acetamido, N-phthalimido, N-oxazolidino, N-imidazolino, N-benzoxazolidino, N-pyrolidinonyl, N(N'-methylbenzimidazolino), N,N-di (C1–C4)alkylamino(C1–C4)alkoxy, N-benzimidazolino; when m and n are independently 0–2, but one or the other of m or n is not 0; $Q_5$ is hydroxy, methoxy, amino, diethylamino, dimethylamino; $R_{10}$ is hydrogen, halo, (C1–C6)alkyl; $R_{11}$ and $R_{12}$ are independently hydrogen, (C1–C6)alkyl, (C1–C6)alkoxy, arylalkyl, cycloalkyl, cycloalkylmethyl, 4-(N-methylpiperidinyl), pyridyl, or $R_{11}$ and $R_{10}$ can be taken together to form a 4, 5, 6, or 7 membered ring, or $R_{11}$ and $R_{12}$ can be taken together to form a 3, 4, 5, 6, or 7 membered ring; $R_{13}$ is hydrogen, (C1–C6) alkyl, 2-methoxyphenyl; $R_{14}$ is 2-pyrimidinyl, N-methyl-2-imidazolyl, 4-chlorophenyl, 2-pyridylmethyl; $R_{15}$ is ($C_1$–C6)alkyl, N-methyl-4-imidazolyl; $R_{16}$ is hydrogen, halo, arylalkyl, aryl,
or a group of the formula

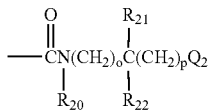

wherein: $Q_2$ is hydrogen, 4-imidazolyl, or $C(O)NR_{24}R_{25}$ when o and p are independently 0–2; $Q_2$ is $OR_{23}$, $NR_{24}R_{25}$, or N-morpholino, when o and p are independently 0–2, but one or the other of o or p is not 0; $R_{20}$ is hydrogen, or (C1–C6)alkyl; $R_{21}$ is hydrogen, (C1–C6)alkyl, or $R_{21}$ and $R_{20}$ can be taken together to form a 4, 5, 6, or 7 membered ring; $R_{22}$ is hydrogen, (C1–C6)alkyl, arylalkyl, aryl, or $R_{21}$ and $R_{22}$ can be taken together to be a 3, 4, 5, 6, 7 membered ring; $R_{23}$ is hydrogen or (C1–C6)alkyl; $R_{24}$ is hydrogen, (C1–C6)alkyl, or $R_{24}$ and $R_{25}$ can be taken together to form a 3, 4, 5, 6, or 7 membered ring, or $R_{24}$ and $R_{20}$ can be taken together to form a 6 or 7 membered ring; $R_{25}$ is hydrogen, (C1–C6)alkyl, or acetyl,
or a group of the formula

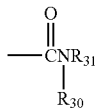

wherein: $R_{30}$ is hydrogen, or (C1–C6)alkyl; $R_{31}$ is hydrogen, (C1–C6)alkyl, 2-pyridyl, pyridylmethyl, amino, or hydroxy, or a group of the formula

wherein: $R_{32}$ and $R_{33}$ are each independently hydrogen, (C1–C6)alkyl, acetyl, alkylsulphonyl, or $R_{32}$ and $R_{33}$ can be taken together to form a 4, 5, 6, or 7 membered ring,
or a group of the formula

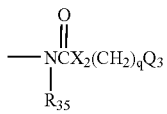

wherein: $X_2$ is $CH_2$, O, or N; q is 2–3 except when $Q_3$ is a bond, q is 0–3; $Q_3$ is $NR_{36}R_{37}$, $OR_{38}$, or a bond; $R_{35}$ is hydrogen, or $R_{35}$ and $Q_3$ (when $Q_3$ is a bond) can be taken together to form a 5 membered ring; $R_{36}$, $R_{37}$, and $R_{38}$ are each independently hydrogen, or (C1–C6)alkyl, or a group of the formula

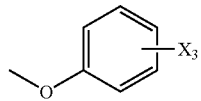

wherein: $X_3$ is cyano, carboxamide, N,N-dimethylcarboxamide, N,N-dimethylthiocarboxamide, N,N-dimethylaminomethyl, 4-methylpiperazin-1yl-methyl or carboxylate,
or a group of the formula

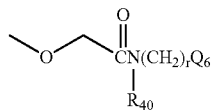

wherein: $Q_6$ is $NR_{41}R_{42}$; r is 2–3; $R_{40}$ is hydrogen, or (C1–C6)alkyl; $R_{41}$ and $R_{42}$ are hydrogen, (C1–C6)alkyl, or $R_{41}$ and $R_{40}$ can be taken together to form a 6 or 7 membered ring,
or a group of the formula

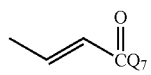

wherein: $Q_7$ is hydroxy, methoxy, or N-piperidinyl;
k is 1–8; R3 is one or more of the following: hydrogen; (C1–C4)alkyl; (C1–C4) alkylhydroxy; hydroxy; N,N-di (C1–C4)alkylamino(C1–C4)alkoxy; benzyl oxymethyl; phenyloxymethyl; oxo; carboxyl; (C1–C4)alkylaryl; benzyloxy; acetoxy; amino(C1–C4)alkyl; (C2–C4)alkenyl; halo; —O—(C1–C4)alkyl; chlorophenethyl; acetonitrile; phenyl; or an optionally substituted phenyl; wherein the substitution may be one or more of the following: (C1–C6)alkoxy, halo, carboxy, or (C1–C6)alkoxycarbonyl; with the proviso that R7' cannot be aryl; heteroaryl; fused aryl; or fused heteroaryl, and the pharmaceutically acceptable salts, esters and prodrugs thereof.

Another preferred embodiment of the invention are compounds of the structure:

Formula (III)

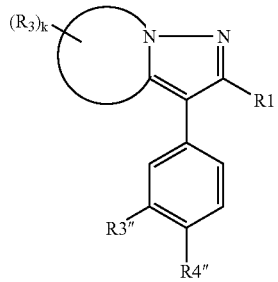

wherein

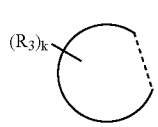

is a five or six membered saturated ring, with the proviso that the ring is a fully saturated carbon ring;

R1 is defined as in claim 1;
R3" is hydrogen; halo; trifluoromethyl;
R4" is hydrogen; halo; (C1–C6)alkyl; (C1–C6)alkoxy; hydroxy; (C1–C6)alkylsulphonyl;
k and R3 are defined as in claim 1;
and the pharmaceutically acceptable salts, esters and prodrugs thereof.

Another preferred embodiment of the invention are compounds of the structure:

Formula (IV)

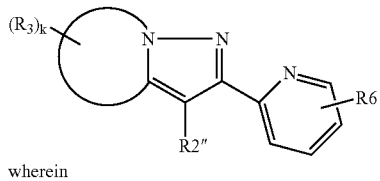

wherein

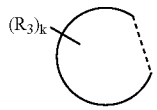

is a five or six membered saturated ring, with the proviso that the ring is a fully saturated carbon ring;

R6 may be one or more of the following: hydrogen, (C1–C6)alkyl, (C2–C6)alkenyl, (C2–C6)alkynyl, (C1–C6) alkoxy, (C2–C6)alkenyloxy, (C2–C6)alkynyloxy, (C1–C6) alkylthio, (C1–C6)alkylsulphinyl, (C1–C6)alkylsulphonyl, (C1–C6)alkylamino, di-[(C1–C6)alkyl]amino, (C1–C6) alkoxycarbonyl, N—(C1–C6)alkylcarbamoyl, N,N-di-[(C1–C6)alkyl]carbamoyl, (C2–C6)alkanoyl, (C2–C6) alkanoyloxy, (C2–C6)alkanoylamino, N—(C1–C6)alkyl-(C2–C6)alkanoylamino, (C3–C6)alkenoylamino, N—(C1–C6)alkyl-(C3–C6)alkenoylamino, (C3–C6) alkynoylamino, N—(C1–C6)alkyl-(C3–C6)alkynoylamino, N—(C1–C6)alkyl sulphamoyl, N,N-di-[(C1–C6)alkyl] sulphamoyl, (C1–C6)alkanesulphonylamino, N—(C1–C6) alkyl-(C1–C6)alkanesulphonylamino, carboxamide, ethylene, thiophenyl, aminophenyl, trifluoromethyl, halo, trifluoromethoxy, hydroxymethyl, N-pyrrolidino, N-morpholino, phenylthio, dialkylaminomethyl, methoxyphenyl, amino, hydroxy, carboxyl, phenyl, arylalky;

R2" is unsubstituted or substituted quinoline-8-yl; unsubstituted or substituted quinoline-6-yl; unsubstituted or substituted 1-naphthyl; unsubstituted or substituted 2-naphthyl; unsubstituted or substituted 3,4-methylenedioxyphenyl; unsbustituted or substituted 3,4-ethylenedioxyphenyl; unsubstituted or substituted benzothiophen-2-yl; wherein the substitution may independently be one or more of the following: (C1–C6)alkyl, (C2–C6)alkenyl, (C2–C6)alkynyl, (C1–C6)alkylhalide, (C1–C6)alkoxy, (C2–C6)alkenyloxy, (C2–C6)alkynyloxy, (C1–C6)alkylthio, (C1–C6) alkylsulphinyl, (C1–C6)alkylsulphonyl, (C1–C6) alkylamino, di-[(C1–C6)alkyl]amino, (C1–C6) alkoxycarbonyl, N—(C1–C6)alkylcarbamoyl, N,N-di-[(C1–C6)alkyl]carbamoyl, aminooxy, N—(C1–C6)alkyl aminooxy, N,N-di-[(C1–C6)alkyl]aminooxy, (C2–C6) alkanoyl, (C2–C6)alkanoyloxy, (C2–C6)alkanoylamino, N—(C1–C6)alkyl-(C2–C6)alkanoylamino, (C3–C6) alkenoylamino, N—(C1–C6)alkyl-(C3–C6)alkenoylamino, (C3–C6)alkynoylamino, N—(C1–C6)alkyl-(C3–C6) alkynoylamino, sulphamoyl, N—(C1–C6)alkylsulphamoyl, N,N-di-[(C1–C6)alkyl]sulphamoyl, (C1–C6) alkanesulphonylamino, N—(C1–C6)alkyl-(C1–C6) alkanesulphonylamino, carboxamide, ethylene, phenyl, thiophenyl, aminophenyl, phenylthio, halo, cyano, pyridinyl, arylalkyl, hydroxy, N-pyrrolidino, N-morpholino, carboxyl, [5-phenyl-1,2,4-oxadiazole-3-yl]methoxy, 6-methyl-pyridazin-3-yloxy, (5-oxo-2-pyrrolidinyl) methoxy, 2-(4,5-dihydro-1H-imidazolyl), N,N-dialkylcarbamoyloxy, 1-hydroxy-1-methylethyl, 4-fluorophenyl, 3,4-methylenedioxyphenyl, trifluoromethyl, trifluoromethoxy, or a group of the formula

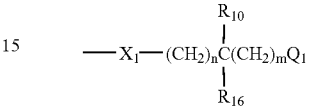

wherein: $X_1$ is O, N, S, $SO_2$, $NR_{13}$, C(O), or bond; $Q_1$ is hydrogen, phenyl, 5-(2,2-difluoro-1,3-benzodioxolyl), C(O) $Q_5$, or pyridyl when m and n are independently 0–2, except when one is 0 the other cannot be 0; $Q_1$ is $OR_{11}$, $NR_{11}R_{12}$, halo, N-morpholino, N-piperazino-N'$R_{13}$, N-imidazolyl, N-pyrazolyl, N-triazolyl, N-(4-piperidinylpiperidine), $SO_2R_{14}$, $SOR_{14}$, $NHSO_2R_{15}$, acetamido, N-phthalimido, N-oxazolidino, N-imidazolino, N-benzoxazolidino, N-pyrolidinonyl, N(N'-methylbenzimidazolino), N,N-di (C1–C4)alkylamino(C1–C4)alkoxy, N-benzimidazolino; when m and n are independently 0–2, but one or the other of m or n is not 0; $Q_5$ is hydroxy, methoxy, amino, diethylamino, dimethylamino; $R_{10}$ is hydrogen, halo, $(C_1-C6)$alkyl; $R_{11}$ and $R_{12}$ are independently hydrogen, (C1–C6)alkyl, (C1–C6)alkoxy, arylalkyl, cycloalkyl, cycloalkylmethyl, 4-N-methylpiperidinyl), pyridyl, or $R_{11}$ and $R_{10}$ can be taken together to form a 4, 5, 6, or 7 membered ring, or $R_{11}$ and $R_{12}$ can be taken together to form a 3, 4, 5, 6, or 7 membered ring; $R_{13}$ is hydrogen, (C1–C6) alkyl, 2-methoxyphenyl; $R_{14}$ is 2-pyrimidinyl, N-methyl-2-imidazolyl, 4-chlorophenyl, 2-pyridylmethyl; $R_{15}$ is (C1–C6)alkyl, N-methyl-4-imidazolyl; $R_{16}$ is hydrogen, halo, arylalkyl, aryl, or a group of the formula

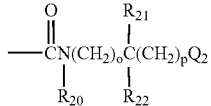

wherein: $Q_2$ is hydrogen, 4-imidazolyl, or $C(O)NR_{24}R_{25}$ when o and p are independently 0–2; $Q_2$ is $OR_{23}$, $NR_{24}R_{25}$, or N-morpholino, when o and p are independently 0–2, but one or the other of o or p is not 0; $R_{20}$ is hydrogen, or (C1–C6)alkyl; $R_{21}$ is hydrogen, (C1–C6)alkyl, or $R_2$, and $R_{20}$ can be taken together to form a 4, 5, 6, or 7 membered ring; $R_{22}$ is hydrogen, (C1–C6)alkyl, arylalkyl, aryl, or $R_2$, and $R_{22}$ can be taken together to be a 3, 4, 5, 6, 7 membered ring; $R_{23}$ is hydrogen or $(C_1-C6)$alkyl; $R_{24}$ is hydrogen, (C1–C6)alkyl, or $R_{24}$ and $R_{25}$ can be taken together to form a 3, 4, 5, 6, or 7 membered ring, or $R_{24}$ and $R_{20}$ can be taken together to form a 6 or 7 membered ring; $R_{25}$ is hydrogen, (C1–C6)alkyl, or acetyl, or a group of the formula

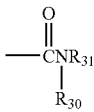

wherein: $R_{30}$ is hydrogen, or (C1–C6)alkyl; $R_{31}$ is hydrogen, (C1–C6)alkyl, 2-pyridyl, pyridylmethyl, amino, or hydroxy, or a group of the formula

wherein: $R_{32}$ and $R_{33}$ are each independently hydrogen, (C1–C6)alkyl, acetyl, alkylsulphonyl, or $R_{32}$ and $R_{33}$ can be taken together to form a 4, 5, 6, or 7 membered ring, or a group of the formula

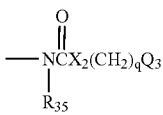

wherein: $X_2$ is $CH_2$, O, or N; q is 2–3 except when $Q_3$ is a bond, q is 0–3; $Q_3$ is $NR_{36}R_{37}$, $OR_{38}$, or a bond; $R_{35}$ is hydrogen, or $R_{35}$ and $Q_3$ (when $Q_3$ is a bond) can be taken together to form a 5 membered ring; $R_{36}$, $R_{37}$, and $R_{38}$ are each independently hydrogen, or (C1–C6)alkyl, or a group of the formula

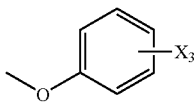

wherein: $X_3$ is cyano, carboxamide, N,N-dimethylcarboxamide, N,N-dimethylthiocarboxamide, N,N-dimethylaminomethyl, 4-methylpiperazin-1yl-methyl or carboxylate, or a group of the formula

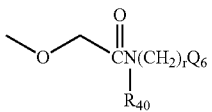

wherein: $Q_6$ is $NR_{41}R_{42}$; r is 2–3; $R_{40}$ is hydrogen, or (C1–C6)alkyl; $R_{41}$ and $R_{42}$ are hydrogen, (C1–C6)alkyl, or $R_{41}$ and $R_{40}$ can be taken together to form a 6 or 7 membered ring, or a group of the formula

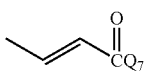

wherein: $Q_7$ is hydroxy, methoxy, dimethylamino, or N-piperidinyl;

k is 1–8; R3 is hydrogen; and the pharmaceutically acceptable salts thereof.

Compounds Exemplified in the Application Include the Following:
a) 6-Bromo-4-(2-pyridin-2-yl-5,6-dihydro-4H-pyrrolo[1,2-b]pyrazol-3-yl)-quinoline,
b) 3-Pyridin-4-yl-2-pyridin-2-yl-5,6-dihydro-4H-pyrrolo[1,2-b]pyrazole,
c) 2-(6-Methyl-pyridin-2-yl)-3-p-tolyl-5,6-dihydro-4H-pyrrolo[1,2-b]pyrazole,
d) 4-[3-(6-Methyl-pyridin-2-yl)-5,6-dihydro-4H-pyrrolo[1,2-b]pyrazol-2-yl]-quinoline,
e) 2-(6-Methyl-pyridin-2-yl)-3-naphthalen-1-yl-5,6-dihydro-4H-pyrrolo[1,2-b]pyrazole,
f) 2-(6-Methyl-pyridin-2-yl)-3-pyridin-3-yl-5,6-dihydro-4H-pyrrolo[1,2-b]pyrazole,
g) 3-(4-Fluoro-naphthalen-1-yl)-2-(6-methyl-pyridin-2-yl)-5,6-dihydro-4H-pyrrolo[1,2-b]pyrazole,
h) 3-(3,4-Difluoro-phenyl)-2-(6-methyl-pyridin-2-yl)-5,6-dihydro-4H-pyrrolo[1,2-b]pyrazole,
i) 1-[2-(4-Methanesulfonyl-phenyl)-1-(6-methyl-pyridin-2-yl)-ethylideneamino]-pyrrolidin-2-one,
j) 7-Methoxy-4-(2-pyridin-2-yl-5,6-dihydro-4H-pyrrolo[1,2-b]pyrazol-3-yl)-quinoline,
k) 7-Benzyloxy-6-methoxy-4-(2-pyridin-2-yl-5,6-dihydro-4H-pyrrolo[1,2-b]pyrazol-3-yl)-quinoline,
l) 6-(2-Pyridin-2-yl-5,6-dihydro-4H-pyrrolo[1,2-b]pyrazol-3-yl)-quinoline,
m) 6-[2-(6-Methyl-pyridin-2-yl)-5,6-dihydro-4H-pyrrolo[1,2-b]pyrazol-3-yl]-quinoline,
n) 3-Naphthalen-2-yl-2-pyridin-2-yl-5,6-dihydro-4H-pyrrolo[1,2-b]pyrazole,
o) 2-(6-Methyl-pyridin-2-yl)-3-naphthalen-2-yl-5,6-dihydro-4H-pyrrolo[1,2-b]pyrazole,
p) 3-(4-Fluoro-phenyl)-2-(6-trifluoromethyl-pyridin-2-yl)-5,6-dihydro-4H-pyrrolo[1,2-b]pyrazole,
q) 4-(Quinolin-4-yl)-3-(5-fluoropyridin-2-yl)-5,6-dihydro-4H-pyrrolo[1,2-b]pyrazole,
r) 4-(7-Bromoquinolin-4-yl)-3-(pyridin-2-yl)-5,6-dihydro-4H-pyrrolo[1,2-b]pyrazole,
s) (Quinolin-4-yl)-3-(2,4-difluorophenyl)-5,6-dihydro-4H-pyrrolo[1,2-b]pyrazole,
t) 4-(2-Pyrazin-2-yl-5,6-dihydro-4H-pyrrolo [1,2-b]pyrazol-3-yl)-quinoline,
u) 4-(5-Methyl-2-pyridin-2-yl-5,6-dihydro-4H-pyrrolo[1,2-b]pyrazol-3-yl)-quinoline,
v) 6-Bromo-4-[2-(6-methyl-pyridin-2-yl)-5,6-dihydro-4H-pyrrolo[1,2-b]pyrazol-3-yl]-quinoline,
w) 4-[2-(6-Methyl-pyridin-2-yl)-5,6-dihydro-4H-pyrrolo[1,2-b]pyrazol-3-yl]-6-trifluoromethyl-quinoline,
x) 3-(3–Chloro-4-fluoro-phenyl)-2-(6-methyl-pyridin-2-yl)-5,6-dihydro-4H-pyrrolo[1,2-b]pyrazole,
y) 3-(2-Chloro-4-fluoro-phenyl)-2-(6-methyl-pyridin-2-yl)-5,6-dihydro-4H-pyrrolo[1,2-b]pyrazole,
z) 3-(4-Fluoro-3-trifluoromethyl-phenyl)-2-(6-methyl-pyridin-2-yl)-5,6-dihydro-4H-pyrrolo[1,2-b]pyrazole,
aa) 2-(6-Methyl-pyridin-2-yl)-3-(2,4,5-trifluoro-phenyl)-5,6-dihydro-4H-pyrrolo[1,2-b]pyrazole,
bb) 8-Fluoro-4-[2-(6-methyl-pyridin-2-yl)-5,6-dihydro-4H-pyrrolo[1,2-b]pyrazol-3-yl]-quinoline,
cc) 7-Bromo-4-[2-(6-methyl-pyridin-2-yl)-5,6-dihydro-4H-pyrrolo[1,2-b]pyrazol-3-yl]-quinoline,
dd) 4-[2-(6-Methyl-pyridin-2-yl)-5,6-dihydro-4H-pyrrolo[1,2-b]pyrazol-3-yl]-6-trifluoromethoxy-quinoline,
ee) 4-[2-(6-Methyl-pyridin-2-yl)-5,6-dihydro-4H-pyrrolo[1,2-b]pyrazol-3-yl]-7-trifluoromethyl-quinoline,
ff) 7-Methoxy-4-[2-(6-methyl-pyridin-2-yl)-5,6-dihydro-4H-pyrrolo[1,2-b]pyrazol-3-yl]-quinoline,
gg) 3-(2-Chloro-pyridin-4-yl)-2-pyridin-2-yl-5,6-dihydro-4H-pyrrolo[1,2-b]pyrazole,
hh) [2-(6-Methyl-pyridin-2-yl)-3-quinolin-4-yl-5,6-dihydro-4H-pyrrolo[1,2-b]pyrazol-6-yl]-methanol,
ii) [3-(7-Bromo-quinolin-4-yl)-2-(6-methyl-pyridin-2-yl)-5,6-dihydro-4H-pyrrolo[1,2-b]pyrazol-6-yl]-methanol,
jj) 4-[2-(6-Chloro-pyridin-2-yl)-5-(4-fluorophenyl)-5,6-dihydro-4H-pyrrolo[1,2-b]pyrazol-3-yl]-quinoline, kk) 4-[2-(6-Ethoxy-pyridin-2-yl)-5-(4-fluoro-phenyl)-5,6-dihydro-4H-pyrrolo[1,2-b]pyrazol-3-yl]-quinoline,
ll) (S)-4-[6-Benzyloxymethyl-2-(6-methyl-pyridin-2-yl)-5,6-dihydro-4H-pyrrolo[1,2-b]pyrazol-3-yl]-7-chloro-quinoline,
mm) (S)-4-[6-Benzyloxymethyl-2-(6-chloro-pyridin-2-yl)-5,6-dihydro-4H-pyrrolo[1,2-b]pyrazol-3-yl]-quinoline,
nn) 4-[2-(6-Methyl-pyridin-2-yl)-3-quinolin-4-yl-5,6-dihydro-4H-pyrrolo[1,2-b]pyrazol-5-yl]-benzoic acid ethyl ester,
oo) 3-(4-Fluoro-phenyl)-5,5-dimethyl-2-(6-methyl-pyridin-2-yl)-5,6-dihydro-4H-pyrrolo[1,2-b]pyrazole,
pp) (R)-6-Benzyloxymethyl-3-(4-fluoro-phenyl)-2-(6-methyl-pyridin-2-yl)-5,6-dihydro-4H-pyrrolo[1,2-b]pyrazole,
qq) 5-(4-Chloro-phenyl)-3-(4-fluoro-phenyl)-2-(6-methyl-pyridin-2-yl)-5,6-dihydro-4H-pyrrolo[1,2-b]pyrazole,
rr) 4-[2-(3-Trifluoromethyl-phenyl)-4,5,6,7-tetrahydro-pyrazolo[1,5-a]pyridin-3-yl]-quinoline,
ss) 4-[2-(4-Trifluoromethyl-phenyl)4,5,6,7-tetrahydro-pyrazolo[1,5-a]pyridin-3-yl]-quinoline,
tt) 4-[2-(4-Chloro-phenyl)-4,5,6,7-tetrahydro-pyrazolo[1,5-a]pyridin-3-yl]-quinoline,
uu) 4-[2-(3-Chloro-phenyl)-4,5,6,7-tetrahydro-pyrazolo[1,5-a]pyridin-3-y]-quinoline,
vv) 4-[2-(3-Fluoro-5-trifluoromethyl-phenyl)-5,6-dihydro-4H-pyrrolo[1,2-b]pyrazol-3-yl]-quinoline,
ww) 4-[2-(3-Fluoro-5-trifluoromethyl-phenyl)-4,5,6,7-tetrahydro-pyrazolo[1,5-a]pyridin-3-yl]-quinoline,
xx) 4-(2-Phenyl-4,5,6,7-tetrahydro-pyrazolo[1,5-a]pyridin-3-yl)-quinoline,
yy) 4-(2-Pyridin-2-yl-4,5,6,7-tetrahydro-pyrazolo[1,5-a]pyridin-3-yl)-[1,10]phenanthroline,
zz) 4-[2-(4-Fluoro-phenyl)-4,5,6,7-tetrahydro-pyrazolo[1,5-a]pyridin-3-yl]-quinoline,
aaa) 4-[2-(3-Trifluoromethoxy-phenyl)-4,5,6,7-tetrahydro-pyrazolo[1,5-a]pyridin-3-yl]-quinoline,
bbb) 4-[2-(2-Fluoro-phenyl)-4,5,6,7-tetrahydro-pyrazolo[1,5-a]pyridin-3-yl]-quinoline,
ccc) 4-(2-Quinolin-2-yl-4,5,6,7-tetrahydro-pyrazolo[1,5-a]pyridin-3-yl)-quinoline,
ddd) 4-[2-(4-Ethyl-pyridin-2-yl)-4,5,6,7-tetrahydro-pyrazolo[1,5-a]pyridin-3-yl]-quinoline,
eee) 4-(2-Quinolin-2-yl-5,6-dihydro-4H-pyrrolo[1,2-b]pyrazol-3-yl)-quinoline,
fff) 2-(3-Quinolin-4-yl-4,5,6,7-tetrahydro-pyrazolo[1,5-a]pyridin-2-yl)-[1,8]naphthyridine,
ggg) 4-[5-(4-Fluoro-phenyl)-2-pyridin-2-yl-5,6-dihydro-4H-pyrrolo[1,2-b]pyrazol-3-yl]-quinoline,
hhh) 4-(6-Hydroxymethyl-2-pyridin-2-yl-5,6-dihydro-4H-pyrrolo[1,2-b]pyrazol-3yl)-quinoline,
iii) 4-(3-Pyridin-2-yl-5,6-dihydro-4H-pyrrolo[1,2-b]pyrazol-2-yl)-quinoline,
jjj) 4-(4-Methyl-2-pyridin-2-yl-5,6-dihydro-4H-pyrrolo[1,2-b]pyrazol-3-yl)-quinoline,
kkk) 4-(5-Benzyl-2-pyridin-2-yl-5,6-dihydro-4H-pyrrolo[1,2-b]pyrazol-3-yl)-quinoline,
lll) 4-(5-Phenethyl-2-pyridin-2-yl-5,6-dihydro-4H-pyrrolo[1,2-b]pyrazol-3-yl)-quinoline,
mmm) 4-(5-Phenyl-2-pyridin-2-yl-5,6-dihydro-4H-pyrrolo[1,2-b]pyrazol-3-yl)-quinoline,
nnn) 4-[2-(3-Trifluoromethylphenyl)-5,6-dihydro-4H-pyrrolo[1,2-b]pyrazol-3-yl]-quinoline,
ooo) 4-[2-(4-Trifluoromethyl-phenyl)-5,6-dihydro-4H-pyrrolo[1,2-b]pyrazol-3-yl]-quinoline,
ppp) 4-(2-Phenyl-5,6-dihydro-4H-pyrrolo[1,2-b]pyrazol-3-yl)-quinoline,
qqq) 2-Chloro-4-(2-pyridin-2-yl-5,6-dihydro-4H-pyrrolo[1,2-b]pyrazol-3-yl)-quinoline,
rrr) 6,8-Dimethoxy-4-[2-(6-methyl-pyridin-2-yl)-5,6-dihydro-4H-pyrrolo[1,2b]pyrazol-3-yl]-quinoline,
sss) 4-[2-(6-Bromo-pyridin-2-yl)-5,6-dihydro-4H-pyrrolo[1,2-b]pyrazol-3-yl]-quinoline,
ttt) 6,8-Dimethoxy-4-[2-pyridin-2-yl-5,6-dihydro-4H-pyrrolo[1,2b]pyrazol-3-yl]-quinoline,
uuu) 3-(4-Fluorophenyl)-2-pyridin-2-yl-5,6-dihydro-4H-pyrrolo[1,2-b]pyrazole,
vvv) 3-(4-Methoxy-phenyl)-2-pyridin-2-yl-5,6-dihydro-4H-pyrrolo[1,2-b]pyrazole,
www) 3-(4-Fluorophenyl)-2-(6-methylpyridin-2-yl)-5,6-dihydro-4H-pyrrolo[1,2-b]pyrazole,
xxx) 3-(4-Methoxyphenyl)-2-(6-methylpyridin-2-yl)-5,6-dihydro-4H-pyrrolo[1,2-b]pyrazole,
yyy) 4-(2-Thiophen-2-yl-5,6-dihydro-4H-pyrrolo[1,2-b]pyrazol-3-yl)quinoline,
zzz) 4-[2-(6-Propylpyridin-2-yl)-5,6-dihydro-4H-pyrrolo[1,2-b]pyrazol-3-yl]-quinoline,
aaaa) 4-[2-(6-Isopropylpyridin-2-yl)-5,6-dihydro-4H-pyrrolo[1,2-b]pyrazol-3-yl]quinoline,
bbbb) 4-[2-(6-Ethyl-pyridin-2-yl)-5,6-dihydro-4H-pyrrolo[1,2-b]pyrazol-3-yl]quinoline,
cccc) 4-[2-(6-Methyl-pyridin-2-yl)-5,6-dihydro-4H-pyrrolo[1,2-b]pyrazol-3-yl]-quinoline,
dddd) 4-[2-(3-Fluorophenyl)-5,6-dihydro-4H-pyrrolo[1,2-b]pyrazol-3-yl]-quinoline,
eeee) 4-[2-(2-Fluorophenyl)-5,6-dihydro-4H-pyrrolo[1,2-b]pyrazol-3-yl]-quinoline,
ffff) 4-[2-(4-Fluoro-phenyl)-5,6-dihydro-4H-pyrrolo[1,2-b]pyrazol-3-yl]-quinoline,
gggg) 4-[2-(3-Trifluoromethoxy-phenyl)-5,6-dihydro-4H-pyrrolo[1,2-b]pyrazol-3-yl]-quinoline,
hhhh) 4-[2-(4-Chloro-pyridin-2-yl)-5,6-dihydro-4H-pyrrolo[1,2-b]pyrazol-3-yl]-quinoline,
iiii) 4-[2-(4-Fluoro-3-trifluoromethyl-phenyl)-5,6-dihydro-4H-pyrrolo[1,2-b]pyrazol-3-yl]quinoline,
jjjj) 4-[2-(2-Fluoro-3-trifluoromethyl-phenyl)-5,6-dihydro-4H-pyrrolo[1,2-b]-pyrazol-3-yl]-quinoline,
kkkk) 4-[5-(3-Methoxy-phenyl)-2-pyridin-2-yl-5,6-dihydro-4H-pyrrolo[1,2-b]pyrazol-3-yl]-quinoline,
llll) 4-[2-(4-Fluoro-3-trifluoromethyl-phenyl)-5-(3-methoxy-phenyl)-5,6-dihydro-4H-pyrrolo[1,2-b]pyrazol-3-yl]-quinoline,
mmmm) 4-(7-Chloro-quinolin-4-yl)-3-(6-methylpyridin-2-yl)-5,6-dihydro-4H-pyrrolo[1,2-b]pyrazole,
nnnn) 4-(7-Ethoxyquinolin-4-yl)-3-(6-methylpyridin-2-yl)-5,6-dihydro-4H-pyrrolo[1,2-b]pyrazole,
oooo) 6-(3-Quinolin-4-yl-5,6-dihydro-4H-pyrrolo[1,2-b]pyrazol-2-yl)-pyridine-2-carboxylic acid hydrochloride,
pppp) 6,7-Difluoro-4-[2-(6-methyl-pyridin-2-yl)-5,6-dihydro-4H-pyrrolo[1,2-b]pyrazol-3-yl]-quinoline,
qqqq) 6,7-Dimethoxy-4-[2-(6-methyl-pyridin-2-yl)-5,6-dihydro-4H-pyrrolo[1,2-b]pyrazol-3-yl]-quinoline,
rrrr) 3-Benzo[1,3]dioxol-5-yl-2-(6-methyl-pyridin-2-yl)-5,6-dihydro-4H-pyrrolo[1,2-b]pyrazole,
ssss) 6-(4-Fluoro-phenyl)-4-[2-(6-methyl-pyridin-2-yl)-5,6-dihydro-4H-pyrrolo[1,2-b]pyrazol-3-yl]-quinoline,
tttt) 6-Benzo[1,3]dioxol-5-yl-4-[2-(6-methyl-pyridin-2-yl)-5,6-dihydro-4H-pyrrolo[1,2-b]pyrazol-3-yl]-quinoline,
uuuu) 4-[2-(6-Methyl-pyridin-2-yl)-5,6-dihydro-4H-pyrrolo[1,2-b]pyrazol-3-yl]-6-thiophen-2-yl-quinoline,
vvvv) 4-[2-(6-Methyl-pyridin-2-yl)-5,6-dihydro-4H-pyrrolo[1,2-b]pyrazol-3-yl]-6-phenyl-quinoline,
wwww) 8-[2-(6-Methyl-pyridin-2-yl)-5,6-dihydro-4H-pyrrolo[1,2-b]pyrazol-3-yl]-quinoline, xxxx) 3-Benzo[b]thiophen-2-yl-2-(6-methyl-pyridin-2-yl)-5,6-dihydro-4H-pyrrolo[1,2-b]pyrazole,
yyyy) 4-(2-Pyridin-2-yl-5,6-dihydro-4H-pyrrolo[1,2-b]pyrazol-3-yl)-quinoline-6-carboxylic acid methyl ester,
zzzz) 4-[2-(6-Methyl-pyridin-2-yl)-5,6-dihydro-4H-pyrrolo[1,2-b]pyrazol-3-yl]-quinoline-6-carboxylic acid methyl ester,
aaaaa) 4-[2-(6-Methyl-pyridin-2-yl)-5,6-dihydro-4H-pyrrolo[1,2-b]pyrazol-3-yl]-quinoline-7-carboxylic acid methyl ester,
bbbbb) 4-[2-Pyridin-2-yl-5,6-dihydro-4H-pyrrolo[1,2-b]pyrazol-3-yl]-quinoline-7-carboxylic acid methyl ester,
ccccc) 2-Pyridin-2-yl-3-quinolin-4-yl-pyrazolo[5,1-c]morpholine,
ddddd) 2-Pyridin-2-yl-3-quinolin-4-yl-pyrazolo[5,1-c]morpholin-4-one,
eeeee) Dimethyl-{3-[4-(2-pyridin-2-yl-5,6-dihydro-4H-pyrrolo[1,2-b]pyrazol-3-yl)-quinolin-7-yloxy]-propyl}-amine,
fffff) {3-[6-Methoxy-4-(2-pyridin-2-yl-5,6-dihydro-4H-pyrrolo[1,2-b]pyrazol-3-yl)-quinolin-7-yloxy]-propyl}-dimethyl-amine,
ggggg) Cyclopropylmethyl-propyl-{3-[4-(2-pyridin-2-yl-5,6-dihydro-4H-pyrrolo[1,2-b]pyrazol-3-yl)-quinolin-7-yloxy]-propyl}-amine,
hhhhh) Diethyl-{3-[4-(2-pyridin-2-yl-5,6-dihydro-4H-pyrrolo[1,2-b]pyrazol-3-yl)-quinolin-7-yloxy]-propyl}-amine,
iiiii) Ethyl-methyl-{3-[4-(2-pyridin-2-yl-5,6-dihydro-4H-pyrrolo[1,2-b]pyrazol-3-yl)-quinolin-7-yloxy]-propyl}-amine,
jjjjj) 3-[4-(2-Pyridin-2-yl-5,6-dihydro-4H-pyrrolo[1,2-b]pyrazol-3-yl)-quinolin-7-yloxy]-propylamine,
kkkkk) 7-[3-(4-Methyl-piperazin-1-yl)-propoxy]-4-(2-pyridin-2-yl-5,6-dihydro-4H-pyrrolo[1,2-b]pyrazol-3-yl)-quinoline,
lllll) Benzyl-methyl-{3-[4-(2-pyridin-2-yl-5,6-dihydro-4H-pyrrolo[1,2-b]pyrazol-3-yl)-quinolin-7-yloxy]-propyl}-amine,
mmmmm) 7-(3-Piperidin-1-yl-propoxy)-4-(2-pyridin-2-yl-5,6-dihydro-4H-pyrrolo[1,2-b]pyrazol-3-yl)-quinoline,
nnnnn) 4-(2-Pyridin-2-yl-5,6-dihydro-4H-pyrrolo[1,2-b]pyrazol-3-yl)-7-(3-pyrrolidin-1-yl-propoxy)-quinoline,
ooooo) 7-(3-Azepan-1-yl-propoxy)-4-(2-pyridin-2-yl-5,6-dihydro-4H-pyrrolo[1,2-b]pyrazol-3-yl)-quinoline,
ppppp) 7-(3-Imidazol-1-yl-propoxy)-4-(2-pyridin-2-yl-5,6-dihydro-4H-pyrrolo[1,2-b]pyrazol-3-yl)-quinoline,
qqqqq) 7-(3-Pyrazol-1-yl-propoxy)-4-(2-pyridin-2-yl-5,6-dihydro-4H-pyrrolo[1,2-b]pyrazol-3-yl)-quinoline,
rrrrr) 1'-{3-[4-(2-Pyridin-2-yl-5,6-dihydro-4H-pyrrolo[1,2-b]pyrazol-3-yl)-quinolin-7-yloxy]-propyl}-[1,4']bipiperidinyl,
sssss) Cyclopropyl-(1-methyl-piperidin-4-yl)-{3-[4-(2-pyridin-2-yl-5,6-dihydro-4H-pyrrolo[1,2-b]pyrazol-3-yl)-quinolin-7-yloxy]-propyl}-amine,
ttttt) 4-(2-Pyridin-2-yl-5,6-dihydro-4H-pyrrolo[1,2-b]pyrazol-3-yl)-7-(3-[1,2,3]triazol-1-yl-propoxy)-quinoline,
uuuuu) Dimethyl-(3-{4-[2-(6-methyl-pyridin-2-yl)-5,6-dihydro-4H-pyrrolo[1,2-b]pyrazol-3-yl]-quinolin-7-yloxy}-propyl)-amine,
vvvvv) Diethyl-(3-{4-[2-(6-methyl-pyridin-2-yl)-5,6-dihydro-4H-pyrrolo[1,2-b]pyrazol-3-yl]-quinolin-7-yloxy}-propyl)-amine,
wwwww) Cyclopropylmethyl-(3-{4-[2-(6-methyl-pyridin-2-yl)-5,6-dihydro-4H-pyrrolo[1,2-b]pyrazol-3-yl]-quinolin-7-yloxy}-propyl)-propyl-amin,
xxxxx) Ethyl-methyl-(3-{4-[2-(6-methyl-pyridin-2-yl)-5,6-dihydro-4H-pyrrolo[1,2-b]pyrazol-3-yl]-quinolin-7-yloxy}-propyl)-amine,
yyyyy) Dimethyl-{2-[4-(2-pyridin-2-yl-5,6-dihydro-4H-pyrrolo[1,2-b]pyrazol-3-yl)-quinolin-7-yloxy]-ethyl}-amine,
zzzzz) Diethyl-{2-[4-(2-pyridin-2-yl-5,6-dihydro-4H-pyrrolo[1,2-b]pyrazol-3-quinolin-7-yloxy]-ethyl}-amine,
aaaaaa) 7-(2-Piperidin-1-yl-ethoxy)-4-(2-pyridin-2-yl-5,6-dihydro-4H-pyrrolo[1,2-b]pyrazol-3-yl)-quinoline,
bbbbbb) Ethyl-methyl-{2-[4-(2-pyridin-2-yl-5,6-dihydro-4H-pyrrolo[1,2-b]pyrazol-3-yl)-quinolin-7-yloxy]ethyl}-amine,
cccccc) 4-(2-Pyridin-2-yl-5,6-dihydro-4H-pyrrolo[1,2-b]pyrazol-3-yl)-7-(2-pyrrolidin-1-yl-ethoxy)-quinoline,
dddddd) 7-[2-(4-Methyl-piperazin-1-yl)-ethoxy]-4-(2-pyridin-2-yl-5,6-dihydro-4H-pyrrolo[1,2-b]pyrazol-3-yl)-quinoline,
eeeeee) Dimethyl-{3-[1-oxy-4-(2-pyridin-2-yl-5,6-dihydro-4H-pyrrolo[1,2-b]pyrazol-3-yl)-quinolin-7-yloxy]-propyl}-amine,
ffffff) 7-Methylsulfanyl-4-(2-pyridin-2-yl-5,6-dihydro-4H-pyrrolo[1,2-b]pyrazol-3-yl)-quinoline,
gggggg) 7-Ethylsulfanyl-4-(2-pyridin-2-yl-5,6-dihydro-4H-pyrrolo[1,2-b]pyrazol-3-yl)-quinoline,
hhhhhh) 6-Methylsulfanyl-4-(2-pyridin-2-yl-5,6-dihydro-4H-pyrrolo[1,2-b]pyrazol-3-yl)-quinoline,
iiiiii) 7-Benzylsulfanyl-4-(2-pyridin-2-yl-5,6-dihydro-4H-pyrrolo[1,2-b]pyrazol-3-yl)-quinoline,
jjjjjj) 3-[4-(2-Pyridin-2-yl-5,6-dihydro-4H-pyrrolo[1,2-b]pyrazol-3-yl)-quinolin-7-ylsulfanyl]-propan-1-ol,
kkkkkk) Dimethyl-{2-[4-(2-pyridin-2-yl-5,6-dihydro-4H-pyrrolo[1,2-b]pyrazol-3-yl)-quinolin-7-ylsulfanyl]-ethyl}-amine,
llllll) Dimethyl [6-(3-quinolin-4-yl-5,6-dihydro-4H-pyrrolo[1,2-b]pyrazol-2-yl)-pyridin-2-yl-methyl]amine,
mmmmmm) 7-(2-Propoxy-ethoxy)-4-(2-pyridin-2-yl-5,6-dihydro-4H-pyrrolo[1,2-b]pyrazol-3-yl)-quinoline,
nnnnnn) N,N-Dimethyl-N'-[4-(2-pyridin-2-yl-5,6-dihydro-4H-pyrrolo[1,2-b]pyrazol-3-yl)-pyridin-2-yl]-ethane-1,2-diamine,
oooooo) N,N-Dimethyl-N'-[4-(2-pyridin-2-yl-5,6-dihydro-4H-pyrrolo[1,2-b]pyrazol-3-yl)-pyridin-2-yl]-propane-1,3-diamine,
pppppp) 3-{3-[4-(2-Pyridin-2-yl-5,6-dihydro-4H-pyrrolo[1,2-b]pyrazol-3-yl)-quinolin-7-yloxy]-propyl}-oxazolidin-2-one,
qqqqqq) 1-{3-[4-(2-Pyridin-2-yl-5,6-dihydro-4H-pyrrolo[1,2-b]pyrazol-3-yl)-quinolin-7-yloxy]-propyl}-imidazolidin-2-one,
rrrrrr) 3-{3-[4-(2-Pyridin-2-yl-5,6-dihydro-4H-pyrrolo[1,2-b]pyrazol-3-yl)-quinolin-7-yloxy)-propyl}-3H-benzooxazol-2-one,
ssssss) Dimethyl-(2-{4-[2-(6-methyl-pyridin-2-yl)-5,6-dihydro-4H-pyrrolo[1,2-b]pyrazol-3-yl]-pyridin-2-ylsulfanyl}-ethyl-amine,
tttttt) 4-(2-Pyridin-2-yl-5,6-dihydro-4H pyrrolo[1,2-b]pyrazol-3-yl)-2pyrrolidin-1-yl-quinoline,
uuuuuu) 2-Phenylsulfanyl-4-(2-pyridin-2-yl-5,6-dihydro-4H-pyrrolo[1,2-b]pyrazol-3-yl)-quinoline,
vvvvvv) 2-Morpholin-4-yl-4-(2-pyridin-2-yl-5,6-dihydro-4H-pyrrolo[1,2-b]pyrazol-3-yl)-quinoline,
wwwwww) 2-Ethylsulfanyl-4-(2-pyridin-2-yl-5,6-dihydro-4H-pyrrolo[1,2-b]pyrazol-3-yl)-quinoline,
xxxxxx) Phenyl-[4-(2-pyridin-2-yl-5,6-dihydro-4H-pyrrolo[1,2-b]pyrazol-3-yl)-quinolin-2-yl]-amine,
yyyyyy) 2-Methoxy-4-(2-pyridin-2-yl-5,6-dihydro-4H-pyrrolo[1,2-b]pyrazol-3-yl)-quinoline, zzzzzz) 2-Ethoxy-4-(2-pyridin-2-yl-5,6-dihydro-4H-pyrrolo[1,2-b]pyrazol-3-yl)-quinoline,
aaaaaaa) 4-[2-(6-Phenylsulfanyl-pyridin-2-yl)-5,6-dihydro-4H-pyrrolo[1,2-b]pyrazol-3-yl]-quinoline,
bbbbbbb) Phenyl-[6-(3-quinolin-4-yl-5,6-dihydro-4H-pyrrolo[1,2-b]pyrazol-2-yl)-pyridin-2-yl]-amine,
ccccccc) 4-{2-[6-(4-Methoxy-phenyl)-pyridin-2-yl]-5,6-dihydro-4H-pyrrolo[1,2-b]pyrazol-3-yl}-quinoline,
ddddddd) 4-[2-(6-Phenyl-pyridin-2-yl)-5,6-dihydro-4H-pyrrolo[1,2-b]pyrazol-3-yl]-quinoline,
eeeeeee) 4-[2-(6-Morpholin-4-yl-pyridin-2-yl)-5,6-dihydro-4H-pyrrolo[1,2-b]pyrazol-3-yl]-quinoline,
fffffff) 4-[2-(6-Pyrrolidin-1-yl-pyridin-2-yl)-5,6-dihydro-4H-pyrrolo[1,2-b]pyrazol-3-yl]-quinoline,
ggggggg) 4-[2-(6-Methoxy-pyridin-2-yl)-5,6-dihydro-4H-pyrrolo[1,2-b]pyrazol-3-yl]-quinoline,
hhhhhhh) 2-{3-[4-(2-Pyridin-2-yl-5,6-dihydro-4H-pyrrolo[1,2-b]pyrazol-3-yl)-quinolin-7-yloxy]-propyl}-isoindole-1,3-dione,
iiiiiii) 7-(3-Fluoro-propoxy)-4-(2-pyridin-2-yl-5,6-dihydro-4H-pyrrolo[1,2-b]pyrazol-3-yl)-quinoline,
jjjjjjj) 7-(3-Fluoro-propoxy)-4-(2-pyridin-2-yl-5,6-dihydro-4H-pyrrolo[1,2-b]pyrazol-3-yl)-quinoline,
kkkkkkk) 7-(3-Chloro-propoxy)-4-(2-pyridin-2-yl-5,6-dihydro-4H-pyrrolo[1,2-b]pyrazol-3-yl)-quinoline,
lllllll) 7-(3-Chloro-propoxy)-6-methoxy-4-(2-pyridin-2-yl-5,6-dihydro-4H-pyrrolo[1,2-b]pyrazol-3-yl)-quinoline,
mmmmmmm) 7-(3-Chloro-propoxy)-4-[2-(6-methyl-pyridin-2-yl)-5,6-dihydro-4H-pyrrolo[1,2-b]pyrazol-3-yl]-quinoline,
nnnnnnn) (1-{3-[7-(2-Chloro-ethoxy)-quinolin-4-yl]-5,6-dihydro-4H-pyrrolo[1,2-b]pyrazol-2-yl}-propenyl)-methylene-amine,
ooooooo) N,N-Diethyl-2-[4-(2-pyridin-2-yl-5,6-dihydro-4H-pyrrolo[1,2-b]pyrazol-3-yl)-quinolin-7-yloxy]-acetamide,
ppppppp) 7-[2-((2R)-1-Methyl-pyrrolidin-2-yl)-ethoxy]-4-(2-pyridin-2-yl-5,6-dihydro-4H-pyrrolo[1,2-b]pyrazol-3-yl)-quinoline,
qqqqqqq) Dimethyl-{4-[4-(2-pyridin-2-yl-5,6-dihydro-4H-pyrrolo[1,2-b]pyrazol-3-yl)-pyridin-2-yloxy]-butyl}-amine,
rrrrrrr) 1-{3-[4-(2-Pyridin-2-yl-5,6-dihydro-4H-pyrrolo[1,2-b]pyrazol-3-yl)-pyridin-2-yloxy]-propyl}-pyrrolidin-2-one,
sssssss) 7-(1-Methyl-piperidin-3-ylmethoxy)-4-(2-pyridin-2-yl-5,6-dihydro-4H-pyrrolo[1,2-b]pyrazol-3-yl)-quinoline,
ttttttt) 7-(3-N,N-Dimethylamino-2-methyl-propyloxy)-4-(2-pyridin-2-yl-5,6-dihydro-4H-pyrrolo[1,2-b]pyrazol-3-yl)-quinoline,
uuuuuuu) 4-[2-(6-Methyl-pyridin-2-yl)-5,6-dihydro-4H-pyrrolo[1,2-b]pyrazol-3-yl]-7-propoxy-quinoline,
vvvvvvv) 4-[6-Benzyloxymethyl-2-(6-methyl-pyridin-2-yl)-5,6-dihydro-4H-pyrrolo[1,2-b]pyrazol-3-yl]-quinoline,
wwwwwww) {4-[2-(6-Methyl-pyridin-2-yl)-5,6-dihydro-4H-pyrrolo[1,2-b]pyrazol-3-yl]-quinolin-7-yloxy}-acetic acid methyl ester,
xxxxxxx) 7-Isopropoxy-4-[2-(6-methyl-pyridin-2-yl)-5,6-dihydro-4H-pyrrolo[1,2-b]pyrazol-3-yl]-quinoline,
yyyyyyy) 4-[2-(6-Methyl-pyridin-2-yl)-5,6-dihydro-4H-pyrrolo[1,2-b]pyrazol-3-yl]-7-(3-morpholin-4-yl-propoxy)-quinoline,
zzzzzzz) 4-(6-Benzyloxymethyl-2-pyridin-2-yl-5,6-dihydro-4H-pyrrolo[1,2-b]pyrazol-6-yl)-quinoline,
aaaaaaaa) 7-Benzyloxy-2-Pyridin-2-yl-3-quinolin-4-yl-pyrazolo[1,5-a]piperidine,
bbbbbbbb) 2-[4-(2-pyridin-2-yl-5,6-dihydro-4H-pyrrolo[1,2-b]pyrazol-3-yl)-quinolin-7-yloxy]-acetamide,
cccccccc) 7-(5-Phenyl-[1,2,4]oxadiazol-3-ylmethoxy)-4-(2-pyridin-2-yl-5,6-dihydro-4H-pyrrolo[1,2-b]pyrazol-3-yl)-quinoline,
dddddddd) 7-(2,2-Difluoro-benzo[1,3]dioxol-5-ylmethoxy)-4-(2-pyridin-2-yl-5,6-dihydro-4H-pyrrolo[1,2-b]pyrazol-3-yl)-quinoline,
eeeeeeee) 7-[2-((2S)-]-Methyl-pyrrolidin-2-yl)-ethoxy]-4-(2-pyridin-2-yl-5,6-dihydro-4H-pyrrolo[1,2-b]pyrazol-3-yl)-quinoline,
ffffffff) 5-[4-(2-Pyridin-2-yl-5,6-dihydro-4H-pyrrolo[1,2-b]pyrazol-3-yl)-quinolin-7-yloxymethyl]-pyrrolidin-2-one,
gggggggg) 4-(6-Phenoxymethyl-2-pyridin-2-yl-5,6-dihydro-4H-pyrrolo[1,2-b]pyrazol-3-yl)-quinoline,
hhhhhhhh) 4-(6-Methylene-2-pyridin-2-yl-5,6-dihydro-4H-pyrrolo[1,2-b]pyrazol-3-yl)-quinoline,
iiiiiiii) 3-(4-Fluoro-phenyl)-6-methylene-2-(6-methyl-pyridin-2-yl)-5,6-dihydro-4H-pyrrolo[1,2-b]pyrazole,
jjjjjjjj) 7-(1-Methyl-piperidin-2-ylmethoxy)-4-(2-pyridin-2-yl-5,6-dihydro-4H-pyrrolo[1,2-b]pyrazol-3-yl)-quinoline hydrochloride,
kkkkkkkk) 7-[2-(1-Methyl-pyrrolidin-2-yl)-ethoxy]-4-(2-pyridin-2-yl-5,6-dihydro-4H-pyrrolo[1,2-b]pyrazol-3-yl)-quinoline hydrochloride,
llllllll) 4-[2-(6-Methyl-1-oxy-pyridin-2-yl)-5,6-dihydro-4H-pyrrolo[1,2-b]pyrazol-3-yl]-quinoline 1-oxide,
mmmmmmmm) 4-[2-(6-Methyl-pyridin-2-yl)-5,6-dihydro-4H-pyrrolo[1,2-b]pyrazol-3-yl]-quinoline 1-oxide,
nnnnnnnn) 4-[2-(6-Methyl-1-oxy-pyridin-2-yl)-5,6-dihydro-4H-pyrrolo[1,2-b]pyrazol-3-yl]-quinoline,
oooooooo) 7-(3-Chloro-propoxy)-4-(2-pyridin-2-yl-5,6-dihydro-4H-pyrrolo[1,2-b]pyrazol-3-yl)-quinoline 1-oxide,
pppppppp) 7-Methanesulfonyl-4-(2-pyridin-2-yl-5,6-dihydro-4H-pyrrolo[1,2-b]pyrazol-3-yl)-quinoline,
qqqqqqqq) 3-(4-Fluoro-phenyl)-2-(6-methyl-1-oxy-pyridin-2-yl)-5,6-dihydro-4H-pyrrolo[1,2-b]pyrazole,
rrrrrrrr) 4-(Quinolin-N1-oxide-4-yl)-3-(6-methylpyridin-2-yl)-5,6-dihydro-4H-pyrrolo[1,2-b]pyrazole,
ssssssss) 6-Methanesulfonyl-4-(2-pyridin-2-yl-5,6-dihydro-4H-pyrrolo[1,2-b]pyrazol-3-yl)-quinoline,
tttttttt) 7-Ethanesulfonyl-4-(2-pyridin-2-yl-5,6-dihydro-4H-pyrrolo[1,2-b]pyrazol-3-yl)-quinoline,
uuuuuuuu) 4-(2-Pyridin-2-yl-5,6-dihydro-4H-pyrrolo[1,2-b]pyrazol-3-yl)-7-[3-(pyrimidine-2-sulfonyl)-propoxy]-quinoline,
vvvvvvvv) 7-[3-(1-Methyl-1H-imidazole-2-sulfonyl)-propoxy]-4-(2-pyridin-2-yl-5,6-dihydro-4H-pyrrolo[1,2-b]pyrazol-3-yl)-quinoline,
wwwwwwww) 7-[3-(4-Chloro-benzenesulfonyl)-propoxy]-4-(2-pyridin-2-yl-5,6-dihydro-4H-pyrrolo[1,2-b]pyrazol-3-yl)-quinoline,
xxxxxxxx) 4-(2-Pyridin-2-yl-5,6-dihydro-4H-pyrrolo[1,2-b]pyrazol-3-yl)-7-[3-(pyridin-2-ylmethanesulfonyl)-propoxy]-quinoline,
yyyyyyyy) 4-(2-Pyridin-2-yl-5,6-dihydro-4H-pyrrolo[1,2-b]pyrazol-3-yl)-7-[3-(pyridin-2-ylmethanesulfinyl)-propoxy]-quinoline,
zzzzzzzz) 4-(Quinolin-1-N-oxide-4-yl)-3-(6-methylpyridin-2-yl-1-N-oxide)-5,6-dihydro-4H-pyrrolo[1,2-b]pyrazole,
aaaaaaaaa) 3-{4-[2-(6-Methyl-pyridin-2-yl)-5,6-dihydro-4H-pyrrolo[1,2-b]pyrazol-3-yl]-quinolin-7-yl}-acrylic acid methyl ester,
bbbbbbbbb) 3-{4-[2-(6-Methylpyridin-2-yl-5,6-dihydro-4H-pyrrolo [1,2-b]pyrazol-3-yl]quinolin-7-yl}-1-piperidin-1-yl-propenone, cccccccc) 3-{4-[2-(6-Methyl-pyridin-2-yl)-5,6-dihydro-4H-pyrrolo[1,2-b]pyrazol-3-yl]-quinolin-6-yl}-acrylic acid methyl ester,
dddddddd) 4-[2-(6-Methyl-pyridin-2-yl)-5,6-dihydro-4H-pyrrolo[1,2-b]pyrazol-3-yl]-7-vinyl-quinoline,
eeeeeeee) 4-[2-(6-Benzyl-pyridin-2-yl)-5,6-dihydro-4H-pyrrolo[1,2-b]pyrazol-3-yl]-quinoline,
ffffffff) 7-Benzyl-4-[2-(6-methyl-pyridin-2-yl)-5,6-dihydro-4H-pyrrolo[1,2-b]pyrazol-3-yl]-quinoline,
gggggggg) 4-[2-(6-Methyl-pyridin-2-yl)-5,6-dihydro-4H-pyrrolo[1,2-b]pyrazol-3-yl]-quinoline-7-carboxylic acid,
hhhhhhhh) 4-[2-(6-Methyl-pyridin-2-yl)-5,6-dihydro-4H-pyrrolo[1,2-b]pyrazol-3-yl]-quinoline-6-carboxylic acid,
iiiiiiii) 3-{4-[2-(6-Methyl-pyridin-2-yl)-5,6-dihydro-4H-pyrrolo[1,2-b]pyrazol-3-yl]-quinolin-7-yl}-acrylic acid,
jjjjjjjj) 3-{4-[2-(6-Methyl-pyridin-2-yl)-5,6-dihydro-4H-pyrrolo[1,2-b]pyrazol-3-yl]-quinolin-7-yl}-propionic acid,
kkkkkkkk) 4-[2-(6-Methyl-pyridin-2-yl)-3-quinolin-4-yl-5,6-dihydro-4H-pyrrolo[1,2-b]pyrazol-5-yl]-benzoic acid,
llllllll) 4-(2-Pyridin-2-yl-5,6-dihydro-4H-pyrrolo[1,2-b]pyrazol-3-yl)-quinoline-7-carboxylic acid cyclopentylamide,
mmmmmmmm) 4-(2-Pyridin-2-yl-5,6-dihydro-4H-pyrrolo[1,2-b]pyrazol-3-yl)-quinoline-7-carboxylic acid (2-morpholin-4-yl-ethyl)-amide,
nnnnnnnn) 4-(2-Pyridin-2-yl-5,6-dihydro-4H-pyrrolo[1,2-b]pyrazol-3-yl)-quinoline-7-carboxylic acid [2-(1H-imidazol-4-yl)-ethyl]-amide,
oooooooo) 4-(2-Pyridin-2-yl-5,6-dihydro-4H-pyrrolo[1,2-b]pyrazol-3-yl)-quinoline-7-carboxylic acid(2-methylamino-ethyl)-amide,
pppppppp) 4-(2-Pyridin-2-yl-5,6-dihydro-4H-pyrrolo[1,2-b]pyrazol-3-yl)-quinoline-7-carboxylic acid(3-methylamino-propyl)-amide,
qqqqqqqq) 4-(2-Pyridin-2-yl-5,6-dihydro-4H-pyrrolo[1,2-b]pyrazol-3-yl)-quinoline-7-carboxylic acid(2-dimethylamino-ethyl)-amide,
rrrrrrrr) (4-Methyl-piperazin-1-yl)-[4-(2-pyridin-2-yl-5,6-dihydro-4H-pyrrolo[1,2-b]pyrazol-3-yl)-quinolin-7-yl]-methanone,
ssssssss) 4-(2-Pyridin-2-yl-5,6-dihydro-4H-pyrrolo[1,2-b]pyrazol-3-yl)-quinoline-7-carboxylic acid cyclobutylamide,
tttttttt) 4-(2-Pyridin-2-yl-5,6-dihydro-4H-pyrrolo[1,2-b]pyrazol-3-yl)-quinoline-7-carboxylic acid cyclopropylamide,
uuuuuuuu) 4-(2-Pyridin-2-yl-5,6-dihydro-4H-pyrrolo[1,2-b]pyrazol-3-yl)-quinoline-7-carboxylic acid(1-ethyl-propyl)-amide,
vvvvvvvv) 4-(2-Pyridin-2-yl-5,6-dihydro-4H-pyrrolo[1,2-b]pyrazol-3-yl)-quinoline-7-carboxylic acid ethyl amide,
wwwwwwww) 4-(2-Pyridin-2-yl-5,6-dihydro-4H-pyrrolo[1,2-b]pyrazol-3-yl)-quinoline-7-carboxylic acid isobutyl-amide,
xxxxxxxx) 4-(2-Pyridin-2-yl-5,6-dihydro-4H-pyrrolo[1,2-b]pyrazol-3-yl)-quinoline-7-carboxylic acid tert-butylamide,
yyyyyyyy) 4-(2-Pyridin-2-yl-5,6-dihydro-4H-pyrrolo[1,2-b]pyrazol-3-yl)-quinoline-7-carboxylic acid isopropylamide,
zzzzzzzz) 4-(2-Pyridin-2-yl-5,6-dihydro-4H-pyrrolo[1,2-b]pyrazol-3-yl)-quinoline-7-carboxylic acid propylamide,
aaaaaaaaa) 4-(2-Pyridin-2-yl-5,6-dihydro-4H-pyrrolo[1,2-b]pyrazol-3-yl)-quinoline-7-carboxylic acid(2-methyl-butyl)-amide,
bbbbbbbbb) 4-(2-Pyridin-2-yl-5,6-dihydro-4H-pyrrolo[1,2-b]pyrazol-3-yl)-quinoline-7-carboxylic acid((2S)-2-methyl-butyl)-amide,
ccccccccc) 4-(2-Pyridin-2-yl-5,6-dihydro-4H-pyrrolo[1,2-b]pyrazol-3-yl)-quinoline-7-carboxylic acid(2S)-sec-butylamide,
ddddddddd) 4-(2-Pyridin-2-yl-5,6-dihydro-4H-pyrrolo[1,2-b]pyrazol-3-yl)-quinoline-7-carboxylic acid(2R)-sec-butylamide,
eeeeeeeee) 4-(2-Pyridin-2-yl-5,6-dihydro-4H-pyrrolo[1,2-b]pyrazol-3-yl)-quinoline-7-carboxylic acid((1R)-1,2-dimethyl-propyl)-amide,
fffffffff) 4-(2-Pyridin-2-yl-5,6-dihydro-4H-pyrrolo[1,2-b]pyrazol-3-yl)-quinoline-7-carboxylic acid(pyridin-4-ylmethyl)-amide,
ggggggggg) 4-(2-Pyridin-2-yl-5,6-dihydro-4H-pyrrolo[1,2-b]pyrazol-3-yl)-quinoline-7-carboxylic acid(pyridin-3-ylmethyl)-amide,
hhhhhhhhh) 4-(2-Pyridin-2-yl-5,6-dihydro-4H-pyrrolo[1,2-b]pyrazol-3-yl)-quinoline-7-carboxylic acid(pyridin-2-ylmethyl)-amide,
iiiiiiiii) 6-(3-Quinolin-4-yl-5,6-dihydro-4H-pyrrolo[1,2-b]pyrazol-2-yl)-pyridine-2-carboxylic acid amide,
jjjjjjjjj) 1-(4-Methyl-piperazin-1-yl)-2-[4-(2-pyridin-2-yl-5,6-dihydro-4H-pyrrolo[1,2-b]pyrazol-3-yl)-quinolin-7-yloxy]-ethanone,
kkkkkkkkk) N-(2-dimethylamino-ethyl)-2-[4-(2-pyridin-2-yl-5,6-dihydro-4H-pyrrolo[1,2-b]pyrazol-3-yl)-quinolin-7-yloxy)-acetamide,
lllllllll) N-(2-dimethylamino-ethyl)-N-methyl-2-[4-(2-pyridin-2-yl-5,6-dihydro-4H-pyrrolo[1,2-b]pyrazol-3-yl)-quinolin-7-yloxy]-acetamide,
mmmmmmmmm) N,N-Dimethyl-3-[4-(2-pyridin-2-yl-5,6-dihydro-4H-pyrrolo[1,2-b]pyrazol-3-yl)-quinolin-7-yloxy]-benzamide,
nnnnnnnnn) 4-(2-Pyridin-2-yl-5,6-dihydro-4H-pyrrolo[1,2-b]pyrazol-3-yl)-quinoline-7-carboxylic acid amide,
ooooooooo) 4-(2-Pyridin-2-yl-5,6-dihydro-4H-pyrrolo[1,2-H]pyrazol-3-yl)-quinoline-7-carboxylic acid(2-dimethylamino-ethyl)-methyl-amide,
ppppppppp) 4-(2-Pyridin-2-yl-5,6-dihydro-4H-pyrrolo[1,2-H]pyrazol-3-yl)-quinoline-7-carboxylic acid(3-dimethylamino-propyl)-methyl-amide,
qqqqqqqqq) 4-(2-Pyridin-2-yl-5,6-dihydro-4H-pyrrolo[1,2-H]pyrazol-3-yl)-quinoline-7-carboxylic acid dimethylamide,
rrrrrrrrr) 4-(2-Pyridin-2-yl-5,6-dihydro-4H-pyrrolo[1,2-H]pyrazol-3-yl)-quinoline-7-carboxylic acid methylamide,
sssssssss) 4-(2-Pyridin-2-yl-5,6-dihydro-4H-pyrrolo[1,2-b]pyrazol-3-yl)-quinoline-7-carboxylic acid pyridin-2-ylamide,
ttttttttt) N-(2,2-Dimethylamino-ethyl)-N-methyl-3-{4-[2-(6-methyl-pyridin-2-yl)-5,6-dihydro-4H-pyrrolo[1,2-b]pyrazol-3-yl]-quinolin-7-yl}-propionamide,
uuuuuuuuu) 2-(6-Methyl-pyridin-2-yl)-5,6-dihydro-4H-pyrrolo[1,2-b]pyrazol-3-yl)-quinoline-6-carboxylic acid (2-dimethylamino-ethyl)-amide,
vvvvvvvvv) 4-[2-(6-Methyl-pyridin-2-yl)-5,6-dihydro-4H-pyrrolo[1,2-b]pyrazol-3-yl]-quinoline-6-carboxylic acid (3-dimethylamino-propyl)-amide,
wwwwwwwww) 4-[2-(6-Methyl-pyridin-2-yl)-5,6-dihydro-4H-pyrrolo[1,2-b]pyrazol-3-yl]-quinoline-6-carboxylic acid(2-morpholin-4-yl-ethyl)-amide,
xxxxxxxxx) 1-[2-(Quinolin-4-yl)-1-(6-methyl-pyridin-2-yl)-5,6-dihydro-4H-pyrrolo[1,2-b]pyrazol-3-yl] quinoline-7-carboxylic acid N,N-dimethylaminoethylamide, yyyyyyyyy) 4-[2-(6-Methylpyridin-2-yl)-5,6-dihydro-4H-pyrrolo[1,2-b]pyrazol-3-yl]quinoline-7-carbox-ylic acid (2-piperidin-1-yl-ethyl)amide, zzzzzzzzzz) N-(2-Dimethylamino-ethyl)-3-{4-[2-(6-methyl-pyridin-2-yl)-5,6-dihydro-4H-pyrrolo[1,2-b] pyrazol-3-yl]-quinolin-7-yl}-propionamide, aaaaaaaaaaa) 4-[2-(6-Methyl-pyridin-2-yl)-5,6-dihydro-4H-pyrrolo[1,2-b]pyrazol-3-yl]-quinoline-7-carboxylic acid (3-dimethylamino-propyl)-amide, bbbbbbbbbbb) 4-[2-(6-Methyl-pyridin-2-yl)-5,6-dihydro-4H-pyrrolo[1,2-b]pyrazol-3-yl]-quinoline-7-carboxylic acid(3-pyrrolidin-1-yl-propyl)-amide, ccccccccccc) 4-[2-(6-Methyl-pyridin-2-yl)-5,6-dihydro-4H-pyrrolo[1,2-b]pyrazol-3-yl]-quinoline-7-carboxylic acid (3-morpholin-4-yl-propyl)-amide, ddddddddddd) 3-{4-[2-(6-Methyl-pyridin-2-yl)-5,6-dihydro-4H-pyrrolo[1,2-b]pyrazol-3-yl]-quinolin-7-yl}-propionamide, eeeeeeeeeee) 4-(2-Pyridin-2-yl-5,6-dihydro-4H-pyrrolo[1,2-b]pyrazol-3-yl)-quinoline-6-carboxylic acid(2-dimethylamino-ethyl)-amide, fffffffffff) 4-(2-Pyridin-2-yl-5,6-dihydro-4H-pyrrolo[1,2-b]pyrazol-3-yl)-quinoline-6-carboxylic acid(2-morpholin-4-yl-ethyl)-amide, ggggggggggg) 4-(2-Pyridin-2-yl-5,6-dihydro-4H-pyrrolo[1,2-b]pyrazol-3-yl)-quinoline-6-carboxylic acid, hhhhhhhhhhh) 4-(2-Pyridin-2-yl-5,6-dihydro-4H-pyrrolo[1,2-b]pyrazol-3-yl)-quinoline-6-carboxylic acid hydrazide, iiiiiiiiiii) 4-(2-Pyridin-2-yl-5,6-dihydro-4H-pyrrolo[1,2-b]pyrazol-3-yl)-quinoline-6-carboxylic acid amide, jjjjjjjjjjj) 4-(2-Pyridin-2-yl-5,6-dihydro-4H-pyrrolo[1,2-b]pyrazol-3-yl)-quinoline-6-carboxylic acid(3-methylamino-propyl)-amide, kkkkkkkkkkk) 4-(2-Pyridin-2-yl-5,6-dihydro-4H-pyrrolo[1,2-b]pyrazol-3-yl)-quinoline-6-carboxylic acid amide, lllllllllll) 4-(2-Pyridin-2-yl-5,6-dihydro-4H-pyrrolo[1,2-b]pyrazol-3-yl)-quinoline-6-carboxylic acid(2-hydroxy-ethyl)-amide, mmmmmmmmmmm) 4-(2-Pyridin-2-yl-5,6-dihydro-4H-pyrrolo[1,2-b]pyrazol-3-yl)-quinoline-7-carboxylic acid hydrazide, nnnnnnnnnnn) 4-(2-Pyridin-2-yl-5,6-dihydro-4H-pyrrolo[1,2-b]pyrazol-3-yl)-quinoline-7-carboxylic acid hydroxyamide, ooooooooooo) 4-(2-Pyridin-2-yl-5,6-dihydro-4H-pyrrolo[1,2-b]pyrazol-3-yl)-quinoline-7-carboxylic acid(2-amino-ethyl)-amide, ppppppppppp) 4-(2-Pyridin-2-yl-5,6-dihydro-4H-pyrrolo[1,2-b]pyrazol-3-yl)-quinoline-7-carboxylic acid(2-hydroxy-ethyl)-amide, qqqqqqqqqqq) 4-(2-Pyridin-2-yl-5,6-dihydro-4H-pyrrolo[1,2-b]pyrazol-3-yl)-quinoline-7-sulfonic acid amide, rrrrrrrrrrr) 4-(2-Pyridin-2-yl-5,6-dihydro-4H-pyrrolo[1,2-b)pyrazol-3-yl)-quinoline-7-sulfonic acid methylamide, sssssssssss) 4-(2-Pyridin-2-yl-5,6-dihydro-4H-pyrrolo[1,2-b]pyrazol-3-yl)-quinoline-7-sulfonic acid dimethylamide, ttttttttttt) 4-(2-Pyridin-2-yl-5,6-dihydro-4H-pyrrolo[1,2-b]pyrazol-3-yl)-quinoline-7-sulfonic acid(3-dimethylamino-propyl)-amide, uuuuuuuuuuu) 4-(2-Pyridin-2-yl-5,6-dihydro-4H-pyrrolo[1,2-b]pyrazol-3-yl)-quinoline-7-sulfonic acid diethylamide, vvvvvvvvvvv) 4-(2-Pyridin-2-yl-5,6-dihydro-4H-pyrrolo[1,2-b]pyrazol-3-yl)-quinoline-7-sulfonic acid(2-piperidin-1-yl-ethyl)-amide, wwwwwwwwwww) 4-(2-Pyridin-2-yl-5,6-dihydro-4H-pyrrolo[1,2-b]pyrazol-3-yl)-quinoline-7-sulfonic acid(2-hydroxy-ethyl)-amide, xxxxxxxxxxx) 4-(2-Pyridin-2-yl-5,6-dihydro-4H-pyrrolo[1,2-b]pyrazol-3-yl)-quinolin-7-ylamine, yyyyyyyyyyy) 2-Dimethylamino-N-[4-(2-pyridin-2-yl-5,6-dihydro-4H-pyrrolo[1,2-b]pyrazol-3-yl)-quinolin-7-yl]-acetamide, zzzzzzzzzzz) 3-Dimethylamino-N-[4-(2-pyridin-2-yl-5,6-dihydro-4H-pyrrolo[1,2-b]pyrazol-3-yl)-quinolin-7-yl] propionamide, aaaaaaaaaaaa) N-[4-(2-Pyridin-2-yl-5,6-dihydro-4H-pyrrolo[1,2-b]pyrazol-3-yl)-quinolin-7-yl]-methanesulfonamide, bbbbbbbbbbbb) N-(2-Pyridin-2-yl-5,6-dihydro-4H-pyrrolo[1,2-b]pyrazol-3-yl)-quinolin-7-yl]-acetamide, cccccccccccc) 4-(2-Pyridin-2-yl-5,6-dihydro-4H-pyrrolo[1,2-b]pyrazol-3-yl)-quinoline-7-carboxylic acid(2-acetylamino-ethyl)-amide, dddddddddddd) N-{3-[4-(2-Pyridin-2-yl-5,6-dihydro-4H-pyrrolo[1,2-b]pyrazol-3-yl)-quinolin-7-yloxy]-propyl}-methanesulfonamide, eeeeeeeeeeee) 1-methyl-1H-imidazole-4-sulfonic acid {3-[4-(2-pyridin-2-yl-5,6-dihydro-4H-pyrrolo[1,2-b]pyrazol-3-yl)-quinolin-7-yloxy]-propyl}-amide, ffffffffffff) 1-(2-Dimethylamino-ethyl)-3-[4-(2-pyridin-2-yl-5,6-dihydro-4H-pyrrolo[1,2-b]pyrazol-3-yl)-quinolin-7-yl]-urea, gggggggggggg) 1-(3-Dimethylamino-propyl)-3-[4-(2-pyridin-2-yl-5,6-dihydro-4H-pyrrolo[1,2-b]pyrazol-3-yl)-quinolin-7-yl]-urea, hhhhhhhhhhhh) 1-(2-Hydroxy-ethyl)-3-[4-(2-pyridin-2-yl-5,6-dihydro-4H-pyrrolo[1,2-b]pyrazol-3-yl)-quinolin-7-yl]-urea, iiiiiiiiiiii) [4-(2-Pyridin-2-yl-5,6-dihydro-4H-pyrrolo[1,2-b]pyrazol-3-yl)-quinolin-7-yl]-carbamic acid methyl ester, jjjjjjjjjjjj) [4-(2-Pyridin-2-yl-5,6-dihydro-4H-pyrrolo[1,2-b]pyrazol-3-yl)-quinolin-7-yl]-carbamic acid 2-hydroxy-ethyl ester, kkkkkkkkkkkk) [4-(2-Pyridin-2-yl-5,6-dihydro-4H-pyrrolo[1,2-b]pyrazol-3-yl)-quinolin-7-yl]-carbamic acid 2-methoxy-ethyl ester, llllllllllll) 1,3-Bis-[4-(2-pyridin-2-yl-5,6-dihydro-4H-pyrrolo[1,2-b]pyrazol-3-yl)-quinolin-7-yl]-urea, mmmmmmmmmmmm) Dimethyl-carbamic acid 4-(2-pyridin-2-yl-5,6-dihydro-4H-pyrrolo[1,2-b]pyrazol-3-yl)-quinolin-7-yl ester, nnnnnnnnnnnn) 7-Bromo-2-isopropyl-4-(2-pyridin-2-yl-5,6-dihydro-4H-pyrrolo[1,2-b]pyrazol-3-yl)-quinoline, oooooooooooo) 2-{4-[2-(6-Methyl-pyridin-2-yl)-5,6-dihydro-4H-pyrrolo[1,2-b]pyrazol-3-yl]-quinolin-6-yl}-propan-2-ol, pppppppppppp) 7-(3-Chloro-propylsulfanyl)-4-(2-pyridin-2-yl-5,6-dihydro-4H-pyrrolo[1,2-b]pyrazol-3-yl)-quinoline, qqqqqqqqqqqq) 7-Bromo-4-(4-chloro-2-pyridin-2-yl-5,6-dihydro-4H-pyrrolo[1,2-b]pyrazol-3-yl)-quinoline, rrrrrrrrrrrr) 8-Chloro-4-(2-pyridin-2-yl-5,6-dihydro-4H-pyrrolo[1,2-b]pyrazol-3-yl)-quinolin-7-ol, ssssssssssss) 8-Bromo-4-(2-pyridin-2-yl-5,6-dihydro-4H-pyrrolo[1,2-b]pyrazol-3-yl)-quinolin-7-ol, tttttttttttt) 3-(7-Bromo-quinolin-4-yl)-2-pyridin-2-yl-5,6-dihydro-4H-pyrrolo[1,2-b]pyrazol-4-ol, uuuuuuuuuuuu) 7-Bromo-4-(4-methoxy-2-pyridin-2-yl-5,6-dihydro-4H-pyrrolo[1,2-b]pyrazol-3-yl)-quinoline, vvvvvvvvvvvv) [3-(7-Bromo-quinolin-4-yl)-2-pyridin-2-yl-5,6-dihydro-4H-pyrrolo[1,2-b]pyrazol-4-yl]-methyl-amine, wwwwwwwwwwww) 3-(7-Bromo-quinolin-4-yl)-2-pyridin-2-yl-5,6-dihydro-pyrrolo[1,2-b]pyrazol-4-one, xxxxxxxxxxxx) 3-[4-(2-Pyridin-2-yl-5,6-dihydro-4H-pyrrolo[1,2-b]pyrazol-3-yl)-quinolin-7-yloxy]-benzamide, yyyyyyyyyyyy) N,N-Dimethyl-3-[4-(2-pyridin-2-yl-5,6-dihydro-4H-pyrrolo[1,2-b]pyrazol-3-yl)-quinolin-7-yloxy]-thiobenzamide, zzzzzzzzzzzz) Dimethyl-{3-[4-(2-pyridin-2-yl-5,6-dihydro-4H-pyrrolo[1,2-b]pyrazol-3-yl)-quinolin-7-yloxy]-benzyl}-amine, aaaaaaaaaaaaa) 4-[2-(6-Methyl-pyridin-2-yl)-5,6-dihydro-4H-pyrrolo[1,2-b]pyrazol-3-yl-1H-quinolin-2-one, bbbbbbbbbbbbb) 4-(2-Pyridin-2-yl-5,6-dihydro-4H-pyrrolo[1,2-b)pyrazol-3-yl)-quinolin-7-ol, ccccccccccccc) 4-[2-(6-Methyl-pyridin-2-yl)-5,6-dihydro-4H-pyrrolo[1,2-b]pyrazol-3-yl]-quinolin-7-ol, ddddddddddddd) 6-Methoxy-4-(2-pyridin-2-yl-5,6-dihydro-4H-pyrrolo[1,2-b]pyrazol-3-yl)-quinolin-7-ol, eeeeeeeeeeeee) 3-{4-[2-(6-Methyl-pyridin-2-yl)-5,6-dihydro-4H-pyrrolo[1,2-b]pyrazol-3-yl]-quinolin-7-yl}-propionic acid methyl ester, fffffffffffff) 4-(6-Methyl-2-pyridin-2-yl-5,6-dihydro-4H-pyrrolo[1,2-b]pyrazol-3-yl)-quinoline, ggggggggggggg) 3-{4-[2-(6-Methyl-pyridin-2-yl)-5,6-dihydro-4H-pyrrolo[1,2-b]pyrazol-3-yl]-quinolin-6-yl}-propionic acid methyl ester, hhhhhhhhhhhhh) 7-Amino-4-[2-(6-Methyl-pyridin-2-yl)-5,6-dihydro-4H-pyrrolo[1,2-b]pyrazol-3-yl]-quinoline, iiiiiiiiiiiii) N,N-Dimethyl-3-{4-[2-(6-methyl-pyridin-2-yl)-5,6-dihydro-4H-pyrrolo[1,2-b]pyrazol-3-yl]-quinolin-7-yl}-propionamide, jjjjjjjjjjjjj) N-{3-[4-(2-Pyridin-2-yl-5,6-dihydro-4H-pyrrolo[1,2-b]pyrazol-3-yl)-quinolin-7-yloxy]-propyl}-acetamide, kkkkkkkkkkkkk) N-Acetyl-N-{4-[2-(6-methyl-pyridin-2-yl)-5,6-dihydro-4H-pyrrolo[1,2-b]pyrazol-3-yl]-quinolin-7-yl}-acetamide, lllllllllllll) 2-Pyridin-2-yl-3-quinolin-4-yl-pyrazolo[1,5-a]piperidin-7-ol, mmmmmmmmmmmmm) 7-Acetoxy-2-pyridin-2-yl-3-quinolin-4-yl-pyrazolo[1,5-a]piperidine, nnnnnnnnnnnnn) Methyl-{3-[4-(2-pyridin-2-yl-5,6-dihydro-4H-pyrrolo[1,2-b]pyrazol-3-yl)-quinolin-7-yloxy]-propyl}-amine, ooooooooooooo) 7-(Piperidin-4-yloxy)-4-(2-pyridin-2-yl-5,6-dihydro-4H-pyrrolo[1,2-b]pyrazol-3-yl)-quinoline, ppppppppppppp) 4-[2-(6-Methyl-pyridin-2-yl)-5,6-dihydro-4H-pyrrolo[1,2-b]pyrazol-3-yl]-quinoline-7-carboxylic acid(2-amino-1,1-dimethyl-ethyl)-amide, qqqqqqqqqqqqq) {6-[3-(4-Fluoro-phenyl)-5,6-dihydro-4H-pyrrolo[1,2-b]pyrazol-2-yl]-methanol, rrrrrrrrrrrrr) [6-(3-Quinolin-4-yl-5,6-dihydro-4H-pyrrolo[1,2-b]pyrazol-2-yl)-pyridin-2-yl]-methanol, sssssssssssss) 4-[2-(6-Methyl-pyridin-2-yl)-5,6-dihydro-4H-pyrrolo[1,2-b]pyrazol-3-yl]-phenol, ttttttttttttt) 7-(1-Methyl-pyrrolidin-3-ylmethoxy)-4-(2-pyridin-2-yl-5,6-dihydro-4H-pyrrolo[1,2-b]pyrazol-3-yl)-quinoline, uuuuuuuuuuuuu) 7-(1-Methyl-piperidin-4-ylmethoxy)-4-(2-pyridin-2-yl-5,6-dihydro-4H-pyrrolo[1,2-b]pyrazol-3-yl)-quinoline, vvvvvvvvvvvvv) 4-[2-(6-Methyl-pyridin-2-yl)-5,6-dihydro-4H-pyrrolo[1,2-b]pyrazol-3-yl]-quinoline-7-carboxylic acid(2-dimethylamino-1,1-dimethyl-ethyl)-amide, wwwwwwwwwwww) (S)-[3-(4-Fluoro-phenyl)-2-(6-methyl-pyridin-2-yl)-5,6-dihydro-4H-pyrrolo[1,2-b]pyrazol-6-yl]-methanol, xxxxxxxxxxxxx) (R)-[3-(4-Fluoro-phenyl)-2-(6-methyl-pyridin-2-yl)-5,6-dihydro-4H-pyrrolo[1,2-b]pyrazol-6-yl]-methanol, yyyyyyyyyyyy) (S)-[3-(4-Fluoro-phenyl)-2-(6-methyl-pyridin-2-yl)-5,6-dihydro-4H-pyrrolo[1,2-b]pyrazol-6-yl]-acetonitrile, zzzzzzzzzzzzz) (R)-[3-(4-Fluoro-phenyl)-2-(6-methyl-pyridin-2-yl)-5,6-dihydro-4H-pyrrolo[1,2-b]pyrazol-6-yl]-acetonitrile, aaaaaaaaaaaaaa) 4-(3-Pyridin-2-yl-5,6-dihydro-4H-pyrrolo[1,2-b]pyrazol-2-yl)-quinoline, bbbbbbbbbbbbbb) 4-(6-Pyridin-2-yl-2,3-dihydro-pyrazolo[5,1-b]oxazol-7-yl)-quinoline, cccccccccccccc) 3-[4-(2-Pyridin-2-yl-5,6-dihydro-4H-pyrrolo[1,2-b]pyrazol-3-yl)-quinolin-7-yl]-oxazolidin-2-one, dddddddddddddd) 1-[4-(2-Pyridin-2-yl-5,6-dihydro-4H-pyrrolo[1,2b]pyrazol-3-yl)-quinolin-7-yl]-imidazolidin-2-one, eeeeeeeeeeeeee) 4-(2-Pyridin-2-yl-5,6-dihydro-4H-pyrrolo[1,2-b]pyrazol-3-yl)-7-(pyridin-4-ylmethoxy)-quinoline, ffffffffffffff) 4-(2-Pyridin-2-yl-5,6-dihydro-4H-pyrrolo[1,2-b]pyrazol-3-yl)-7-(3-pyridin-3-yl-propoxy)-quinoline, gggggggggggggg) 7-(4,5-Dihydro-1H-imidazol-2-yl)-4-(2-pyridin-2-yl-5,6-dihydro-4H-pyrrolo[1,2-b]pyrazol-3-yl)-quinoline, hhhhhhhhhhhhhh) 4-[5-(4-Fluoro-phenyl)-2-(6-methyl-pyridin-2-yl)-5,6-dihydro-4H-pyrrolo[1,2-b]pyrazol-3-yl]-quinoline (Enantiomer A), iiiiiiiiiiiiii) 4-[5-(4-Fluoro-phenyl)-2-(6-methyl-pyridin-2-yl)-5,6-dihydro-4H-pyrrolo[1,2-b]pyrazol-3-yl]-quinoline (Enantiomer B), jjjjjjjjjjjjjj) 2-Pyridin-2-yl-3-quinolin-4-yl-pyrazolo[5,1-c]morpholine, kkkkkkkkkkkkkk) 4-[2-(6-Vinyl-pyridin-2-yl)-5,6-dihydro-4H-pyrrolo[1,2-b]pyrazol-3-yl)-quinoline, llllllllllllll) 3-{4-[2-(6-Methyl-pyridin-2-yl)-5,6-dihydro-4H-pyrrolo[1,2]pyrazol-3-yl]-quinolin-6-yl}-acrylic acid, mmmmmmmmmmmmmm) 7-(6-Methyl-pyridazin-3-yloxy)-4-(2-pyridin-2-yl-5,6-dihydro-4H-pyrrolo[1,2-b]pyrazol-3-yl)-quinoline, nnnnnnnnnnnnnn) 4-(2-Pyridin-2-yl-5,6-dihydro-4H-pyrrolo[1,2-b]pyrazol-3-yl)-7-[4-(4-pyrimidin-2-yl-piperazin-1-yl)-butoxy]-quinoline, oooooooooooooo) 7-{3-[4-(2-Methoxy-phenyl)-piperazin-1-yl]-propoxy}-4-(2-pyridin-2-yl-5,6-dihydro-4H-pyrrolo[1,2-b]pyrazol-3-yl)-quinoline, pppppppppppppp) Pyridin-2-yl-{3-[4-(2-pyridin-2-yl-5,6-dihydro-4H-pyrrolo[1,2-b]pyrazol-3-yl)-quinolin-7-yloxy]-propyl}-amine, qqqqqqqqqqqqqq) 4-[2-(6-Methyl-pyridin-2-yl)-5,6-dihydro-4H-pyrrolo[1,2-b]pyrazol-3-yl]-quinoline-7-carboxylic acid(2-dimethylamino-1-methyl-ethyl)-amide, rrrrrrrrrrrrrr) 4-[2-(6-Methyl-pyridin-2-yl)-5,6-dihydro-4H-pyrrolo[1,2-b]pyrazol-3-yl]-quinoline-7-carboxylic acid amide, ssssssssssssss) 4-(2-Pyridin-2-yl-5,6-dihydro-4H-pyrrolo[1,2-b]pyrazol-3-yl)-quinoline-7-carboxylic acid(3-dimethylamino-propyl)-amide, tttttttttttttt) 4-[2-(6-Methyl-pyridin-2-yl)-5,6-dihydro-4H-pyrrolo[1,2-b]pyrazol-3-yl]-quinoline-7-carboxylic acid (2-dimethylamino-ethyl)-methyl-amide, uuuuuuuuuuuuuu) N,N-Dimethyl-3-{4-[2-(6-methyl-pyridin-2-yl)-5,6-dihydro-4H-pyrrolo[1,2-b]pyrazol-3-yl]-quinolin-7-yl}-acrylamide, vvvvvvvvvvvvvv) 4-(2-Pyridin-2-yl-5,6-dihydro-4H-pyrrolo[1,2-b]pyrazol-3-yl)-quinoline-1-oxide, wwwwwwwwwwwwww) 7-Benzyloxy-4-[2-(6-methyl-pyridin-2-yl)-5,6-dihydro-4H-pyrrolo[1,2-b]pyrazol-3-yl]-quinoline, xxxxxxxxxxxxxx) 4-[2-(6-Chloro-6-dihydro-4H-pyrrolo loro-pyridin-2-yl)-5 [1,2-b]pyrazol-3-yl]-quinoline, yyyyyyyyyyyyyy) 6-(3-Quinolin-4-yl-5,6-dihydro-4H-pyrrolo[1,2-b]pyrazol-2-yl)pyridine-2-carboxylic acid methyl ester, zzzzzzzzzzzzzz) 4-(7-Chloroquinolin-4-yl)-3-(pyridin-2-yl)-5,6-dihydro-4H-pyrrolo[1,2☐b]pyrazole, aaaaaaaaaaaaaaa) 4-(2-Furan-2-yl-5,6-dihydro-4H-pyrrolo[1,2-b]pyrazol-3-yl)-quinoline, bbbbbbbbbbbbbbb) 3-{4-[2-(6-Methyl-pyridin-2-yl)-5,6-dihydro-4H-pyrrolo[1,2-b]pyrazol-3-yl]-quinolin-6-yl}-acrylic acid methyl ester, ccccccccccccccc) 4-[2-(2-Methyl-thiazol-4-yl)-5,6-dihydro-4H-pyrrolo[1,2-b]pyrazol-3-yl]-quinoline, ddddddddddddddd) 3-(4-Fluoro-phenyl)-2-(2-methyl-thiazol-4-yl)-5,6-dihydro-4H-pyrrolo[1,2-b]pyrazole, eeeeeeeeeeeeeee) 4-[2-(2-Methyl-2H-pyrazol-3-yl)-5,6-dihydro-4H-pyrrolo[1,2-b]pyrazol-3-yl]-quinoline, fffffffffffffff) 4-(2-Thiazol-2-yl-5,6-dihydro-4H-pyrrolo[1,2-b]pyrazol-3-yl)-quinoline, ggggggggggggggg) 4-[2-(1-Methyl-1H-imidazol-2-yl)-5,6-dihydro-4H-pyrrolo[1,2-b]pyrazol-3-yl]-quinoline, hhhhhhhhhhhhhhh) 6,7-Dichloro-4-[2-(6-methyl-pyridin-2-yl)-5,6-dihydro-4H-pyrrolo[1,2-b]pyrazol-3-yl]-quinoline, iiiiiiiiiiiiiii) (S)-6-Benzyloxymethyl-3-(4-fluoro-phenyl)-2-(6-methyl-pyridin-2-yl)-5,6-dihydro-4H-pyrrolo[1,2-b]pyrazole, jjjjjjjjjjjjjjj) N,N-Dimethyl-3-{4-[2-(6-methyl-pyridin-2-yl)-5,6-dihydro-4H-pyrrolo[1,2-b]pyrazol-3-yl]-quinolin-7-yl}-acrylamide, and the pharmaceutically acceptable salts, esters and prodrugs thereof.

The compounds exemplified above are merely representative of the invention and are not limiting in any fashion.

The compounds disclosed herein can be made according to the following schemes and examples. The examples should in no way be understood to be limiting in any way as to how the compounds may be made.

The skilled artisan will appreciate that the introduction of certain substituents will create asymmetry in the compounds of Formula (I). The present invention contemplates all enantiomers and mixtures of enantiomers, including racemates. It is preferred that the compounds of the invention containing chiral centers are single enantiomers.

The compounds of the present invention can be prepared by a variety of procedures, some of which are illustrated in the Schemes below. It will be recognized by one of skill in the art that the individual steps in the following schemes may be varied to provide the compounds of Formula (I). The particular order of steps required to produce the compounds of Formula (I) is dependent upon the particular compound being synthesized, the starting compound, and the relative lability of the substituted moieties.

SCHEME I:

Method A:

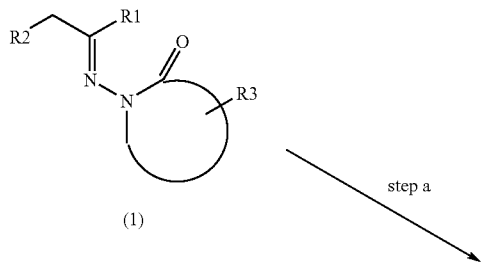

(1)

step a

Method B:

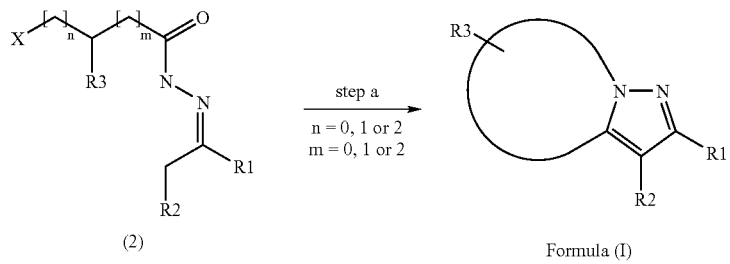

(2)

step a
n = 0, 1 or 2
m = 0, 1 or 2

Formula (I)

Method C:

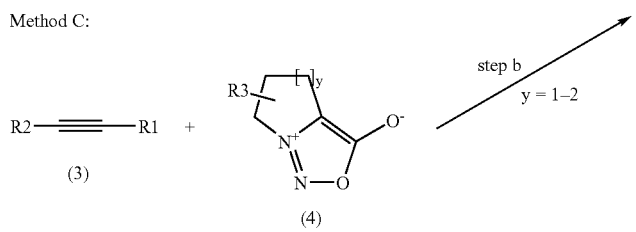

(3)     (4)

step b
y = 1–2

The Compounds of Formula (I) may be prepared from several synthetic methods. In Scheme I, Methods A and B employ a cyclization of an appropriately substituted alkylideneamino-pyrrolidin-2-one (I), Method A, or an appropriately substituted alkanone-alkene-hydrazide (2), Method B. One skilled in the art would also appreciate Method C, a condensation of an appropriately substituted alkyne (3) with a substituted synthon (4) to afford compounds of Formula (I).

Another variation a skilled artisan would appreciate is Method C for the formation of Formula (I), in Scheme I, is step b, which is known and appreciated in the art (Ranganathan, Darshan; Bamezai, Shakti, *Tetrahedron Lett.,* 1983, 1067–1070). For example, an alkyne of (3) is reacted with a compound of (4) in a suitable solvent, such as tetrahydrofuran, N,N-dimethylformamide, or toluene, xylene, preferably xylene at temperatures of about 0 to 150° C. The products can be isolated and purified by techniques described above.

SCHEME II:

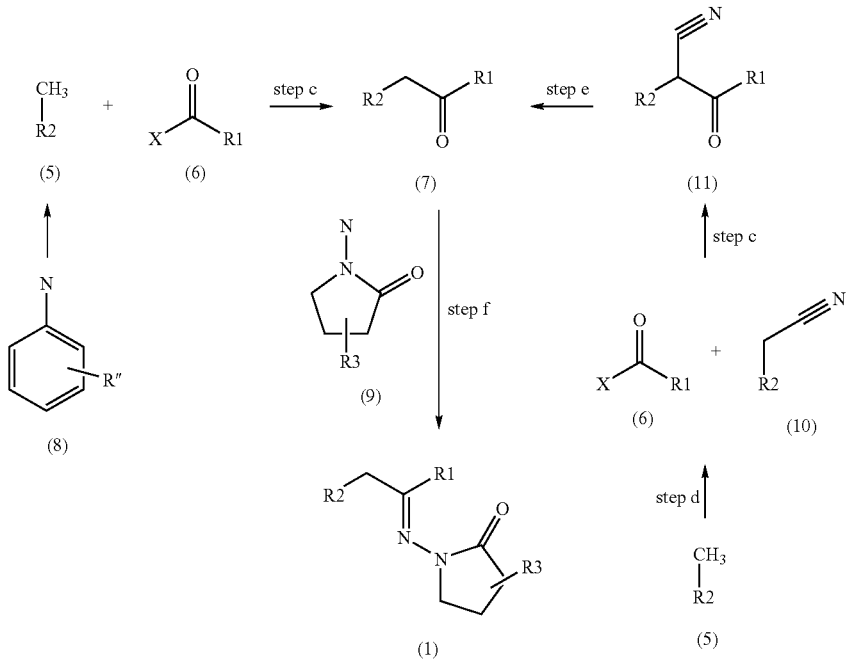

Step a depicts a cyclization of a compound of formula (1) or a substituted compound of formula (2), where the R group(s) can be any group(s), previously defined as said for R1, R2 or R3 of Formula (I) from here on. Typically, the appropriate compound of formula (1) is contacted to a suitable base that can form the anion of the hydrazone, such as lithium diisopropylamide, potassium bis(trimethylsilyl) amide, lithium bis(trimethylsilyl)amide, sodium bis (trimethylsilyl)amide, sodium hydride, lithium hydride, potassium hydride, sodium alkoxides (sodium hydoxide, sodium methoxide, or sodium ethoxide) or potassium alkoxides (potassium hydroxide, potassium methoxide, potassium t-butoxide or potassium ethoxide), with sodium hydride being the preferred base. The reaction is carried out in a suitable solvent, such as tetrahydrofuran, N,N-dimethylformamide, dimethylsulfoxide or toluene, preferably N,N-dimethylformamide at temperatures of about 0 to 100° C. The products can be isolated and purified by techniques well known in the art, such as precipitation, filtration, extraction, evaporation, trituration, chromatography, and recrystallization. Optionally, a variation of step b of Scheme 1, may be appropriate for the formation of 4,5,6,7-tetrahydro-pyrazolo[1,5-a]pyridine derivatives, when n equals to 2, to give the corresponding derivatives of Formula (1) as shown in Method B.

Scheme II, step c, depicts an acylation of an appropriate aromatic and/or heteroaromatic compound of formula (5) and an appropriate carbonyl ester of formula (6) to give a compound of formula (7). The aromatic and/or heteroaromatic compounds of formula (5) are commercially available or can be produced a condensation-cyclization by the use of an appropriate substituted aryl-heteroaryl-amine of formula (8), where R″ is previously described as substitutions for the R2 groups of Formula (I). For an example, methyl vinyl ketone can be reacted with formula (8) in the presence of an acid to afford aromatic-heteroaromatic-methyl compounds of formula (5). The acylation of formula (5) requires that X, of formula (6), to be a suitable leaving group, such as C1–C6 alkoxy, disubstituted amino, halo, C1–C6 thioether or arly thio, preferably disubstituted amino. The reaction is typically carried out in the presence of a suitable base that can create an anion of the compound of formula (5), such as lithium diisopropylamide, potassium bis(trimethylsilyl) amide, lithium bis(trimethylsilyl)amide, sodium bis (trimethylsilyl)amide, sodium hydride, lithium hydride, potassium hydride, sodium alkoxides (sodium methoxide, or sodium ethoxide) or potassium alkoxides (potassium methoxide, potassium t-butoxide or potassium ethoxide), with potassium bis(trimethylsilyl)amide being the preferred base. Generally, the reaction is carried out in suitable solvents, such as tetrahydrofuran and toluene or a combination of such, at temperatures of about –78° C. to ambient temperature. The product, formula (7), can be isolated and purified by techniques well known in the art, such as precipitation, filtration, extraction, evaporation, trituration, chromatography, and recrystallization. Another variation of the acylation step c, is to use a nitrile compound of formula (10) in place of the aromatic- or heteroaromatic-methyl compounds of formula (5). The product, formula (11), can be transformed to formula (7) by hydrolysis of the nitrile group and then subsequent decarboxylation. Generally, a compound of formula (11) is dissolved in a hydrogen halide acid solution, preferably hydrogen chloride. The reaction is carried out at temperatures of about ambient to refluxing for about 24 hours. This type of reaction is well known and appreciated in the art (Larock, R. C., *Comprehensive Organic Transformations*, copyright 1989, VCH, pp 993). Compounds of formula (10) can be acquired by treatment of an appropriate substituted aromatic- or heteroaromatic-methyl group with a halogenating reagent, such as N-halosuccinimides, preferably N-bromosuccinimide in carbon tetrachloride and subsequently reacting the aromatic-halomethylene intermediate with a nitrile source, such as lithium cyanide, potassium cyanide, or trimethylsilyl cyanide, preferably sodium cyanide. The reaction is carried out at ambient temperatures for about 24 hours, as shown in step d, to afford the acetonitrile compounds of formula (10), (Larock, R. C., *Comprehensive Organic Transformations*, copyright 1989, VCH, pp 313; Eur. J. Org. Chem. 1999, 2315–2321).

In Scheme II, step f, compound of formula (7) is contacted to an appropriate compound of formula (9), this type of compound is known and appreciated in the art (Taylor, Edward C.; Haley, Neil F.; Clemens, Robert J., *J. Amer. Chem. Soc.*, 1981, 7743–7752), to give the compound of formula (1). Typically, the reaction is carried out in an acidic solvent, such as acetic acid and a suitable acid scavenger such as pyridine, or triethylamine. The reaction is carried out at temperatures of about 60° C. to ambient for 4–24 hours. The products can be isolated and purified by techniques described above.

compounds of formula (6) and formula (13) is a suitable leaving group as previously described, preferably a C1–C6 alkoxy group. The Claisen condensation is well known and appreciated in the art (March, J., *Advanced Organic Chemistry*, copyright 1985, John Wiley and Sons, Inc., pp 437–439). The products of formula (14) can be isolated and purified by techniques described above.

In Scheme III, step f conditions can be applied to a compound of formula (14) with the appropriate compound of formula (9), to give the compound of formula (15). Typically, the reaction is carried out in a suitable solvent such as ethanol, N-methylpyrrolidinone or pyridine with pyridine being the preferred solvent. The reaction is carried out at temperatures of about 60° C. to ambient for 4–24 hours. The products can be isolated and purified by techniques described above.

Step c, as described above, depicts the cyclization of a compound of formula (15) to give an optionally substituted compound of formula (16). Typically, the appropriate compound of formula (15) is reacted with to a suitable base that can form the anion of the hydrazone, sodium hydride being the preferred base in a suitable solvent preferably N,N-dimethylformamide at temperatures of about 0 to 100° C. Optionally, a hydrolysis of the carboxyl ester of formula (16) can be performed. The products can be isolated and purified by techniques described above.

Step h depicts the transformation of a carboxylic acid, formula (16), to a halide of formula (17). This transformation is well known and appreciated in the art (Larock, R. C., *Comprehensive Organic Transformations*, 2$^{nd}$ Ed., copyright 1999, John Wiley & Sons, pp 741–742). The halide of formula (17) can be used as a leaving group in combination with a substituted aryl- or heteroarylboronic acid or ester in the presence of a suitable palladium catalyst, preferably tetrakis(triphenylphosphine)palladium(0), and a suitable base such as potassium carbonate to further give compounds

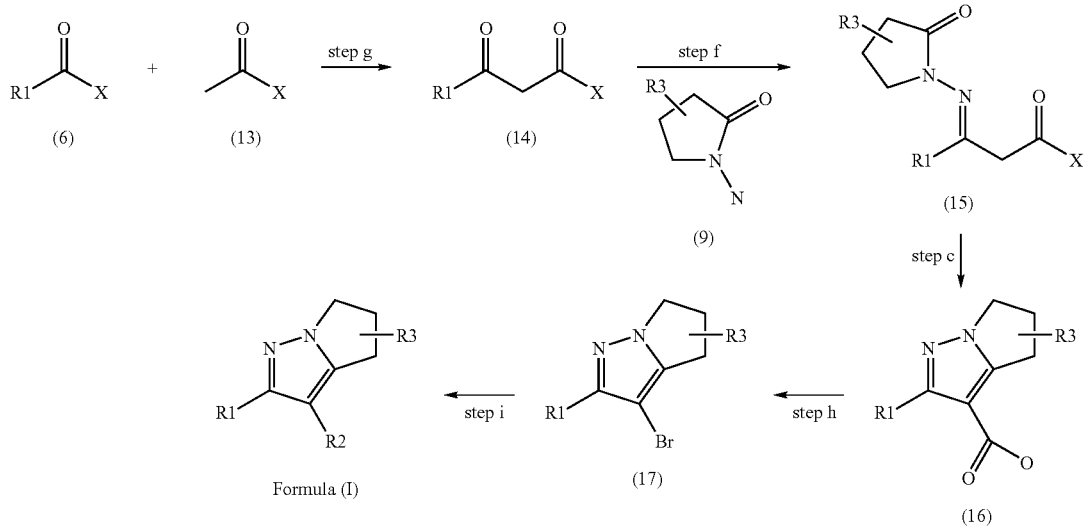

SCHEME III:

Another variation a skilled artisan would appreciate in the formation of Formula (1) is shown in Scheme III.

Scheme III, step g, depicts a Claisen condensation of two appropriate substituted carbonyl esters, where X for both of Formula (I) (Suzuki reaction see: Miryaura, N.; Yanagi, T.; Suzuki, A. The Palladium-Catalyzed Cross Coupling Reaction of Phenylboronic Acid with Haloarenes in the Presence of Bases. *Synth. Commun.*, 1981, 513–518).

SCHEME IV:

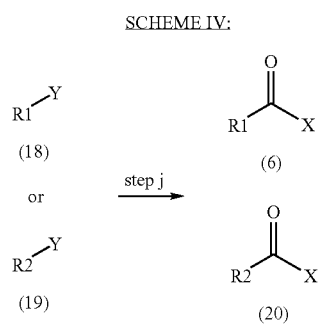

Scheme IV, step j, depicts a carbonylation reaction for the formation of compounds of formula (6) and (20), where X is a suitable leaving group described as above, preferably a halogen. Compounds of formula (18) and (19) are used in the formation of formula (6) and (20), respectively. The carbonyl group of formula (6) and (20) can further undergo a synthetic transformation to incorporate the leaving group X, where X is previously described. The Y group can be an aromatic or heteroaromatic halide and the reaction can be carried out in the presence of carbon monoxide, a suitable nucleophile, such as an amine or an alcohol, with a palladium (0) or palladium (II) catalyst, such as 1,1'-bis (diphenylphosphino) ferrocene]dichloropalladium(II): dichloromethane, tetrakis(triphenylphosphine)-palladium (0), bis(triphenylphosphine)palladium (II) chloride or palladium(II) acetate, tetrakis(triphenylphosphine) palladium(0), tris-(benzylideneacetone)dipalladium(0), palladium dichloride, palladium bis(trifluoroacetate), or preferably 1,1'-bis(diphenylphosphino)ferrocene] dichloropalladium(II):dichloromethane. All reagents of the reagents are combined in a suitable solvent, typically terahydrofuran, toluene or ethylene glycol dimethyl ether, stirred at temperatures of about 0 to 80° C. All products can be isolated and purified by techniques described above.

Scheme V depicts the conversion of optionally substituted heteroaryls to optionally substituted carboxylic acid derivatives. Reaction sequences of this type are well known and appreciated in the art (Fife, Wilmer K., *J. Org. Chem.,* 1983, 1375–1377). A representative example of these reactions are as follow. For example, in step k, an optionally substituted pyridine compound of formula (21), where R is previously described as the substitutions for R1 or R2 of Formula (I), is treated with hydrogen peroxide in acetic acid, at reflux. Formula (23) is produced from the crude intermediate, formula (22), and results from the removal of the solvent in step k, the addition of a nitrile source, preferably trimethylsilyl cyanide along with a disubstituted carbamyl halide, such as dimethylcarbamyl chloride. The reaction is carried out at ambient temperatures for about 24 hours. All products can be isolated and purified by techniques described above.

Scheme V, step e, the nitrile compounds of formula (23) are hydrolized by an acid to give the carboxylic acid of formula (24). Generally, a compound of formula (23) is dissolved in a hydrogen halide acid solution, preferably hydrogen chloride. The reaction is carried out at temperatures of about ambient to reflux for about 24 hours. This type of reaction is well known and appreciated in the art (Larock, R. C., *Comprehensive Organic Transformations,* copyright 1989, VCH, pp 993). Formula (24) can then be converted to the appropriate carbonyl leaving group, where X is a suitable leaving group described as above as shown in step m. This conversion is well known and appreciated in the art (Larock, R. C., *Comprehensive Organic Transformations,* copyright 1989, VCH, pp 966).

Alternatively, the carboxylic acid of formula (24) can be reduced to the corresponding alcohol by borane in tetrahydrofuran and then converted to a leaving group. Theses transformations are well known and appreciated in the art (Larock, R. C., *Comprehensive Organic Transformations,* copyright 1989, VCH, pp 552 reduction; pp 335 conversion to leaving group). The desired products may be isolated and purified by techniques described above.

SCHEME V:

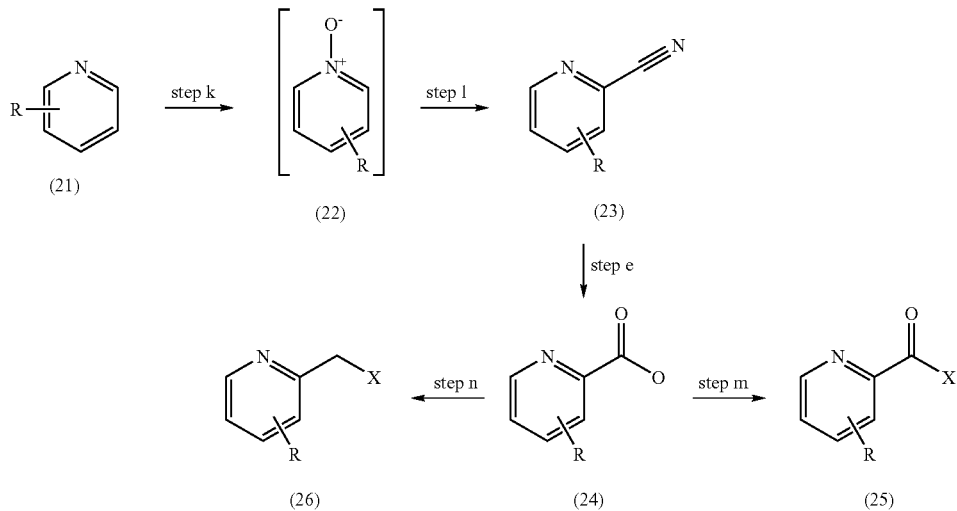

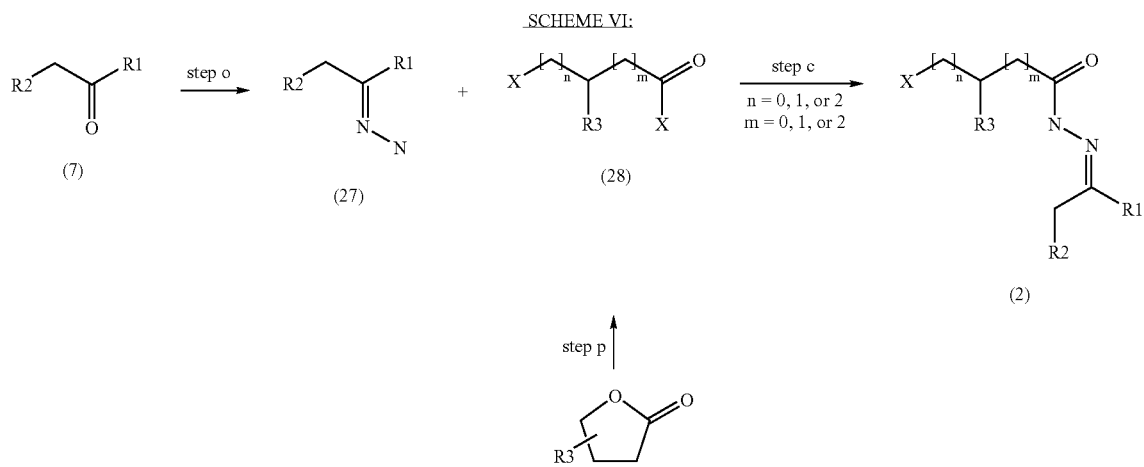

Scheme VI, step o, depicts a hydrazination of formula (7) affording a hydrazone compound of formula (27). Typically the reaction is carried out with a suitable source of hydrazine, preferably anhydrous hydrazine in an acidic solution consisting of an alcohol, such as methanol, ethanol, or propanol, and a hydrogen halo acid, preferably hydrogen chloride, is used as the solvent. The product can be isolated and purified by techniques described above. Compounds of formula (28) are commercially available or can be produced by a ring opening of appropriate substituted cyclic-carbonyl esters. Step p depicts these ring openings which can be accomplished by an acid hydrolysis using such as; hydrogen bromide with acetic acid or trimethyl aluminum can give the corresponding carboxylic acid derivatives to be further transformed to give compound of formula (28).

Scheme VI, step c previously described, transforms the hydrazones of formula (27) to the hydrazides of formula (2), by acylation with compounds formula (28). The compound of formula (28) can be an appropriate carboxylic acid derivative, where X can be a leaving group previously described, preferably a halogen, most preferably a chloride, and where n and m can equal 1 or 2 carbons. The reaction is carried out in the presence of an acid scavenger such as pyridine or triethylamine. The reagents are combined, and products isolated and purified by techniques described above. The conversion of amines to an amides by acylation is well known and appreciated in the art (Larock, R. C., *Comprehensive Organic Transformations*, copyright 1989, VCH, pp 979).

SCHEME VII:

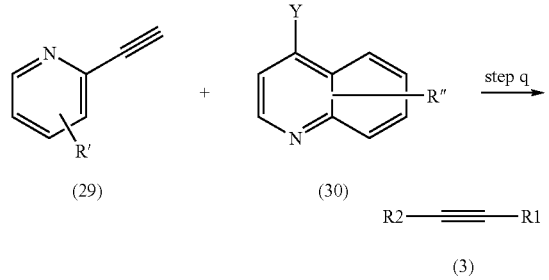

One skilled in the art would appreciate the formation of formula (3) by the palladium-promoted coupling reaction of an alkyne and an aromatic halide. Such a reaction is known and appreciated in the art (Reisch, Johannes; Gunaherath, G. M. Kamal B., *J. Heterocycl. Chem.*, 1993; 1057–1060, Inouye, Masahiko; Miyake, Toshiyuki; Furusyo, Masaru; Nakazumi, Hiroyuki, *J. Amer. Chem. Soc.*, 1995; 12416–12425). For example, in Scheme VII, step q, an appropriate substituted alkyne of formula (29) and a variably substituted compound of formula (30), where R' and R" are previously described as substitutions for R1 and R2 groups, respectively, for Formula (I) and where Y can be an appropriate leaving group such as a halide and the R group(s) can be one or more groups as previously described. Typically, the reaction is carried out by combining a compound of formula (30) with a palladium (0) or palladium (II) catalyst as described previously, preferably bis(triphenylphosphine) palladium (II) chloride with a suitable base, such as trialkylamine or pyridine, preferably triethylamine along with a copper(I) halide to facilitate coupling to a compound of formula (29). All reagents are combined in a suitable solvent, typically terahydrofuran, toluene or ethylene glycol dimethyl ether, stirred at temperatures of about 0 to 80° C. All products can be isolated and purified by techniques described above.

SCHEME VIII:

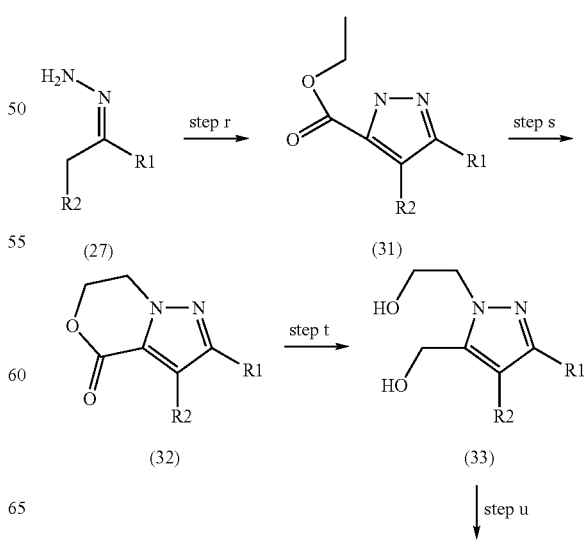

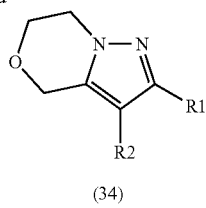

(34)

Scheme VIII, depicts the incorporation of a heteroatom into the acyclic ring portion of Formula (I). In step r, an appropriate compound of formula (27) is reacted with an oxalic acid monoalkyl ester derivative, such as ethyl oxalyl chloride to give a compound of formula (31). Generally, the reaction is carried out in a suitable solvent, such as pyridine, at temperatures from ambient to reflux. The products can be isolated and purified by techniques described above.

The reaction of step s, a compound of formula (31) is converted to a lactone of formula (32), by a sequence of reactions. An appropriate compound of formula (31) is dissolved in a suitable solvent, such as tetrahydrofuran, N,N-dimethylformamide, or toluene, preferably N,N-dimethylformamide at temperatures of about 0 to 80° C. A suitable base, such as sodium carbonate, sodium bicarbonate, cesium carbonate, cesium bicarbonate, lithium carbonate, potassium carbonate, preferably cesium carbonate, is used in 1–3 molar equivalence, along with an appropriate alkylating reagent, such as a halo-alcohol, preferably 2-bromo-ethanol. The products can be isolated and purified by techniques described above.

Step t depicts a ring opening and reduction of a compound of formula (32) to give a di-alcohol compound of formula (33). Typically, the reaction is carried out with a suitable reducing agent, such as boranes (sodium borohydride, borane-methyl sulfide complex or potassium borohydride), or aluminum hydrides (lithium aluminum hydride, sodium aluminum hydride or potassium aluminum hydride, preferably lithium aluminum hydride). All of the reagents are combined in a suitable solvent, typically dichloromethane, chloroform, tetrahydrofuran, dioxane, or diethyl ether and are stirred from 1 to 72 hours at a temperature of from ambient to about the refluxing temperature of the solvent. The desired product may be isolated and purified by techniques described above.

The reaction in step u depicts a ring formation of a compound of formula (33) to give a compound of formula (34), a compound derivative of Formula (I). The di-hydroxy compound of formula (33) is mixed with a suitable base, such as sodium hydride, potassium hydride, typically at approximately 2–4 molar equivalents of base per molar equivalent of the di-alcohol. A suitable sulfonylating agent, such as p-toluenesulfonyl chloride, p-nitro-benzenesulfonyl chloride, trifluoromethanesulfonic anhydride, or preferably methanesulfonyl chloride, is added in the reaction for the conversion of the hydroxy group of formula (33) into a suitable leaving group. The reaction is carried out in a suitable solvent, such as dichloromethane, chloroform, tetrahydrofuran, dioxane, or diethyl ether, preferably tetrahydrofuran, and stirred for 1 to 24 hours at a temperature of about 0° C. to ambient. The desired product may be isolated and purified by techniques described above.

SCHEME IX:

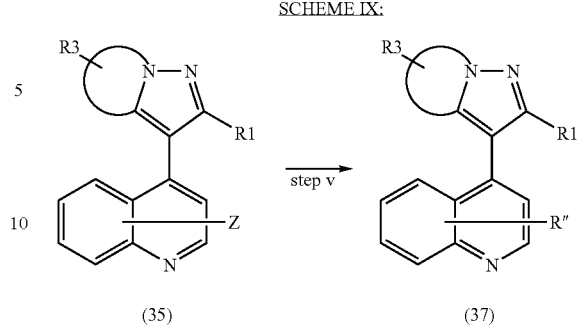

(35)      (37)

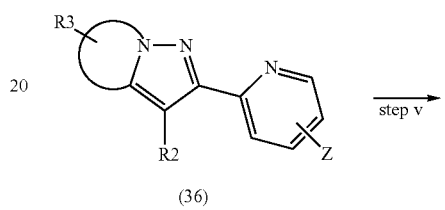

(36)

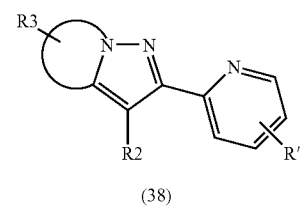

(38)

Scheme IX, elaborates substitution of the R1 and R2 groups of Formula (1). A representative transformation is seen in step v, a nucleophilic addition of appropriate compounds of formula (35) and (36), where Z is an halide, such as chloro, bromo, or iodo, or a sulfonic ester derivative substituted anywhere upon the aromatic ring, can undergo a nucleophilic substitution with appropriate nucleophiles, where the R group(s) is described above, to give compounds of formula (37) and (38), respectively. Typically, the reaction is carried out in the presence of C1–C6 alkoxide or variably substituted amine neat or in N,N-dimethylformamide, toluene or xylene, preferably N,N-dimethylformamide at temperatures of about 100° C. to reflux. Alternatively, a metal-nucleophile, such as trialkylstannyls, or boranes with a suitable base such as, sodium alkoxides (sodium methoxide, or sodium ethoxide) or potassium alkoxides (potassium methoxide, or potassium ethoxide) can be used with a palladium catalyst, previously described, preferably tetrakis(triphenylphosphine)palladium (0). Or a skilled artisan can use as the metal-nucleophile a magnesium-halogen reagent (Grignard reagent) along with the palladium catalyst, to further elaborate the aryl-substituents at the C3 and C4 positions of the pyrazole of Formula (1). All reagents of the reagents are combined in a suitable solvent, typically tetrahydrofuran, toluene or ethylene glycol dimethyl ether, stirred at temperatures from room temperature to reflux. All products can be isolated and purified by techniques described above.

SCHEME X:

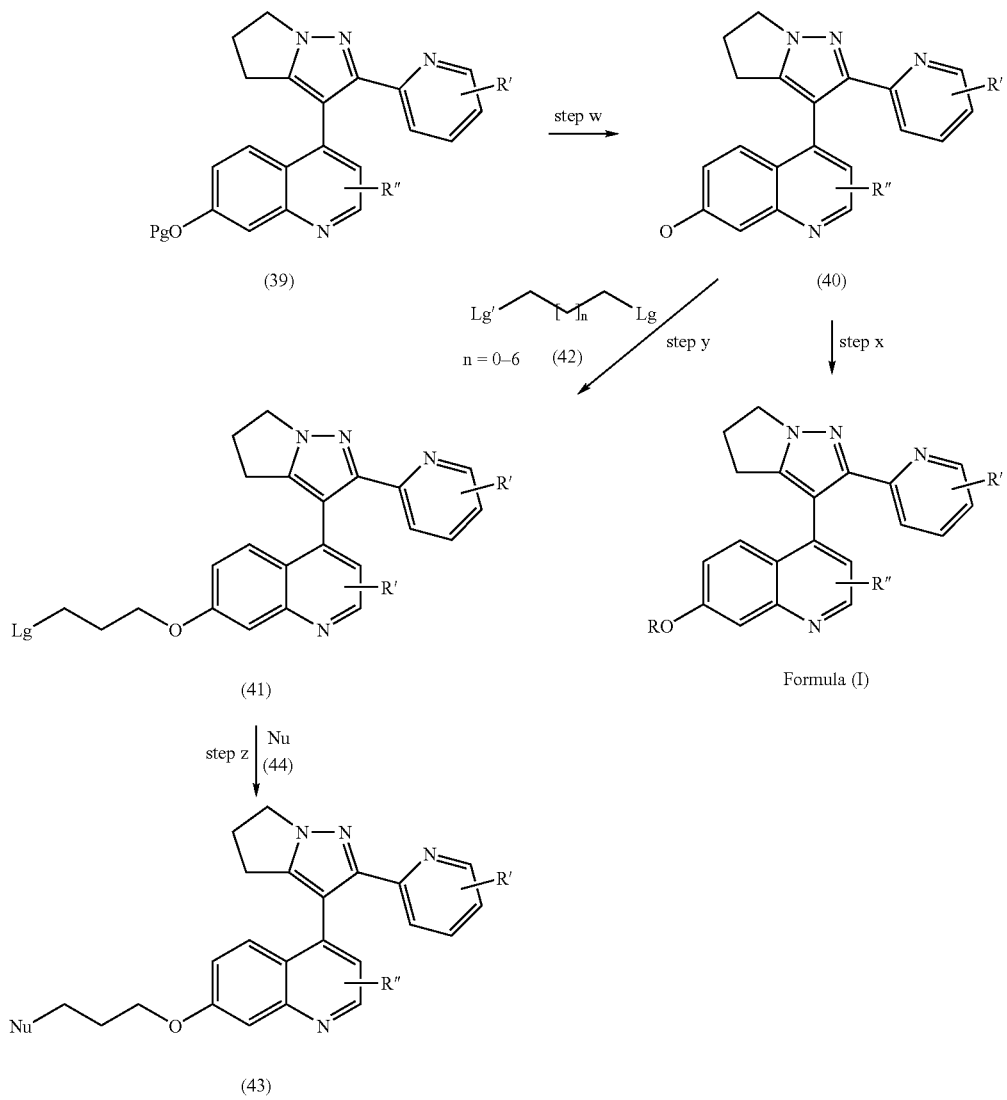

Scheme X depicts the manipulation of hydroxy-aryl compounds of formula (40) for further alkylations and transformations to enable the scope of this invention, where the R group(s) are previously described. Representative conversions are shown in Scheme X.

Step w, depicts the deprotection of a protected aromatic-hydroxy group of formula (39) to give a compound of formula (40), where the "Pg" can be an alkoxide. The deprotection is well known and appreciated in the art (Greene T. W., Wuts, P. G. M. *Protective Groups in Organic Synthesis*, copyright 1991, John Wiley and Sons, Inc., pp146–149). The product of formula (40) can be isolated and purified by techniques previous described.

Step x, depicts the formation of an aryl ether compound of formula (40) to give the compounds of Formula (1). The formation of an aryl ether is well known and appreciated in the art (March, J., *Advanced Organic Chemistry*, copyright 1985, John Wiley and Sons, Inc., pp342–343, 589 and Mundy, B. P., Ellerd, M. G. *Name Reactions and Reagents in Organic Synthesis*, copyright 1988, John Wiley and Sons, Inc., pp 242, 530; Sawyer, J. S., Schmittling, E. A., Palkowitz, J. A., Smith, III, W. J., J. Org. Chem., 1998, 63, 6338–6343). The products can be isolated and purified by techniques described above.

Step y depicts an alkyation of a compound of formula (40) to give a variably substituted compound of formula (41), where the leaving group(s) "Lg" and "Lg'" can include such leaving groups, but are not limited to, halides, oxonium ions, alkyl perchlorates, ammonioalkanesulfonate esters, alkyl fluorosulfonates, nonaflates, tresylates, triflates, and sulfonic esters, preferably the mesylate or tosylate, given "Lg" and "Lg'" are not the same group. Typically, the appropriate compound of formula (40) is reacted with a suitable base that can form the anion of the phenol, such as lithium carbonate, sodium carbonate, potassium carbonate, cesium carbonate, sodium hydride, lithium hydride, potassium hydride, with cesium carbonate being the preferred base, in the presence of a compound of formula (42). The reaction is carried out in a suitable solvent, such as tetrahydrofuran, N,N-dimethylformamide, dimethylsulfoxide, dimethyl acetamide or toluene, preferably N,N-dimethylformamide at temperatures of about 0 to 100° C. The products can be isolated and purified by techniques described above.

Step z depicts the nucleophilic substitution of leaving group "Lg", by a nucleophile to form a compound of the formula (43). Nucleophilic substitution is well known and appreciated in the art (March, J., *Advanced Organic Chemistry*, copyright 1985, John Wiley and Sons, Inc., pp 255–446). Typically, the compound of formula (41) is reacted with a nucleophile of formula (44), which is typically, but not limited to, primary amines, secondary amines, alcohols or thiols. The reaction is carried out in a suitable solvent, such as tetrahydrofuran, N,N-dimethylformamide, dimethylsulfoxide, dimethyl acetamide or toluene, preferably N,N-dimethylformamide at temperatures of about 0 to 100° C. The products can be isolated and purified by techniques described above.

SCHEME XI:

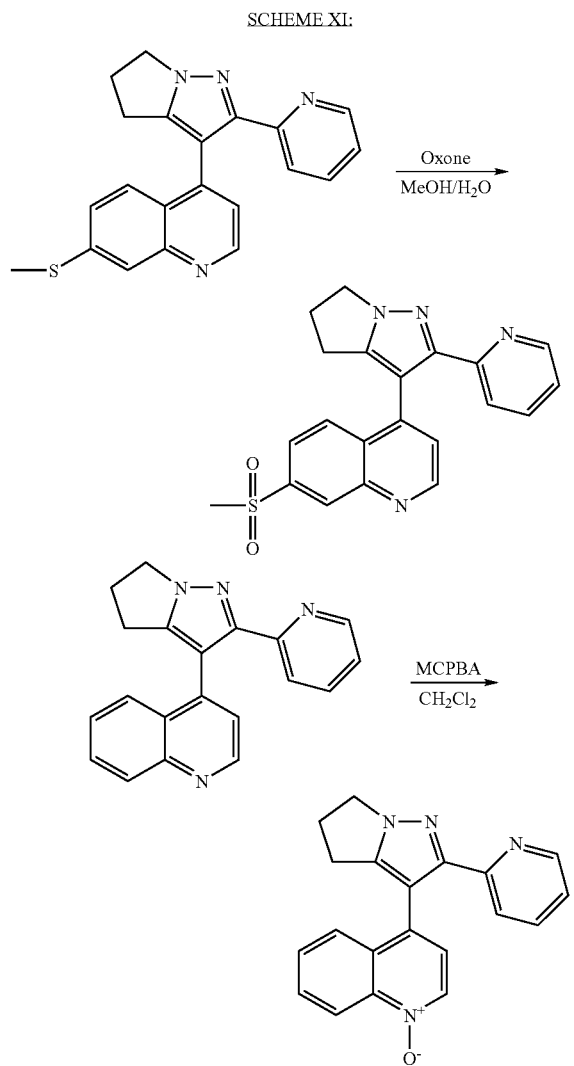

A skilled artisan would appreciate oxidation reactions on compounds of Formula (I) to further elaborate the scope of this invention. Representative examples are shown in Scheme XI. For example, a sulfur- or nitrogen-containing compound can be oxidized to an oxide (nitrogen or sulfur) or a bis oxide (sulfur) by oxidizing reagents. Typically, a compound of Formula (I) is contacted to an oxidant which is typically, but not limited to, hydrogen peroxide, acetoyl peroxide, benzoyl peroxide, tert-butyl peroxide, ozone, Oxone®, preferably Oxone®, in the presence of an acid which is typically, but not limited to, hydrochloric, sulfuric, nitric, phosphoric, acetic, trifluoroacetic acids, preferably acetic acid. The reaction is carried out in a suitable solvent, such as tetrahydrofuran, water, an alcohol, such as, but not limited to, ethanol, or methanol, preferably a mixture of water and tetrahydrofuran at temperatures of about 0 to 100° C. Oxidations are well known and appreciated in the art (March, J., *Advanced Organic Chemistry*, copyright 1985, John Wiley and Sons, Inc., pp 1089–1090).

SCHEME XII:

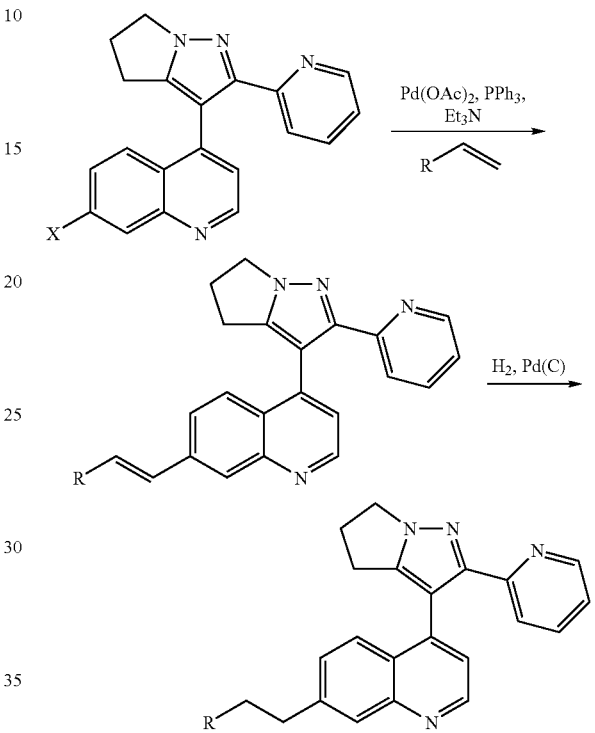

A skilled artisan would appreciate palladium catalyzed couplings to elaborate the scope of the invention as shown in Scheme XII.

Aryl substitutions of may be accomplished, through the use of a halo or sulfonyl leaving group, X, in combination with a substituted aryl- or heteroarylboronic acid or ester in the presence of a suitable palladium catalyst and a suitable base such as potassium carbonate as previously described in Scheme III. Another palladium catalyzed reaction, incorporates alkenyl substitutions may be realized by reacting the corresponding aryl halide with an alkene in the presence of a suitable base such as triethylamine, a palladium catalyst, and a suitable ligand, such as triphenylphosphine. The resulting alkene may be reduced via hydrogenation to provide a substituted alkane-linked derivative (Heck reaction see: Whitcombe, N.J.; Hii, K. K.; Gibson, S. E. Advances in the Heck chemistry of aryl bromides and chlorides, *Tetrahedron*, 2001, 57(35), 7449–7476).

A skilled artisan would also appreciate a carbonylation using an aromatic halide along with a palladium catalyst and an atmosphere of carbon monoxide in a suitable solvent such as methanol as previously described in Scheme IV.

SCHEME XIII:

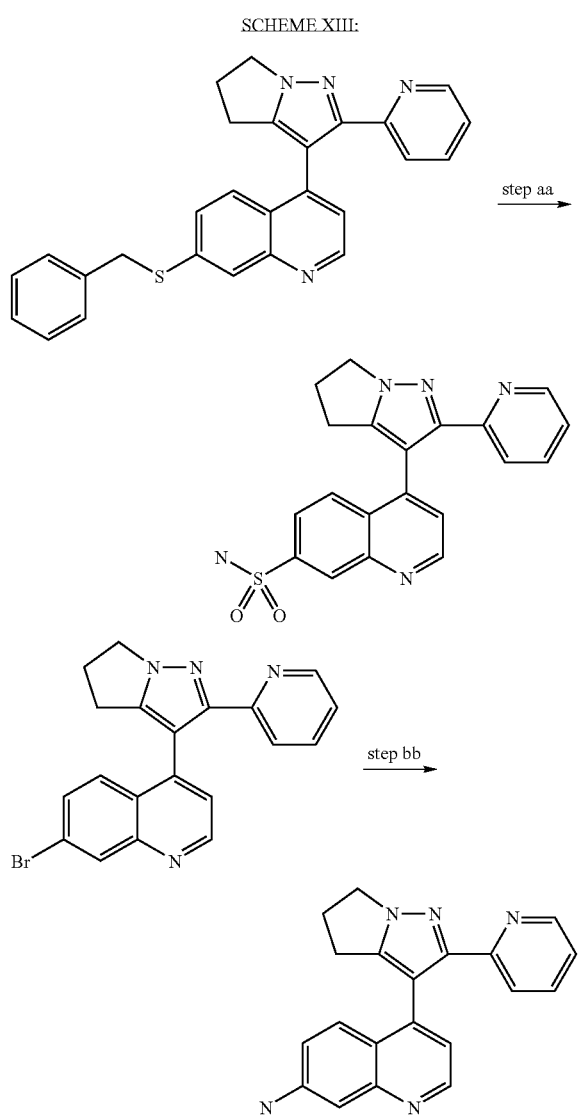

SCHEME XIV:

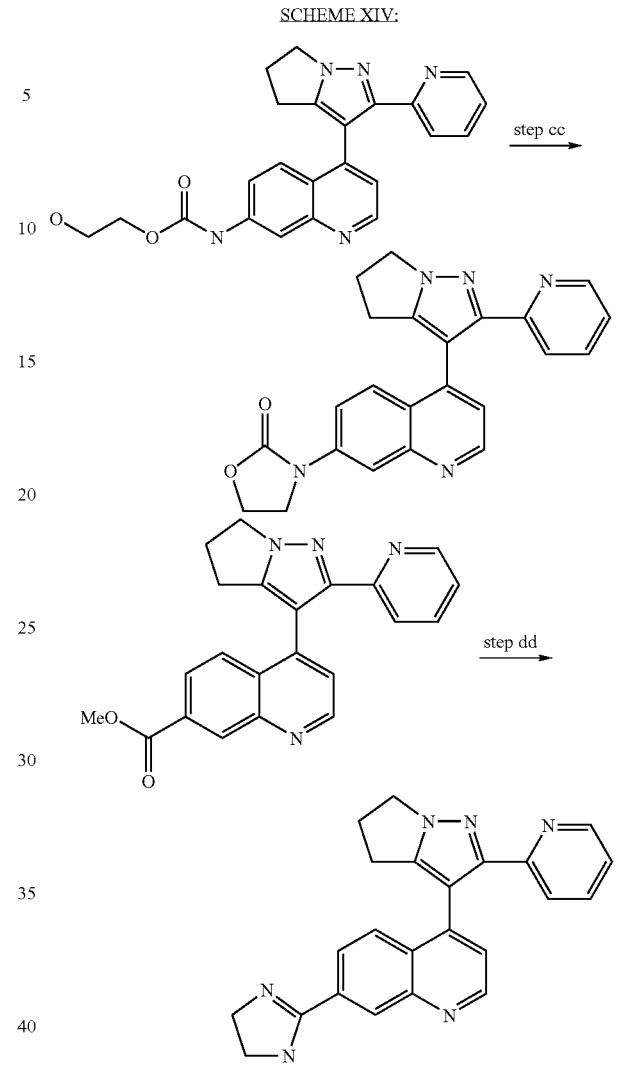

Scheme XIII also elaborates compounds of Formula (I) to further enable the scope of this invention. A transformation of a benzylthio-aryl to a sulfonamide formation is depicted in step aa. A typical reaction is the treatment of a benzylthio-aryl with molecular chlorine in aqueous acetic acid solution and with the removal of the solvent then coupling the product to an appropriate substituted amine. One skilled in the art would also appreciate the conversion of an arylhalide of Formula (I) to the corresponding amine, shown in step bb. For example, the arylhalide is treated with benzophenone imine and a suitable base such as sodium methoxide, sodium iso-propoxide or preferably sodium tert-butoxide also using a palladium catalyst as previously described, preferably bis(dibenzylideneacetone)-palladium with an appropriate ligand such as 2,2'-bis(diphenylphosphino)-1,1'-binaphthyl, this type of amination transformation is well known and appreciated in the art (Prashad, M.; Hu, B.; Lu, Y.; Draper, R.; Har, D.; Repic, O.; Blacklock, T. J., *J. Org. Chem.*, 2000, 65, 2612–1614).

One skilled in the art would also appreciate other transformations of hetrocyclic substitutions, as shown in Scheme XIV.

Step cc, depicts a cyclization of a hydroxyethyl-carbamic ester, to give an oxazolidinone. This type of cyclization is well known in the art (Mistunobu, O., *Synthesis*, 1981, 1–28).

Step dd, depicts a transformation of the aryl carboxylic ester, to a 4,5-dihydro-1H-imidazole by use of a Lewis acid such as trimethylaluminum. This type of transformation is well known in the art (Neef, G.; Eder, U.; Sauer, G.; *J. Org. Chem.*, 1981, 46, 2824–2826).

Many of the compounds of the present invention are not only inhibitors of TGF-beta receptor kinase, but are also useful intermediates for the preparation of additional compounds of the present invention. For example, ester moieties may be reduced or hydrolized to the corresponding alcohols or carboxylic acid (Larock, R. C., *Comprehensive Organic Transformations*, 2$^{nd}$ Ed., copyright 1999, John Wiley & Sons, pp 1959–1968). These alcohols may then be activated and displaced by a number of nucleophiles to provide other compounds of the invention (see Larock, *Comprehensive Organic Transformations*, 2$^{nd}$ Ed., John Wiley & Sons, New York, pg. 779–780 (1999)).

Additionally, in order to substitute alcohol derivatives with a corresponding amine, the skilled artisan would appreciate that necessary intermediates would incorporate certain appropriate leaving groups. Such leaving groups include, but are not limited to, halides, oxonium ions, alkyl perchlorates, ammonioalkanesulfonate esters, alkyl fluorosulfonates, nonaflates, tresylates, triflates, and sulfonic esters, preferably the mesylate or tosylate. Techniques for the introduction of these groups are also well known to the skilled artisan; see, for example, March, *Advanced Organic Chemistry*, 5$^{th}$ Ed., John Wiley and Sons, New York, pg. 445–449 (2001). The skilled artisan will appreciate the secondary amine moiety can be reacted with an appropriate reagent to introduce a suitable amino protecting group "Pg", such as a formyl group, acetyl group, or preferably a tert-butoxycarbonyl moeity. These protecting groups may be removed at any convenient point in the synthesis of the compounds of the present invention. Methods of formation and removal of an amino-protecting group are well known in the art; see, for example, Greene and Wuts, *Protective Groups in Organic Synthesis*, 3$^{rd}$ Ed., John Wiley and Sons, New York, Chapter 7 (1999).

For example, secondary amines may be acylated, alkylated or coupled with simple carboxylic acids or amino acids under standard conditions, in the presence of a peptide coupling reagent, optionally in the presence of a catalyst. Suitable peptide coupling reagents include N,N'-carbonyldiimidazole (CDI), N,N'-dicyclohexylcarbodiimide (DCC), 1-(3-dimethylaminopropyl)-3-ethylcarbodiimide hydrochloride (EDC), and 1-(3-(1-pyrrolidinyl)propyl)-3-ethylcarbodiimide (PEPC). Polymer supported forms of EDC (*Tetrahedron Letters*, 34(48), 7685 (1993)) and PEPC (U.S. Pat. No. 5,792,763) have been described, and are very useful for the preparation of the compounds of the present invention. Suitable catalysts for the coupling reaction include N,N-dimethyl-4-aminopyridine (DMAP). Such coupling reactions are well known and appreciated in the art (Larock, R. C., *Comprehensive Organic Transformations*, 2$^{nd}$ Ed., copyright 1999, John Wiley & Sons, pp 1941–1949). Also One skilled in the art would appreciate the treatment of a secondary amine with a phosgene reagent, with a suitable base such as pyridine and quenching the reaction with an amine or an alcohol to afford the appropriate ureas and carbamates of Formula (I) (March, J., *Advanced Organic Chemistry*, copyright 1985, John Wiley and Sons, Inc., pp 370–371).

A skilled artisan would recognize several other transformations that can be applied to the synthetic process for production of useful and reactive intermediates. Such transformations include but are not limited to alkylation or acylations of the appropriate amine, O-alkylation of the hydroxy intermediates, or hydroxy-halogen exchange (Larock, *Comprehensive Organic Transformations*, 2$^{nd}$ Ed., John Wiley & Sons, New York, pg. 689–697 (1999)).

The skilled artisan will also appreciate that not all of the substituents in the compounds of Formula (I) will tolerate certain reaction conditions employed to synthesize the compounds. These moieties may be introduced at a convenient point in the synthesis, or may be protected and then deprotected as necessary or desired. Furthermore, the skilled artisan will appreciate that in many circumstances, the order in which moieties are introduced is not critical.

The skilled artisan will appreciate that the compounds of Formula (I) in Methods A, B or C may be formed into acid addition salts using pharmaceutically acceptable acids. The formation of acid-addition salts is well known and appreciated in the art.

The following preparations and examples further illustrate the preparation of compounds of the present invention and should not be interpreted in any way as to limit the scope. Those skilled in the art will recognize that various modifications may be made while not departing from the spirit and scope of the invention. All publications mentioned in the specification are indicative of the level of those skilled in the art to which this invention pertains.

Preparation 1

4,5-Dihydroxy-pentanoic acid ethyl ester

A solution of ethyl pent-4-enoate (11.7 g, 91.3 mmol) in tetrahydrofuran (420 mL) and water (40 mL) is treated with osmium tetroxide (1.0 g, 4.2 mmol) and 4-methylmorpholine N-oxide (32.5 mL, 50% in water) at room temperature and stired for 3 h, at which time no more starting material is detectable by TLC (SiO$_2$, 2% methanol/dichloromethane, R$_f$=0.40). The mixture is concentrated in vacuo and the residue chromatographed on SiO$_2$ (2% methanol/ethyl acetate) to afford the title compound 14.37 g (96%) as a colorless oil.

$^1$H NMR (CDCl$_3$): δ 4.10 (q, J=7 Hz, 2H), 3.60–3.80 (m, 2H), 3.45 (dd, J=7, 11 Hz, 1H), 3.00 (bs, 2H), 2.45 (dd, J=1.3, 7 Hz, 2H), 1.70–1.85 (m, 2H), 1.25 (t, J=7 Hz, 3H).

Preparation 2

5-(tert-Butyl-dimethyl-silyloxy)-4-hydroxy-pentanoic acid ethyl ester

A solution of 4,5-dihydroxy-pentanoic acid ethyl ester, (7 g, 43.2 mmol) and 4-dimethylaminopyridine (0.2 g, 1.73 mmol) in dichloromethane (145 mL) at room temperature under nitrogen is treated with tert-butyl-dimethyl-silyl chloride (7.8 g, 51.85 mmol) and triethylamine (6.9 mL, 47.52 mmol) and stirred 18 h. The mixture is diluted with dichloromethane (100 mL), washed with water (100 mL), saturated ammonium chloride solution, and brine. The solution is filtered and concentrated in vacuo to yield the title compound, 11.85 g (99%), as a colorless oil.

$^1$H NMR (CDCl$_3$): δ 4.05 (q, J=7 Hz, 2H), 3.50–3.65 (m, 2H), 3.30–3.40 (m, 1H), 2.30–2.45 (m, 3H), 1.60–1.75 (m, 2H), 1.20 (t, J=7 Hz, 3H), 0.90 (s, 9H), 0.10 (s, 6H).

Preparation 3

(2-Amino-2-methyl-propyl)-carbamic acid tert-Butyl ester

Di-tert-butyl dicarbonate (2.5 g, 11.3 mmol) is added portionwise to a solution of 2-methyl-propane-1,2-diamine (3.0 g, 34.0 mmol) in 1,4-dioxane (50 mL). The mixture is stirred at room temperature for 18 h concentrated in vacuo. The residue is purified by flash chromatography (methanol/dichloromethane (5:95)) and yielded the title compound 2.47 g (40%) as a white solid.

$^1$H NMR (CDCl$_3$) δ 5.07–4.87 (m, 1H), 3.08–2.92 (m, 2H), 1.54–1.41 (m, 9H), 1.09 (s, 6H).

Preparation 4

1-Benzyloxy-4-phenyl-butan-2-ol

Benzyloxy-acetaldehyde (3.0 g, 20 mmol) is dissolved in tetrahydrofuran (200 mL), cooled to −78° C. This solution is treated with phenylethylmagnesium chloride (1.0 M in tetrahydrofuran, 24 mL, 24 mmol), and stirred for one hour. The mixture is allowed to warm to room temperature and stirred for 4 h. The mixture is treated with hydrochloric acid (1 M, 40 mL) and extracted with ethyl acetate. The combined organic extracts are washed with water and brine, dried over sodium sulfate, and filtered. The filtrate is concentrated in vacuo to provide the title compound, 4.0 g (80%), as a colorless liquid.

$^1$H NMR (CDCl$_3$) δ 7.37–7.10 (m, 10H), 4.56 (s, 2H), 3.85–3.72 (m, 1H), 3.5–3.41 (m, 1H), 3.39–3.29 (m, 1H), 2.9–2.6 (m, 2H), 1.8–1.67 (m, 2H).

Preparation 5

1-Benzyloxy-4-phenyl-butan-2-one

To a solution of 1-benzyloxy-4-phenyl-butan-2-ol, (8.4 g, 32.8 mmol) in dichloromethane (400 mL) is added a mixture of pyridinium chlorochromate (14.1 g, 65.6 mmol) with SiO$_2$ (14 g) and stirred for 3 h at room temperature. The mixture is filtered through a pad of SiO$_2$ and concentrated to provide the title compound 5.7 g (68%) as a colorless liquid.

$^1$H NMR (CDCl$_3$) δ 7.4–7.14 (m, 10H), 4.6 (s, 2H), 4.03 (s, 2H), 2.9–2.82 (m, 2H), 2.8–2.72 (m, 2H).

Preparation 6

4-Acetoxy-3-phenyl-butyric acid methyl ester

A mixture of 4-acetoxy-3-phenyl-but-2-enoic acid methyl ester, (1.0 g, 4.27 mmol), 10 wt. % palladium on activated carbon (1.0 g), acetic acid (10 mL) is shaken under an atmosphere of hydrogen on a Parr® Shaker. The mixture is filtered through a pad of Celite® and rinsed with methanol. The solution is concentrated in vacuo to yield 0.93 g (92%) of the title compound.

$^1$H NMR (CDCl$_3$) δ 7.40–7.10 (m, 5H), 4.30–4.05 (m, 2H), 3.60 (s, 3H), 3.55–3.40 (m, 1H), 2.80–2.50 (m, 2H), 2.10 (s, 3H).

Preparation 7

Acetic Acid 2-oxo-2-phenyl-ethyl ester

A solution of 2-hydroxyaceto-phenone (10 g, 73.4 mmol), pyridine (17.4 g, 220.2 mmol), dichloromethane (734 mL), 3 crystals of 4-dimethylaminopyridine is cooled to –78° C. To this solution is added acetic anhydride (13.9 mL, 146.9 mmol) then warmed to room temperature and stirred for 18 h. The mixture is washed with water (200 mL) and brine (200 mL) then dried over sodium sulfate. The mixture is filtered and concentrated in vacuo to yield the title compound, 13 g (99%), as a colorless liquid.

$^1$H NMR (CDCl$_3$) δ 7.9–7.2 (m, 5H), 5.32 (s, 2H), 2.20 (s, 3H).

Preparation 8

4-(3-Methoxy-phenyl)-5H-furan-2-one

3-Methoxy-phenyl-boronic acid (2.16 g, 14.2 mmol) and trifluoromethansulfonic acid 5-oxo-2,5-dihydro-furan-3-yl ester[1] (3 g, 12.92 mmol) in tetrahydrofuran (110 mL) is dissolved and de-gassed for 15 min. To this solution is added sodium carbonate (3.42 g, 32.3 mmol) in water (10 mL) and tetrakis-triphenylphosphine-palladium(0) (0.75 g, 0.646 mmol). The reaction mixture is refluxed for 45 min, cooled to room temperature, diluted with ether (50 mL) and filtered through a Celite® pad. The filtrate is washed with water and brine, dried over magnesium sulfate, filtered, and concentrated in vacuo. The residue is chromatographed on SiO$_2$ (3:7 ethyl acetate/hexanes) to yield the title compound, 1.9 g (71%), as a white crystalline solid.

[1]) Grigg, R.; Kennewell, P.; Savic, V. *Tetrahedron*, 1994, 5489–5494.

$^1$H NMR (CDCl$_3$): δ 7.35 (m, 1H), 7.00–7.20 (m, 3H), 6.30 (s, 1H), 5.20 (s, 2H), 3.80 (s, 3H).

Preparation 9

4-(4-Fluoro-phenyl)-5H-furan-2-one

A method similar to PREPARATION 7, except employing 4-fluoro-phenyl-boronic acid, is used to yield the title compound as a white crystalline solid.

$^1$H NMR (CDCl$_3$): δ 7.50–7.60 (m, 2H), 7.15–7.25 (m, 2H), 6.35 (s, 1H), 5.20 (s, 2H).

Preparation 10

4-(3-Methoxy-phenyl)-dihydro-furan-2-one

To a solution of 4-(3-methoxy-phenyl)-5H-furan-2-one, (1.9 g, 10 mmol) in tetrahydrofuran (100 mL) and is added Raney nickel (7.6 g, 50% suspension in water) the mixture is stirred under hydrogen (ambient pressure) 18 h at room temperature. The mixture is filtered through Celite® and concentrated in vacuo to yield the title compound, 1.54 g (80%), as a white crystalline solid.

$^1$H NMR (CDCl$_3$): δ 7.25 (m, 1H), 6.75–6.90 (m, 3H), 4.65 (dd, J=7.9 Hz, J=9 Hz, 1H), 4.25 (dd, J=7.9 Hz, J=9 Hz, 1H), 3.80 (s, 3H), 3.70–3.85 (m, 1H), 2.90 (dd, J=8.7, 17.5 Hz, 1H), 2.65 (dd, 1H, J=8.7, 17.5 Hz).

Preparation 11

4-(4-Fluoro-phenyl)-dihydro-furan-2-one

A method similar to PREPARATION 9, except employing 4-(4-fluoro-phenyl)-5H-furan-2-one, (1.4 g, 7.86 mmol), is used to yield the title compound, 1.38 g (97.6%), as a white crystalline solid.

$^1$H NMR (CDCl$_3$): δ 7.15–7.35 (m, 2H), 7.00–7.10 (m, 2H), 4.65 (dd, J=7.8, 9 Hz, 1H), 4.20 (dd, J=7.8, 9 Hz, 1H), 3.70–3.90 (m, 1H), 2.90 (dd, J=9, 17.5 Hz, 1H), 2.60 (dd, J=9, 17.5 Hz, 1H).

Preparation 12

4-Benzyl-dihydro-furan-2-one

A mixture of 3-benzoylpropionic acid (18 g, 101 mmol), potassium carbonate (10 g, 75 mmol), water (45 mL) and formaldehyde (36% in water, 7.8 mL, 101 mmol) is stirred at room temperature for 5 days, warmed to 30° C. and stirred for 3 additional days. To this mixture is added concentrated hydrochloric acid (10 mL) to pH 5.0, heated at 50° C. for 30 min. and cooled to room temperature. The mixture is extracted with chloroform (4×200 mL) and the combined organic extracts washed with sodium carbonate (10% in water, 3×100 mL). The solution is dried with anhydrous sodium sulfate and filtered. The filtrate is concentrated in vacuo to yield 4-benzoyl-dihydro-furan-2-one (12 g) as a colorless liquid.

To a solution of 4-benzoyl-dihydro-furan-2-one (5 g) in methanol (250 mL) in a Parr® reactor is added palladium chloride (0.25 g). The mixture is shaken under hydrogen (50 PSI) for 3 h. The mixture is filtered through a pad of Celite® (40 g) and the filtrate concentrated. The residue is chromatographed on SiO$_2$ (10% ethyl acetate/hexanes, then 30% ethyl acetate/hexanes) to yield the title compound, (2.5 g, 34% from 3-benzoylpropionic acid), as a colorless liquid.

$^1$H NMR (CDCl$_3$) δ 7.40–7.05 (m, 5H), 4.38–4.30 (m, 1H), 4.02–3.98 (m, 1H), 2.98–2.70 (m, 2H), 2.68–2.55 (m, 1H), 2.38–2.25 (m, 1H).

Preparation 13

4-Phenethyl-dihydro-furan-2-one

A mixture of 3-benzyloxymethyl-5-phenyl-pent-2-enoic acid methyl ester, (3.2 g, 13.5 mmol), 10 wt. % palladium on activated carbon (3.2 g), and acetic acid (40 mL) is placed in a Parr® Shaker under hydrogen (45 PSI) and shaken 4 h. The mixture is filtered through a pad of Celite® and concentrated in vacuo. The residue is dissolved in toluene (30 mL), treated with p-tolunesulfonic acid (0.1 g), refluxed for 2 h and concentrated in vacuo. The residue is chromatographed on $SiO_2$ (10% ethyl acetate/hexanes then 50% ethyl acetate/hexanes) to yield the title compound 1.2 g (62%) as a colorless liquid.

$^1$H NMR ($CDCl_3$) δ 7.38–7.15 (m, 5H), 4.50–4.40 (m, 1H), 4.00–3.92 (m, 1H), 2.70–2.50 (m, 4H), 2.25–2.15 (m, 1H), 1.90–1.80 (m., 2H).

Preparation 14

4-Methyl-dihydro-furan-2-one

A method similar to PREPARATION 13, except employing 4-methyl-5H-furan-2-one (3 g, 30.6 mmol), is used to yield the title compound, 3.06 g (100%) as a colorless liquid.

$^1$H NMR ($CDCl_3$) δ 4.45–4.37 (m, 1H), 3.93–3.80 (m, 1H), 2.71–2.56 (m, 2H), 2.20–1.99 (m, 1H), 1.21–1.09 (m, 3H).

Preparation 15

4-Phenyl-dihydro-furan-2-one

A solution of 4-acetoxy-3-phenyl-butyric acid methyl ester, (4.5 g, 19.2 mmol) in 1,4-dioxane (29 mL) and sulfuric acid (29 mL) is stirred at room temperature for one hour then heated at 45° C. for 18 h. Volatile solvents are evaporated and the residue is extracted with toluene. The combined organic extracts are extracted with water and brine, filtered, and concentrated to yield the title compound, 2.2 g (71%), as a colorless liquid.

$^1$H NMR ($CDCl_3$) δ 7.38–7.1 (m, 5H), 4.73–4.65 (m, 1H), 4.3–4.22 (m, 1H), 3.85–3.7 (m, 1H), 3.0–2.9 (m, 1H), 2.75–2.55 (m, 1H).

Preparation 16

(R)-5-Benzyloxymethyl-dihydro-furan-2-one

To a solution of (R)-5-hydroxymethyl-dihydro-furan-2-one (5 g, 43.06 mmol) in tetrahydrofuran (130 mL) is added sodium hydride (2.58 g, 60% oil dispersion, 64.59 mmol) and tetrabutylammonium iodide (spatula) and stirred for 30 min. To the mixture is added benzyl bromide (6.18 mL, 51.67 mmol) and refluxed for 3 h. The mixture is cooled and diluted with ethyl acetate (150 mL), washed with a saturated solution of ammonium chloride (150 mL) and brine. The mixture is dried over magnesium sulfate, filtered and concentrated in vacuo to yield the title compound, 8.87 g (100%), as a pale yellow oil.

$^1$H NMR ($CDCl_3$): δ 7.25–7.40 (m, 5H), 4.63–4.72 (m, 1H), 4.56 (s, 2H), 3.68 (dd, J=10.7, 4.0 Hz, 1H), 3.58 (dd, J=10.7, 4.0 Hz, 1H), 2.04–2.68 (m, 4H).

Preparation 17

(S)-5-Benzyloxymethyl-dihydro-furan-2-one

A method similar to PREPARATION 16, except employing (S)-5-hydroxymethyl-dihydro-furan-2-one (4.0 g, 34 mmol), is used to yield the title compound, 7.1 g (>98%), as a colorless oil.

$^1$H NMR ($CDCl_3$): δ 7.25–7.40 (m, 5H), 4.63–4.72 (m, 1H), 4.56 (s, 2H), 3.68 (dd, J=10.7, 4.0 Hz, 1H), 3.58 (dd, J=10.7, 4.0 Hz, 1H), 2.04–2.68 (m, 4H).

Preparation 18

4-(5-Methoxy-tetrahydro-furan-3-yl)-benzoic acid ethyl ester

A solution of sodium nitrite (1.67 g, 24.2 mmol) in water (14 mL) is added dropwise to an ice cold mixture of ethyl 4-aminobenzoate (4.0 g, 24.2 mmol) and tetrafluoroboric acid (7.8 mL, 48%, 59.78 mmol) and stirred for 30 min. Methanol (28.5 mL), 2,5-dihydrofuran (3.66 mL, 48.4 mmol) and palladium(II) acetate (70 mg, 0.31 mmol) are added and the mixture refluxed for 30 min. The mixture is filtered through Celite® pad and the filtrate diluted with dichloromethane (100 mL). The organic layer is separated and concentrated in vacuo. The residue is chromatographed on $SiO_2$ (10% ethyl acetate/hexanes) to yield the title compound, 2.45 g (42%), as a white solid.

$^1$H NMR ($CDCl_3$): δ 7.98 (d, J=8.3 Hz, 2H), 7.27–7.39 (m, 2H), 5.18 (m, 1H), 4.27–4.40 (m, 3H), 3.61–3.87 (m, 2H), 3.40 (s, 3H), 2.28–2.70 (m, 1H), 1.91–2.18 (m, 1H), 1.38 (t, J=7.1 Hz, 3H).

Preparation 19

4-(4-Chloro-phenyl)-2-methoxy-tetrahydro-furan

A method similar to PREPARATION 18, except employing 4-chloroaniline (10.0 g, 78.4 mmol), is used to yield the title compound, 6.7 g (40%), as a pale yellow oil.

$^1$H NMR ($CDCl_3$): δ 7.13–7.28 (m, 4H), 5.14 (m, 1H), 4.14–4.31 (m, 1H), 3.54–3.82 (m, 2H), 3.32–3.41 (m, 3H), 2.28–2.63 (m, 1H), 1.87–2.08 (m, 1H).

Preparation 20

4-(5-Oxo-tetrahydro-furan-3-yl)-benzoic acid ethyl ester

To a solution of 75% 3-chloroperbenzoic acid (2.7 g, 11.76 mmol) in dichloromethane (35 mL) is added magnesium sulfate (2.0 g, 16.6 mmol) and the mixture stirred for 30 min. Solids are removed by filtration and the filtrate treated with borontrifluoride etherate (0.5 mL, 3.92 mmol) and 4-(5-methoxy-tetrahydro-furan-3-yl)-benzoic acid ethyl ester (2.45 g, 9.8 mmol) in dichloromethane (5 mL). The mixture is stirred at room temperature 18 h, diluted with ether (200 mL) and washed with a 10% solution of sodium thiosulfite (150 mL), a saturated solution of sodium bicarbonate (150 mL) and brine. The mixture is dried over magnesium sulfate, filtered and concentrated in vacuo. The residue is chromatographed on $SiO_2$ (elute with 20% ethyl acetate/hexanes) to yield the title compound, 2.2 g (96%), as an off-white solid.

$^1$H NMR ($CDCl_3$): δ 8.04 (d, J=8.3 Hz, 2H), 7.31 (d, J=8.3 Hz, 2H), 4.69 (dd, J=9.0, 7.9 Hz, 1H), 4.26–4.42 (m, 3H), 3.82–3.95 (m, 1H), 2.96 (dd, J=17.5, 8.7 Hz, 1H), 2.68 (dd, J=17.5, 8.7 Hz, 1H), 1.39 (t, J=7.1 Hz, 3H).

Preparation 21

4-(4-Chloro-phenyl)-dihydro-furan-2-one

A method similar to PREPARATION 20, except employing 4-(4-chloro-phenyl)-2-methoxy-tetrahydro-furan (6.78 g, 32 mmol), is used to yield the title compound, 6.2 g (98%), as an off-white solid.

¹H NMR (CDCl₃): δ 7.34 (d, J=8.5 Hz, 2H), 7.17 (d, J=8.5 Hz, 2H), 4.65 (dd, J=9.1, 7.8 Hz, 1H), 4.23 (dd, J=9.1, 7.8 Hz, 1H), 3.70–3.84 (m, 1H), 2.92 (dd, J=17.5, 8.8 Hz, 1H), 2.63 (dd, J=17.5, 8.8 Hz, 1H).

Preparation 22

4-Hydroxy-3-(3-methoxy-phenyl)-butyric acid benzhydrylidene-hydrazide

Trimethylaluminum (12 mL, 2 M in hexane, 24 mmol) is added dropwise to a solution of benzophenone hydrazone (1.57 g, 8 mmol) in dichloromethane (20 mL) at room temperature and under nitrogen. After the mixture is stirred for 30 min, 4-(3-methoxy-phenyl)-dihydro-furan-2-one, (1.54 g, 8 mmol) in dichloromethane (5 mL) is added. The mixture is refluxed for 5 h cooled to room temperature and diluted with dichloromethane (30 mL). The mixture is treated with 4 N sodium hydroxide (30 mL) and stirred one hour. The organic layer is separated, washed with brine and, dried over magnesium sulfate. The mixture is filtered, concentrated in vacuo and chromatographed on SiO₂ (2% methanol/dichloromethane) to yield the title compound, 2.25 g (73%) as a pale yellow oil.

¹H NMR (CDCl₃): δ 8.35 (bs, 1H), 7.15–7.60 (m, 11H), 6.75–6.95 (m, 3H), 3.80–3.90 (m, 2H), 3.80 (s, 3H), 3.45–3.6 (m, 1H), 3.15–3.40 (m, 2H), 2.15 (m, 1H).

Preparation 23

3-(4-Fluoro-phenyl)-4-hydroxy-butyric acid benzhydrylidene-hydrazide

A method similar to PREPARATION 22, except employing 4-(4-fluoro-phenyl)-dihydro-furan-2-one (1.38 g, 7.67 mmol), is used to yield the title compound, 2.8 g (90%), as a white crystalline solid.

¹H NMR (CDCl₃): δ 8.30 (bs, 1H), 7.15–7.60 (m, 12H), 6.95–7.15 (m, 2H), 3.75–3.95 (m, 2H), 3.40–3.60 (m, 1H), 3.20–3.35 (m, 3H).

Preparation 24

5-(tert-Butyl-dimethyl-silyloxy)-4-hydroxy-pentanoic acid benzhydrylidene-hydrazide A method similar to PREPARATION 22, except employing 5-(tert-butyl-dimethyl-silyloxy)-4-hydroxy-pentanoic acid ethyl ester (6.41 g, 23.2 mmol), is used to yield the title compound, 6.2 g (63%), as a yellow foam.

¹H NMR (CDCl₃): δ 8.30 (bs, 1H), 7.20–7.60 (m, 10H), 3.65–3.85 (m, 2H), 3.50–3.60 (m, 1H), 3.00–3.10 (m, 2H), 2.80 (d, J=4 Hz, 1H), 1.70–2.00 (m, 2H), 0.90 (s, 9H), 0.10 (s, 6H).

Preparation 25

Methansulfonic acid 3-(benzhydrylidene-hydrazinocarbonyl)-2-(3-methoxy-phenyl)-propyl ester A solution of 4-hydroxy-3-(3-methoxy-phenyl)-butyric acid benzhydrylidene-hydrazide and (1.7 g, 4.38 mmol) and 4-dimethylaminopyridine (26 mg, 0.22 mmol) in pyridine (15 mL) is cooled to 0° C. treated with methanesulfonyl chloride (0.4 mL, 5.25 mmol) and stirred 18 h at room temperature. The mixture is diluted with dichloromethane (30 mL) and washed with 1 N hydrochloric acid (30 mL), a saturated solution of sodium bicarbonate and brine. The mixture is dried over magnesium sulfate, filtered, concentrated in vacuo and chromatographed on SiO₂ (2% methanol/dichloromethane) to yield the title compound, 1.64 g (80%), as yellow foam.

¹H NMR (CDCl₃): δ 8.35 (bs, 1H), 7.15–7.60 (m, 10H), 6.75–6.95 (m, 4H), 4.50 (m, 2H), 3.80 (m, 4H), 3.20–3.40 (m, 2H), 2.85 (s, 3H).

Preparation 26

Methanesulfonic acid 3-(benzhydrylidene-hydrazinocarbonyl)-2-(4-fluoro-phenyl)-propyl ester A method similar to PREPARATION 25, except employing 3-(4-fluoro-phenyl)-4-hydroxy-butyric acid benzhydrylidene-hydrazide (2.78 g, 7.4 mmol), is used to yield the title compound, 2.1 g (62%), as a yellow foam.

¹H NMR (CDCl₃): δ 8.30 (bs, 1H), 7.20–7.70 (m, 12H), 6.90–7.10 (m, 2H), 4.40–4.50 (m, 2H), 3.75 (m, 1H), 3.25–3.35 (m, 2H), 2.90 (s, 3H).

Preparation 27

Methansulfonic acid 3-(benzhydrylidene-hydrazinocarbonyl)-1-(tert-butyl-dimethyl-silyloxymethyl)-propyl ester A method similar to PREPARATION 25, except employing 5-(tert-butyl-dimethyl-silyloxy)-4-hydroxy-pentanoic acid benzhydrylidene-hydrazide (5.55 g, 13 mmol), is used to yield the title compound, 6.08 g (93%), as a yellow foam.

¹H NMR (CDCl₃): δ 8.30 (bs, 1H), 7.50–7.60 (m, 5H), 7.30–7.40 (m, 5H), 4.80–4.90 (m, 1H), 3.70–3.80 (m, 2H), 3.00–3.15 (m, 5H), 2.00–2.20 (m, 2H), 0.90 (s, 9H), 0.10 (s, 6H).

Preparation 28

1-Amino-4-(3-methoxy-phenyl)-pyrrolidin-2-one

Concentrated hydrochloric acid (0.35 mL) is added to a suspension of 1-(benzhydrylidene-amino)-4-(3-methoxy-phenyl)-pyrrolidin-2-one, (0.8 g, 2.16 mmol) in water (17 mL) and refluxed for one hour. The mixture is concentrated in vacuo and water azeotroped away using ethanol and toluene. The residue is dissolved in methanol (5 mL) and loaded on SCX resin (5 g). The resin is washed with methanol and 2 M solution of ammonia in methanol. Appropriate fractions are concentrated to yield the title compound, 402 mg (92%), as a white crystalline solid.

¹H NMR (CDCl₃): δ 7.25 (t, J=8 Hz, 1H), 6.75–6.85 (m, 3H), 4.20 (bs, 2H), 3.85 (m, 1H), 3.80 (s, 3H), 3.45–3.60 (m, 2H), 2.80 (dd, J=9, 17 Hz, 1H), 2.50 (dd, J=9, 17 Hz, 1H).

By the previous method the following compounds are prepared (unless otherwise specified):

| PREP # | Product (Chemical Name) | Physical Data |
|---|---|---|
| 29 | (S)-1-Amino-5-benzyloxymethyl-pyrrolidin-2-one | $^1$H NMR(CDCl$_3$): δ 7.26–7.37(m, 5H), 4.53(s, 2H), 3.89(bs, 2H), 3.68–3.89(m, 2H), 3.46–3.54 (m, 1H), 2.26–2.53(m, 2H), 1.90–2.15(m, 2H) |
| 30 | 4-(1-Amino-5-oxo-pyrrolidin-3-yl)-benzoic acid ethyl ester | $^1$H NMR(CDCl$_3$): δ 8.02(dd, J=6.7, 1.7Hz, 2H), 7.28(dd, J=6.7, 1.7Hz, 2H), 4.37(t, J=7.1Hz, 2H), 4.14(bs, 2H), 3.93(dd, J=8.4, 7.4Hz, 1H), 3.51–3.68(m, 2H), 2.87(dd, J=17.0, 9.0Hz, 1H), 2.53(dd, J=17.0, 7.8Hz, 1H), 1.39 (t, J=7.1Hz, 3H) |
| 31 | 1-Amino-4,4-dimethyl-pyrrolidin-2-one | $^1$H NMR(CDCl$_3$): δ 4.20(bs, 2H), 3.25(s, 2H), 1.93(s, 2H), 1.22(s, 6H) |
| 32 | (R)-1-Amino-5-benzyloxymethyl-pyrrolidin-2-one | $^1$H NMR(CDCl$_3$): δ 7.26–7.37(m, 5H), 4.53(s, 2H), 3.89(bs, 2H), 3.68–3.89(m, 2H), 3.46–3.54 (m, 1H), 2.26–2.53(m, 2H), 1.90–2.15(m, 2H) |
| 33 | 1-Amino-4-(4-chloro-phenyl)-pyrrolidin-2-one | $^1$H NMR(CDCl$_3$): δ 7.31–7.41(m, 4H), 4.03(t, J=7.7Hz, 1H), 3.72–3.88(m, 1H), 3.59(t, J=7.7Hz, 1H), 2.91(dd, J=17.4, 8.9Hz, 1H), 2.57 (dd, J=17.4, 8.9Hz, 1H) |
| 34 | 1-Amino-4-(4-fluoro-phenyl)-pyrrolidin-2-one | $^1$H NMR(CDCl$_3$): δ 7.15–7.30(m, 2H), 7.00–7.10 (m, 2H), 4.20(bs, 2H), 3.80–3.95(m, 1H), 3.45–3.6(m, 2H), 2.80(dd, J=9.3, 23.6Hz, 1H), 2.50(dd, J=8.4, 23.6Hz, 1H). |
| 35 | 1-Amino-5-hydroxymethyl-pyrrolidin-2-one | $^1$H NMR(CDCl$_3$): δ 4.20(bs, 2H), 4.00(dd, J=2.4, 12Hz, 1H), 3.65–3.80(m, 1H), 3.60(dd, J=4.4, 12Hz, 1H), 3.45(s, 1H), 2.30–2.55(m, 2H), 2.00–2.15(m, 1H), 1.75–1.90(m, 1H). |
| 36 | 1-amino-3-methylpyrrolidin-2-one hydrochloride | $^1$H NMR(CDCl$_3$) δ: 1.21(d, 1H), 1.79(m, 1H), 2.36(m, 1H), 2.60(m, 1H), 3.93(m, 1H), 7.10 (bd s, 1H) MS ES$^+$ m/e 115(M + 1). |
| 37 | 1-amino-3-benzylpyrrolidin-2-one hydrochloride | $^1$H NMR(DMSO-d$_6$) δ: 1.66(m, 1H), 1.99(m, 1H), 2.62(m, 1H), 2.74(m, 1H), 3.01(m, 1H), 3.39(m, 2H), 7.18–7.30(m, 5H). |

Preparation 38

1-Aminopyrrolidin-2-one hydrochloride

4-Chlorobutyryl chloride (57 mL, 510 mmol) is added to a solution of benzophenone hydrazone (100 g, 510 mmol) and pyridine (41 mL, 510 mmol) in anhydrous dichloromethane (520 mL) under nitrogen at a rate that maintains a gentle reflux throughout the addition. The mixture is stirred for 0.5 h and poured into water (1 L). The layers are separated and the organic layer washed with brine, dried (sodium sulfate), filtered, and concentrated in vacuo to yield 4-chloro-butyric acid benzhydrylidene-hydrazide as a residue.

MS ES$^+$ m/e 303.1 (M+1).

The residue is dissolved in tetrahydrofuran (1.5 L), cooled in an ice-water bath, treated with portions 60% sodium hydride suspended in mineral oil (20 g, 498 mmol) and stirred for 1 h. To the mixture is added saturated aqueous ammonium chloride solution (1 L) and ethyl acetate (1 L). The layers are separated and the organic solution washed with brine, dried (sodium sulfate), filtered and concentrated in vacuo to yield 1-(benzhydrylideneamino)pyrrolidin-2-one as a residue.

$^1$H NMR (CDCl$_3$): δ 7.58–7.62 (m, 2H), 7.39–7.46 (m, 4H), 7.29–7.36 (m, 4H) 3.31 (t, J=7 Hz, 2H), 2.32 (t, J=7 Hz, 2H), 1.91 (quintet, J=7 Hz, 2H); MS ES$^+$ m/e 267.1 (M+1).

The residue is suspended in water (3 L), treated with concentrated hydrochloric acid (80 mL), and heated to reflux for 1.5 h. The solution is cooled to room temperature and extracted twice with dichloromethane. The aqueous portion is concentrated in vacuo followed by azeotropic removal of water with three portions of absolute ethanol and three portions of toluene to yield the title compound, 56 g (81%), as a white solid.

$^1$H NMR (DMSO-d$_6$): δ 3.58 (t, J=7 Hz, 2H), 2.33 (t, J=7 Hz, 2H), 2.04 (quintet, J=7 Hz, 2H), TOF MS ES$^+$ exact mass calculated for C$_4$H$_8$N$_2$ (P+1): m/z=100.0637. Found: 100.0641.

Preparation 39

(L)-N-Nitrosoproline

A solution of 30 g L-proline in 100 mL water and 20 mL concentrated hydrochloric acid is cooled in ice bath and treated with 25 g sodium nitrite over 10 min. The mixture is stirred 1 h and concentrated in vacuo with minimal heat. The mixture is diluted with 1 N hydrochloric acid (100 mL) and extracted with chloroform (150 mL) and dichloromethane (2×200 mL). Organic portions are combined, dried (magnesium sulfate) and concentrated in vacuo. The residue was crystallized from dichloromethane-hexane to yield 5.58 g (L)-N-nitrsoproline.

MS ES$^+$ m/e 145 (M+1), MS ES$^-$ m/e 143 (M−1).

Preparation 40

3a H-pyrrolidino[1,2-C]1,2,3-oxadiazolin-3-one (L)-N-Nitrsoproline (1.08 g, 7 mmol) is dissolved in ether (180 mL). This solution is added to trifluoroacetic anhydride (1.5 mL) cooled in an ice bath. The mixture is stirred 6 h in ice bath, evaporated with minimum heat, and chromatographed on SiO$_2$ (0 to 100% ethyl acetate in hexane) to yield (0.75 g, 85%) of the title compound as an oil.

MS ES$^+$ m/e 127 (M+1).

Preparation 41

1-(Benzylidene-amino)-3-methyl-pyrrolidin-2-one

To an ice-cooled solution of water (48 mL) and concentrated hydrochloric acid (20.4 mL) added, with stirring, a solution of sodium nitrite (16.5 g, 240 mmol) dissolved in water (48 mL) over 20 min. The sodium nitrite solution is added to a solution of 3-methypyrrolidinone (10.11 g, 102 mmol) in water (60 mL) over 30 min while cooling the reaction mixture in an ice-salt bath. The reaction mixture is stirred 3 h in an ice-salt bath and extracted with methylene chloride (2×300 mL). The organic layers are combined, dried (magnesium sulfate), and evaporated to yield 9.22 g, (71%) of the intermediate N-nitroso compound as an oil. Product formation is confirmed by TLC (5% methanol in chloroform). The crude N-nitroso product (9.22 g, 72.0 mmol) is dissolved in glacial acetic acid (37.5 mL) and cooled in an ice bath. Zinc dust (17.5 g, 270 mmol) is added such that the reaction temperature does not exceed 21° C. The reaction mixture is diluted with water (125 mL) after 1 h, filtered, and the zinc salts washed with water (25 mL). Benzaldehyde (5.3 g, 50 mmol) is added to the filtrate and the mixture stirred for 2 h. The white precipitate is collected by filtration and washed with water to yield the title compound.

MS ES$^+$ m/e 203 (M+1).

Preparation 42

1-Chloromethyl-4-fluoronaphthalene

A solution of 1-fluoronaphthalene (5.5 g, 37.6 mmol), paraformaldehyde (2.5 g, 83 mmol), glacial acetic acid (3.5 mL), phosphoric acid (2 mL) and concentrated hydrochloric acid (5 mL) is heated at 85° C. for 15 h. The reaction mixture is poured into water and extracted three times with dichloromethane. The organic extracts are combined and washed with water and brine, dried (sodium sulfate), filtered, and evaporated to yield the title compound, 6.53 g (98%, as a yellow solid.

$^1$H NMR (CDCl$_3$): δ 8.12–8.19 (m, 2H), 7.67 (ddd, J=8, 7, 1 Hz,1H), 7.61 (ddd, J=8, 7, 1 Hz,1H), 7.46 (dd, J=8, 5 Hz, 1H), 7.09 (dd, J=10, 8 Hz, 1H), 5.02 (s, 2H).

Preparation 43

2-(Benzyloxy)-1-methoxy-4-nitrobenzene

A solution of 2-methoxy-5-nitrophenol (54.3 g, 321 mmol), benzyl bromide (26.5 mL, 223 mmol,) and cesium carbonate (73 g, 223 mmol) is stirred in N,N-dimethylformamide (250 mL) for 24 h at room temperature. The mixture is partitioned between water and ethyl acetate. The layers are separated and the organic layer washed three times with water, once with brine, dried (sodium sulfate), filtered and evaporated to give a crude solid. The crude product is recrystallized from ethyl acetate to yield the title compound, 56.4 g (68%), as a white crystalline solid.

MS ES$^+$ m/e 260 (M+1).

Preparation 44

3-Benzyloxy-4-methoxy-phenylamine

To a solution of 2-(benzyloxy)-1-methoxy-4-nitrobenzene (35.35 g, 136 mmol) in 1:1 ethyl acetate: ethanol (640 mL) at 80° C. is added tin(II) chloride hydrate in portions over 25 minutes. The mixture is heated at this temperature for 5 h. The mixture is allowed to cool to room temperature and stirred for 2 days. The mixture is poured into water (1 L) and neutralized with solid sodium bicarbonate. The mixture is extracted three times with ethyl acetate. The combined organic extracts are washed with water and brine, dried (sodium sulfate), filtered and evaporated to yield the title compound as a dark brown oil.

MS ES$^+$ m/e 230 (M+1).

Preparation 45

2-Bromo-5-fluoropyridine

This preparation is conducted in a manner similar to that described for the preparation of 2-bromopyridine from 2-aminopyridine in *Org. Syn. Coll. Vol.* 3, p. 136, except that 2-amino-5-fluoropyridine is used to yield the title compound, 47.5 g (55%), as a red oil.

$^1$H NMR (CDCl$_3$) δ 7.3 (ddd, 1H), 7.5 (dd, 1H), 8.3 (d, 1H).

PREPARATION 46

Ethyl 5-fluoropyridine-2-carboxylate

A mixture of 2-bromo-5-fluoropyridine (5.00 g, 28.4 mmol), sodium acetate (9.33 g, 114 mmol), and 1-1'bis(diphenylphosphino)ferrocene]dichloropalladium(II):CH$_2$Cl$_2$ (0.464 g, 0.57 mmol) in ethanol (80 mL) in a Parr® high pressure stainless steel reactor vessel is placed under an atmosphere of 50 psi carbon monoxide and heated at 80–100° C. for 4 h. The vessel is cooled, volatiles removed in vacuo, and the residue partitioned between ethyl acetate and water. The ethyl acetate extract is washed with water and brine, dried over sodium sulfate, filtered, and evaporated to give a dark solid. The residue is chromatographed on SiO$_2$ (10% ethyl acetate/hexanes) to yield the title compound 2.8 g (58%) as a white solid that is recrystallized from hexanes to give white crystals: mp 61–63° C.

Preparation 47

6-Methyl-pyridine-2-carboxylic acid methyl ester

To a suspension of 6-methyl-pyridine-2-carboxylic acid (10 g, 72.9 mmol) in methylene chloride (200 mL) cooled to 0° C. is added methanol (10 mL), 4-dimethylaminopyridine (11.6 g, 94.8 mmol), and EDC (18.2 g, 94.8 mmol). The mixture is stirred at room temperature for 6 h, washed with water and brine, and dried over sodium sulfate. The mixture is filtered and concentrated in vacuo. The residue is chromatographed on SiO$_2$ (50% ethyl acetate/hexanes) to yield the title compound, 9.66 g (92%), as a colorless liquid.

$^1$H NMR (CDCl$_3$) δ 7.93–7.88 (m, 1H), 7.75–7.7 (m, 1H), 7.35–7.3 (m, 1H), 4.00 (s, 3H), 2.60 (s, 3H).

Preparation 48

6-Propylpyridine-2-carboxylic acid

A solution of 6-propyl-pyridine-2-carbonitrile (9.1 g, 61.9 mmol) in 6 N hydrochloric acid is heated at reflux for 18 h. The mixture is cooled to room temperature and concentrated in vacuo. The residue is partitioned between dichloromethane and water. The aqueous portion is adjusted to pH 6 with saturated aqueous sodium bicarbonate solution and extracted five times with dichloromethane. The organic extracts are combined, dried (sodium sulfate), filtered, and concentrated in vacuo to yield the title compound, 8.32 g (81%), as a white solid.

TOF MS ES$^+$ exact mass calculated for C$_9$H$_{12}$NO$_2$ (p+1): m/z 166.0868. Found: 166.0874.

Preparation 49

6-Isopropylpyridine-2-carboxylic acid

A method similar to PREPARATION 48, except employing 6-isopropyl-pyridine-2-carbonitrile (6.35 g, 43.4 mmol), is used to yield the title compound, 6.62 g (92%), as a white solid.

TOF MS ES+ exact mass calculated for $C_9H_{12}NO_2$ (p+1): m/z=166.0868. Found: 166.0867.

Preparation 50

6-Ethylpyridine-2-carboxylic acid hydrochloride

A method similar to PREPARATION 48 is used except employing 6-ethyl-pyridine-2-carbonitrile (7.94 g, 60.1 mmol) in 6 N hydrochloric acid (150 mL), heating at reflux for 18 h, cooling to room temperature, concentrating the mixture in vacuo, and co-evaporating with toluene four times to yield the title compound, 12.5 g (72%), as a white solid.

TOF MS ES+ exact mass calculated for $C_8H_{10}NO_2$ (p+1): m/z 152.0712. Found: 152.0701.

Preparation 51

Methyl 3-fluorobenzoate

A solution of 3-fluorobenzoic acid (3.0 g, 21.4 mmol) in methanol (71 mL) at 0° C. is treated dropwise with thionyl chloride (3.1 mL, 42.8 mmol). The solution is stirred for 15 min at 0° C., 2.5 h at room temperature, and 2 h at 50° C. The reaction is concentrated in vacuo and the residue dissolved in ethyl acetate (150 mL). The organic solution is washed with saturated aqueous sodium bicarbonate (2×100 mL), brine (100 mL), and dried over sodium sulfate. The solution is decanted and concentrated to yield the title compound, 2.61 g (79%), as a clear, colorless oil.

$^1$H NMR (CDCl$_3$): δ 7.85 (m, 1H), 7.75 (m, 1H), 7.32 (m, 1H), 7.21 (m, 1H), 3.85 (s, 3H).

By the previous method the following compounds are essentially prepared (unless otherwise specified):

| PREP # | Product (Chemical Name) | Physical Data |
| --- | --- | --- |
| 52 | Methyl 2-fluorobenzoate | $^1$H NMR(CDCl$_3$): δ 7.91(m, 1H), 7.42 (m, 1H), 7.12(m, 2H), 4.32(s, 3H) |
| 53 | Methyl 4-fluorobenzoate | $^1$H NMR(CDCl$_3$): δ 8.03(m, 2H), 7.05 (m, 2H), 3.92(s, 3H) |
| 54 | Methyl quinoline-2-carboxylate | $^1$H NMR(CDCl$_3$): δ 8.28(m, 2H), 8.10 (m, 1H), 7.93(m, 1H), 7.78(m, 1H), 7.52(m, 1H), 4.03(s, 3H) |
| 55 | Methyl 4-ethylpyridine-2-carboxylate | $^1$H NMR(CDCl$_3$): δ 8.58(m, 1H), 7.95 (s, 1H), 7.32(m, 1H), 3.95(s, 3H), 2.63 (m, 2H), 1.21(m, 3H) |
| 56 | Methyl 1,8-naphthridine-2-carboxylate | $^1$H NMR(CDCl$_3$): δ 9.18(m, 1H), 8.22 (m, 3H), 7.51(m, 1H), 3.92(s, 3H) |
| 57 | Methyl 6-chloropicolinate | $^1$H NMR(CDCl$_3$): δ 8.05(m, 1H), 7.73 (m, 1H), 7.42(m, 1H), 3.95(s, 3H) |
| 58 | Methyl 4-chloropicolinate | $^1$H NMR(CDCl$_3$): (NMR shows 2 rotamers in ~4:1 ratio; data for major conformer given) δ 8.53(m, 1H), 8.06 (m, 1H), 7.41(m, 1H), 3.92(s, 3H) |
| 59 | 4-Fluoro-3-trifluoromethyl-benzoic acid methyl ester | $^1$H NMR(CDCl$_3$): δ 8.30–8.50(m, 2H), 7.25(m, 1H), 3.90(s, 3H) |
| 60 | 2-Fluoro-3-trifluoromethyl-benzoic acid methyl ester | $^1$H NMR(CDCl$_3$): δ 8.15(t, J=5Hz, 1H), 7.75(t, J=5Hz, 1H), 7.35(t, J=5Hz, 1H), 3.90(s, 3H) |
| 61 | 6-Propylyridine-2-carboxylic acid methyl ester | TOF MS ES+ exact mass calculated for $C_{10}H_{14}NO_2$ (p + 1): m/z = 180.1025 Found: 180.1030 |
| 62 | 6-Isopropylpyridine-2-carboxylic acid methoxymethylamide | $^1$H NMR(CDCl$_3$): δ 7.69(t, J=8Hz, 1H), 7.46(br s, 1H), 7.23(d, J=8Hz, 1H), 3.81(br s, 3H), 3.41(br s, 3H), 3.10(septet, J=7Hz, 1H), 1.30(d, J=7Hz, 2H) |
| 63 | 6-Ethylpyridine-2-carboxylic acid methoxymethylamide | $^1$H NMR(CDCl$_3$): δ 7.67(t, J=8Hz, 1H), 7.45(br s, 1H), 7.23(d, J=8Hz, 1H), 3.78(br s, 3H), 3.40(br s, 3H), 2.86(q, J=8Hz, 2H), 1.31(t, J=8Hz, 3H) |
| 65 | 6-methyl-pyridine-2-carboxylic acid methoxy-methyl-amide | MS ES+ m/e 181 (M + 1) |

Preparation 66

Pyrazine-2-carboxylic acid methoxy-methyl-amide

To a solution of pyrazine-2-carboxylic acid (2.0 g, 16.1 mmol) in methylene chloride (54 mL) at 0° C. is added oxalyl chloride (7.1 mL, 80.6 mmol) and N,N-dimethylformamide (0.12 mL, 1.6 mmol). The cooling bath is removed after 10 min and the reaction mixture stirred 18 h at room temperature. The reaction mixture is concentrated in vacuo. The residual oil is dissolved in methylene chloride (54 mL) and treated with N,O-dimethylhydroxylamine hydrochloride (2.36 g, 24.15 mmol) and triethylamine (11.2 mL, 80.6 mmol). The reaction mixture is stirred for 3 h at room temperature and diluted with methylene chloride. The resulting mixture is washed with water (50 mL), saturated aqueous bicarbonate (50 mL), and brine (100 mL), and concentrated in vacuo to yield the title compound, 2.35 g (88%), as a brown oil.

¹H NMR (CDCl₃): δ 8.92 (s, 1H), 8.63 (s, 1H), 8.52 (s, 1H), 3.72 (s, 3H), 3.51 (s, 3H). MS (CI, methane) m/e 168 (M+1).

By the previous method the following compounds are similarly prepared (unless otherwise specified):

| PREP # | Product (Chemical Name) | Physical Data |
|---|---|---|
| 67 | 6-Chloro-pyridine-2-carboxylic acid methoxy-methyl-amide | ¹H NMR(CDCl₃): δ 7.75(t, J=8.00Hz, 1H), 7.50–7.70(m, 1H), 7.40(d, J=8.0Hz, 1H), 3.80(s, 3H), 3.38(s, 3H) |
| 68 | 6-Methyl-pyridine-2-carboxylic acid methoxy-methyl-amide | ¹H NMR(CDCl₃): δ 7.67(m, 1H), 7.43 (m, 1H), 7.20(m, 1H), 3.75(s, 3H), 3.39(s, 3H), 2.58(s, 3H) |

Preparation 69

3-Benzyloxymethyl-5-phenyl-pent-2-enoic acid methyl ester

Methyl(triphenylphosphoranylidiene)-acetate (1 eq) and 1-benzyloxy-4-phenyl-butan-2-one (1 eq) are combined in toluene and refluxed for 18 h. Additional methyl (triphenylphosphoranylidiene)-acetate is added and refluxed for another 18 h. The solvent is removed in vacuo, and the residue suspended in hexanes and filtered. The filtrate is concentrated in vacuo to yield the title compound.

¹H NMR (CDCl₃) δ 7.4–7.1 (m, 10H), 6.08 (s, 1H), 4.5 (s, 2H), 3.9 (s, 2H), 3.65 (s, 3H), 2.9–2.55 (m, 4H)

By the previous method the following compound is similarly prepared (unless otherwise specified):

| PREP # | Product (Chemical Name) | Physical Data |
|---|---|---|
| 70 | 4-Acetoxy-3-phenyl-but-2-enoic acid methyl ester | ¹H NMR(CDCl₃) δ 7.4–7.1 (m, 5H), 6.05–5.59(m, 1H), 4.8–4.77(m, 2H), 3.6(s, 3H), 2.1(s, 3H) |

Preparation 71

(4-Fluoronaphthalen-1-yl)acetonitrile

A solution of 1-chloromethyl-4-fluoronaphthalene (5.45 g, 5.66 mmol), sodium cyanide (333 mg, 6.79 mmol), and water (2 mL) in N,N-dimethylformamide (30 mL) is stirred for 8 h, then heated at 70° C. for 15 h. The mixture is cooled to room temperature and partitioned between saturated sodium bicarbonate solution and ethyl acetate. The organic portion is washed with three portions of water, one portion of brine, dried (sodium sulfate), filtered and evaporated. The residue is chromatographed on SiO₂ (30% ethyl acetate/hexane) to yield the title compound, 4.67 g (90%), as a light brown solid. ¹H NMR (CDCl₃): δ 8.19 (d, J=8 Hz, 1H), 7.87 (d, J=8 Hz, 1H), 7.68 (ddd, J=8, 7, 1 Hz, 1H), 7.63 (ddd, J=8, 7, 1 Hz, 1H), 7.51 (dd, J=8, 5 Hz, 1H), 7.14 (dd, J=10, 8 Hz, 1H), 4.09 (s, 2H).

By the previous method the following compound is similarly prepared (unless otherwise specified):

| PREP # | Product (Chemical Name) | Physical Data |
|---|---|---|
| 72 | (4-methanesulfonyl-phenyl)-acetonitrile | MS ES⁺ m/e 196 (M + 1) |

Preparation 73

Quinolin-6-yl-acetonitrile

A solution of 6-methyl-quinoline (3.00 g, 20.6 mmol), N-bromosuccinimide (3.96 g, 22.0 mmol), and benzoyl peroxide (0.51 g, 2.10 mmol) in carbon tetrachloride (100 mL) is stirred at reflux for 2 h. The reaction is cooled to room temperature then washed with saturated aqueous sodium bisulfite (50 mL). The organic phase is passed through 30 g SiO₂ (2×) eluting with dichloromethane then diethyl ether. N,N-Dimethylformamide (83 mL) is added to the combined organic fractions and solvent removed under reduced pressure leaving only the reaction mixture in N,N-dimethylformamide. To the reaction mixture in N,N-dimethylformamide is added sodium cyanide (1.22 g, 24.9 mmol) and potassium bicarbonate (2.51 g, 24.9 mmol). The reaction mixture is allowed to stir at 50° C. for 2 h. The cooled reaction mixture is poured into pH 7 buffer (75 mL) and extracted with ethyl acetate (2×100 mL). The organic layers are combined, washed with saturated aqueous sodium chloride (100 mL), dried over solid sodium chloride, and concentrated under reduced pressure to afford an oil that is purified by normal phase flash chromatography (120 g Biotage KP-Sil 40L: 10% ethyl acetate in hexanes for 5 min, 20% ethyl acetate in hexanes for 20 min, 40% ethyl acetate in hexanes for 20 min, 60% ethyl acetate in hexanes for 20 min, then 60–100% ethyl acetate in hexanes ramp over 20 min) to provids 645 mg (18%) of the title compound. MS ES⁺ m/e 169 (M+1).

By the previous method the following compounds are essentially prepared (unless otherwise specified):

| PREP # | Product Name | Physical Data |
|---|---|---|
| 74 | 6-Propyl-pyridine-2-carbonitrile | TOF MS ES+ exact mass calculated for $C_9H_{10}N_2$ (p + 1): m/z = 146.0844 Found: 146.0832. |
| 75 | 6-Isopropylpyridine-2-carbonitrile | TOF MS ES+ exact mass calculated for $C_9H_{10}N_2$ (p + 1): m/z = 146.0844 Found: 146.0849 |
| 76 | 6-Ethylpyridine-2-carbonitrile | TOF MS ES+ exact mass calculated for $C_8H_8N_2$ (p + 1): m/z = 132.0687. Found: 132.0691. |

Preparation 77

2-Ethynyl-6-methyl-pyridine

A solution of 2-bromo-6-methylpyridine (0.5 g, 2.9 mmol) and (trimethylsilyl)acetylene (0.29 g, 2.9 mmol) in triethylamine (15 mL) is purged with argon. Copper(I) iodide (11 mg, 0.06 mmol) and $(PPh_3)_2PdCl_2$ (42 mg, 0.06 mmol) are added and the reaction is stirred under argon at room temperature for 2 h. The solvent is removed in vacuo and the residue is diluted in ethyl acetate (50 mL) and water (50 mL). The organic is separated and washed with brine. The solvent is removed to afford a dark oil. This oil is diluted in methanol (50 mL) and treated with a 1 N sodium hydroxide solution (10 mL) and stirred for 3 h at room temperature. The aqueous is neutralized with 1 N hydrochloric acid and extracted with ethyl acetate. The solvent is removed in vacuo to afford a dark oil that is purified by $SiO_2$ column chromatography to yield 1.16 g (24%) of the title compound as a light yellow oil.

MS ES+ m/e 118 (M+1).

Preparation 78

(6-Methyl-pyridin-2-yl)-propinoic acid ethyl ester

A solution of 2-ethynyl-6-methyl-pyridine (0.5 g, 4.3 mmol) in tetrahydrofuran (20 mL) is cooled to −78° C. and treated with 1.6 M N-butyllithium in hexanes (2.9 mL, 4.7 mmol) and stirred for 0.5 h. This solution is then treated with ethyl chloroformate (2.85 mL, 30 mmol) and stirred for 3 h while the solution warms to room temperature. The reaction is quenched with saturated ammonium chloride solution and extracted with ethyl acetate. The solvent is removed to yield 0.67 g (83%) of desired product as a light yellow oil.

MS ES+ m/e 190 (M+1).

Preparation 79

4-(2-(2-Pyridyl)ethynyl)quinoline

A mixture of triphenyphosphine oxide (5.56 g, 10 mmol) in 1,2-dichloroethane (30 mL) is cooled in an ice bath. Trifluoromethanesulfonic anhydride (1.57 mL, 10 mmol) is added dropwise over 15 min. To this mixture is added a solution of 1-(2-pyridyl)-2-(4-quinolyl)ethan-1-one (2.5 g, 10 mmol) in 1,2-dichloroethane (10 mL) and triethylamine (2.84 mL, 20 mmol). The ice bath is removed and the mixture heated at reflux for 16 h. The mixture is diluted with dichloromethane (100 mL) and washed with water (3×100 mL), dried (magnesium sulfate), filtered, concentrated in vacuo, and chromatographed on $SiO_2$ (0 to 100% hexane in ethyl acetate) to yield 1 g of title compound as an oil.

MS ES+ m/e 231 (M+1).

Preparation 80

4-Pyridin-2-ylethynyl-quinoline-2-carboxylic acid ethyl ester

A mixture of ethyl 4-bromoquinoline-2-carboxylate (2.80 g, 10.0 mmol, J. Org. Chem. 1947, 12, 456), triethylamine (1.7 mL, 12 mmol), bis(triphenylphosphine)-palladium(II) chloride (0.561 g, 0.80 mmol), CuI (0.114 g, 0.60 mmol), and 2-ethynylpyridine (1.11 g, 10.8 mmol) in $CH_3CN$ (80 mL) is heated at 75–80° C. for 18 h in a sealed tube. Additional triethylamine (0.85 ml, 6.1 mmol), bis(triphenylphosphine)palladium (II) chloride (0.23 g, 0.40 mmol), and CuI (0.055 g, 0.29 mmol) is added and the mixture heated for an additional 18 h. The mixture is concentrated in vacuo and partitioned between water and chloroform. The chloroform extracts are washed with brine and evaporated. The residue is chromatographed on $SiO_2$ (50% ethyl acetate/hexanes) to yield 1.52 g (50%) of a yellow solid. Precipitation from ethyl acetate gave the title compound as yellow crystals: mp 129–131° C.; MS ES+ m/e 303 (M+1).

Preparation 81

3-Benzyl-4-bromo-butyric acid

A mixture of 4-benzyl-dihydrofuran-2-one (1.0 g, 5.6 mmol), acetic acid (1.7 mL), HBr (33% in acetic acid, 2.0 mL) is heated at 80° C. for 4 h. The mixture is cooled to room temperature, poured into ice-water (20 mL), and extracted with chloroform (2×30 mL). The combined organic extracts are washed with water and brine, dried with anhydrous sodium sulfate, filtered, and concentrated in vacuo to yield 3-benzyl-4-bromo-butyric acid, 1.5 g (99%), as a colorless liquid.

$^1$H NMR (CDCl$_3$) δ 7.30–7.12 (m, 5H), 3.58–3.35 (m, 2H), 2.80–2.38 (m, 5H).

By the previous method the following compounds are prepared (unless otherwise specified):

| PREP # | Product | Physical Data |
|---|---|---|
| 82 | 3-Bromomethyl-5-phenyl-pentanoic acid | $^1$H NMR(CDCl$_3$) δ 7.40–7.20(m, 5H), 3.70–3.65 (m, 2H), 2.85–2.50(m, 4H), 2.40–2.30(m, 1H), 1.90–1.70(m, 2H) |
| 83 | 4-Bromo-3-phenyl-butyric acid | $^1$H NMR(CDCl$_3$) δ 11.3–10.5(br s, 1H), 7.4–7.2 (m, 5H), 3.7–3.42(m, 3H), 3.1–2.98(m, 1H), 2.8–2.68 (m, 1H) |
| 84 | 4-Bromo-3-methyl-butyric acid | $^1$H NMR(CDCl$_3$) δ 3.55–3.33(m, 2H), 2.69–2.55 (m, 1H), 2.41–2.21(m, 2H), 1.17–1.02(m, 3H) |

Preparation 85

3-Benzyl-4-bromo-butyric acid (1-pyridin-2-yl-2-quinolin-4-yl-ethylidene)-hydrazide A mixture of 3-benzyl-4-bromo-butyric acid (2.0 g, 7.78 mmol) and thionyl chloride (6.0 mmol) is heated to 80° C. for 2 h. The thionyl chloride is evaporated to yield 3-benzyl-4-bromo-butyryl chloride 2.1 g (99%), as a colorless liquid.

$^1$H NMR (CDCl$_3$) δ 7.25–7.11 (m, 5H), 3.55–3.48 (m, 1H), 3.40–3.35 (m, 1H), 3.20–3.10 (m, 1H), 3.00–2.90 (m, 1H), 2.80–2.70 (m, 2H), 2.60–2.57 (m, 1H).

A solution of (1-pyridin-2-yl-2-quinolin-4-yl-ethylidene)-hydrazine (2.25 g, 8.40 mmol) in anhydrous dichloromethane (100 mL) and pyridine (1.81 mL, 22.4 mmol) is cooled to −78° C., treated with a solution of 3-benzyl-4-bromo-butyryl chloride (2.1 g, 7.8 mmol) in dichloromethane (10 mL), and stirred for 2 h. The mixture is treated with methanol (3 mL), stirred for 10 min, and diluted with saturated ammonium chloride solution (30 mL). The mixture is diluted with dichloromethane (300 mL), washed with water (2×50 mL) and brine (50 mL), dried with anhydrous sodium sulfate, filtered, and concentrated in vacuo. The residue is precipitated from ether to yield the title compound, 2.3 g (60%), as a pale yellowish solid.

$^1$H NMR (CDCl$_3$) δ 8.88–8.82 (m, 1H), 8.68–8.60 (m, 2H), 8.30–8.15 (m, 2H), 7.80–7.65 (m, 2H), 7.40–7.20 (m, 7H), 7.00–6.92 (m, 1H), 4.85 (s, 2H), 3.60–3.40 (m, 2H), 3.18–3.05 (m, 1H), 2.98–2.80 (m, 3H), 2.70–2.60 (m, 1H).

By the previous method the following compounds are prepared (unless otherwise specified):

| PREP # | Product (Chemical Name) | Physical Data |
|---|---|---|
| 86 | 3-Benzyl-4-bromo-butyric acid(1-pyridin-2-yl-2-quinolin-4-yl-ethylidene)-hydrazide | $^1$H NMR(CDCl$_3$) δ 8.70–8.65(m, 1H), 8.50–8.55 (m, 1H), 8.30–8.12(m, 3H), 7.88–7.60(m, 4H), 7.30–7.10(m, 5H), 6.95–6.90(m, 1H), 4.82(s, 2H), 3.70–3.50(m, 2H), 3.20–3.05(m, 1H), 2.90–2.10 (m, 6H) |
| 87 | 4-Bromo-3-phenyl-butyric acid(1-pyridin-2-yl-2-quinolin-4-yl-ethyldiene)-hydrazide | $^1$H NMR(CDCl$_3$) δ 8.75–8.61(m, 2H), 2.27–8.0(m, 2H), 7.8–7.6(m, 2H), 7.53–7.45(m, 2H), 7.2–7.1 (m, 6H), 6.88–6.8(m, 1H), 5.25–5.2(m, 1H), 4.78–4.7 (m, 1H), 3.4–3.33(m, 1H), 3.15–3.05(m, 1H), 2.7–2.48(m, 2H), 2.4–2.3(m, 1H) |
| 88 | 4-Chloro-butyric acid [2-quinolin-4-yl-1-(3-trifluoromethyl-phenyl)-ethylidene]-hydrazide | $^1$H NMR(CDCl$_3$) δ 8.82–8.86(m, 1H), 8.12–8.18 (m, 1H), 7.81–7.60(m, 3H), 7.36–7.46(m, 2H), 7.20–7.40(m, 3H), 4.3–4.38(m, 2H), 2.60–2.86(m, 4H) |
| 89 | 4-Chloro-butyric acid [2-quinolin-4-yl-1-(4-trifluoromethyl-phenyl)-ethylidene]-hydrazide | $^1$H NMR(CDCl$_3$) δ 9.10–9.00(s, 1H), 9.80–9.70 (m, 1H), 8.22–8.00(m, 2H), 7.85–7.55(m, 6H), 6.90–6.80(m, 1H), 4.50(s, 2H), 3.60–3.50(m, 2H), 2.02–1.90(m, 2H) |
| 90 | 5-Chloro-pentanoic acid [2-quinolin-4-yl-1-(3-trifluoromethyl-phenyl)-ethylidene]-hydrazide | $^1$H NMR(CDCl$_3$) δ 8.75–8.70(s, 1H), 8.30–8.05 (m, 2H), 7.98–7.60(m, 6H), 6.95–6.90(m, 1H), 4.50(s, 2H), 3.60–3.50(m, 2H), 2.85–2.75(m, 2H), 2.00–1.70(m, 4H) |
| 91 | 5-Chloro-pentanoic acid [2-quinolin-4-yl-1-(4-trifluoromethyl-phenyl)-ethylidene]-hydrazide | $^1$H NMR(CDCl$_3$) δ 8.75–8.70(s, 1H), 8.20–7.95 (m, 3H), 7.80–7.40(m, 4H), 7.15–7.05(m, 1H), 6.90–6.80(m, 1H), 4.50(s, 2H), 3.60–3.50(m, 2H), 2.85–2.75(m, 2H), 2.00–1.70(m, 4H) |
| 92 | 5-Chloro-pentanoic acid[1-(4-chloro-phenyl)-2-quinolin-4-yl-ethylidene]-hydrazide | $^1$H NMR(CDCl$_3$) δ 8.9–8.7(m, 1H), 8.25–8.0(m, 3H), 7.85–7.5(m, 4H), 7.34–7.15(m, 1H), 6.97–6.87 (m, 1H), 4.4(s, 2H), 3.63–3.4(m, 2H), 2.8–2.7(m, 2H), 3.37–2.3(m, 2H), 1.9–1.5(m, 2H) |
| 93 | 5-Chloro-pentanoic acid[1-(3-chloro-phenyl)-2-quinolin-4-yl-ethylidene]-hydrazide | $^1$H NMR(CDCl$_3$) δ 8.9–8.7(m, 1H), 8.25–8.1(m, 1H), 8.05–7.95(m, 2H), 7.82–7.65(m, 2H), 7.5–7.45 (m, 1H), 7.35–7.2(m, 2H), 6.9–6.85(m, 1H), 4.45 (s, 2H), 3.7(s, 1H), 3.6–3.4(m, 2H), 2.8–2.7(m, 2H), 2.37–2.3(m, 2H), 1.9–1.5(m, 2H) |
| 94 | 4-Chloro-butyric acid [1-(3-fluoro-5-trifluoromethyl-phenyl)-2- | $^1$H NMR(CDCl$_3$) δ 9.15–9.05(s, 1H), 8.80–8.70 (m, 1H), 8.26–8.20(m, 1H), 8.10–8.05(m, 1H), 7.85–7.60(m, 4H), 7.40–7.30(m, 1H), 6.90–6.85 |

| PREP # | Product (Chemical Name) | Physical Data |
|---|---|---|
| | quinolin-4-yl-ethylidene]-hydrazide | (m, 1H), 4.50(s, 2H), 3.60–3.50(m, 2H), 2.02–1.90 (m, 2H) |
| 95 | 5-Chloro-pentanoic acid [2-quinolin-4-yl-1-(3-fluoro-5-trifluoromethyl-phenyl)-ethylidene]-hydrazide | $^1$H NMR(CDCl$_3$) δ 8.75–8.70(s, 1H), 8.30–8.05 (m, 2H), 7.98–7.60(m, 6H), 6.95–6.90(m, 1H), 4.50(s, 2H), 3.60–3.50(m, 2H), 2.85–2.75(m, 2H), 2.00–1.70(m, 4H) |
| 96 | 5-Chloro-pentanoic acid (1-phenyl-2-quinolin-4-yl-ethylidene)-hydrazide | $^1$H NMR(CDCl$_3$) δ 8.80–8.70(m, 1H), 8.25–8.05 (m, 2H), 7.95–7.65(m, 4H), 7.45–7.40(m, 3H), 7.00–6.90(m, 1H), 4.50(s, 2H), 3.60–3.50(m, 2H), 2.0–1.80(m, 4H) |
| 97 | 4-Chloro-butyric acid(1-phenyl-2-quinolin-4-yl-ethylidene)-hydrazide | $^1$H NMR(CDCl$_3$) δ 8.80–8.75(m, 1H), 8.15–7.95 (m, 2H), 7.80–7.50(m, 4H), 7.40–7.10(m, 4H), 4.60(s, 2H), 3.35–3.25(m, 2H), 2.30–2.20(m, 2H), 1.70–1.55(m, 2H) |
| 98 | 5-Chloro-pentanoic acid (2-[1,10]phenanthrolin-4-yl-1-pyridin-2-yl-ethylidene)-hydrazide | $^1$H NMR(CDCl$_3$) δ 9.2–9.12(m, 1H), 9.0–8.9(m, 2H), 8.45–8.38(m, 1H), 8.3–8.1(m, 3H), 7.9–7.6 (m, 3H), 7.3–7.2(m, 1H), 7.1–7.03(m, 1H), 3.6–3.45 (m, 2H), 2.5–2.43(m, 2H), 1.9–1.63(m, 4H) |
| 99 | 4-Chloro-butyric acid [2-(2-chloro-quinolin-4-yl)-1-pyridin-2-yl-ethylidene]-hydrazide | $^1$H NMR(CDCl$_3$) δ 8.90–8.80(s, 1H), 8.55–8.50 (m, 1H), 8.30–8.10(m, 3H), 7.90–7.65(m, 3H), 7.40–7.30(m, 1H), 6.85(m, 1H), 4.70(s, 2H), 3.70–3.60 (m, 2H), 3.10–3.00(m, 2H), 2.15–2.00(m, 2H) |
| 100 | 4-Chloro-butyric acid [2-(6,8-dimethoxy-quinolin-4-yl)-1-(6-methyl-pyridin-2-yl)-ethylidene]-hydrazide | $^1$H NMR(CDCl$_3$ ) δ 8.70–8.65(m, 1H), 7.97–7.9(m, 1H), 7.75–7.60(m, 2H), 7.30–7.23(m, 1H), 7.20–7.13 (m, 1H), 6.77–6.67(m, 1H), 4.70(s, 2H), 3.82 (s, 3H), 3.7(s, 3H), 3.65–3.55(m, 2H), 2.6–2.45(m, 5H), 2.18–1.98(m, 2H) |
| 101 | 4-Chloro-butyric acid [1-(6-bromo-pyridin-2-yl)-2-quinolin-4-yl-ethylidene]-hydrazide | $^1$H NMR(CDCl$_3$) δ 9.20–9.0(br, 1H), 8.80–8.75 (m, 1H), 8.22–8.10(m, 2H), 7.80–7.55(m, 3H), 7.45–7.40(m, 1H), 7.31–7.26(m, 1H), 6.95–6.90 (m, 1H), 4.75(s, 2H), 3.65–3.45(m, 2H), 3.00–2.90 (m, 2H), 2.10–2.00(m, 2H) |
| 102 | 4-Chloro-butyric acid [2-(6,8-dimethoxy-quinolin-4-yl)-1-pyridin-2-yl-ethylidene]-hydrazide | $^1$H NMR(CDCl$_3$) δ 8.80(s, 1H), 8.65–8.50(m, 2H), 7.8–7.7(m, 1H), 7.35–7.2(m, 2H), 7.0–6.93 (m, 1H), 6.8–6.7(m, 1H), 4.70(s, 2H), 3.82(s, 3H), 3.7(s, 3H), 3.65–3.55(m, 2H), 2.55–2.45(m, 2H), 2.18–1.98(m, 2H) |
| 103 | 5-Chloro-pentanoic acid [1-(6-methyl-pyridin-2-yl)-2-quinolin-4-yl-ethylidene]-hydrazide | $^1$H NMR(CDCl$_3$) δ 8.95–8.88(m, 1H), 8.60–8.55 (m, 1H), 8.38–8.30(m, 1H), 8.2–8.12(m, 1H), 8.0–7.90 (m, 1H), 7.87–7.80(m, 2H), 7.36–7.30(m, 1H), 7.17–7.08(m, 1H), 5.0(s, 2H), 3.80–3.72(m, 2H), 3.07–2.99(m, 2H), 2.63(s, 3H), 2.10–1.99(m, 4H) |
| 104 | 4-Chloro-butyric acid [1-(3-fluoro-phenyl)-2-quinolin-4-yl-ethylidene]-hydrazide | MS APCI$^+$ m/e 384 (M + 1) |
| 105 | 4-Chloro-butyric acid [1-(2-fluoro-phenyl)-2-quinolin-4-yl-ethylidene]-hydrazide | MS APCI$^+$ m/e 384 (M + 1) |
| 106 | 4-Chloro-butyric acid [1-(4-fluoro-phenyl)-2-quinolin-4-yl-ethylidene]-hydrazide | MS APCI$^+$ m/e 384 (M + 1) |
| 107 | 4-Chloro-butyric acid [2-quinolin-4-yl-1-(3-trifluoromethoxy-phenyl)-ethylidene]-hydrazide | MS APCI$^+$ m/e 450 (M + 1) |
| 108 | 5-Chloro-pentanoic acid [1-(4-fluoro-phenyl)-2-quinolin-4-yl-ethylidene]-hydrazide | MS APCI$^+$ m/e 398 (M + 1) |
| 109 | 5-Chloro-pentanoic acid [2-quinolin-4-yl-1-(3-trifluoromethoxy-phenyl)-ethylidene]-hydrazide | MS APCI$^+$ m/e 464 (M + 1) |
| 110 | 5-Chloro-pentanoic acid [1-(2-fluoro-phenyl)-2-quinolin-4-yl-ethylidene]-hydrazide | MS APCI$^+$ m/e 398 (M + 1) |
| 111 | 5-Chloro-pentanoic acid (2-quinolin-4-yl-1-quinolin-2-yl-ethylidene)-hydrazide | MS APCI$^+$ m/e 431 (M + 1) |

-continued

| PREP # | Product (Chemical Name) | Physical Data |
|---|---|---|
| 112 | 5-Chloro-pentanoic acid [1-(4-ethyl-pyridin-2-yl)-2-quinolin-4-yl-ethylidene]-hydrazide | MS APCI$^+$ m/e 409 (M + 1) |
| 113 | 4-Chloro-butyric acid(2-quinolin-4-yl-1-quinolin-2-yl-ethylidene)-hydrazide | MS APCI$^+$ m/e 417 (M + 1) |
| 114 | 5-Chloro-pentanoic acid (1-[1,8]naphthyridin-2-yl-2-quinolin-4-yl-ethylidene)-hydrazide | MS APCI$^+$ m/e 432 (M + 1) |
| 115 | 4-(4-Pyridin-2-yl-3-quinolin-4-yl-1H-pyrrol-2-yl)-butyric acid methyl ester | MS APCI$^+$ m/e 373 (M + 1) |
| 116 | 4-Chloro-butyric acid [1-(6-chloro-pyridin-2-yl)-2-quinolin-4-yl-ethylidene]-hydrazide | MS APCI$^+$ m/e 402 (M + 1) |
| 117 | 4-Chloro-butyric acid [1-(4-chloro-pyridin-2-yl)-2-quinolin-4-yl-ethylidene]-hydrazide | MS APCI$^+$ m/e 401 (M + 1) |
| 118 | 4-Chloro-butyric acid benzhydrylidene-hydrazide | $^1$H NMR(CDCl$_3$): δ 2.20(q, J=9Hz, 2H), 3.00(t, J=9Hz, 2H), 3.70(t, J=9Hz, 2H), 7.20(m, 2H), 7.40(m, 2H), 7.50(m, 6H), 8.50(bs, 1H) |
| 119 | 4-Chloro-butyric acid [1-(2-fluoro-3-trifluoromethyl-phenyl)-2-quinolin-4-yl-ethylidene]-hydrazide | $^1$H NMR(CDCl$_3$): δ 8.80(m, 1H), 8.00–8.20(m, 1H), 7.50–7.82(m, 3H), 6.80–7.40(m, 5H), 4.60(s, 2H), 3.45–3.75(m, 2H), 2.80(m, 2H), 2.00–2.20 (m, 2H) |
| 120 | N-[1-Aza-2-(6-methyl-pyridyl-2-yl)-3-(4-quinolyl)prop-1-enyl]-4-chlorobutanamide | MS ES$^+$ m/e 381 (M + 1), and MS ES$^-$ m/e 379 (M − 1) |
| 121 | 1-[2-(6,7-Dimethoxy-quinolin-4-yl)-1-(6-methyl-pyridin-2-yl)-ethylideneamino]-pyrrolidin-2-one | MS ES$^+$ m/e 405 (M + 1) |
| 122 | (1-Pyrazin-2-yl-2-quinolin-4-yl-ethylidene)-hydrazine | MS APCI$^+$ m/e 264 (M + 1) |
| 123 | 4-Bromo-butyric acid(1-pyrazin-2-yl-2-quinolin-4-yl-ethylidene)-hydrazide | MS APCI$^+$ m/e 412/414 (M + 1) |
| 124 | 4-Bromo-3-methyl-butyric acid(1-pyridin-2-yl-2-quinolin-4-yl-ethylidene)-hydrazide | $^1$H NMR(CDCl$_3$) δ 9.21(s, 1H), 8.73–8.70(m, 1H), 8.52–8.47(m, 1H), 8.27–8.11(m, 3H), 7.80–7.62 (m, 3H), 7.31–7.27(m, 1H), 6.92–6.87(m, 1H), 4.82(s, 2H), 3.41–3.32(m, 2H), 2.98–2.85(m, 1H), 2.67–2.52(m, 1H), 2.28–2.12(m, 1H), 1.04–0.98 (m, 3H) |
| 125 | (R)-5-Benzyloxy-4-hydroxy-pentanoic acid benzhydrylidene-hydrazide | $^1$H NMR(CDCl$_3$): δ 8.40(s, 1H), 7.45–7.55(m, 5H), 7.20–7.40(m, 10H), 4.55(s, 2H), 3.90–4.00 (m, 1H), 3.55(dd, J=9.5, 3.9Hz, 1H), 3.45(dd, J=9.5, 7.2Hz, 1H), 3.00–3.10(m, 2H), 2.95(d, J=3.7Hz, 1H), 1.90–2.05(m, 2H) |
| 126 | 4-[2-(Benzhydrylidene-hydrazinocarbonyl)-1-hydroxymethyl-ethyl]-benzoic acid ethyl ester | $^1$H NMR(CDCl$_3$): δ 8.36(bs, 1H), 8.02(d, J=8.3Hz, 2H), 7.18–7.54(m, 12H), 4.36(q, J=7.1Hz, 2H), 3.85–3.95(m, 2H), 3.55–3.65(m, 1H), 3.24–3.38 (m, 2H), 2.18(m, 1H), 1.38(t, J=7.1Hz, 3H) |
| 127 | 4-Hydroxy-3,3-dimethyl-butyric acid benzhydrylidene-hydrazide | $^1$H NMR(CDCl$_3$): δ 8.44(bs, 1H), 7.22–7.58(m, 10H), 3.42(s, 1H), 2.89(s, 2H), 1.56(s, 2H), 1.09 (s, 6H). |
| 128 | (S)-5-Benzyloxy-4-hydroxy-pentanoic acid benzhydrylidene-hydrazide | $^1$H NMR(CDCl$_3$): δ 8.40(s, 1H), 7.45–7.55(m, 5H), 7.20–7.40(m, 10H), 4.55(s, 2H), 3.90–4.00 (m, 1H), 3.55(dd, J=9.5, 3.9Hz, 1H), 3.45(dd, J=9.5, 7.2Hz, 1H), 3.00–3.10(m, 2H), 2.95(d, J=3.7Hz, 1H), 1.90–2.05(m, 2H) |
| 129 | 3-(4-Chloro-phenyl)-4-hydroxy-butyric acid benzhydrylidene-hydrazide | $^1$H NMR(CDCl$_3$): δ 8.35(bs, 1H), 7.17–7.55(m, 14H), 3.86(m, 2H), 3.48(m, 1H), 3.18–3.38(m, 2H) |

Preparation 130

7-Methyl-4-methyl-quinoline

A solution of 3-methyl-phenylamine (1 eq), in 1,4-dioxane is stirred and cooled to approximately 12° C. Sulfuric acid (2 eq.) is slowly added and heated at reflux. Methylvinyl ketone (1.5 eq) is added dropwise into the refluxing solution. The solution is heated for 1 h after addition is complete. The reaction solution is evaporated to dryness and dissolved in methylene chloride. The solution is adjusted to pH 8 with 1 M sodium carbonate and extracted with three times with water. The residue is chromatographed on $SiO_2$ (70/30 hexane/ethylacetate) to yield the title compound.

MS $ES^+$ m/e=158.2 (M+1).

By the previous method of the following compounds are prepared (unless otherwise specified):

| PREP # | Product Name | Physical Data |
|---|---|---|
| 131 | 7-Ethoxy-4-methyl-quinoline | TOF MS $ES^+$ exact mass calculated for $C_{12}H_{14}NO$ (p + 1): m/z = 188.1075 Found: 188.1059 |
| 132 | 6,7-Dimethoxy-4-methyl-quinoline | TOF MS $ES^+$ exact mass calculated for $C_{12}H_{14}NO_2$ (p + 1): m/z = 204.1025 Found: 204.1010 |
| 133 | 6-Ethoxy-4-methyl-quinoline | TOF MS $ES^+$ exact mass calculated for $C_{12}H_{14}NO$ (p + 1): m/z = 188.1075. Found: 188.1079 |
| 134 | 6,7-Dichloro-4-methyl-quinoline | MS $ES^+$ m/e 212 (M + 1) |
| 135 | 6,7-Difluoro-4-methyl-quinoline | MS $ES^+$ m/e 178 (M + 1) |
| 136 | 4-Methyl-quinolin-6-ylamine | MS $ES^+$ m/e 159 (M + 1) |
| 137 | 7-Methoxy-4-methyl-quinoline | MS $ES^+$ m/e 174 (M + 1) |
| 138 | 7-Fluoro-4-methyl-quinoline | MS $ES^+$ m/e 162 (M + 1) |
| 139 | 8-Methoxy-4-methyl-quinoline | MS $ES^+$ m/e 174 (M + 1) |
| 140 | 8-Ethoxy-4-methyl-quinoline | MS $ES^+$ m/e 188 (M + 1) |
| 141 | 4,7-Dimethyl-quinoline | MS $ES^+$ m/e 158 (M + 1) |
| 142 | 6-Bromo-4-methyl-quinoline | $^1$H NMR(CDCl$_3$) δ 8.78–8.75(m, 1H), 8.16–8.11 (m, 1H), 7.99–7.91(m, 1H), 7.81–7.72(m, 1H), 7.28–7.19(m, 1H), 2.67(s, 3H) |
| 143 | 8-Fluoro-4-methyl-quinoline | $^1$H NMR(CDCl$_3$) δ 8.80–8.75(m, 1H), 7.85–7.80 (m, 3H), 7.60–7.30(m, 3H), 3.70(s, 3H) |
| 144 | 7-Bromo-4-methyl-quinoline | $^1$H NMR(CDCl$_3$) δ 8.80–8.75(m, 1H), 8.30(s, 1H), 7.90–7.85(m, 1H), 7.70–7.65(m, 1H), 7.25–7.20 (m, 1H), 2.65(s, 3H) |
| 145 | 6-Trifluoromethoxy-4-methyl-quinoline | $^1$H NMR(CDCl$_3$) δ 8.81(m, 1H), 8.16(m, 1H), 7.80(br s, 1H), 7.58(m, 1H), 7.30(m, 1H), 2.70 (s, 3H) |
| 146 | 6-Trifluoromethyl-4-methyl-quinoline | $^1$H NMR(CDCl$_3$) δ 8.80–8.75(m, 1H), 8.15–8.10 (m, 1H), 7.80(s, 1H), 7.60–7.55(m, 1H), 7.30–7.27 (m, 1H), 2.70(s, 3H) |
| 147 | 7-Methoxy-4-methyl-quinoline | $^1$H NMR(CDCl$_3$) δ 8.80–8.75(m, 1H), 7.90–7.85 (m, 1H), 7.40(s, 1H), 7.22–7.18(m, 1H), 7.10–7.08 (m, 1H), 4.00(s, 3H), 2.70(s, 3H) |

Preparation 148

1-(2-Pyridyl)-2-(4-quinolyl)ethan-1-one

In a 3-neck 3-liter round bottom flask equipped with two addition funnels is dissolved lepidine (10.0 mL, 75.63 mmol) in tetrahydrofuran (200 mL). One addition funnel is charged with ethyl picolinate (20.43 mL, 151.26 mmol) and the other with 0.5 M potassium bis(trimethylsilyl)amide (166.4 mL, 83.19 mmol) in toluene. The solution is cooled to −78° C. and the base added to the reaction mixture dropwise over 40 min. The reaction mixture is stirred an additional 1.5 h and ethyl picolinate is added rapidly. The ice bath is removed and the reaction mixture stirred at ambient temperature for 3 h. The reaction is quenched with water (20 mL) and after 5 min formic acid added until the pH is slightly less than 7. The mixture is concentrated in vacuo and partitioned between ethyl acetate (300 mL) and brine-sodium bicarbonate (300 mL) mixture. The organic layer is washed with brine and sodium bicarbonate, dried over sodium sulfate, and concentrated. The product is chromatographed on $SiO_2$ (27–30% acetone in hexane) to yield 15.31 g (82%) of a yellow-brown solid.

MS $ES^+$ m/e 249 (M+1).

By the previous method the following compounds are prepared (unless otherwise specified):

| PREP # | Product (Chemical Name) | Physical Data |
|---|---|---|
| 149 | 1-pyridin-2-yl-2-quinolin-4-yl-ethanone | |
| 150 | 2-Quinolin-4-yl-1-(3-trifluoromethyl-phenyl)-ethanone | $^1$H NMR(CDCl$_3$) δ 8.8(m, 1H), 8.3(s, 1H), 8.12–8.28(m, 2H), 7.80–7.90(m, 2H), 7.59–7.78(m, 3H), 7.21–7.29(m, 1H), 4.80(s, 2H) |
| 152 | 2-Quinolin-4-yl-1-(4-chloro-phenyl)-ethanone | $^1$H NMR (CDCl$_3$) δ 8.9–8.85(d, 1H), 8.21–8.15(d, 1H), 8.0–7.9(d, 2H), 7.85–7.78 (d, 1H), 7.73–7.69(t, 1H), 7.55–7.5 (t, 1H), 7.46–7.4(d, 2H), 7.25–7.19(d, 1H), 4.7(s, 2H) |
| 153 | 1-(3-Chloro-phenyl)-2-quinolin-4-yl-ethanone | $^1$H NMR (CDCl$_3$) δ 8.9–8.85(m, 1H), 8.21–8.15(m, 1H), 8.0–7.9(m, 2H), 7.85–7.78 (m, 1H), 7.73–7.69(m, 1H), 7.55–7.5 (m, 1H), 7.46–7.4(m, 2H), 7.25–7.19(m, 1H), 4.7(s, 2H) |
| 154 | 1-(3-Fluoro-5-trifluoromethyl-phenyl)-2-quinolin-4-yl-ethanone | $^1$H NMR (CDCl$_3$) δ 8.90–8.88(m, 1H), 8.22–8.12(m, 2H), 7.98–7.75(m, 3H), 7.60–7.52(m, 2H), 7.30–7.25(m, 1H), 4.78(s, 2 H) |
| 155 | 1-Phenyl-2-quinolin-4-yl-ethanone | $^1$H NMR (CDCl$_3$) δ 8.80–8.75(m, 1 H), 8.20–8.12(m, 3H), 7.80–7.52(m, 3H), 7.35–7.05(m, 4H), 4.78(s, 2H) |
| 156 | 2-(2-Chloro-quinolin-4-yl)-1-pyridin-2-yl-ethanone | $^1$H NMR (CDCl$_3$) δ 8.90–8.88(m, 1H), 8.10–7.80(m, 3H), 7.85–7.75(m, 1H), 7.60–7.52(m, 2H), 7.40(s, 1H), 5.00(s, 2H) |
| 157 | 2-(6,8-Dimethoxy-quinolin-4-yl)-1-(6-methyl-pyridin-2-yl)-ethanone | $^1$H NMR (CDCl$_3$) δ 8.70–8.65(m, 1H), 7.87–7.8(m, 1H), 7.75–7.67(m, 1H), 7.40–7.3(m, 2H), 6.9–6.85(m, 1H), 6.70–6.65 (m, 1H), 4.9(s, 2H), 4.05(s, 3H), 3.85(s, 3H), 2.70(s, 3H) |
| 158 | 1-(6-Bromo-pyridin-2-yl)-2-quinolin-4-yl-ethanone | $^1$H NMR (CDCl$_3$) δ 8.90–8.85(m, 1H), 8.20–8.00(m, 3 H), 7.80–7.40(m, 5 H), 4.98(s, 2 H) |
| 159 | 2-(6,8-Dimethoxy-quinolin-4-yl)-1-pyridin-2-yl-ethanone | $^1$H NMR (CDCl$_3$) δ 8.80–8.68(m, 2H), 8.1–8.01(m, 1H), 7.9–7.8(m, 1H), 7.55–7.48 (m, 1H), 7.42–7.38(m, 1H), 6.9–6.85 (m, 1H), 6.70–6.65(m, 1H), 4.9(s, 2H), 4.05(s, 3H), 3.85(s, 3H) |
| 160 | 1-(6-Methyl-pyridin-2-yl)-2-quinolin-4-yl-ethanone | $^1$H NMR (CDCl$_3$) δ 8.85–8.8(m, 1H), 8.1–8.0(m, 2H), 7.85–7.87(m, 1H), 7.73–7.6 (m, 2H), 7.50–7.43(m, 1H), 7.4–7.3 (m, 2H), 5.00(s, 2H), 2.70(s, 3H) |
| 161 | 2-[1,10]Phenanthrolin-4-yl-1-pyridin-2-yl-ethanone | $^1$H NMR (CDCl$_3$) δ 9.20–9.10(m, 2H), 8.80–8.75(m, 1H), 8.25–8.20(m, 1H), 8.05–7.95(m, 2H), 7.90–7.75(m, 2H), 7.65–7.50(m, 3H), 5.20(s, 2H) |
| 162 | 2-Quinolin-4-yl-1-thiophen-2-yl-ethanone | TOF MS $ES^+$ exact mass calculated for $C_{15}H_{12}NOS$ (p + 1): m/z = 254.0640 Found: 254.0657 |
| 163 | 1-Furan-2-yl-2-quinolin-4-yl-ethanone | TOF MS $ES^+$ exact mass calculated for $C_{15}H_{12}NO_2$ (p + 1): m/z = 238.0868 Found: 238.0888 |
| 164 | 1-(6-Propylpyridin-2-yl)-2-quinolin-4-yl-ethanone | TOF MS $ES^+$ exact mass calculated for $C_{19}H_{19}N_2O$ (p + 1): |

-continued

| PREP # | Product (Chemical Name) | Physical Data |
|---|---|---|
| 165 | 1-(6-Isopropylpyridin-2-yl)-2-quinolin-4-yl-ethanone | m/z = 291.1497<br>Found: 291.1504<br>TOF MS ES+ exact mass calculated for $C_{19}H_{19}N_2O$ (p + 1):<br>m/z = 291.1497<br>Found: 291.1496 |
| 166 | 1-(6-Ethylpyridin-2-yl)-2-quinolin-4-yl-ethanone | TOF MS ES+ exact mass calculated for $C_{18}H_{17}N_2O$ (p + 1):<br>m/z = 277.1341<br>Found: 277.1339;<br>Anal. Calcd for $C_{18}H_{16}N_2O$: C, 78.24; H, 5.84; N, 10.14. Found: C, 77.67; H, 5.92; N, 10.16 |
| 167 | 1-(3-Fluoro-phenyl)-2-quinolin-4-yl-ethanone | $^1$H NMR (CDCl$_3$): δ 8.87(m, 1H), 8.14 (m, 1H), 7.83(m, 2H), 7.70(m, 2H), 7.55 (m, 2H), 7.42(m, 2H), 4.72(s, 2H) |
| 168 | 1-(4-Fluoro-phenyl)-2-quinolin-4-yl-ethanone | MS CI+ 266 (M + 1) |
| 169 | 2-(Quinolin-4-yl)-1-(3-trifluoro methoxy-phenyl)-ethanone | MS APCI+ m/e 332 (M + 1) |
| 170 | 1-Quinolin-2-yl-2-quinolin-4-yl-ethanone | MS APCI+ m/e 299 (M + 1) |
| 171 | 1-(4-Ethyl-pyridin-2-yl)-2-quinolin-4-yl-ethanone | MS APCI+ m/e 277 (M + 1) |
| 172 | 1-[1,8] Naphthyridin-2-yl-2-quinolin-4-yl-ethanone | MS APCI+ m/e 300 (M + 1) |
| 173 | 1-(6-Chloro-pyridin-2-yl)-2-quinolin-4-yl-ethanone | $^1$H NMR (CDCl$_3$): δ 8.81(m, 1H), 8.08 (m, 1H), 7.96(m, 2H), 7.76(m, 1H), 7.63 (m, 1H), 7.41(m, 2H), 7.34(m, 1H), 4.94 (s, 2H) |
| 174 | 1-(4-Chloro-pyridin-2-yl)-2-quinolin-4-yl-ethanone | MS APCI+ m/e 283 (M + 1) |
| 175 | 1-(2-Fluoro-3-trifluoromethyl-phenyl)-2-quinolin-4-yl-ethanone | $^1$H NMR (CDCl$_3$): δ 8.20(d, J=4Hz, 1H), 8.15(d, J=7Hz, 1H), 7.95–8.10(m, 1H), 7.60–7.80(m, 3H), 7.50(m, 1H), 7.15–7.35(m, 2H), 4.80(s, 2H) |
| 176 | 1-(4-Fluoro-3-trifluoromethyl-phenyl)-2-quinolin-4-yl-ethanone | $^1$H NMR (CDCl$_3$): δ 8.85(d, J=4Hz, 1H), 8.35(d, J=6Hz, 1H), 8.25(m, 1H), 8.15(d, J=6Hz, 1H), 7.80(d, J=8Hz, 1H), 7.70(t, J=8Hz, 1H), 7.55(t, J=8Hz, 1H), 7.35(t, J=8Hz, 1H), 7.25(s, 1H), 4.70(s, 2H) |
| 177 | Dimethyl 6-[2-(4-quinolyl)acetyl]pyridyl-2-carboxylate | MS ES− m/e 305 (M − 1) |
| 178 | 2-Quinolin-4-yl-1-(3-trifluoromethylphenyl)-ethanone | MS ES+ m/e 315.9 (M + 1) |
| 179 | 1-(5-Chloropyridin-2-yl)-2-(quinolin-4-yl)ethanone | mp 123–125° C. |
| 180 | 1-(5-Fluoropyridin-2-yl)-2-(quinolin-4-yl)ethanone | MS ES+ m/e 267 (M + 1) |
| 181 | 1-(Pyridin-2-yl)-2-(7-chloroquinolin-4-yl)ethanone | mp 87–91° C.<br>MS ES+ m/e 283 (M + 1), 285 (M + 3) |
| 182 | 1-(6-Methylpyridin-2-yl)-2-(7-chloroquinolin-4-yl)ethanone | mp 88–90° C.<br>EA Calcd. for $C_{17}H_{13}ClN_2O$: C, 68.81; H, 4.41; O, 9.44; Found: C, 48.48; H, 4.38; N, 9.63 |
| 183 | 1-(6-Methylpyridin-2-yl)-2-(7-ethoxyquinolin-4-yl)ethanone | MS ES+ m/e 308 (M + 2) |
| 184 | 2-(4-Fluoronaphthalen-1-yl)-1-(6-methyl-pyridin-2-yl)-ethanone | MS ES+ m/e 280 (M + 1) |
| 185 | 2-Quinolin-4-yl-1-(4-trifluoro methyl-phenyl)-ethanone | $^1$H NMR (CDCl$_3$) δ 8.80(m, 1H), 8.20–8.12 (m, 3H), 7.90–7.52(m, 5H), 7.25–7.30 (m, 1H), 4.78(s, 2H) |
| 186 | 1-(2-Fluoro-phenyl)-2-quinolin-4-yl-ethanone | MS CI+ 266 (M + 1) |
| 187 | Methyl 6-(2-quinolin-4-yl-acetyl)-pyridine-2-carboxylic acid methyl ester | MS ES− m/e 305 (M − 1) |
| 188 | 2-(6-Bromo-quinolin-4-yl)-1-pyridin-2-yl-ethanone | MS ES+ m/e 326.9 & 328.9 (M + 1). |
| 189 | 1-Pyridin-2-yl-2-pyridin-4-yl-ethanone | MS ES+ m/e = 199.2 (M + 1) |
| 190 | 2-(6-Methylpyridin-2-yl)-1-quinolin-4-yl-ethanone | MS ES− m/e 308 (M + 1) |

-continued

| PREP # | Product (Chemical Name) | Physical Data |
|---|---|---|
| 191 | 2-(7-Methoxy-quinolin-4-yl)-1-pyridin-2-yl-ethanone | MS ES+ m/e 279 (M + 1) |
| 192 | 2-(7-Benzyloxy-6-methoxy-quinolin-4-yl)-1-pyridin-2-yl-ethanone | MS ES+ m/e 385 (M + 1) |
| 193 | 1-Pyrazin-2-yl-2-quinolin-4-yl-ethanone | MS APCI+ m/e 250 (M + 1) |
| 194 | 2-(6-Bromo-quinolin-4-yl)-1-(6-methyl-pyridin-2-yl)-ethanone | $^1$H NMR (CDCl$_3$) δ 8.89–8.81(m, 1H), 8.40(s, 1H), 8.03–7.99(m, 1H), 7.90–7.85 (m, 1H), 7.79–7.67(m, 2H), 7.49–7.38(m, 2H), 4.97(s, 2H), 2.71(s, 3H) |
| 195 | 1-(6-Methyl-pyridin-2-yl)-2-(6-trifluoromethyl-quinolin-4-yl)-ethanone | $^1$H NMR (CDCl$_3$) δ 8.97–8.94(m, 1H), 8.55–8.51(m, 1H), 8.25–8.20(m, 1H), 7.98–7.93(m, 1H), 7.89–7.83(m, 1H), 7.77–7.69(m, 1H), 7.54–7.50(m, 1H), 7.41–7.32(m, 1H), 5.00(s, 2H), 2.69(s, 3H) |
| 196 | 2-(8-Fluoro-quinolin-4-yl)-1-(6-methyl-pyridin-2-yl)-ethanone | $^1$H NMR (CDCl$_3$) δ 8.90–8.85(m, 1H), 7.90–7.70(m, 2H), 7.50–7.30(m, 3H), 5.05(s, 2H), 2.70(s, 3H) |
| 197 | 2-(7-Bromo-quinolin-4-yl)-1-(6-methyl-pyridin-2-yl)-ethanone | $^1$H NMR (CDCl$_3$) δ 8.85(m, 1H), 8.30(s, 1H), 8.00–7.60(m, 4H), 7.45–7.35(m, 2H), 5.05(s, 2H), 2.65(s, 3H). |
| 198 | 2-(6-Trifluoromethoxy-quinolin-4-yl)-1-(6-methyl-pyridin-2-yl)-ethanone | $^1$H NMR (CDCl$_3$) δ 8.92(m, 1H), 8.42(s, 1H), 8.20(m, 1H), 7.88(m, 1H), 7.80–7.70 (m, 2H), 7.53(m, 1H), 7.40(m, 1H), 5.02(s, 2H), 2.64(s, 3H). |
| 199 | 2-(7-Trifluoromethyl-quinolin-4-yl)-1-(6-methyl-pyridin-2-yl)-ethanone | $^1$H NMR (CDCl$_3$) δ 8.88(m, 1H), 8.15–8.10 (m, 1H), 8.00(s, 1H), 7.98–7.80(m, 2H), 7.75–7.65(m, 1H), 7.50(m, 1H), 7.35–7.33(m, 1H), 5.00(s, 2H), 2.70(s, 3H) |
| 200 | 2-(7-Methoxy-quinolin-4-yl)-1-(6-methyl-pyridin-2-yl)-ethanone | $^1$H NMR (CDCl$_3$) δ 8.88(m, 1H), 8.15–8.10 (m, 1H), 8.00(s, 1H), 7.98–7.80(m, 2H), 7.75–7.65(m, 1H), 7.50(m, 1H), 7.35–7.33(m, 1H), 5.00(s, 2H), 2.70(s, 3H) |
| 201 | 2-(7-Bromo-quinolin-4-yl)-1-pyridin-2-yl-ethanone | $^1$H NMR (CDCl$_3$) δ 8.85(m, 1H), 8.30(s, 1H), 8.00–7.60(m, 4H), 7.45–7.35(m, 3H), 5.05(s, 2H) |
| 202 | 2-(2-Chloro-pyridin-4-yl)-1-pyridin-2-yl-ethanone | $^1$H NMR (CDCl$_3$) δ 8.85(m, 1H), 8.30(s, 1H), 8.00–7.60(m, 4H), 7.45–7.35(m, 3H), 5.05(s, 2H) |
| 203 | 1-(6-Chloro-pyridin-2-yl)-2-quinolin-4-yl-ethanone | $^1$H NMR (CDCl$_3$): δ 8.88(d, J=4.4Hz, 1H), 8.13(d, J=8.0Hz, 1H), 7.97–8.02 (m, 2H), 7.80–7.87(m, 1H), 7.72(t, J=8.0Hz, 1H), 7.53–7.60(m, 2H), 7.43(d, J=4.4Hz, 1H), 4.99(s, 2H) |
| 204 | 1-(6-Methyl-pyridin-2-yl)-2-quinolin-4-yl-ethanone | $^1$H NMR (CDCl$_3$): δ 8.54(d, J=4.4Hz, 1H), 8.11(dd, J=8.4, 0.9Hz, 1H), 8.07 (dd, J=8.4, 0.9Hz, 1H), 7.85(d, J=7.7Hz, 1H), 7.66–7.86(m, 2H), 7.54(td, J=7.0, 1.3Hz, 1H), 7.35–7.45(m, 2H), 5.02 (s, 2H), 2.67(s, 3H). |
| 204a | 2-Quinolin-4-yl-1-thiazol-2-yl-ethanone | ES MS 269.3 (M + 1) |
| 204b | 1-(1-Methyl-1H-imidazol-2-yl)-2-quinolin-4-yl-ethanone | MS (ES) m/e 252.3 (M+) |
| 204c | 2-(4-Fluoro-phenyl)-1-(5-methyl-4H-pyrrol-2-yl)-ethanone | MS (ES) m/e 236.3 (M+) |
| 204d | 1-pyridin-2-yl-2-quinolin-4-yl-ethanone | ES MS 249 (M + 1) |
| 204e | 2-quinolin-4-yl-1-thiazol-2-yl-ethanone | MS (ES) m/e 255 (M+) |
| 204f | 1-(1-methyl-1H-imidazol-2-yl)-2-quinolin-4-yl-ethanone | MS (ES) m/e 252 (M+) |

Preparation 205

2-(4-Fluoro-phenyl)-3-oxo-3-(6-trifluoromethyl-pyridin-2-yl)-propionitrile

A solution of 4-fluorophenylacetonitrile (0.12 mL, 1.0 mmol) in dry tetrahydrofuran (2 mL) is treated dropwise with potassium bis(trimethylsilyl)amide (0.5 M toluene, 3.0 mL, 1.5 mmol) at 0° C. under an atmosphere of nitrogen. The mixture is stirred 10 min then 6-trifluoromethyl-pyridine-2-carbothioic acid S-(4-chloro-phenyl) ester is added all at once. The mixture is allowed to warn to room temperature then warmed to reflux for 10 min, at which time the reaction is complete by TLC (methylene chloride). The mixture is allowed to cool then poured into 10% citric acid and extracted into methylene chloride. The methylene chloride solution is dried over magnesium sulfate and concentrated in vacuo. The residue is purified on a silica gel cartridge prepared with hexane then eluted with methylene chloride to yield 204 mg (66%) 2-(4-fluoro-phenyl)-3-oxo-3-(6-trifluoromethyl-pyridin-2-yl)-propionitrile. MS ES⁻ m/z 307 (M−1).

Preparation 206

2-(3-Chloro-4-fluoro-phenyl)-1-(6-methyl-pyridin-2-yl)-ethanone

A dispersion of sodium hydride, (60% in mineral oil, 0.7 g, 17.7 mmol) is added to ethanol (25 mL). When gas evolution ceases, 3-chloro-4-fluorophenylacetonitrile (Fluorochemicals, 2.0 g, 11.8 mmol) and 6-methyl-pyridine-2-carboxylic acid methyl ester (1.8 g, 11.8 mmol), are added. The mixture is refluxed for 2.5 h and adjusted to pH 7 with 1 N hydrochloric acid. The mixture is concentrated in vacuo. Concentrated hydrochloric acid (50 mL) is added to the mixture after which it is refluxed for 1.5 h. The mixture is poured over ice and adjusted to pH 8 with 5 N sodium hydroxide. The mixture is extracted with methylene chloride and the organic portions dried over anhydrous sodium sulfate. The mixture is filtered and concentrated in vacuo to yield the title compound, 2.1 g (68%), as a yellowish solid.

¹H NMR (CDCl₃) δ 7.86–7.83 (m, 1H), 7.73–7.71 (m, 1H), 7.42–7.33 (m, 2H), 7.26–7.04 (m, 2H), 4.49 (s, 2H), 2.65 (s, 3H).

By the previous method the following compounds are prepared (unless otherwise specified)

| PREP # | Product (Chemical Name) | Physical Data |
| --- | --- | --- |
| 207 | 2-(2-Chloro-4-fluoro-phenyl)-1-(6-methyl-pyridin-2-yl)-ethanone | ¹H NMR(CDCl₃) δ 7.87–7.85(m, 1H), 7.74–7.69(m, 1H), 7.36–7.34(m, 1H), 7.27–7.14(m, 2H), 6.99–6.93(m, 1H), 4.68(s, 2H), 2.65(s, 3H) |
| 208 | 1-(6-Methyl-pyridin-2-yl)-2-(2,4,5-trifluoro-phenyl)-ethanone | ¹H NMR(CDCl₃) δ 7.87–7.85(m, 1H), 7.75–7.70(m, 1H), 7.37–7.34(m, 1H), 7.15–7.07(m, 1H), 6.98–6.89(m, 1H), 4.55(s, 2H), 2.64(s, 3H) |
| 209 | 2-(4-Fluoro-3-trifluoromethyl-phenyl)-1-(6-methyl-pyridin-2-yl)-ethanone | ¹H NMR(CDCl₃) δ 7.86–7.84(m, 1H), 7.74–7.62(m, 2H), 7.53–7.49(m, 1H), 7.36–7.33(m, 1H), 7.16–7.10(m, 1H), 4.55(s, 2H), 2.65(s, 3H) |
| 210 | 2-(4-Fluoro-phenyl)-1-(6-methyl-pyridin-2-yl)-ethanone | ¹H NMR(CDCl₃): δ 7.84(d, J=7.7Hz, 1H), 7.69(t, J=7.7Hz, 1H), 7.25–7.35(m, 4H), 6.95–7.05(m, 1H), 4.50(s, 2H), 2.64(s, 3H). |

Preparation 211

1-(6-Methylpyridin-2-yl)-2-p-tolyl-ethanone

To a slurry of magnesium turnings (406 mg, 16.7 mmol) in toluene (10 mL) is added 4-methylbenzylchloride (10 mg, 0.06 mmol) dropwise in tetrahydrofuran (0.2 mL). Two drops of 1,2-dibromoethane are added, the mixture heated to 50° C., and allowed to cool to room temperature. This process is repeated until reaction initiates. 4-Methylbenzylchloride (1.5 g, 10 mmol) in tetrahydrofuran (7 mL) is added slowly while keeping the internal temperature below 32° C. After the addition is complete the reaction is stirred at room temperature for 1 h. The reaction mixture is added dropwise over 5 minutes to a solution of 6-methyl-pyridine-2-carboxylic acid methoxy-methyl-amide (Prep 250, 1 g, 5.6 mmol) in toluene (5 mL). The reaction is stirred for an additional 45 minutes. The reaction is quenched with 1 N hydrochloric acid and stirred for 30 minutes. The aqueous layer is neutralized with saturated sodium bicarbonate and extracted twice with ethyl acetate. The combined organic extracts are washed with brine, dried (sodium sulfate), filtered and concentrated in vacuo. The crude residue is chromatographed on SiO₂ (50% ethyl acetate/hexane to 75% ethyl acetate/hexane) to yield the title compound, 633 mg (25%), as a brown oil.

MS ES⁺ m/e 226 (M+1)

By the previous method of the following compounds are essentially prepared: (unless otherwise specified)

| PREP # | Product Name | Physical Data |
| --- | --- | --- |
| 212 | 1-(6-Methyl-pyridin-2-yl)-2-naphthalen-1-yl-ethanone | MS ES⁺ m/e 262 (M + 1) |

Preparation 213

2-(4-Fluoro-phenyl)-1-(6-trifluoromethyl-pyridin-2-yl)-ethanone

A slurry of 2-(4-fluoro-phenyl)-3-oxo-3-(6-trifluoromethyl-pyridin-2-yl)-propionitrile (1.4 g, 4.4 mmol) in 48% HBr is warmed to reflux for 8 h, allowed to stand at ambient temperature 16 h, then warmed at reflux for 8 h. The mixture is extracted with ether, treated with a small amount of sodium bicarbonate, extracted with ether, made basic with solid sodium hydroxide, and extracted again with ether. Ethereal extracts are combined, dried over magnesium sulfate, and concentrated in vacuo to a dark oil. The residual oil is purified on a silica gel cartridge prepared with hexane then eluted with methylene chloride to yield 816 mg (65%) of the title compound as a dark oil.

MS ES⁻ m/z 282 (M−1).

By the previous method the following compounds are prepared (unless otherwise specified):

| PREP # | Product (Chemical Name) | Physical Data |
|---|---|---|
| 214 | 1-Pyridin-2-yl-2-quinolin-6-yl-ethanone | MS ES+ m/e 249 (M + 1) |
| 215 | 1-(6-Methyl-pyridin-2-yl)-2-quinolin-6-yl-ethanone | MS ES+ m/e 263 (M + 1) |
| 216 | 2-Naphthalen-2-yl-1-pyridin-2-yl-ethanone | MS ES+ m/e 248 (M + 1) |
| 217 | 1-(6-Methyl-pyridin-2-yl)-2-naphthalen-2-yl-ethanone | MS ES+ m/e 262 (M + 1) |
| 218 | 2-(4-Methanesulfonyl-phenyl)-1-(6-methyl-pyridin-2-yl)-ethanone | MS ES+ m/e 290 (M + 1) |
| 219 | 1-(6-Methyl-pyridin-2-yl)-2-pyridin-3-yl-ethanone | MS ES+ m/e 213 (M + 1) |
| 220 | 1-(3-Fluorophenyl)-2-(4-fluorophenyl)-ethanone | MS ES+ m/e 233 (M + 1) |
| 221 | 2-(4-Fluoro-naphthalen-1-yl)-1-(6-methyl-pyridin-2-yl)-ethanone | MS ES+ m/e 280 (M + 1) |
| 222 | 2-(3,4-Difluoro-phenyl)-1-(6-methyl-pyridin-2-yl)-ethanone | MS ES+ m/e 248 (M + 1) |
| 223 | 2-(4-Methoxyphenyl)-1-(6-methylpyridin-2-yl)-ethanone | TOF MS ES+ exact mass calculated for $C_9H_{10}N_2$ (p + 1): m/z = 146.0844. Found: 146.0832. |
| 224 | 2-(4-Fluorophenyl)-1-pyridin-2-yl-ethanone | MS FAB+ m/z = 216.1 (M + 1). |
| 225 | 2-(4-Methoxyphenyl)-1-pyridin-2-yl-ethanone | MS ES+ m/e 228.1 (M + 1) |
| 226 | 2-(4-Fluorophenyl)-1-(6-methylpyridin-2-yl)ethanone | MS ES+ m/e 230.1 (M + 1) |
| 227 | 2-(4-Methoxyphenyl)-3-(6-methylpyridin-2-yl)-3-oxo-propionitrile | TOF MS ES+ exact mass calculated for $C_{16}H_{15}N_2O_2$ (p + 1): m/z = 267.1134. Found: 267.1125 |
| 228 | 1-Pyridin-2-yl-2-(4-trifluoro methylphenyl)ethanone | MS ES+ m/e 266.1 (M + 1) |

Preparation 229

[2-Quinolin-4-yl-1-(3-trifluoromethyl-phenyl)-ethylidene]-hydrazine

A solution of 2-quinolin-4-yl-1-(3-trifluoromethyl-phenyl)-ethanone (1.0 g, 3.2 mmol) in ethanol (13 mL) is cooled to 0° C. and treated with hydrazine (0.6 g, 19 mmol) and concentrated hydrochloric acid (0.13 mL, 1.6 mmol). The mixture is refluxed for 2 h and concentrated in vacuo. The residue is taken up in dichloromethane and washed with saturated sodium bicarbonate (30 mL), water (2×30 mL), and brine (30 mL). The solution is dried over anhydrous sodium sulfate and filtered. The filtrate is concentrated to yield the title compound, 1.0 g (97%), as a pale yellow foam.
$^1$H NMR (CDCl$_3$) δ 8.80 (m, 1H), 8.28–8.05 (m, 3H), 7.90–7.40 (m, 4H), 7.20–7.05 (m, 2H), 5.50 (s, 2H), 4.45 (m, 2H).

By the previous method the following compounds are prepared (unless otherwise specified).

| PREP # | Product (Chemical Name) | Physical Data |
|---|---|---|
| 230 | (1-Pyridin-2-yl-2-quinolin-4-yl-ethylidene)-hydrazine | $^1$H NMR(CDCl$_3$) δ 8.70–8.61(m, 1H), 8.50–8.40(m, 1H), 8.25–8.03(m, 3H), 7.80–7.55(m, 3H), 7.31–7.10(m, 2H), 5.50(s, 2H), 4.80(s, 2H) |
| 231 | [2-Quinolin-4-yl-1-(4-trifluoromethyl-phenyl)-ethylidene]-hydrazine | $^1$H NMR(CDCl$_3$) δ 8.82–8.78(m, 1H), 8.20–8.05(m, 2H), 7.85–7.60(m, 5H), 7.30–7.10(m, 2H), 5.55(s, 2H), 4.44(s, 2H) |
| 232 | [1-(4-Chloro-phenyl)-2-quinolin-4-yl-ethylidene]-hydrazine | $^1$H NMR(CDCl$_3$) δ 8.79–8.7(m, 1H), 8.22–8.15(d, 1H), 8.13–8.03(d, 2H), 7.84–7.75(m, 1H), 7.72–7.63(m, 1H), 7.6–7.52(d, 2H), 7.38–7.25(m, 1H), 7.1–7.0(m, 1H), 5.45(s, 2H), 4.4(s, 2H) |
| 233 | [1-(3-Chloro-phenyl)-2-quinolin-4-yl-ethylidene]-hydrazine | $^1$H NMR(CDCl$_3$) δ 8.79–8.7(m, 1H), 8.22–8.00(m, 3H), 7.8–7.69(m, 2H), 7.84–7.5–7.42(m, 1H), 7.3–7.2(m, 2H), 7.10–6.98(m, 1H), 5.50(s, 2H), 4.40(s, 2H) |
| 234 | [1-(3-Fluoro-5-trifluoromethyl-phenyl)-2-quinolin-4-yl-ethylidene]-hydrazine | $^1$H NMR(CDCl$_3$) δ 8.82–8.78(m, 1H), 8.20–8.05(m, 2H), 7.85–7.70(m, 3H), 7.55–7.48(m, 1H), 7.30–7.22(m, 1H), 7.05–7.00(m, 1H), 5.60(s, 2H), 4.40(s, 2H) |
| 235 | (1-Phenyl-2-quinolin-4-yl-ethylidene)-hydrazine | $^1$H NMR(CDCl$_3$) δ 8.82–8.78(m, 1H), 8.30–8.05(m, 2H), 7.80–7.60(m, 4H), 7.40–7.15(m, 4H), 5.40(s, 2H), 4.50(s, 2H) |

| PREP # | Product (Chemical Name) | Physical Data |
|---|---|---|
| 236 | [2-(2-Chloro-quinolin-4-yl)-1-pyridin-2-yl-ethylidene]-hydrazine | $^1$H NMR(CDCl$_3$) δ 8.50–8.45(m, 1H), 8.20–8.00(m, 3H), 7.80–7.60(m, 3H), 7.25–7.18(m, 1H), 7.00(s, 1H), 5.60(s, 2H), 4.70(s, 2H) |
| 237 | [2-(6,8-Dimethoxy-quinolin-4-yl)-1-(6-methyl-pyridin-2-yl)-ethylidene]-hydrazine | $^1$H NMR(CDCl$_3$) δ 8.70–8.65(m, 1H), 7.87–7.80(m, 1H), 7.75–7.67(m, 1H), 7.20–7.13(m, 1H), 7.10–7.03(m, 1H), 6.90–6.85(m, 1H), 6.7–6.65(m, 1H), 5.50(s, 2H), 4.70(s, 2H), 4.05(s, 3H), 3.85(s, 3H), 2.70(s, 3H) |
| 238 | [1-(6-Bromo-pyridin-2-yl)-2-quinolin-4-yl-ethylidene]-hydrazine | $^1$H NMR(CDCl$_3$) δ 8.82–8.78(m, 1H), 8.25–8.00(m, 3H), 7.85–7.60(m, 3H), 7.40–7.35(m, 1H), 7.10–7.05(m, 1H), 5.55(s, 2H), 4.70(s, 2H) |
| 239 | [2-(6,8-Dimethoxy-quinolin-4-yl)-1-pyridin-2-yl-ethylidene]-hydrazine | $^1$H NMR(CDCl$_3$) δ 8.69–8.50(m, 2H), 8.10–8.01(m, 1H), 7.75–7.67(m, 1H), 7.25–7.10(m, 2H), 6.90–6.85(m, 1H), 6.70–6.65(m, 1H), 5.57(s, 2H), 4.67(s, 2H), 4.05(s, 3H), 3.85(s, 3H) |
| 240 | [1-(6-Methyl-pyridin-2-yl)-2-quinolin-4-yl-ethylidene]-hydrazine | $^1$H NMR(CDCl$_3$) δ 8.75–8.68(m, 1H), 8.27–8.20(d, 1H), 8.19–8.1(d, 1H), 7.90–7.82(m, 1H), 7.80–7.69(m, 2H), 7.65–7.50(m, 1H), 7.10–7.00(m, 2H), 5.50(s, 2H), 4.80(s, 2H), 2.45(s, 3H) |
| 241 | (2-[1,10]Phenanthrolin-4-yl-1-pyridin-2-yl-ethylidene)-hydrazine | $^1$H NMR(CDCl$_3$) δ 9.20–9.05(m, 2H), 8.85–8.80(m, 1H), 8.45–8.40(m, 1H), 8.30–8.05(m, 3H), 7.90–7.75(m, 2H), 7.65–7.50(m, 2H), 5.60(br s, 2H), 4.90(s, 2H) |
| 242 | [1-(3-Fluoro-phenyl)-2-quinolin-4-yl-ethylidene]-hydrazine | $^1$H NMR(CDCl$_3$): δ 8.75(m, 1H), 8.05(m, 2H), 7.68(m, 1H), 7.51(m, 1H), 7.32(m, 3H), 6.93(m, 1H), 6.86(m, 1H), 5.45(s, 2H), 4.32(s, 2H) |
| 243 | [1-(2-Fluoro-phenyl)-2-quinolin-4-yl-ethylidene]-hydrazine | $^1$H NMR(CDCl$_3$, 1:1 mixture of rotamers): δ 8.73(m, 1H), 8.07(m, 2H), 7.51(m, 2H), 6.81(m, 2H), 5.38(m, 2H), 4.30(m, 2H) |
| 244 | [1-(4-Fluoro-phenyl)-2-quinolin-4-yl-ethylidene]-hydrazine | MS Calcd. 279; MS (CI) (M + 1) 280 |
| 245 | [2-Quinolin-4-yl-1-(3-trifluoromethoxy-phenyl)-ethylidene]-hydrazine | $^1$H NMR(CDCl$_3$): δ 8.78(m, 1H), 8.21(m, 2H), 7.62(m, 4H), 7.22(m, 3H), 5.53(s, 2H), 4.42(s, 2H) |
| 246 | (2-Quinolin-4-yl-1-quinolin-2-yl-ethylidene)-hydrazine | MS Calcd. 312; MS (APCI) (M + 1) 313 |
| 247 | [1-(4-Ethyl-pyridin-2-yl)-2-quinolin-4-yl-ethylidene]-hydrazine | MS Calcd. 290; MS (API) (M + 1) 291 |
| 248 | (1-[1,8]Naphthyridin-2-yl-2-quinolin-4-yl-ethylidene)-hydrazine | MS Calcd. 313; MS (APCI) (M + 1) 314 |
| 249 | [1-(6-Chloropyridin-2-yl)-2-quinolin-4-yl-ethylidene]-hydrazine | MS Calcd. 296; MS (APCI) (M + 1) 297 |
| 250 | [1-(4-Chloropyridin-2-yl)-2-quinolin-4-yl-ethylidene]-hydrazine | MS Calcd. 296; MS (APCI) (M + 1) 297 |
| 251 | [1-(2-Fluoro-3-trifluoromethyl-phenyl)-2-quinolin-4-yl-ethylidene]-hydrazine | $^1$H NMR(CDCl$_3$): δ 8.80(m, 1H), 7.95–8.20(m, 2H), 7.40–7.80(m, 4H), 7.00–7.30(m, 2H), 5.80(s, 2H), 4.45(s, 2H) |

Preparation 252

4-Benzyl-1-(1-pyridin-2-yl-2-quinolin-4-yl-ethylideneamino)-pyrrolidin-2-one

A mixture of 3-benzyl-4-bromo-butyric acid(1-pyridin-2-yl-2-quinolin-4-yl-ethylidene)-hydrazide (PREP. 70, 0.8 g, 1.6 mmol) in tetrahydrofuran (26 mL) at 0° C. is treated with NaH (60% in mineral oil, 0.086 g, 2.2 mmol). The mixture is warmed to room temperature and stirred for 2 h. Saturated ammonium chloride (2 mL) is added and volatiles removed in vacuo. The residue is chromatographed on SiO$_2$ (90% ethyl acetate/hexanes followed by dichloromethane:methanol:ammonium hydroxide/94:5:1) to yield the title compound, 0.4 g (45%), as a yellowish foam.

$^1$H NMR (CDCl$_3$) δ 8.86–8.82 (m, 1H), 8.70–8.60 (m, 1H), 8.30–8.05 (m, 3H), 7.80–7.30 (m, 4H), 7.30–7.20 (m, 5H), 6.85–6.80 (m, 1H), 5.20–4.85 (m, 2H), 3.05–2.95 (m, 2H), 2.30–2.15 (m, 3H), 2.00–1.90 (m, 2H).

By the previous method the following compounds are essentially prepared:

| PREP # | Product (Chemical Name) | Physical Data |
|---|---|---|
| 253 | 1-(1-Pyridin-2-yl-2-quinolin-4-yl-ethylideneamino)-pyrrolidin-2-one | ¹H NMR(CDCl₃) δ 8.80–8.70(m, 2H), 8.20–8.00(m, 3H), 7.80–7.66(m, 3H), 7.60–7.40(m, 1H), 7.30–7.10(m, 5H), 6.95–6.90(m, 1H), 5.20–5.10(m, 1H), 4.80–4.70(m, 1H), 3.00–3.85(m, 2H), 2.70–2.60(m, 1H), 2.40–2.10(m, 6H) |
| 254 | 4-Phenyl-1-(1-pyridin-2-yl-2-quinolin-4-yl-ethylidene amino)-pyrrolidin-2-one | ¹H NMR(CDCl₃) δ 8.75–8.61(m, 2H), 2.27–8.00(m, 2H), 7.80–7.60(m, 2H), 7.53–7.45(m, 2H), 7.20–7.10(m, 6H), 6.88–6.80(m, 1H), 5.25–5.20(m, 1H), 4.78–4.70(m, 1H), 3.40–3.33(m, 1H), 3.15–3.05(m, 1H), 2.7–2.48(m, 2H), 2.40–2.30(m, 1H) |
| 255 | 1-[2-Quinolin-4-yl-1-(3-trifluoromethylphenyl)-ethylideneamino]-pyrrolidin-2-one | ¹H NMR(CDCl₃) δ 8.98(s, 1H), 8.72–8.80(m, 1H), 8.20–8.25(m, 1H), 8.00–8.10(m, 2H), 7.60–7.88(m, 3H), 7.40–7.50(m, 1H), 6.78–6.90(m, 1H), 4.51(s, 2H), 3.55–3.65(m, 2H), 2.88–2.98(m, 2H), 2.00–2.20(m, 2H) |
| 256 | 1-[2-Quinolin-4-yl-1-(4-trifluoromethyl-phenyl)-ethylideneamino]-pyrrolidin-2-one | ¹H NMR(CDCl₃) δ 8.80–8.00(m, 1H), 8.20–8.10(m, 2H), 8.00–7.60(m, 5H), 7.25–7.10(m, 2H), 3.48–3.40(m, 2H), 2.35–2.25(m, 2H), 1.80–1.65(m, 2H) |
| 257 | 1-(1-Phenyl-2-quinolin-4-yl-ethylideneamino)-pyrrolidin-2-one | ¹H NMR(CDCl₃) δ 8.80–8.75(m, 1H), 8.15–8.00(m, 2H), 7.80–7.50(m, 3H), 7.40–7.10(m, 5H), 4.60(s, 2H), 3.35–3.30(m, 2H), 2.30–2.20(m, 2H), 1.70–1.60(m, 2H) |
| 258 | 1-[2-(2-Chloro-quinolin-4-yl)-1-pyridin-2-yl-ethylideneamino]-pyrrolidin-2-one | ¹H NMR(CDCl₃) δ 8.70–8.60(m, 1H), 8.20–7.95(m, 2H), 7.80–7.65(m, 2H), 7.60–7.10(m, 4H), 4.90(s, 2H), 3.10–3.05(m, 2H), 2.25–2.15(m, 2H), 1.60–1.40(m, 2H) |
| 259 | 1-[2-(6,8-Dimethoxy-quinolin-4-yl)-1-(6-methyl-pyridin-2-yl)-ethylidene amino]-pyrrolidin-2-one | ¹H NMR(CDCl₃) δ 8.70–8.65(m, 1H), 7.90–7.83(m, 1H), 7.65–7.57(m, 1H), 7.25–7.15(m, 2H), 6.9–6.87(m, 1H), 6.67–6.63(m, 1H), 4.80(s, 2H), 4.00(s, 3H), 3.70(s, 3H), 2.95–2.87(m, 2H), 2.60(s, 3H), 2.20–2.08(m, 2H), 1.4–1.3(m, 2H) |
| 260 | 1-[1-(6-Bromo-pyridin-2-yl)-2-quinolin-4-yl-ethylideneamino]-pyrrolidin-2-one | ¹H NMR(CDCl₃) δ 8.80–8.75(m, 1H), 8.15–8.10(m, 2H), 7.95–7.90(m, 1H), 7.70–7.45(m, 4H), 7.20–7.15(m, 1H), 4.85(s, 2H), 3.10–3.00(m, 2H), 2.20–2.15(m, 2H), 1.50–1.30(m, 2H) |
| 261 | 1-[2-(6,8-Dimethoxy-quinolin-4-yl)-1-pyridin-2-yl-ethylidene amino]-pyrrolidin-2-one | ¹H NMR(CDCl₃) δ 8.7–8.4(m, 3H), 7.83–7.70(m, 1H), 7.4–7.2(m, 2H), 6.9–6.87(m, 1H), 6.67–6.63(m, 1H), 4.80(s, 2H), 4.10–3.80(m, 7H), 3.7(s, 3H), 2.20–2.08(m, 2H) |
| 262 | 1-[1-(3-Fluoro-phenyl)-2-quinolin-4-yl-ethylideneamino]-pyrrolidin-2-one | MS APCI⁺ m/e 348 (M + 1) |
| 263 | 1-[1-(2-Fluoro-phenyl)-2-quinolin-4-yl-ethylideneamino]-pyrrolidin-2-one | |
| 264 | 1-[1-(4-Fluoro-phenyl)-2-quinolin-4-yl-ethylideneamino]-pyrrolidin-2-one | MS APCI⁺ m/e 348 (M + 1) |
| 265 | 1-[2-Quinolin-4-yl-1-(3-trifluoromethoxy-phenyl)-ethylideneamino]-pyrrolidin-2-one | ¹H NMR(CDCl₃): δ 8.75(m, 1H), 8.15(m, 2H), 7.55(m, 4H), 7.48(m, 1H), 7.12(m, 2H), 4.55(s, 2H), 3.44(m, 2H), 2.24(m, 2H), 1.63(m, 2H) |
| 266 | 4-[2-(4-Fluoro-phenyl)-4,5,6,7-tetrahydro-pyrazolo[1,5-a]pyridin-3-yl]-quinoline | MS APCI⁺ m/e 344 (M + 1) |
| 267 | 1-(2-Quinolin-4-yl-1-quinolin-2-yl-ethylideneamino)-pyrrolidin-2-one | MS APCI⁺ m/e 381 (M + 1) |
| 268 | 1-[1-(6-Chloro-pyridin-2-yl)-2-quinolin-4-yl-ethylideneamino]-pyrrolidin-2-one | MS APCI⁺ m/e 365 (M + 1) |
| 269 | 1-[1-(4-Chloro-pyridin-2-yl)-2-quinolin-4-yl-ethylideneamino]-pyrrolidin-2-one | MS APCI⁺ m/e 365 (M + 1) |
| 270 | 1-[1-(2-Fluoro-3-trifluoromethyl-phenyl)-2- | ¹H NMR(CDCl₃): δ 8.70–8.80(m, 1H), 8.00–8.20(m, 2H), 7.50–7.70(m, 4H), 7.00–7.30(m, |

| PREP # | Product (Chemical Name) | Physical Data |
|---|---|---|
| | quinolin-4-yl-ethylideneamino]-pyrrolidin-2-one | 2H), 4.50(s, 2H), 3.60(m, 2H), 2.10–2.40(m, 2H), 1.75–2.00(m, 2H) |
| 271 | 1-(Benzhydrylidene-amino)-pyrrolidin-2-one | $^1$H NMR(CDCl$_3$): δ 1.80(q, J=9Hz, 2H), 2.30(t, J=9Hz, 2H), 3.30(t, J=9Hz, 2H), 7.30(m, 8H), 7.50(m, 2H) |
| 272 | 1-(Benzhydrylidene-amino)-4-(4-fluoro-phenyl)-pyrrolidin-2-one | $^1$H NMR(CDCl$_3$): δ 7.65(d, J=8Hz, 2H), 7.20–7.50(m, 10H), 6.95(d, J=6Hz, 2H), 3.70(dd, J=7, 9Hz, 1H), 3.25–3.50(m, 2H), 2.75(dd, J=9, 17Hz, 1H), 2.45(dd, J=7, 17Hz, 1H,) |
| 273 | 1-(Benzhydrylidene-amino)-4-(3-methoxy-phenyl)-pyrrolidin-2-one | $^1$H NMR(CDCl$_3$): δ 7.60(m, 2H), 7.22–7.45(m, 9H), 6.75(dd, J=2.5, 8Hz, 1H), 6.60(m, 2H), 3.80(s, 3H), 3.65(m, 1H), 3.30–3.45(m, 2H), 2.85(dd, J=9, 17Hz, 1H), 2.45(dd, J=9, 17Hz, 1H) |
| 274 | 1-(Benzhydrylidene-amino)-5-(tert-butyl-dimethyl-silyloxymethyl)-pyrrolidin-2-one | $^1$H NMR(CDCl$_3$): δ 7.50–7.60(m, 5H), 7.30–7.40(m, 5H), 3.95(dd, J=4, 10.5Hz, 1H), 3.70–3.80(m, 1H), 3.60(dd, J=4, 10.5Hz, 1H), 2.30–2.45(m, 1H), 2.10–2.25(m, 1H), 1.90–2.05(m, 2H), 0.90(s, 9H), 0.10(s, 6H) |
| 275 | 1-[1-(6-Methyl-pyridin-2-yl)-2-quinolin-4-yl-ethylideneamino]-pyrrolidin-2-one | MS APCI$^+$ m/e 346 (M + 1) |
| 276 | 1-[2-(6,7-Dimethoxy-quinolin-4-yl)-1-(6-methyl-pyridin-2-yl)-ethylideneamino]-pyrrolidin-2-one | MS ES$^+$ m/e 405 (M + 1) |
| 278 | 1-(1-Pyrazin-2-yl-2-quinolin-4-yl-ethylideneamino)-pyrrolidin-2-one | $^1$H NMR(CDCl$_3$): δ 9.39(s, 1H), 8.77(m, 1H), 8.65(m, 1H), 8.58(m, 1H), 8.13(m, 1H), 7.96(m, 1H), 7.72(m, 1H), 7.51(m, 1H), 7.18(m, 1H), 4.84(s, 2H), 3.15(m, 2H), 2.21(m, 2H), 1.47(m, 2H) |
| 279 | 4-Methyl-1-(1-pyridin-2-yl-2-quinolin-4-yl-ethylideneamino)-pyrrolidin-2-one | $^1$H NMR(CDCl$_3$) δ 8.80–8.73(m, 1H), 8.70–8.63(m, 1H), 8.20–8.00(m, 3H), 7.81–7.68(m, 2H), 7.55–7.47(m, 1H), 7.40–7.35(m, 1H), 7.21–7.18(m, 1H), 5.17–5.07(m, 1H), 4.80–4.72(m, 1H), 3.07–2.99(m, 1H), 2.90–2.82(m, 1H), 2.39–2.23(m, 1H), 1.87–1.55(m, 2H), 0.79–0.67(m, 3H) |
| 280 | 1-[1-(6-Methyl-pyridin-2-yl)-2-(6-trifluoromethyl-quinolin-4-yl)-ethylideneamino]-pyrrolidin-2-one | $^1$H NMR(CDCl$_3$) δ 8.89–8.80(m, 1H), 8.59(s, 1H), 8.24–8.17(m, 1H), 7.91–7.78(m, 2H), 7.65–7.55(m, 1H), 7.41–7.39(m, 1H), 7.20–7.13(m, 1H), 4.91(s, 2H), 3.22–3.13(m, 2H), 2.49(s, 3H), 2.37–2.29(m, 2H), 1.72–1.57(m, 2H) |
| 281 | (S)-1-(Benzhydrylidene-amino)-5-benzyloxy methyl-pyrrolidin-2-one | $^1$H NMR(CDCl$_3$): δ 7.56–7.60(m, 2H), 7.24–7.46(m, 13H), 4.55–4.72(m, 2H), 3.90(m, 1H), 3.76(dd, J=9.8, 4.3Hz, 1H), 3.60(dd, J=9.8, 3.2Hz, 1H), 1.95–2.39(m, 4H). |
| 282 | 4-[1-(Benzhydrylidene-amino)-5-oxo-pyrrolidin-3-yl]-benzoic acid ethyl ester | $^1$H NMR(CDCl$_3$): δ 7.93(d, J=8.0Hz, 2H), 7.63(dd, J=8.0, J=0.7Hz, 2H), 7.29–7.54(m, 10H), 4.36(q, J=7.1Hz, 2H), 3.78(dd, J=9.3, 8.1Hz, 1H), 3.46–3.63(m, 1H), 3.36(dd, J=9.3, 6.0Hz, 1H), 2.81(dd, J=17.0, 9.2Hz, 1H), 2.45(dd, J=17.0, 6.9Hz, 1H), 1.39(t, J=7.1Hz, 3H) |
| 283 | 1-(Benzhydrylidene-amino)-4,4-dimethyl-pyrrolidin-2-one | $^1$H NMR(CDCl$_3$): δ 7.27–7.64(m, 10H), 3.03(s, 2H), 2.14(s, 2H), 0.97(s, 6H) |
| 284 | (R)-1-(Benzhydrylidene-amino)-5-benzyloxy methyl-pyrrolidin-2-one | $^1$H NMR(CDCl$_3$): δ 7.56–7.60(m, 2H), 7.24–7.46(m, 13H), 4.55–4.72(m, 2H), 3.90(m, 1H), 3.76(dd, J=9.8, 4.3Hz, 1H), 3.60(dd, J=9.8, 3.2Hz, 1H), 1.95–2.39(m, 4H) |
| 285 | 1-(Benzhydrylidene-amino)-4-(4-chloro-phenyl)-pyrrolidin-2-one | $^1$H NMR(CDCl$_3$): δ 7.61(m, 2H), 7.21–7.47(m, 10H), 6.93(m, 2H), 3.75(dd, J=9.2, 7.9Hz, 1H), 3.25–3.48(m, 2H), 2.78(dd, J=17.2, 9.0Hz, 1H), 2.40(dd, J=17.2, 6.8Hz, 1H) |
| 285a | 1-[1-(4-Methyl-thiazol-2-yl)-2-quinolin-4-yl-ethylideneamino]-pyrrolidin-2-one | ES MS 351.4 (M + 1) |
| 285b | 1-[1-(1-Methyl-1H-imidazol-2-yl)-2-quinolin-4-yl-ethylideneamino]-pyrrolidin-2-one | MS (ES) m/e 334.4 (M$^+$) |

-continued

| PREP # | Product (Chemical Name) | Physical Data |
|---|---|---|
| 285c | 1-[2-(4-Fluoro-phenyl)-1-(4-methyl-thiazol-2-yl)-ethylideneamino]-pyrrolidin-2-one | MS (ES) m/e 318.4 (M+) |
| 285d | 1-pyridin-2-yl-2-quinolin-4-yl-ethanone | ES MS 249 (M + 1) |
| 285e | 1-(2-quinolin-4-yl-1-thiazol-2-yl-ethylideneamino)-pyrrolidin-2-one | MS (ES) m/e 337 (M+) |
| 285f | 1-[1-(1-methyl-1H-imidazol-2-yl)-2-quinolin-4-yl-ethylideneamino]-pyrrolidin-2-one | MS (ES) m/e 334 (M+) |
| 285g | 1-[2-(6,7-Dichloro-quinolin-4-yl)-1-(6-methyl-pyridin-2-yl)-ethylideneamino]-pyrrolidin-2-one | MS ES+ m/e 413 (M + 1) |

Preparation 286

4-(3-Methoxy-phenyl)-1-(1-pyridin-2-yl-2-quinolin-4-yl-ethylideneamino)-pyrrolidin-2-one A solution of 1-pyridin-2-yl-2-quinolin-4-yl-ethanone, (0.25 g, 1 mmol) and pyridine (0.242 mL, 3 mmol) in acetic acid (2 mL) is added to 1-amino-4-(3-methoxy-phenyl)-pyrrolidin-2-one, (0.2 g, 1 mmol) at room temperature under nitrogen. The mixture is stirred 18 h and concentrated in vacuo. The residue is chromatographed on $SiO_2$ (2% methanol/dichloromethane) to yield the title compound, 0.25 g (57%), as a yellow foam.

$^1$H NMR (CDCl$_3$): δ 8.75 (d, J=4.5 Hz, 1H), 8.65 (d, J=4.5 Hz, 1H), 7.70–8.20 (m, 3H), 7.20–7.60 (m, 3H), 6.70–6.85 (m, 3H), 6.40–6.55 (m, 3H), 5.25 (d, J=16.7 Hz, 1H), 4.70 (d, J=16.7 Hz, 1H), 3.70 (s, 3H), 3.45–3.60 (m, 1H), 3.10 (dd, J=8, 9.3 Hz, 1H), 2.25–2.80 (m, 3H).

By the previous method the following compounds are prepared (unless otherwise specified):

| PREP # | Product (Chemical Name) | Physical Data |
|---|---|---|
| 287 | 1-[1-(4-Fluoro-3-trifluoromethyl-phenyl)-2-quinolin-4-yl-ethylideneamino]-pyrrolidin-2-one | $^1$H NMR(CDCl$_3$): δ 8.70(d, J=4Hz, 1H), 8.10(t, J=8Hz, 2H), 7.80–7.95(m, 2H), 7.70(t, J=8Hz, 1H), 7.55(t, J=8Hz, 1H), 7.00–7.20(m, 2H), 4.50(s, 2H), 3.45(t, J=7Hz, 2H), 2.25(t, J=7Hz, 2H), 1.75(q, J=7Hz, 2H) |
| 288 | 1-[1-(4-Fluoro-3-trifluoromethyl-phenyl)-2-quinolin-4-yl-ethylideneamino]-4-(3-methoxy-phenyl)-pyrrolidin-2-one | $^1$H NMR(CDCl$_3$): δ 8.80(d, J=4.5Hz, 1H), 8.15(d, J=8.5Hz, 1H), 7.65–8.00(m, 4H), 7.00–7.40(m, 4H), 6.55–6.80(m, 3H), 4.65(s, 2H), 3.75(m, 5H), 3.15(m, 1H), 2.75(dd, J=8.5, 17Hz, 1H), 2.50(dd, J=8.5, 17Hz, 1H) |
| 289 | 4-(4-Fluoro-phenyl)-1-(1-pyridin-2-yl-2-quinolin-4-yl-ethylideneamino)-pyrrolidin-2-one | $^1$H NMR(CDCl$_3$): δ 8.80(d, J=4.5Hz, 1H), 8.70(d, J=4.5Hz, 1H), 8.00–8.25(m, 3H), 7.60–7.90(m, 2H), 7.45–7.60(m, 2H), 7.15–7.25(m, 2H), 6.75–6.85(m, 3H), 5.20(d, J=16.8Hz, 1H), 4.70(d, J=16.8Hz, 1H), 3.30 (t, J=9Hz, 1H), 3.15(t, J=9Hz, 1H), 2.70(m, 1H), 2.55(dd, J=9, 16.8Hz, 1H), 2.25(dd, J=9, 16.8Hz, 1H) |
| 290 | 5-Hydroxymethyl-1-(1-pyridin-2-yl-2-quinolin-4-yl-ethylideneamino)-pyrrolidin-2-one | $^1$H NMR(CDCl$_3$): δ 8.70(d, J=4.5Hz, 1H), 8.00–8.15(m, 2H), 7.80(d, J=8Hz, 1H), 7.15–7.75(m, 6H), 4.95(d, J=16.5Hz, 1H), 4.85(d, J=16.5Hz, 1H), 3.25–3.45(m, 2H), 3.10–3.20(m, 1H), 2.10–2.40(m, 3H), 1.20–1.60(m, 2H) |
| 291 | 4-(4-Fluoro-phenyl)-1-[1-(6-methyl-pyridin-2-yl)-2-quinolin-4-yl-ethylideneamino]-pyrrolidin-2-one | $^1$H NMR(CDCl$_3$): δ 8.85(d, J=4.5Hz, 1H), 7.95–8.25(m, 3H), 7.20–7.60(m, 5H), 6.80–6.90(m, 4H), 5.25(d, J=16.6Hz, 1H), 4.70 (d, J=16.6Hz, 1H), 3.10– 3.35(m, 2H), 2.60–2.70(m, 1H), 2.40–2.50(m, 1H), 2.55(s, 3H), 2.20–2.40(m, 1H) |

-continued

| PREP # | Product (Chemical Name) | Physical Data |
|---|---|---|
| 292 | 3-Benzyl-1-[1-(6-methyl-pyridin-2-yl)-2-quinolin-4-yl-ethylideneamino]-pyrrolidin-2-one | MS ES+ m/e 421 (M + 1) |
| 293 | 3-Ethyl-1-[1-(6-methyl-pyridin-2-yl)-2-quinolin-4-yl-ethylideneamino]-pyrrolidin-2-one | MS ES+ m/e 359 (M + 1) |
| 294 | 1-(1-Pyridin-2-yl-2-quinolin-4-yl-ethylideneamino)-piperidine-2,6-dione | MS ES+ m/e 359.0 (M + 1) |
| 295 | 1-[2-(7-Chloroquinolin-4-yl)-1-(pyridin-2-yl)ethylideneamino]pyrrolidin-2-one | mp 87–91° C.<br>MS ES+ m/e 283 (M + 1), 285 (M + 3) |
| 296 | 1-[2-(7-Chloroquinolin-4-yl)-1-(6-methylpyridin-2-yl)ethylideneamino]pyrrolidin-2-one | mp 151–153° C.<br>EA Calcd for $C_{21}H_{19}N_4O$: C, 66.58; H, 5.06; N, 14.79; Found: C, 66.48; H, 5.15; N, 14.42 |
| 297 | 1-[2-(7-Ethoxyquinolin-4-yl)-1-(6-methylpyridin-2-yl)ethylideneamino]pyrrolidin-2-one | MS ES+ m/e 390 (M + 2) |
| 298 | 1-[2-(4-Fluorophenyl)-1-pyridin-2-yl-ethylideneamino]pyrrolidin-2-one | MS ES+ m/e 298.1 (M + 1). |
| 299 | 1-[2-(4-Methoxyphenyl)-1-pyridin-2-yl-ethylideneamino]pyrrolidin-2-one | MS ES+ m/e 310.1 (M + 1). |
| 300 | 1-[2-(4-Fluorophenyl)-1-(6-methylpyridin-2-yl)-ethylideneamino]pyrrolidin-2-one | MS ES+ m/e 312.1 (M + 1) |
| 301 | 1-[2-(4-Methoxyphenyl)-1-(6-methylpyridin-2-yl)ethylideneamino]pyrrolidin-2-one | MS ES+ m/e 324.1 (M + 1). |
| 302 | 1-(2-Quinolin-4-yl-1-thiophen-2-yl-ethylideneamino)pyrrolidin-2-one | MS ES+ m/e 336.1 (M + 1) |
| 303 | 4-(2-Furan-2-yl-5,6-dihydro-4H-pyrrolo[1,2-b]pyrazol-3-yl)-quinoline | TOF MS ES+ exact mass calculated for $C_{19}H_{16}N_3O$ (p + 1): m/z = 302.1293. Found: 302.1312 |
| 304 | 1-[1-(6-Propylpyridin-2-yl)-2-quinolin-4-yl-ethylideneamino]pyrrolidin-2-one | MS ES+ m/e 373.1 (M + 1) |
| 305 | 1-[1-(6-Isopropylpyridin-2-yl)-2-quinolin-4-yl-ethylideneamino]pyrrolidin-2-one | MS ES+ m/e 373.1 (M + 1) |
| 306 | 1-(1-Pyridin-2-yl-2-quinolin-4-yl-ethylideneamino)-pyrrolidin-2-one | MS ES+ m/e 330.9 (M + 1) |
| 307 | 3-Methyl-1-[(pyridin-2-yl-quinolin-4-yl-methylene)-amino]-pyrrolidin-2-one | MS ES+ m/e 345 (M + 1) |
| 308 | 6-[1-(2-Oxo-pyrrolidin-1-ylimino)-2-quinolin-4-yl-ethyl]-pyridine-2-carboxylic acid methyl ester | MS ES+ m/e 389 (M + 1) |
| 309 | 6-[1-(2-Oxo-pyrrolidino-1-ylimino)-2-quinolin-4-yl-ethyl]pyridine-2-carboxylic acid methyl ester | MS ES+ m/e 389 (M + 1) |
| 310 | 1-Pyridin-2-yl-2-quinolin-6-yl-ethanone | MS ES+ m/e 249 (M + 1) |
| 311 | 1-(6-Methyl-pyridin-2-yl)-2-quinolin-6-yl-ethanone | MS ES+ m/e 263 (M + 1) |
| 312 | 2-Naphthalen-2-yl-1-pyridin-2-yl-ethanone | MS ES+ m/e 248 (M + 1) |
| 313 | 1-(6-Methyl-pyridin-2-yl)-2-naphthalen-2-yl-ethanone | MS ES+ m/e 262 (M + 1) |

-continued

| PREP # | Product (Chemical Name) | Physical Data |
|---|---|---|
| 314 | 1-[2-(4-Fluoro-phenyl)-1-(6-trifluoromethyl-pyridin-2-yl)-ethylideneamino]-pyrrolidin-2-one | MS ES+ m/z 366 (M + 1). |
| 315 | 1-[2-(6-Bromo-quinolin-4-yl)-1-pyridin-2-yl-ethylideneamino]-pyrrolidin-2-one | MS ES+ m/e 408.7 & 410.7 (M + 1) |
| 316 | 1-(2-Pyridin-4-yl-1-pyridin-2-yl-ethylideneamino)-pyrrolidin-2-one | MS ES+ m/e 281.3 (M + 1) |
| 317 | 1-[1-(6-Methylpyridin-2-yl)-2-p-tolyl-ethylideneamino]-pyrrolidin-2-one | MS ES+ m/e 308 (M + 1) |
| 318 | 1-[2-(6-Methylpyridin-2-yl)-1-quinolin-4-yl-ethylideneamino]-pyrrolidin-2-one | MS ES+ m/e 245 (M + 1) |
| 319 | 1-[1-(6-Methylpyridin-2-yl)-2-naphthalen-1-yl-ethylideneamino]-pyrrolidin-2-one | MS ES+ m/e 344 (M + 1) |
| 320 | 1-[1-(6-Methylpyridin-2-yl)-2-pyridin-3-yl-ethylideneamino]-pyrrolidin-2-one | MS ES+ m/e 295 (M + 1) |
| 321 | 1-[2-(4-Fluorophenyl)-1-(3-fluorophenyl)-ethylideneamino]-pyrrolidin-2-one | MS ES+ m/e 315 (M + 1) |
| 323 | 1-[2-(4-Fluoronaphthalen-1-yl)-1-(6-methylpyridin-2-yl)-ethylideneamino]-pyrrolidin-2-one | MS ES+ m/e 362 (M + 1) |
| 324 | 1-[2-(3,4-Difluorophenyl)-1-(6-methylpyridin-2-yl)-ethylideneamino]-pyrrolidin-2-one | MS ES+ m/e 329.9 (M + 1) |
| 325 | 1-[2-(4-Methanesulfonyl-phenyl)-1-(6-methyl-pyridin-2-yl)-ethylideneamino]-pyrrolidin-2-one | MS ES+ m/e 372 (M + 1) |
| 326 | 1-[2-(7-Methoxy-quinolin-4-yl)-1-pyridin-2-yl-ethylideneamino]-pyrrolidin-2-one | MS ES+ m/e 361 (M + 1) |
| 327 | 1-[2-(7-Benzyloxy-6-methoxy-quinolin-4-yl)-1-pyridin-2-yl-ethylideneamino]-pyrrolidin-2-one | MS ES+ m/e 467 (M + 1) |
| 328 | 1-[2-(6-Bromo-quinolin-4-yl)-1-(6-methyl-pyridin-2-yl)-ethylideneamino]-pyrrolidin-2-one | $^1$H NMR(CDCl$_3$) δ 8.74–8.70(m, 1H), 8.39–8.35(m, 1H), 7.96–7.84(m, 2H), 7.78–7.72(m, 1H), 7.64–7.56(m, 1H), 7.34–7.28(m, 1H), 7.21–7.15(m, 1H), 4.80(s, 2H), 3.34–3.27(m, 2H), 2.54(s, 3H), 2.38–2.30(m, 2H), 1.73–1.59(m, 2H) |
| 329 | 1-[2-(3-Chloro-4-fluoro-phenyl)-1-(6-methyl-pyridin-2-yl)-ethylideneamino]-pyrrolidin-2-one | $^1$H NMR(CDCl$_3$) δ 7.89–7.87(m, 1H), 7.62–7.57(m, 1H), 7.30–7.27(m, 1H), 7.19–7.17(m, 1H), 7.10–7.07(m, 1H), 7.01–6.95(m, 1H), 4.38(s, 2H), 3.49–3.44(m, 2H), 2.58(s, 3H), 2.46–2.40(m, 2H), 1.93–1.88(m, 2H) |
| 340 | 1-[2-(2-Chloro-4-fluoro-phenyl)-1-(6-methyl-pyridin-2-yl)-ethylideneamino]-pyrrolidin-2-one | $^1$H NMR(CDCl$_3$) δ 8.62–8.61(m, 1H), 7.90–7.87(m, 1H), 7.60–7.55(m, 1H), 7.30–7.25(m, 1H), 7.14–7.02(m, 1H), 6.86–6.80(m, 1H), 4.44(s, 2H), 3.52–3.47(m, 2H), 2.52(s, 3H), 2.42–2.36(m, 2H), 1.94–1.86(m, 2H) |
| 341 | 1-[2-(4-Fluoro-3-trifluoromethyl-phenyl)-1-(6-methyl-pyridin-2-yl)-ethylideneamino]-pyrrolidin-2-one | $^1$H NMR(CDCl$_3$) δ 7.89–7.87(m, 1H), 7.62–7.53(m, 2H), 7.45–7.41(m, 1H), 7.28–7.19(m, 1H), 7.16–7.01(m, 1H), 4.43(s, 2H), 3.52–3.47(m, 2H), 2.56(s, 3H), 2.46–2.41(m, 2H), 1.98–1.90(m, 2H) |
| 342 | 1-[1-(6-Methyl-pyridin-2-yl)-2-(2,4,5-trifluorophenyl)-ethylideneamino]-pyrrolidin-2-one | $^1$H NMR(CDCl$_3$) δ 8.63–8.61(m, 1H), 7.91–7.88(m, 1H), 7.65–7.58(m, 1H), 7.31–7.14(m, 1H), 6.87–6.78(m, 1H), 4.32(s, 2H), 3.59–3.55(m, 2H), 2.55(s, 3H), 2.50–2.44(m, 2H), 2.04–1.99(m, 2H) |

-continued

| PREP # | Product (Chemical Name) | Physical Data |
|---|---|---|
| 343 | 1-[2-(8-Fluoro-quinolin-4-yl)-1-(6-methyl-pyridin-2-yl)-ethylideneamino]-pyrrolidin-2-one | $^1$H NMR(CDCl$_3$) δ 8.80–8.75(m, 1H), 7.95–7.85(m, 2H), 7.70–7.60(m, 1H), 7.45–7.20(m, 4H), 4.90(s, 2H), 3.10–3.00(m, 2H), 2.20–2.15(m, 2H), 1.48–1.35(m, 2H). |
| 344 | 1-[2-(7-Bromo-quinolin-4-yl)-1-(6-methyl-pyridin-2-yl)-ethylideneamino]-pyrrolidin-2-one | $^1$H NMR(CDCl$_3$) δ 8.72(m, 1H), 8.28(m, 1H), 8.00–7.90(m, 2H), 7.70–7.55(m, 2H), 7.30–6.20(m, 2H), 4.90(s, 2H), 3.10–3.00(m, 2H), 2.52(s, 3H), 2.20–2.15(m, 2H), 1.48–1.35(m, 2H) |
| 345 | 1-[2-(6-Trifluoromethoxy-quinolin-4-yl)-1-(6-methyl-pyridin-2-yl)-ethylideneamino]-pyrrolidin-2-one | $^1$H NMR(CDCl$_3$) δ 8.75(m, 1H), 8.22(m, 1H), 7.98(s, 1H), 7.86(m, 1H), 7.62(m, 1H), 7.53(m, 1H), 7.35(m, 1H), 7.20–7.10(m, 1H), 4.82(s, 2H), 3.14(m, 2H), 2.52(s, 3H), 2.26(m, 2H), 1.52(m, 2H) |
| 346 | 1-[2-(7-Trifluoromethyl-quinolin-4-yl)-1-(6-methyl-pyridin-2-yl)-ethylideneamino]-pyrrolidin-2-one | $^1$H NMR(CDCl$_3$) δ 8.80–8.75(m, 1H), 8.35(s, 1H), 8.22–8.18(m, 1H), 7.90–7.85(m, 1H), 7.65–7.52(m, 2H), 7.25–7.10(m, 2H), 4.90(s, 2H), 3.10–3.00(m, 2H), 2.50(s, 3H), 2.20–2.15(m, 2H), 1.48–1.35(m, 2H) |
| 347 | 1-[2-(7-Methoxy-quinolin-4-yl)-1-(6-methyl-pyridin-2-yl)-ethylideneamino]-pyrrolidin-2-one | $^1$H NMR(CDCl$_3$) δ 8.62(m, 1H), 7.94(m, 2H), 7.62(m, 1H), 7.41(m, 1H), 7.21(m, 1H), 7.12(m, 2H), 4.89(s, 2H), 3.94(m, 3H), 3.05(m, 2H), 2.55(s, 3H), 1.61(m, 2H), 1.37(m, 2H). |
| 348 | 1-[2-(7-Bromo-quinolin-4-yl)-1-pyridin-2-yl-ethylideneamino]-pyrrolidin-2-one | $^1$H NMR(CDCl$_3$) δ 8.72(d, J=4.5Hz, 1H), 8.60(d, J=4.5Hz, 1H), 8.30(d, J=2.0Hz, 1H), 8.15(dd, J=7.8, 1.0Hz, 1H), 7.95(d, J=9.0Hz, 1H), 7.80(dt, J=2.0, 7.8Hz, 1H), 7.58(dd, J=2.0, 9.0Hz, 1H), 7.40(dd, J=4.5, 7.8Hz, 1H), 7.20(m, 1H), 4.90(s, 2H), 3.10(t, J=6.8Hz, 2H), 2.22(t, J=6.8Hz, 2H), 1.44(q, J=6.8Hz, 2H) |
| 349 | 1-[2-(2-Chloro-pyridin-4-yl)-1-pyridin-2-yl-ethylideneamino]-pyrrolidin-2-one | $^1$H NMR(CDCl$_3$) δ 8.63(m, 1H), 8.22(d, J=4.5Hz, 1H), 8.11(m, 1H), 7.75(dd, J=7.0, 2.0Hz, 1H), 7.36(m, 1H), 7.16(m, 1H), 7.07(m, 1H), 4.45(s, 2H), 3.51(t, J=7.0Hz, 1H), 2.41(t, J=7.0Hz, 2H), 2.35(s, 3H), 1.87(m, 2H) |
| 350 | 5-Hydroxymethyl-1-[1-(6-methyl-pyridin-2-yl)-2-quinolin-4-yl-ethylideneamino]-pyrrolidin-2-one | $^1$H NMR(CDCl$_3$): δ 8.65(d, J=4.5Hz, 1H), 8.00–8.15(m, 2H), 7.80(d, J=9.0Hz, 1H), 7.40–7.75(m, 3H), 7.20–7.35(m, 2H), 4.80–5.00(m, 2H), 3.20–3.50(m, 2H), 3.10(dd, J=9.0, 4.5Hz, 1H), 2.55(s, 3H), 2.10–2.40(m, 2H), 1.20–1.60(m, 2H) |
| 351 | 1-[2-(7-Bromo-quinolin-4-yl)-1-(6-methyl-pyridin-2-yl)-ethylideneamino]-5-hydroxymethyl-pyrrolidin-2-one | $^1$H NMR(CDCl$_3$): δ 8.75(d, J=4.4Hz, 1H), 8.28(d, J=2.0Hz, 1H), 7.97(d, J=7.0Hz, 1H), 7.88(d, J=6.0Hz, 1H), 7.15–7.75(m, 4H), 4.95(d, J=15Hz, 1H), 4.85(d, J=15Hz, 1H), 3.30–3.60(m, 2H), 3.10–3.21(m, 1H), 2.55(s, 3H), 2.05–2.40(m, 2H), 1.30–1.70(m, 2H). |
| 352 | 1-[1-(6-Chloro-pyridin-2-yl)-2-quinolin-4-yl-ethylideneamino]-4-(4-fluoro-phenyl)-pyrrolidin-2-one | $^1$H NMR(CDCl$_3$): δ 8.85(d, J=4.4Hz, 1H), 8.00–8.25(m, 3H), 7.40–7.80(m, 3H), 7.05–7.35(m, 6H), 5.25(d, J=16.6Hz, 1H), 4.75(d, J=16.6Hz, 1H), 3.10–3.45(m, 2H), 2.70–2.95(m, 2H), 2.35–2.55(m, 1H) |
| 353 | (S)-5-Benzyloxymethyl-1-[1-(6-chloro-pyridin-2-yl)-2-quinolin-4-yl-ethylideneamino]-pyrrolidin-2-one | $^1$H NMR(CDCl$_3$): δ 8.68(d, J=4.4Hz, 1H), 8.08(d, J=7.7Hz, 1H), 7.95–8.00(m, 2H), 7.62–7.71(m, 2H), 7.42–7.50(m, 1H), 7.15–7.38(m, 7H), 4.82–4.86(m, 2H), 4.28(s, 2H), 3.42–3.50(m, 1H), 3.05–3.12(m, 2H), 2.32–2.44(m, 1H), 2.08–2.15(m, 1H), 1.45–1.65(m, 2H) |
| 354 | (S)-5-Benzyloxymethyl-1-[2-(7-chloro-quinolin-4-yl)-1-(6-methyl-pyridin-2-yl)-ethylideneamino]-pyrrolidin-2-one | $^1$H NMR(CDCl$_3$): δ 8.77(d, J=4.4Hz, 1H), 8.01–8.11(m, 2H), 7.15–7.88(m, 10H), 4.86(d, J=2.9Hz, 2H), 4.50–4.60(m, 1H), 4.33(d, J=2.9Hz, 2H), 3.70–3.90(m, 2H), 3.45–3.60(m, 2H), 2.47(s, 3H), 2.15–2.42(m, 2H) |
| 355 | 4-{1-[1-(6-Methyl-pyridin-2-yl)-2-quinolin-4-yl-ethylideneamino]-5-oxo-pyrrolidin-3-yl}-benzoic acid ethyl ester | $^1$H NMR(CDCl$_3$): δ 8.76(d, J=4.5Hz, 1H), 8.15(d, J=8.5Hz, 1H), 8.09(d, J=8.3Hz, 1H), 7.97(d, J=7.9Hz, 1H), 7.85(d, J=8.3Hz, 1H), 7.50–7.75(m, 5H), 7.15–7.25(m, 1H), 6.93(d, J=8.3Hz, 2H), 5.24(d, J=16.6Hz, 1H), 4.72(d, J=16.6Hz, 1H), 4.35(q, J=7.1Hz, 2H), 3.35(t, J=8.8Hz, 1H), 3.16(t, J=8.8Hz, 1H), 2.51–2.78(m, 4H), |

-continued

| PREP # | Product (Chemical Name) | Physical Data |
|---|---|---|
| | | 2.32(dd, J=9.2, 17.0Hz, 1H), 1.45–1.55(m, 1H), 1.40(t, J=7.1Hz, 3H). |
| 356 | 1-(Benzhydrylidene-amino)-3-benzyl-pyrrolidin-2-one | MS ES+ m/e 355 (M + 1) |
| 357 | 1-(Benzhydrylidene-amino)-3-ethyl-pyrrolidin-2-one | MS ES+ m/e 293 (M + 1) |

Preparation 358

(R)-5-Benzyloxymethyl-1-[2-(4-fluoro-phenyl)-1-(6-methyl-pyridin-2-yl)-ethylideneamino]-pyrrolidin-2-one Boron trifluoride etherate (0.25 mL, 1.98 mmol) is added to a solution of 2-(4-fluoro-phenyl)-1-(6-methyl-pyridin-2-yl)-ethanone (0.45 g, 1.98 mmol) in tetrahydrofuran (6.6 mL) under nitrogen and stirred for 30 min. A solution of (R)-1-amino-5-benzyloxymethyl-pyrrolidin-2-one (0.43 g, 1.98 mmol) in tetrahydrofuran (1.0 mL) is added and the resulting mixture is stirred for 1 h. The mixture is concentrated in vacuo and the residue chromatographed on a SiO$_2$ column (30% ethyl acetate/hexanes) to yield the title compound, 380 mg (45%), as a yellow foam.

$^1$H NMR (CDCl$_3$): δ 7.81 (d, J=7.8 Hz, 1H), 7.55 (t, J=7.8 Hz, 1H), 7.11–7.32 (m, 8H), 6.81 (td, J=8.7, 2.0 Hz, 2H), 4.45 (s, 2H), 4.30–4.43 (m, 2H), 3.80 (m, 1H), 3.39–3.51 (m, 2H), 2.51–2.63 (m, 4H), 2.23–2.41 (m, 1H), 1.86–2.04 (m, 2H).

Preparation 359

4-(4-Chloro-phenyl)-1-[2-(4-fluoro-phenyl)-1-(6-methyl-pyridin-2-yl)-ethylideneamino]-pyrrolidin-2-one A method similar to PREPARATION 358, except employing 1-amino-4-(4-chloro-phenyl)-pyrrolidin-2-one (1.47 g, 7.0 mmol), is used to yield the title compound, 1.56 g (53%), as a yellow foam.

$^1$H NMR (CDCl$_3$): δ 7.55–7.66 (m, 1H), 7.15–7.45 (m, 7H), 6.89–7.07 (m, 3H), 4.61 (d, J=15.4 Hz, 1H), 4.28 (d, J=15.4 Hz, 1H), 3.54–3.71 (m, 2H), 3.26–3.42 (m, 1H), 2.75–2.89 (m, 1H), 2.58 (s, 3H), 2.46–2.56 (m, 1H).

Preparation 360

(S)-5-Benzyloxymethyl-1-[2-(4-fluoro-phenyl)-1-(6-methyl-pyridin-2-yl)-ethylideneamino]-pyrrolidin-2-one A mixture of (S)-1-amino-5-benzyloxymethyl-pyrrolidin-2-one (0.5 g, 2.27 mmol) and 2-(4-fluoro-phenyl)-1-(6-methyl-pyridin-2-yl)-ethanone (0.52 g, 2.27 mmol) in toluene (2.5 mL) in a round bottom flask equipped with a Dean-Stark apparatus is refluxed for 1 h. The mixture is concentrated in vacuo and the residue chromatographed on SiO$_2$ (40% ethyl acetate/hexanes) to yield the title compound, 500 mg (52%), as a pale yellow oil.

$^1$H NMR (CDCl$_3$): δ 7.81 (d, J=7.8 Hz, 1H), 7.55 (t, J=7.8 Hz, 1H), 7.11–7.32 (m, 8H), 6.81 (td, J=8.7, 2.0 Hz, 2H), 4.45 (s, 2H), 4.30–4.43 (m, 2H), 3.80 (m, 1H), 3.39–3.51 (m, 2H), 2.51–2.63 (m, 4H), 2.23–2.41 (m, 1H), 1.86–2.04 (m, 2H).

Preparation 361

4-(2-Pyridin-2-yl-5,6-dihydro-4H-pyrrolo[1,2-b]pyrazol-3-yl)-7-[3-(pyrimidin-2-ylsulfanyl)-propoxy]-quinoline 7-(3-Chloro-propoxy)-4-(2-pyridin-2-yl-5,6-dihydro-4H-pyrrolo[1,2-b]pyrazol-3-yl)-quinoline (0.060 g, 0.148 mmol), 2-mercaptopyrimidine (0.033 g, 0.296 mmol, 2.0 equiv) and potassium iodide (0.010 g, 0.120 mmol, 0.80 equiv) are combined in N,N-dimethylformamide (1.0 mL) and the reaction is heated at 60° C. for 72 h. The mixture is placed on a 10 g SCX resin column. The resin is washed sequentially with 9:1 dichloromethane: methanol (2×120 mL), 4:1 dichloromethane: methanol (2 N ammonia) (2×125 mL), and methanol (2 N ammonia) (125 mL). The ammonia washes are evaporated to dryness and the residue is subjected to chromatography on silica gel (20 g, 99:1 dichloromethane: methanol (2 N ammonia)) to yield 0.054 g (76%) of the desired product as a tan solid.

MS ES+ m/e 482 (M+1).

By a similar method the following compounds are prepared (unless otherwise specified):

| PREP # | Product Name | Physical Data |
|---|---|---|
| 362 | 7-[3-(1-Methyl-1H-imidazol-2-ylsulfanyl)-propoxy]-4-(2-pyridin-2-yl-5,6-dihydro-4H-pyrrolo[1,2-b]pyrazol-3-yl)-quinoline | MS ES+ m/e 484 (M + 1) |
| 363 | 7-[3-(4-Chloro-phenylsulfanyl)-propoxy]-4-(2-pyridin-2-yl-5,6-dihydro-4H-pyrrolo[1,2-b]pyrazol-3-yl)-quinoline | MS ES+ m/e 514 (M + 1) |

-continued

| PREP # | Product Name | Physical Data |
|---|---|---|
| 364 | 4-(2-Pyridin-2-yl-5,6-dihydro-4H-pyrrolo[1,2-b]pyrazol-3-yl)-7-[3-(4-pyrimidin-2-yl-piperazin-1-yl)-propoxy]-quinoline | MS ES+ m/e 534 (M + 1) |
| 365 | 7-{3-[4-(2-Methoxy-phenyl)-piperazin-1-yl]-propoxy}-4-(2-pyridin-2-yl-5,6-dihydro-4H-pyrrolo[1,2-b]pyrazol-3-yl)-quinoline | MS ES+ m/e 562 (M + 1) |
| 366 | Pyridin-2-yl-{3-[4-(2-pyridin-2-yl-5,6-dihydro-4H-pyrrolo[1,2-b]pyrazol-3-yl)-quinolin-7-yloxy]-propyl}-amine | MS ES+ m/e 463 (M + 1) |
| 367 | 4-(2-Pyridin-2-yl-5,6-dihydro-4H-pyrrolo[1,2-b]pyrazol-3-yl)-7-[3-(pyridin-2-ylmethylsulfanyl)-propoxy]-quinoline | MS ES+ m/e 495 (M + 1) |

Preparation 368

2-(6-Methyl-pyridin-2-yl)-5,6-dihydro-4H-pyrrolo[1,2-b]pyrazole-3-carboxylic acid ethyl ester A solution of (6-methyl-pyridin-2-yl)-propynoic acid ethyl ester (3 g, 15.9 mmol) and 3a H-pyrrolidino[1,2-C]1,2,3-oxadiazolin-3-one (2 g, 15.9 mmol) is heated in xylene (50 mL) at 150° C. for 48 h. The mixture is cooled and concentrated in vacuo. The crude residue is chromatographed on $SiO_2$ (ethyl acetate) to give the title compound, 1.6 g (37%), as a brown solid.

MS ES+ m/e 272 (M+1).

Preparation 369

2-(6-Methyl-pyridin-2-yl)-5,6-dihydro-4H-pyrrolo[1,2-b]pyrazole-3-carboxylic acid A solution of 2-(6-methyl-pyridin-2-yl)-5,6-dihydro-4H-pyrrolo[1,2-b]pyrazole-3-carboxylic acid ethyl ester (1.6 g, 5.9 mmol) and 2 N sodium hydroxide (6 mL, 29 mmol) in absolute ethanol (50 mL) is refluxed for 5 h. The mixture is cooled to room temperature and concentrated in vacuo. The residue is suspended in water and acidified to pH 5 with 1 N hydrochloric acid. The aqueous solution is extracted three times with dichloromethane. The organic extracts are combined, dried (sodium sulfate), filtered, and concentrated in vacuo to yield the title compound, 1.4 g (97%), as a white solid.

MS ES− m/e 242 (M−1).

Preparation 370

3-Bromo-2-(6-methyl-pyridin-2-yl)-5,6-dihydro-4H-pyrrolo[1,2-b]pyrazole

A solution of 2-(6-methyl-pyridin-2-yl)-5,6-dihydro-4H-pyrrolo[1,2-b]pyrazole-3-carboxylic acid (1.4 g, 5.8 mmol) in N,N-dimethylformamide (20 mL) is treated with N-bromosuccinamide (1 g, 5.6 mmol) and stirred at room temperature for 16 h. The mixture is diluted with ethyl acetate and washed three times with water, once with brine, dried (sodium sulfate), filtered, and concentrated in vacuo to yield the title compound, 1.5 g (94%), as light yellow solid.

MS ES+ m/e 278 (M+1).

Preparation 371

4-(2-Pyridin-2-yl-5,6-dihydro-4H-pyrrolo[1,2-b]pyrazol-3-yl)-quinoline-7-carboxylic acid Lithium hydroxide monohydrate (0.65 g, 15.6 mmol) is added to a solution of 4-(2-pyridin-2-yl-5,6-dihydro-4H-pyrrolo[1,2-b]pyrazol-3-yl)-quinoline-7-carboxylic acid methyl ester (1.44 g, 3.89 mmol) in 2:1 tetrahydrofuran/water (30 mL), stirred at room temperature for 18 h, and concentrated in vacuo. The residue is purified by SCX resin, (2 N ammonia in methanol), to yield the title compound, 1.22 g (88%), as a tan solid.

$^1$H NMR (DMSO-d$_6$): δ 8.91 (m, 1H), 8.55 (m, 1H), 7.48–7.85 (m, 7H), 7.41 (m, 1H), 7.09 (m, 1H), 4.22 (m, 2H), 2.81 (m, 2H), 2.60 (m, 2H).

By a similar method the following compounds are prepared (unless otherwise specified):

| PREP # | Product Name | Physical Data |
|---|---|---|
| 372 | 6-(3-Quinolin-4-yl-5,6-dihydro-4H-pyrrolo[1,2-b]pyrazol-2-yl)pyridine-2-carboxylic acid dihydrochloride | MS ES+ m/e 357 (M + 1) |
| 373 | 3-{4-[2-(6-Methyl-pyridin-2-yl)-5,6-dihydro-4H-pyrrolo[1,2-b]pyrazol-3-yl]-quinolin-7-yl}-propionic acid | $^1$H NMR(CDCl$_3$) δ 8.85–8.79(m, 1H), 8.20(s, 1H), 7.75–7.66(m, 1H), 7.35–7.23(m, 3H), 1H), 4.41–4.28(m, 2H), 3.29–3.18(m, 2H), 2.90–2.76(m, 4H), 2.75–2.60(m, 2H), 2.29(s, 3H) |

Preparation 374

(S)-6-Benzyloxymethyl-3-(4-fluoro-phenyl)-2-(6-methyl-pyridin-2-yl)-5,6-dihydro-4H-pyrrolo[1,2-b]pyrazole A method similar to PREPARATION 360, except employing (8)-5-benzyloxymethyl-1-[2-(4-fluoro-phenyl)-1-(6-methyl-pyridin-2-yl)-ethylideneamino]-pyrrolidin-2-one (0.5 g, 1.16 mmol), is used to yield the title compound, 325 mg (68%), as pale brown oil.

$^1$H NMR (CDCl$_3$): δ 7.50 (t, J=8.8 Hz, 1H), 7.17–7.47 (m, 8H), 6.96–7.06 (m, 3H), 4.61 (m, 1H), 4.50 (s, 2H), 3.98 (dd, J=9.8, 3.2 Hz, 1H), 3.87 (dd, J=9.8, 5.6 Hz, 1H), 2.68–3.05 (m, 4H), 2.54 (s, 3H).

MS APCI+ m/e 414 (M+1).

Preparation 375

5-Chloromethyl-2,2-difluoro-benzo[1,3]dioxole

A solution of (2,2-difluoro-benzo[1,3]dioxol-5-yl)-methanol (1.0 g, 5.32 mmol) in carbon tetrachloride (10.6 mL) is added to polymer-supported triphenylphospine (3.5 g, 3 mmol/g, 10.6 mmol) at room temperature. The reaction is heated for 3 h at 80° C., cooled to room temperature, filtered, and the solids washed with dichloromethane. The filtrate is concentrated in vacuo to yield the title compound, 0.79 g (72%), as a clear, orange oil.

MS CI+ m/e 207 (M+1).

By the previous method the following compounds are essentially prepared (unless otherwise specified):

mg, 0.07 mmol) and 4-dimethylaminopyridine (catalytic) in pyridine (0.2 mL) is cooled to 0° C. and treated with methanesulfonyl chloride (8 mL, 0.105 mmol) and stirred for 30 min. The mixture is stirred at room temperature for 30 min, diluted with ethyl acetate (20 mL), washed with water and brine, dried over magnesium sulfate, filtered, and concentrated in vacuo to yield the title compound, 30 mg (86%,) as a yellow oil.

$^1$H NMR (CDCl$_3$): δ 8.90 (d, J=4.0 Hz, 1H), 8.45 (d, J=4.0 Hz, 1H), 8.15 (d, J=8.5 Hz, 1H), 7.55–7.70 (m, 2H), 7.36–7.48 (m, 2H), 7.05–7.30 (m, 3H), 4.80–4.90 (m, 2H), 4.65–4.75 (m, 1H), 2.65–3.05 (m, 7H).

By a similar method the following compounds are prepared (unless otherwise specified):

| PREP # | Product Name | Physical Data |
|---|---|---|
| 379 | (R)-Methanesulfonic acid 3-(benzhydrylidene-hydrazinocarbonyl)-1-benzyloxymethyl-propyl ester | $^1$H NMR(CDCl$_3$): δ 8.63(bs, 1H), 7.22–7.63(m, 15H), 4.95–5.14(m, 1H), 4.52–4.65(m, 2H), 3.68–3.73(m, 2H), 3.00–3.13(m, 5H), 2.05–2.28(m, 2H) |
| 380 | 4-[2-(Benzhydrylidene-hydrazinocarbonyl)-1-methanesulfonyloxymethyl-ethyl] benzoic acid ethyl ester | $^1$H NMR(CDCl$_3$): δ 8.32(s, 1H), 8.02(d, J=8.3Hz, 2H), 7.17–7.57(m, 12H), 4.49(dd, J=6.5, 1.9Hz, 2H), 4.36(q, J=7.1Hz, 2H), 3.67–3.90(m, 1H), 3.31–3.43(m, 2H), 2.86(s, 3H), 1.38(t, J=7.1Hz, 3H) |
| 381 | Methanesulfonic acid 3-(benzhydrylidene-hydrazino carbonyl)-2,2-dimethyl-propyl ester | $^1$H NMR(CDCl$_3$): δ 8.35(bs, 1H), 7.22–7.61(m, 10H), 4.20(s, 2H), 3.01(s, 3H), 2.92(s, 2H), 1.18(s, 6H) |
| 382 | (S)-Methanesulfonic acid 3-(benzhydrylidene-hydrazinocarbonyl)-1-benzyloxymethyl-propyl ester | $^1$H NMR(CDCl$_3$): δ 8.63(bs, 1H), 7.22–7.63(m, 15H), 4.95–5.14(m, 1H), 4.52–4.65(m, 2H), 3.68–3.73(m, 2H), 3.00–3.13(m, 5H), 2.05–2.28(m, 2H) |
| 383 | Methanesulfonic acid 3-(benzhydrylidene-hydrazinocarbonyl)-2-(4-chloro-phenyl)-propyl ester | $^1$H NMR(CDCl$_3$): δ 8.32(bs, 1H), 7.15–7.57(m, 14H), 4.41–4.52(m, 2H), 3.71–3.81(m, 1H), 3.24–3.36(m, 2H), 2.88(s, 3H) |
| 384 | (R)-Methanesulfonic acid 3-(4-fluoro-phenyl)-2-(6-methyl-pyridin-2-yl)-5,6-dihydro-4H-pyrrolo[1,2-b]pyrazol-6-ylmethyl ester | $^1$H NMR(CDCl$_3$): δ 7.40–7.51(m, 1H), 6.92–7.25(m, 6H), 4.58–4.79(m, 3H), 2.81–3.18(m, 6H), 2.61–2.72(m, 1H), 2.54(s, 3H) |
| 385 | Methanesulfonic acid 5-chloro-pentyl ester | $^1$H NMR(DMSO-d$_6$): δ 4.22(m, 2H), 3.53(m, 2H), 2.95(s, 3H), 1.81(m, 4H), 1.55(m, 2H) |
| 386 | Methanesulfonic acid tetrahydro-furan-2-ylmethyl ester | $^1$H NMR(DMSO-d$_6$): δ 4.21(m, 3H), 3.82(m, 2H), 3.05(s, 3H), 1.84–2.05(m, 3H), 1.68(m, 1H) |

| PREP # | Product Name | Physical Data |
|---|---|---|
| 376 | 4-[2-(6-Chloromethyl-pyridin-2-yl)-5,6-dihydro-4H-pyrrolo[1,2-b]pyrazol-3-yl]quinoline | MS ES+ m/e 361 (M + 1). |
| 377 | 3-Chloromethyl-pyrrolidine-1-carboxylic acid benzyl ester | MS CI+ m/e 254 (M + 1) |

Preparation 378

Methanesulfonic acid 2-pyridin-2-yl-3-quinolin-4-yl-5,6-dihydro-4H-pyrrolo[1,2-b]pyrazol-6-ylmethyl ester A solution of [2-(6-methyl-pyridin-2-yl)-3-quinolin-4-yl-5,6-dihydro-4H-pyrrolo[1,2-b]pyrazol-6-yl]-methanol (30

Preparation 387

4-[4-(2-Pyridin-2-yl-5,6-dihydro-4H-pyrrolo[1,2-b]pyrazol-3-yl)-quinolin-7-yloxy]-piperidine-1-carboxylic acid tert-butyl ester To a suspension of 4-(2-pyridin-2-yl-5,6-dihydro-4H-pyrrolo[1,2-b]pyrazol-3-yl)-quinolin-7-ol (0.27 g, 0.84 mmol) in N,N-dimethylformamide (15 mL) is added 4-bromo-piperidine-1-carboxylic acid tert-butyl ester (0.29 mL, 2.28 mmol) and cesium carbonate (1.5 g, 4.57 mmol. The mixture is heated at 80° C. for 48 h and concentrated in vacuo. The residue is taken up in dichloromethane, washed with water and brine, dried over sodium sulfate, and concentrated in vacuo. Purification by flash chromatography (SiO$_2$, 7% methanol in dichloromethane) yields the title compound, 262 mg (61%,) as a yellow oil.

MS ES+ m/e 512 (M+1).

By the previous method the following compounds are essentially prepared (unless otherwise specified):

| PREP # | Product Name | Physical Data |
|---|---|---|
| 388 | 4-[4-(2-Pyridin-2-yl-5,6-dihydro-4H-pyrrolo[1,2-b]pyrazol-3-yl)-quinolin-7-yloxy]-piperidine-1-carboxylic acid tert-butyl ester | MS ES+ m/e 560 (M + 1) |
| 389 | 7-(5-Chloro-pentyloxy)-4-(2-pyridin-2-yl-5,6-dihydro-4H-pyrrolo[1,2-b]pyrazol-3-yl)-quinoline | MS APC+ m/e 433 (M + 1). |
| 390 | 3-[4-(2-Pyridin-2-yl-5,6-dihydro-4H-pyrrolo[1,2-b]pyrazol-3-yl)-quinolin-7-yloxymethyl]-pyrrolidine-1-carboxylic acid benzyl ester | MS APC+ m/e 546 (M + 1) |
| 391 | Dimethyl-{5-[4-(2-pyridin-2-yl-5,6-dihydro-4H-pyrrolo[1,2-b]pyrazol-3-yl)-quinolin-7-yloxy]-pentyl}-amine | mp: 115–118° C. MS APC+ m/e 424 (M + 1) |
| 392 | Methyl-{5-[4-(2-pyridin-2-yl-5,6-dihydro-4H-pyrrolo[1,2-b]pyrazol-3-yl)-quinolin-7-yloxy]-pentyl}-amine | MS APC+ m/e 428 (M + 1) |
| 393 | 1,3-Bis-{3-[4-(2-pyridin-2-yl-5,6-dihydro-4H-pyrrolo[1,2-b]pyrazol-3-yl)-quinolin-7-yloxy]-propyl}-1,3-dihydro-benzoimidazol-2-one | MS APC+ m/e 872 (M + 1) |

Preparation 394

4-(2-Pyridin-2-yl-5,6-dihydro-4H-pyrrolo[1,2-b]pyrazol-3-yl)-quinoline-2-carboxylic acid ethyl ester and 4-(3-Pyridin-2-yl-5,6-dihydro-4H-pyrrolo[1,2-b]pyrazol-2-yl)-quinoline-2-carboxylic acid ethyl ester

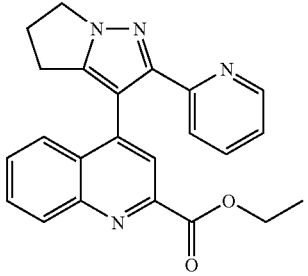

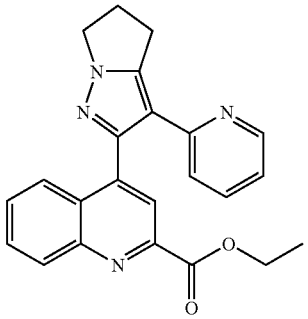

A mixture of 3a H-pyrrolidino[1,2-C]1,2,3-oxadiazolin-3-one (28 mg, 0.22 mmol) and 4-pyridin-2-ylethynyl-quinoline-2-carboxylic acid ethyl ester (0.11 g, 0.33 mmol) in xylene (2.2 mL) is refluxed in an oil bath for 96 h. The solvent is removed in vacuo and the residue chromatographed on SiO$_2$ (0 to 1% methanol in chloroform with 3 drops ammonium hydroxide per 150 mL solvent) to yield 9.1 mg of regioisomer 1 and 28.6 mg of regioisomer 2.

Regioisomer 1: $^1$H NMR (CDCl$_3$) δ: 8.26 (d, 2h), 8.04 (s, 1H), 7.69 (d, 1H), 7.63 (t, 1H), 7.39 (t, 1H), 7.35 (t, 1H), 7.25 (d, 1H), 6.79 (t, 1H), 4.47 (quartet, 2H), 4.31 (t, 2H), 2.82 (m, 2H), 2.65 (quintet, 2H), 1.40 (t, 3H); MS ES$^+$ m/e 385 (M+1).

Regioisomer 2: $^1$H NMR (CDCl$_3$) δ: 8.39 (d, 1H), 8.27 (d, 1H), 8.20 (s, 1H), 7.90 (d, 1H), 7.65 (t, 1H), 7.37 (t, 1H), 7.18 (t, 1H), 6.57 (d, 1H), 4.26 (t, 2H), 3.26 (t, 2H), 2.70 (quintet, 2H), 1.38 (t, 3H); MS ES$^+$ m/e 385 (M+1).

Preparation 395

2-(2-Hydroxyethyl)-3-hydroxymethyl-5-pyridin-2-yl-4-quinolin-4-yl-pyrazole

To a solution of 2-pyridin-2-yl-3-quinolin-4-yl-pyrazolo[5,1-c]morpholin-4-one (0.50 g, 1.46 mmol) in tetrahydrofuran (20 mL) is added LiAlH$_4$ (0.50 g, 13.1 mmol) at room temperature. The mixture is stirred for 2 h quenched with 1 N sodium hydroxide solution, and partitioned between dichloromethane and water. The organic portion is dried (sodium sulfate), filtered, and concentrated in vacuo. The residue is chromatographed on SiO$_2$ (10% methanol/dichloromethane) to yield the title compound, 0.35 g (70%), as an off-white solid.

TOF MS ES+ exact mass calculated for C$_{20}$H$_{19}$N$_4$O$_2$ (p+1): m/z=347.1508. Found: 347.1496.

By the previous method the following compound is essentially prepared (unless otherwise specified):

| PREP # | Product Name | Physical Data |
|---|---|---|
| 396 | (2,2-Difluoro-benzo[1,3]dioxol-5-yl)-methanol | $^1$H NMR(DMSO-d$_6$): δ 7.18(s, 1H), 6.96(s, 2H), 4.61(m, 2H) |

Preparation 397

3-Ethoxycarbonyl-5-pyridin-2-yl-4-quinolin-4-yl-pyrazole

A solution of 2-quinolin-4-yl-1-pyridin-2-yl ethanone (1.00 g, 4.0 mmol) and hydrazine monohydrate (1.0 mL) in ethanol (200 mL) is heated at reflux for 2 h. The mixture is concentrated in vacuo to dryness, the residue dissolved in pyridine (50 mL), cooled to 0° C., and treated with ethyl oxalyl chloride (0.60 mL, 5.4 mmol) dropwise over 20 min. The mixture is warmed to room temperature, stirred for 2 h, and heated at reflux for 3 h. The mixture is concentrated in vacuo and the residue partitioned between dichloromethane and water. The organic portion is dried (sodium sulfate), filtered, and concentrated in vacuo to yield the title compound, 0.6 g (44%,) as a white solid which is crystallized from ether.

$^1$H NMR (CDCl$_3$): δ 12.43 (br s, 1H), 9.02 (d, J=5 Hz, 1H), 8.56 (br s, 1H), 8.32 (d, J=7 Hz, 1H), 7.76 (t, J=7 Hz, 1H), 7.65 (d, J=8 Hz, 1H), 7.46 (m, 2H), 7.33 (br s, 1H), 7.17 (t, J=7 Hz, 1H), 4.11 (m, 1H), 0.90 (t, J=7 Hz, 1H). MS ES$^+$ m/e 345.0 (M+1).

Preparation 398

5-Pyridin-2-yl-4-quinolin-4-yl-2H-pyrazol-3-ol

To a solution of (1-pyridin-2-yl-2-quinolin-4-yl-ethylidene)-hydrazine (2.0 g, 7.6 mmol) in pyridine (20 mL)

at 0° C. is added ethyl chloroformate (2 mL) dropwise. The mixture is warmed to room temperature and stirred for 2 h. The solution is refluxed for 12 h and concentrated in vacuo. The residue is treated with dichloromethane/methanol and the precipitate collected by vacuum filtration. The precipitate is triturated with ethanol to yield the title compound, 300 mg (13%), as a white solid.

MS ES+ m/e 288.9 (M+1).

Preparation 399

[2-Methyl-2-({4-[2-(6-methyl-pyridin-2-yl)-5,6-dihydro-4H-pyrrolo[1,2-b]pyrazol-3-yl]-quinoline-7-carbonyl}-amino)-propyl]-carbamic acid tert-butyl ester To a solution of 4-[2-(6-methyl-pyridin-2-yl)-5,6-dihydro-4H-pyrrolo[1,2-b]pyrazol-3-yl]-quinoline-7-carboxylic acid (0.16 g, 0.43 mmol), (2-amino-2-methyl-propyl)-carbamic acid tert-butyl ester (0.09 g, 0.47 mmol), EDC (0.09 g, 0.47 mmol), 1-hydroxybenzotriazole (0.06 g, 0.47 mmol) in dichloromethane (8.6 mL) is added N,N-diisopropylethylamine (0.25 mL, 1.29 mmol). The mixture is stirred at room temperature for 18 h and concentrated in vacuo. The residue is taken up in ethyl acetate, washed with water and saturated aqueous sodium chloride, dried over sodium sulfate and concentrated in vacuo. The residue is chromatographed on SiO$_2$ (methanol/dichloromethane/2:98) to yield the title compound 0.21 g (91%) as a white solid.

$^1$H NMR (CDCl$_3$) δ 8.93–8.86 (m, 1H), 8.51 (s, 1H), 7.79 (s, 2H), 7.39–7.23 (m, 2H), 7.08–7.00 (m, 1H), 6.93–6.85 (m, 1H), 5.32–5.20 (m, 1H), 4.424.31 (m, 2H), 3.41–3.32 (m, 2H), 2.89–2.78 (m, 2H), 2.75–2.61 (m, 2H), 2.26 (s, 3H), 1.54–1.41 (m, 15H).

By the previous method the following compounds is prepared (unless otherwise specified):

| PREP # | Product Name | Physical Data |
|---|---|---|
| 400 | 6-tert-Butoxycarbonylamino-2-{[4-(2-pyridin-2-yl-5,6-dihydro-4H-pyrrolo[1,2-b]pyrazol-3-yl)-quinoline-7-carbonyl]-amino}-hexanoic acid methyl ester | MS APC+ m/e 599 (M + 1) |

Preparation 401

4-[4-(2-Pyridin-2-yl-5,6-dihydro-4H-pyrrolo[1,2-b] pyrazol-3-yl)-quinolin-7-yloxy]-piperidine-1-carboxylic acid tert-butyl ester To a suspension of 4-(2-pyridin-2-yl-5,6-dihydro-4H-pyrrolo[1,2-b]pyrazol-3-yl)-quinolin-7-ol (0.27 g, 0.84 mmol) in N,N-dimethylformamide (15 mL) is added 4-bromo-piperidine-1-carboxylic acid tert-butyl ester (0.29 mL, 2.28 mmol) and cesium carbonate (1.5 g, 4.57 mmol). The mixture is heated at 80° C. for 48 h and concentrated in vacuo. The residue is taken up in dichloromethane, washed with water and saturated aqueous sodium chloride, dried over sodium sulfate, and concentrated in vacuo. The residue is chromatographed on SiO$_2$ (7% methanol in dichloromethane) to yield the title compound, 262 mg (61%), as a yellow oil.

MS ES+ m/e 512 (M+1).

By the previous method the following compound is prepared (unless otherwise specified):

| PREP # | Product Name | Physical Data |
|---|---|---|
| 402 | 4-[4-(2-Pyridin-2-yl-5,6-dihydro-4H-pyrrolo[1,2-b]-pyrazol-3-yl)-quinolin-7-yloxy]-piperidine-1-carboxylic acid tert-butyl ester | MS ES+ m/e 560 (M + 1) |

Preparation 403

[4-(2-Pyridin-2-yl-5,6-dihydro-4H-pyrrolo[1,2-b] pyrazol-3-yl)-quinolin-7-yloxy]-acetic acid To a solution of [4-(2-pyridin-2-yl-5,6-dihydro-4H-pyrrolo[1,2-b]pyrazol-3-yl)-quinolin-7-yloxy]-acetic acid ethyl ester (250 mg, 0.6 mmol) in methanol (4 mL) at room temperature is added 1 N lithium hydroxide (1.2 mL, 1.2 mmol). The mixture is heated at 60° C. for 4 h. The mixture is cooled to room temperature and concentrated in vacuo. The residue is taken up in water and acidified to pH=6 with 1 N hydrochloric acid. The aqueous solution is extracted with dichloromethane 5 times. The combined organic extracts are dried (sodium sulfate), filtered, and concentrated in vacuo to yield the title compound, 150 mg (65%), as an off white solid. MS ES− m/e 385 (M−1).

Preparation 404

4-(2-Pyridin-2-yl-5,6-dihydro-4H-pyrrolo[1,2-b] pyrazol-3-yl)-7-(tetrahydro-furan-2-ylmethoxy)-quinoline A mixture of methanesulfonic acid tetrahydro-furan-2-ylmethyl ester (0.70 g, 3.66 mmol), 4-(2-pyridin-2-yl-5,6-dihydro-4H-pyrrolo[1,2-b]pyrazol-3-yl)-quinolin-7-ol (400 mg, 1.22 mmol), and cesium carbonate (2.38 g, 7.32 mmol) in N,N-dimethylformamide (2.5 mL) is heated at 60° C. for 42 h. The mixture is concentrated in vacuo and the residue chromatographed to yield the title compound, 79 mg (15%), as a tan solid.

MS APC+ m/e 413 (M+1).

By the previous method the following compounds is prepared. Unless otherwise specified.

| PREP # | Product (Chemical Name) | Physical Data |
|---|---|---|
| 405 | 1,5-Bis-(4-(2-pyridin-2-yl-5,6-dihydro-4H-pyrrolo[1,2-b]pyrazol-3-yl)-quinolin-7-oxy)-pentane | mp: 154–156° C. MS APC+ m/e 725 (M + 1) |

EXAMPLE 1

6-Bromo-4-(2-pyridin-2-3,1-5,6-dihydro-4H-pyrrolo[1,2-b]pyrazol-3-yl)-quinoline

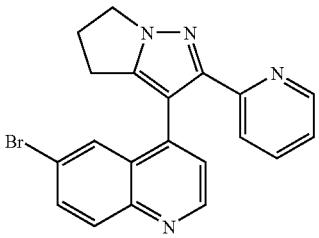

To a suspension of hexane-washed sodium hydride (60% dispersion in mineral oil, 347 mg, 50 mmol) in N,N-dimethylformamide (20 mL) is added 1-[2-(6-bromo-quinolin-4-yl)-1-pyridin-2-yl-ethylideneamino]-pyrrolidin-2-one (2.2 g, 5.37 mmol). The resulting mixture is heated at 80–85° C. under nitrogen atmosphere for 18 h. The reaction is adjusted to pH 2 and neutralized with solid sodium carbonate. The product is extracted with ethyl acetate, dried over sodium sulfate, and concentrated in vacuo. The residue is chromatographed on $SiO_2$ (dichloromethane to 2% methanol/dichloromethane) to yield a colorless solid, 1.145 g (54%).

MS $ES^+$ m/e 391.2 & 393.2 (M+1).

By the above method, the following compounds are prepared (unless otherwise specified):

| EXAMPLE # | Product (Chemical Name) | Physical Data |
|---|---|---|
| 2 | 3-Pyridin-4-yl-2-pyridin-2-yl-5,6-dihydro-4H-pyrrolo[1,2-b]pyrazole | MS $ES^+$ m/e 262.3 (M + 1) |
| 3 | 2-(6-Methyl-pyridin-2-yl)-3-p-tolyl-5,6-dihydro-4H-pyrrolo[1,2-b]pyrazole | TOF MS $ES^+$ exact mass calculated for $C_{19}H_{20}N_3$ (p + 1): m/z = 290.1657 Found: 290.1667 |
| 4 | 4-[3-(6-Methyl-pyridin-2-yl)-5,6-dihydro-4H-pyrrolo[1,2-b]pyrazol-2-yl]-quinoline | TOF MS $ES^+$ exact mass calculated for $C_{21}H_{19}N_4$ (p + 1): m/z = 327.1609. Found: 327.1628 |
| 5 | 2-(6-Methyl]-pyridin-2-yl)-3-naphthalen-1-yl-5,6-dihydro-4H-pyrrolo[1,2-b]pyrazole | TOF MS $ES^+$ exact mass calculated for $C_{22}H_{20}N_3$ (p + 1): m/z = 326.1657. Found: 326.1666 |
| 6 | 2-(6-Methylpyridin-2-yl)-3-pyridin-3-yl-5,6-dihydro-4H-pyrrolo[1,2-b]pyrazole | TOF MS $ES^+$ exact mass calculated for $C_{17}H_{17}N_4$ (p + 1): m/z = 277.1453. Found: 277.1452 |
| 7 | 4-[5-(4-Fluorophenyl)-2-(6-methyl-pyridin 2-yl)-5,6-dihydro-4H-pyrrolo[1,2-b]pyrazol-3-yl]-quinoline | MS $APCI^+$ m/e 421 (M + 1). |
| 8 | 3-(4-Fluor-naphthalen-1-yl)-2-(6-methyl-pyridin-2-yl)-5,6-dihydro-4H-pyrrolo[1,2-b]pyrazole | TOF MS $ES^+$ exact mass calculated for $C_{22}H_{19}FN_3$ (p + 1): m/z = 344.1563. Found: 344.1548 |
| 9 | 3-(3,4-Difluorophenyl)-2-(6-methyl-pyridin-2-yl)-5,6-dihydro-4H-pyrrolo[1,2-b]pyrazole | TOF MS $ES^+$ exact mass calculated for $C_{18}H_{16}F_2N_3$ (p + 1): m/z = 312.1312. Found: 312.1309 |
| 10 | 1-[2-(4-Methanesulfonyl-phenyl)-1-(6-methyl-pyridin-2-yl)-ethylideneamino]-pyrrolidin-2-one | TOF MS $ES^+$ exact mass calculated for $C_{19}H_{20}N_3O_2S$ (p + 1): m/z = 354.1276. Found: 354.1281 |
| 11 | 7-Methoxy-4-(2-pyridin-2-yl-5,6-dihydro-4H-pyrrolo[1,2-b]pyrazol-3-yl)-quinoline | TOF MS $ES^+$ exact mass calculated for $C_{21}H_{19}N_4O$ (p + 1): m/z = 343.1559. Found: 343.1574 |
| 12 | 7-Benzyloxy-6-methoxy-4-(2-pyridin-2-yl-5,6-dihydro-4H-pyrrolo[1,2-b]pyrazol-3-yl)-quinoline | TOF MS $ES^+$ exact mass calculated for $C_{28}H_{25}N_4O_2$ (p + 1): m/z = 449.1978. Found: 449.1994 |
| 13 | 6-(2-Pyridin-2-yl-5,6-dihydro-4H-pyrrolo[1,2-b]pyrazol-3-yl)-quinoline | MS $ES^+$ m/e 313 (M + 1) |
| 14 | 6-[2-(6-Methyl-pyridin-2-yl)-5,6-dihydro-4H-pyrrolo[1,2-b]pyrazol-3-yl]-quinoline | MS $ES^+$ m/e 327 (M + 1) |
| 15 | 3-Naphthalen-2-yl-2-pyridin-2-yl-5,6-dihydro-4H-pyrrolo[1,2-b]pyrazole | MS $ES^+$ m/e 312 (M + 1) |
| 16 | 2-(6-Methyl-pyridin-2-yl)-3-naphthalen-2-yl-5,6-dihydro-4H-pyrrolo[1,2-b]pyrazole | MS $ES^+$ m/e 326 (M + 1) |
| 17 | 3-(4-Fluoro-phenyl)-2-(6-trifluoromethyl-pyridin-2-yl)-5,6-dihydro-4H-pyrrolo[1,2-b]pyrazole | MS $ES^+$ m/e 348 (M + 1) |
| 18 | 4-(Quinolin-4-yl)-3-(5-fluoropyridin-2-yl)-5,6-dihydro-4H-pyrrolo[1,2-b]pyrazole | mp 62–66° C.; MS $ES^+$ m/e 331 (M + 1) |

-continued

| EXAMPLE # | Product (Chemical Name) | Physical Data |
|---|---|---|
| 19 | 4-(7-Bromoquinolin-4-yl)-3-(pyridin-2-yl)-5,6-dihydro-4H-pyrrolo[1,2-b]pyrazole | mp 214–216° C.; MS ES+ m/e 391 (M + 1), 393 (M + 3) |
| 20 | (Quinolin-4-yl)-3-(2,4-difluorophenyl)-5,6-dihydro-4H-pyrrolo[1,2-b]pyrazole | mp 76–83° C.; MS ES+ m/e 348 (M + 1) |
| 21 | 4-(2-Pyrazin-2-yl-5,6-dihydro-4H-pyrrolo[1,2-b]pyrazol-3-yl)-quinoline | MS (CI, methane) m/e 314 (M + 1). |
| 22 | 4-(5-Methyl-2-pyridin-2-yl-5,6-dihydro-4H-pyrrolo[1,2-b]pyrazol-3-yl)-quinoline | MS APCI+ m/e 327 (M + 1) |
| 23 | 6-Bromo-4-[2-(6-methyl-pyridin-2-yl)-5,6-dihydro-4H-pyrrolo[1,2-b]pyrazol-3-yl]-quinoline | MS APCI+ m/e 405/407 (M + 1). |
| 24 | 4-[2-(6-Methyl-pyridin-2-yl)-5,6-dihydro-4H-pyrrolo[1,2-b]pyrazol-3-yl]-6-trifluoromethyl-quinoline | MS APCI+ m/e 395 (M + 1) |
| 25 | 3-(3-Chloro-4-fluoro-phenyl)-2-(6-methyl-pyridin-2-yl)-5,6-dihydro-4H-pyrrolo[1,2-b]pyrazole | MS (CI, methane) 328 (M + 1) |
| 26 | 3-(2-Chloro-4-fluoro-phenyl)-2-(6-methyl-pyridin-2-yl)-5,6-dihydro-4H-pyrrolo[1,2-b]pyrazole | MS (CI, methane) 328 (M + 1) |
| 27 | 3-(4-Fluoro-3-trifluoromethyl-phenyl)-2-(6-methyl-pyridin-2-yl)-5,6-dihydro-4H-pyrrolo[1,2-b]pyrazole | MS (CI, methane) 362 (M + 1) |
| 28 | 2-(6-Methyl-pyridin-2-yl)-3-(2,4,5-trifluoro-phenyl)-5,6-dihydro-4H-pyrrolo[1,2-b]pyrazole | MS (CI, methane) 330 (M + 1) |
| 29 | 8-Fluoro-4-[2-(6-methyl-pyridin-2-yl)-5,6-dihydro-4H-pyrrolo[1,2-b]pyrazol-3-yl]-quinoline | MS APCI+ m/e 345 (M + 1) |
| 30 | 7-Bromo-4-[2-(6-methyl-pyridin-2-yl)-5,6-dihydro-4H-pyrrolo[1,2-b]pyrazol-3-yl]-quinoline | MS APCI+ m/e 405/407 (M + 1) |
| 31 | 4-[2-(6-Methyl-pyridin-2-yl)-5,6-dihydro-4H-pyrrolo[1,2-b]pyrazol-3-yl]-6-trifluoromethoxy-quinoline | MS APCI+ m/e 411 (M + 1) |
| 32 | 4-[2-(6-Methyl-pyridin-2-yl)-5,6-dihydro-4H-pyrrolo[1,2-b]pyrazol-3-yl]-7-trifluoromethyl-quinoline | MS APCI+ m/e 395 (M + 1) |
| 33 | 7-Methoxy-4-[2-(6-methyl-pyridin-2-yl)-5,6-dihydro-4H-pyrrolo[1,2-b]pyrazol-3-yl]-quinoline | MS APCI+ m/e 357 (M + 1) |
| 34 | 3-(2-Chloro-pyridin-4-yl)-2-pyridin-2-yl-5,6-dihydro-4H-pyrrolo[1,2-b]pyrazole | MS APCI+ m/e 297 (M + 1) |
| 35 | [2-(6-Methyl-pyridin-2-yl)-3-quinolin-4-yl-5,6-dihydro-4H-pyrrolo[1,2-b]pyrazol-6-yl]-methanol | MS APCI+ m/e 357 (M + 1) |
| 36 | [3-(7-Bromo-quinolin-4-yl)-2-(6-methyl-pyridin-2-yl)-5,6-dihydro-4H-pyrrolo[1,2-b]pyrazol-6-yl]-methanol | MS APCI+ m/e 435/437 (M + 1) |
| 37 | 4-[2-(6-Chloro-pyridin-2-yl)-5-(4-fluorophenyl)-5,6-dihydro-4H-pyrrolo[1,2-b]pyrazol-3-yl]-quinoline | MS APCI+ m/e 441 (M + 1) |
| 38 | 4-[2-(6-Ethoxy-pyridin-2-yl)-5-(4-fluoro-phenyl)-5,6-dihydro-4H-pyrrolo[1,2-b]pyrazol-3-yl]-quinoline | MS APCI+ m/e 451 (M + 1) |
| 39 | (S)-4-[6-Benzyloxymethyl-2-(6-methyl-pyridin-2-yl)-5,6-dihydro-4H-pyrrolo[1,2-b]pyrazol-3-yl]-7-chloro-quinoline | MS APCI+ m/e 481 (M + 1). |
| 40 | (S)-4-[6-Benzyloxymethyl-2-(6-chloro-pyridin-2-yl)-5,6-dihydro-4H-pyrrolo[1,2-b]pyrazol-3-yl]-quinoline | MS APCI+ m/e 467 (M + 1). |
| 41 | 4-[2-(6-Methyl-pyridin-2-yl)-3-quinolin-4-yl-5,6-dihydro-4H-pyrrolo[1,2-b]pyrazol-5-yl]-benzoic acid ethyl ester | MS APCI+ m/e 475 (M + 1). |
| 42 | 3-(4-Fluoro-phenyl)-5,5-dimethyl-2-(6-methyl-pyridin-2-yl)-5,6-dihydro-4H-pyrrolo[1,2-b]pyrazole | MS APCI+ m/e 322 (M + 1). mp: 117–118° C. |
| 43 | (R)-6-Benzyloxymethyl-3-(4-fluoro-phenyl)-2-(6-methyl-pyridin-2-yl)-5,6-dihydro-4H-pyrrolo[1,2-b]pyrazole | MS APCI+ m/e 414 (M + 1). |
| 44 | 5-(4-Chloro-phenyl)-3-(4-fluoro-phenyl)-2-(6-methyl-pyridin-2-yl)-5,6-dihydro-4H-pyrrolo[1,2-b]pyrazole | MS APCI+ m/e 404 (M + 1). |

-continued

| EXAMPLE # | Product (Chemical Name) | Physical Data |
|---|---|---|
| 45 | 4-[2-(3-Trifluoromethyl-phenyl)-4,5,6,7-tetrahydro-pyrazolo[1,5-a]pyridin-3-yl]-quinoline | MS APCI$^+$ m/e 394 (M + 1). |
| 46 | 4-[2-(4-Trifluoromethyl-phenyl)-4,5,6,7-tetrahydro-pyrazolo[1,5-a]pyridin-3-yl]-quinoline | MS APCI+ m/e 394 (M + 1) |
| 47 | 4-[2-(4-Chlorophenyl)-4,5,6,7-tetrahydro-pyrazolo[1,5-a]pyridin-3-yl]-quinoline | MS APCI$^+$ m/e 360 (M + 1) |
| 48 | 4-[2-(3-Chlorophenyl)-4,5,6,7-tetrahydro-pyrazolo[1,5-alpyridin-3-y]-quinoline | MS APCI$^+$ m/e 360 (M + 1) |
| 49 | 4-[2-(3-Fluoro-5-trifluoromethyl-phenyl)-5,6-dihydro-4H-pyrrolo[1,2-b]pyrazol-3-yl]-quinoline | MS APCI$^+$ m/e 398 (M + 1) |
| 50 | 4-[2-(3-Fluoro-5-trifluoromethyl-phenyl)-4,5,6,7-tetrahydro-pyrazolo[1,5-a]pyridin-3-yl]-quinoline | MS APCI$^+$ m/e 412 (M + 1) |
| 51 | 4-(2-Phenyl-4,5,6,7-tetrahydro-pyrazolo[1,5-a]pyridin-3-yl)-quinoline | MS APCI$^+$ m/e 326 (M + 1) |
| 52 | 4-(2-Pyridin-2-yl-4,5,6,7-tetrahydro-pyrazolo[1,5-a]pyridin-3-yl)-[1,10]phenanthroline | MS APCI$^+$ m/e 378 (M + 1) |
| 53 | 4-[2-(4-Fluoro-phenyl)-4,5,6,7-tetrahydro-pyrazolo[1,5-a]pyridin-3-yl]-quinoline | MS APCI$^+$ m/e 344 (M + 1) |
| 54 | 4-[2-(3-Trifluoromethoxy-phenyl)-4,5,6,7-tetrahydro-pyrazolo[1,5-a]pyridin-3-yl]-quinoline | MS APCI$^+$ m/e 410 (M + 1) |
| 55 | 4-[2-(2-Fluoro-phenyl)-4,5,6,7-tetrahydro-pyrazolo[1,5-a]pyridin-3-yl]-quinoline | APCI$^+$ m/e 344 (M + 1) |
| 56 | 4-(2-Quinolin-2-yl-4,5,6,7-tetrahydro-pyrazolo[1,5-a]pyridin-3-yl)-quinoline | MS APCI$^+$ m/e 377 (M + 1) |
| 57 | 4-[2-(4-Ethyl-pyridin-2-yl)-4,5,6,7-tetrahydro-pyrazolo[1,5-a]pyridin-3-yl]-quinoline | MS APCI$^+$ m/e 355 (M + 1) |
| 58 | 4-(2-Quinolin-2-yl-5,6-dihydro-4H-pyrrolo[1,2-b]pyrazol-3-yl)-quinoline | MS APCI$^+$ m/e 363 (M + 1) |
| 59 | 2-(3-Quinolin-4-yl-4,5,6,7-tetrahydro-pyrazolo[1,5-a]pyridin-2-yl)-[1,8]naphthyridine | MS APCI$^+$ m/e 378 (M + 1) |
| 60 | 4-[5-(4-Fluoro-phenyl)-2-pyridin-2-yl-5,6-dihydro-4H-pyrrolo[1,2-b]pyrazol-3-yl]-quinoline | MS APCI$^+$ m/e 407 (M + 1) |
| 61 | 4-(6-Hydroxymethyl-2-pyridin-2-yl-5,6-dihydro-4H-pyrrolo[1,2-b]pyrazol-3yl)-quinoline | MS APCI$^+$ m/e 343 (M + 1) |
| 62 | 4-(3-Pyridin-2-yl-5,6-dihydro-4H-pyrrolo[1,2-b]pyrazol-2-yl)-quinoline | MS ES$^+$ m/e 313 (M + 1) |
| 63 | 4-(4-Methyl-2-pyridin-2-yl-5,6-dihydro-4H-pyrrolo[1,2-b]pyrazol-3-yl)-quinoline | MS ES$^+$ m/e 327 (M + 1) |
| 64 | 4-(5-Benzyl-2-pyridin-2-yl-5,6-dihydro-4H-pyrrolo[1,2-b]pyrazol-3-yl)-quinoline | MS APCI$^+$ m/e 403 (M + 1) |
| 65 | 4-(5-Phenethyl-2-pyridin-2-yl-5,6-dihydro-4H-pyrrolo[1,2-b]pyrazol-3-yl)-quinoline | MS APCI$^+$ m/e 417.4 (M + 1) |
| 66 | 4-(5-Phenyl-2-pyridin-2-yl-5,6-dihydro-4Hpyrrob[1,2-b]pyrazol-3-yl)-quinoline | MS APCI$^+$ m/e 399 (M + 1) |
| 67 | 4-[2-(3-Trifluoromethylphenyl)-5,6-dihydro-4H-pyrrolo[1,2-b]pyrazol-3-yl]-quinoline | MS APCI$^+$ m/e 380 (M + 1) |
| 68 | 4-[2-(4-Trifluoromethyl-phenyl)-5,6-dihydro-4H-pyrrolo[1,2-b]pyrazol-3-yl]-quinoline | MS APCI$^+$ m/e 380 (M + 1) |
| 69 | 4-(2-Phenyl-5,6-dihydro-4H-pyrrolo[1,2-b]pyrazol-3-yl)-quinoline | MS APCI$^+$ m/e 312 (M + 1) |
| 70 | 2-Chloro-4-(2-pyridin-2-yl-5,6-dihydro-4H-pyrrolo[1,2-b]pyrazol-3-yl)-quinoline | MS APCI$^+$ m/e 347 (M + 1) |
| 71 | 6,8-Dimethoxy-4-[2-(6-methyl-pyridin-2-yl)-5,6-dihydro-4H-pyrrolo[1,2b]pyrazol-3-yl]-quinoline | MS APCI$^+$ m/e 387 (M + 1) |
| 72 | 4-[2-(6-Bromo-pyridin-2-yl)-5,6-dihydro-4H-pyrrolo[1,2-b]pyrazol-3-yl]-quinoline | MS calcd. 391; MS (M + 1) 391,393 |
| 73 | 6,8-Dimethoxy-4-[2-pyridin-2-yl-5,6-dihydro-4H-pyrrolo[1,2b]pyrazol-3-yl]-quinoline | MS APCI$^+$ m/e 373 (M + 1) |
| 74 | 3-(4-Fluorophenyl)-2-pyridin-2-yl-5,6-dihydro-4H-pyrrolo[1,2-b]pyrazole | MS ES$^+$ m/e 280.1 (M + 1). |
| 75 | 3-(4-Methoxy-phenyl)-2-pyridin-2-yl-5,6-dihydro-4H-pyrrolo[1,2-b]pyrazole | TOF MS ES$^+$ exact mass calculated for $C_{18}H_{18}N_3O$ |

-continued

| EXAMPLE # | Product (Chemical Name) | Physical Data |
|---|---|---|
| 76 | 3-(4-Fluorophenyl)-2-(6-methylpyridin-2-yl)-5,6-dihydro-4H-pyrrolo[1,2-b]pyrazole | (p + 1): m/z 292.1450. Found: 292.1466. TOF MS ES$^+$ exact mass calculated for $C_{18}H_{17}N_3F$ (p + 1): m/z 294.1407. Found: 294.1416. |
| 77 | 3-(4-Methoxyphenyl)-2-(6-methylpyridin-2-yl)-5,6-dihydro-4H-pyrrolo[1,2-b]pyrazole | TOF MS ES$^+$ exact mass calculated for $C_{19}H_{20}N_{3O}$ (p + 1): m/z 306.1606. Found: 306.1584. |
| 78 | 4-(2-Thiophen-2-yl-5,6-dihydro-4H-pyrrolo[1,2-b]pyrazol-3-yl)quinoline | TOF MS ES$^+$ exact mass calculated for $C_{19}H_{16}N_3S$ (p + 1): m/z = 318.1065 Found: 318.1051 |
| 79 | 4-[2-(6-Propylpyridin-2-yl)-5,6-dihydro-4H-pyrrolo[1,2-b]pyrazol-3-yl]-quinoline | TOF MS ES$^+$ exact mass calculated for $C_{23}H_{23}N_4$ (p + 1): m/z 355.1923 Found: 355.1909 |
| 80 | 4-[2-(6-Isopropylpyridin-2-yl)-5,6-dihydro-4H-pyrrolo[1,2-b]pyrazol-3-yl]quinoline | TOF MS ES$^+$ exact mass calculated for $C_{23}H_{23}N_4$ (p + 1): m/z 355.1923 Found: 355.1912 |
| 81 | 4-[2-(6-Ethyl-pyridin-2-yl)-5,6-dihydro-4H-pyrrolo[1,2-b]pyrazol-3-yl]quinoline | TOF MS ES$^+$ exact mass calculated for $C_{22}H_{21}N_4$ (p + 1): m/z 341.1766 Found: 341.1766 |
| 82 | 4-[2-(6-Methyl-pyridin-2-yl)-5,6-dihydro-4H-pyrrolo[1,2-b]pyrazol-3-yl]-quinoline | MS ES$^+$ m/e 327 (M + 1) |
| 83 | 4-[2-(3-Fluorophenyl)-5,6-dihydro-4H-pyrrolo[1,2-b]pyrazol-3-yl]-quinoline | MS APCI$^+$ m/e 330 (M + 1) |
| 84 | 4-[2-(2-Fluoro-phenyl)-5,6-dihydro-4H-pyrrolo[1,2-b]pyrazol-3-yl]-quinoline | MS APCI$^+$ m/e 330 (M + 1) |
| 85 | 4-[2-(4-Fluoro-phenyl)-5,6-dihydro-4H-pyrrolo[1,2-b]pyrazol-3-yl]-quinoline | MS APCI$^+$ m/e 330 (M + 1) |
| 86 | 4-[2-(3-Trifluoromethoxy-phenyl)-5,6-dihydro-4H-pyrrolo[1,2-b]pyrazol-3-yl]-quinoline | MS APCI$^+$ m/e 396 (M + 1) |
| 87 | 4-[2-(4-Chloro-pyridin-2-yl)-5,6-dihydro-4H-pyrrolo[1,2-b]pyrazol-3-yl]-quinoline | MS APCI$^+$ m/e 347 (M + 1) |
| 88 | 4-[2-(4-Fluoro-3-trifluoromethyl-phenyl)-5,6-dihydro-4H-pyrrolo[1,2-b]pyrazol-3-yl]quinoline | MS APCI$^+$ m/e 398.3 (M + 1) |
| 89 | 4-[2-(2-Fluoro-3-trifluoromethyl-phenyl)-5,6-dihydro-4H-pyrrolo[1,2-b]-pyrazol-3-yl]-quinoline | MS APCI$^+$ m/e 398.1 (M + 1) |
| 90 | 4-[5-(3-Methoxy-phenyl)-2-pyridin-2-yl-5,6-dihydro-4H-pyrrolo[1,2-b]pyrazol-3-yl]-quinoline | MS APCI$^+$ m/e 419 (M + 1) |
| 91 | 4-[2-(4-Fluoro-3-trifluoromethyl-phenyl)-5-(3-methoxy-phenyl)-5,6-dihydro-4H-pyrrolo[1,2-b]pyrazol-3-yl]-quinoline | MS APCI$^+$ m/e 504 (M + 1) |
| 92 | 3-(7-Chloro-quinolin-4-yl)-2-(6-methylpyridin-2-yl)-5,6-dihydro-4H-pyrrolo[1,2-b]pyrazole | mp 178–182° C. MS ES$^+$ m/e 361 (M + 1) |
| 93 | 3-(7-Ethoxyquinolin-4-yl)-2-(6-methylpyridin-2-yl)-5,6-dihydro-4H-pyrrolo[1,2-b]pyrazole | mp 164–166° C. MS ES$^+$ m/e 371 (M + 1), 372 (M + 2) |
| 94 | 6-(3-Quinolin-4-yl-5,6-dihydro-4H-pyrrolo[1,2-b]pyrazol-2-yl)-pyridine-2-carboxylic acid hydrochloride | $^1$H NMR(DMSO-d$_6$) δ: 2.65 (quintet, 2H), 2.89(m, 2H), 4.33(t, 2H), 7.59(t, 2H), 7.72(d, 1H), 7.84(d, 1H), 7.85–8.00(m, 2H), 8.06(d, 1H), 8.22(m, 1H), 8.40(d, 1H), 9.11(d, 1H) |
| 95 | 6,7-Difluoro-4-[2-(6-methyl-pyridin-2-yl)-5,6-dihydro-4H-pyrrolo[1,2-b]pyrazol-3-yl]-quinoline | ESIMS m/e 363 (M ++ 1) |
| 96 | 6,7-Dimethoxy-4-[2-(6-methyl-pyridin-2-yl)-5,6-dihydro-4H-pyrrolo[1,2-b]pyrazol-3-yl]-quinoline | MS ES$^+$ m/e 387 (M + 1) |

-continued

| EXAMPLE # | Product (Chemical Name) | Physical Data |
|---|---|---|
| 97 | 4-[2-(6-Ch,6-dihydro-4H-pyrrolo loro-pyridin-2-yl)-5[1,2-b]pyrazol-3-yl]-quinoline | MS Calcd. 346; MS (APCI) (M + 1) 347 |
| 98 | 6-(3-Quinolin-4-yl-5,6-dihydro-4H-pyrrolo[1,2-b]pyrazol-2-yl)pyridine-2-carboxylic acid methyl ester | MS ES+ m/e 371 (M + 1) |
| 99 | 4-(7-Chloroquinolin-4-yl)-3-(pyridin-2-yl)-5,6-dihydro-4H-pyrrolo[1,2-b]pyrazole | mp 208–211° C. C,68.67; H, 4.55; N, 15.50; Found: C, 68.96; H, 4.30; N, 15.28 |
| 100 | (4-(2-Furan-2-yl-5,6-dihydro-4H-pyrrolo[1,2-b]pyrazol-3-yl)-quinoline | TOF MS exact mass calculated for $C_{19}H_{16}N_{3}O$ (p + 1): m/z = 302.1293 Found: 302.1312 |
| 101 | 3-{4-[2-(6-Methyl-pyridin-2-yl)-5,6-dihydro-4H-pyrrolo[1,2-b]pyrazol-3-yl]-quinolin-6-yl}-acrylic acid methyl ester | MS APCI+ m/e 411 (M + 1) |
| 102 | 4-[2-(2-Methyl-thiazol-4-yl)-5,6-dihydro-4H-pyrrolo[1,2-b]pyrazol-3-yl]-quinoline | ES MS 333.4 (M + 1) |
| 103 | 3-(4-Fluoro-phenyl)-2-(2-methyl-thiazol-4-yl)-5,6-dihydro-4H-pyrrolo[1,2-b]pyrazole | MS (ES) m/e 300.4 (M + 1) |
| 104 | 4-[2-(2-Methyl-2H-pyrazol-3-yl)-5,6-dihydro-4H-pyrrolo[1,2-b]pyrazol-3-yl]-quinoline | MS (ES) m/e 316.4 (M+) |
| 105 | 4-(2-thiazol-2-yl-5,6-dihydro-4H-pyrrolo[1,2-b]pyrazol-3-yl)-quinoline | MS (ES) m/e 319 (M+) |
| 106 | 4-[2-(1-methyl-1H-imidazol-2-yl)-5,6-dihydro-4H-pyrrolo[1,2-b]pyrazol-3-yl]-quinoline | MS (ES) m/e 316 (M+) |
| 107 | 6,7-Dichloro-4-[2-(6-methyl-pyridin-2-yl)-5,6-dihydro-4H-pyrrolo[1,2-b]pyrazol-3-yl]-quinoline | MS ES+ m/e 395 (M + 1) |
| 108 | (S)-6-Benzyloxymethyl-3-(4-fluoro-phenyl)-2-(6-methyl-pyridin-2-yl)-5,6-dihydro-4H-pyrrolo[1,2-b]pyrazole | MS CI+ m/e 414 (M + 1) |

EXAMPLE 109

3-Benzo[1,3]dioxol-5-yl-2-(6-methyl-pyridin-2-yl)-5,6-dihydro-4H-pyrrolo[1,2-b]pyrazole

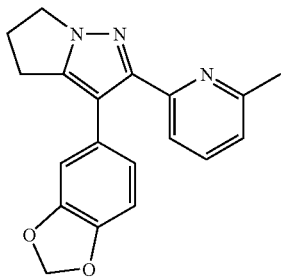

A mixture of 3-bromo-2-(6-methyl-pyridin-2-yl)-5,6-dihydro-4H-pyrrolo[1,2-b]pyrazole (99 mg, 0.36 mmol), 3,4-methylenedioxyphenylboronic acid (65 mg, 0.39 mmol), (PPh$_3$)$_4$Pd (20 mg, 0.02 mmol), 1 N aqueous sodium carbonate solution (500 μL, 0.5 mmol) in toluene (5 mL) and methanol (1 mL) is purged with argon for 10 min and heated at 80° C. under nitrogen for 30 h. The mixture is cooled and partitioned between water and ethyl acetate, and the organic portion washed with water and brine, dried (sodium sulfate), filtered, and concentrated in vacuo. The crude residue is chromatographed on SiO$_2$ (ethyl acetate) to yield the title compound, 10 mg (9%), as a yellow solid.

MS ES+ m/e 320 (M+1).

By the above method the following compounds are prepared (unless otherwise specified):

| EXAMPLE # | Product (Chemical Name) | Physical Data |
|---|---|---|
| 110 | 6-(4-Fluoro-phenyl)-4-[2-(6-methyl-pyridin-2-yl)-5,6-dihydro-4H-pyrrolo[1,2-b]pyrazol-3-yl]-quinoline | MS APCI+ m/e 421 (M + 1) |
| 111 | 6-Benzo[1,3]dioxol-5-yl-4-[2-(6-methyl-pyridin-2-yl)-5,6-dihydro-4H-pyrrolo[1,2-b]pyrazol-3-yl]-quinoline | MS APCI+ m/e 447 (M + 1) |

-continued

| EXAMPLE # | Product (Chemical Name) | Physical Data |
|---|---|---|
| 112 | 4-[2-(6-Methyl-pyridin-2-yl)-5,6-dihydro-4H-pyrrolo[1,2-b]pyrazol-3-yl]-6-thiophen-2-yl-quinoline | MS APCI+ m/e 409 (M + 1) |
| 113 | 4-[2-(6-Methyl-pyridin-2-yl)-5,6-dihydro-4H-pyrrolo[1,2-b]pyrazol-3-yl]-6-phenyl-quinoline | MS APCI+ m/e 403 (M + 1) |
| 114 | 8-[2-(6-Methyl-pyridin-2-yl)-5,6-dihydro-4H-pyrrolo[1,2-b]pyrazol-3-yl]-quinoline | MS (ES) m/e 327 (M+) |
| 115 | 3-Benzo[b]thiophen-2-yl-2-(6-methyl-pyridin-2-yl)-5,6-dihydro-4H-pyrrolo[1,2-b]pyrazole | MS (ES) m/e 332 (M+) |

EXAMPLE 116

4-(2-Pyridin-2-yl-5,6-dihydro-4H-pyrrolo[1,2-b]pyrazol-3-yl)-quinoline-6-carboxylic acid methyl ester

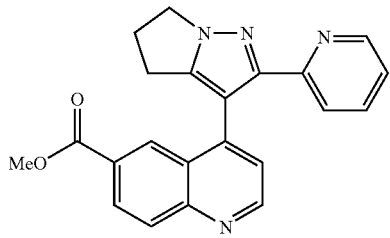

To a mixture of sodium acetate (0.84 g, 10.2 mmol) and [1,1'-bis(diphenylphosphino)ferrocene]dichloropalladium (II):CH₂Cl₂ (42 mg, 0.05 mmol) in methanol (40 mL) is added 6-bromo-4-(2-pyridin-2-yl-5,6-dihydro-4H-pyrrolo[1,2-b]pyrazol-3-yl)-quinoline (1.0 g, 2.56 mmol). The mixture is heated at 90° C. under 68 psi carbon monoxide for 24 h. The mixture is cooled, filtered, and concentrated in vacuo. The product is partitioned between ethyl acetate and: water. The organic layer is dried over sodium sulfate and concentrated in vacuo. The residue is chromatographed on SiO₂ (dichloromethane to 2% methanol/dichloromethane) to yield a solid, 918 mg (97%).

MS ES⁺ m/e 371.2 (M+1).

By the above method, the following compounds are prepared (unless otherwise specified):

EXAMPLE 120

2-Pyridin-2-yl-3-quinolin-4-yl-pyrazolo[5,1-c]morpholine

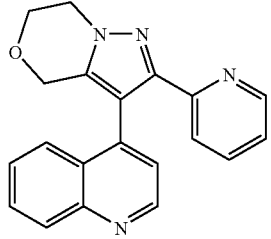

To a solution of 2-(2-hydroxyethyl)-3-hydroxymethyl-5-pyridin-2-yl-4-quinoline-4-yl-pyrazole, (0.10 g, 0.29 mmol) in tetrahydrofuran (10 mL) cooled at 0° C. is added NaH (0.04 g, 50% in mineral oil). The mixture is stirred for 2 h at room temperature and methanesulfonyl chloride (0.065 g, 0.57 mmol) is added dropwise over 30 min. The reaction is quenched with water and extracted into ethyl acetate. The organic layer is washed with water, dried (sodium sulfate), filtered, and concentrated in vacuo. The residue is chromatographed on SiO₂ (10% methanol/dichloromethane) to yield the title compound, 31 mg (33%), as a white solid.

TOF MS ES⁺ exact mass calculated for $C_{20}H_{16}N_4O$ (p+1): m/z=329.1402. Found: 329.1409.

| EXAMPLE # | Product (Chemical Name) | Physical Data |
|---|---|---|
| 117 | 4-[2-(6-Methyl-pyridin-2-yl)-5,6-dihydro-4H-pyrrolo[1,2-b]pyrazol-3-yl]-quinoline-6-carboxylic acid methyl ester | MS APCI⁺ m/e 385 (M + 1) |
| 118 | 4-[2-(6-Methyl-pyridin-2-yl)-5,6-dihydro-4H-pyrrolo[1,2-b]pyrazol-3-yl]-quinoline-7-carboxylic acid methyl ester | MS APCI⁺ m/e 385 (M + 1) |
| 119 | 4-[2-Pyridin-2-yl-5,6-dihydro-4H-pyrrolo[1,2-b]pyrazol-3-yl]-quinoline-7-carboxylic acid methyl ester | MS APCI⁺ m/e 371 (M + 1) |

EXAMPLE 121

2-Pyridin-2-yl-3-quinolin-4-yl-pyrazolo[5,1-c]morpholin-4-one

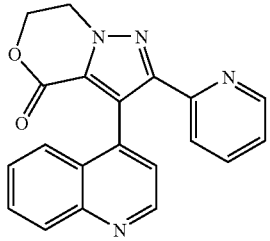

A mixture of 3-ethoxycarbonyl-5-pyridin-2-yl-4-quinolin-4-yl-pyrazole (0.35 g, 1.00 mmol), 2-bromoethanol (0.15 g, 1.12 mmol), and cesium carbonate (0.50 g, 1.5 mmol) in N,N-dimethylformamide (20 mL) is heated at 60° C. for 2 h. The mixture is cooled to room temperature and poured into ethyl acetate (60 mL). The organic portion is washed with water, dried (sodium sulfate), filtered, and concentrated in vacuo. The residue is chromatographed on $SiO_2$ (ethyl acetate/hexane) to yield the title compound, 110 mg (32%).

TOF MS ES+ exact mass calculated for $C_{20}H_{15}N_4O_2$ (p+1): m/z=343.1195. Found: 343.1179.

EXAMPLE 122

5 Dimethyl-{3-[4-(2-pyridin-2-yl-5,6-dihydro-4H-pyrrolo[1,2-b]pyrazol-3-yl)-quinolin-7-yloxy]-propyl}-amine

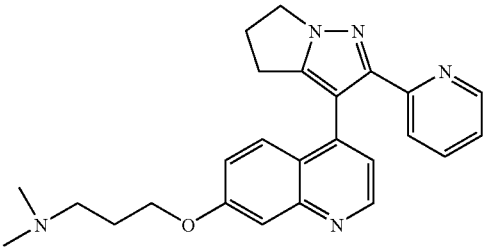

A solution of 7-(3-chloro-propoxy)-4-(2-pyridin-2-yl-5,6-dihydro-4H-pyrrolo[1,2-b]pyrazol-3-yl)-quinoline (54 mg, 0.13 mmol), sodium iodide (5 mg, 0.03 mmol), and 2 N dimethylamine in tetrahydrofuran (3 mL, 6 mmol) in N,N-dimethylformamide (5 mL) is heated at 100° C. for 48 h. The mixture is cooled and concentrated in vacuo. The residue is chromatographed on $SiO_2$ (100% ethyl acetate to 10% methanol in ethyl acetate) to yield the title compound, 41 mg (74%), as a brown solid.

TOF MS ES+ exact mass calculated for $C_{25}H_{28}N_5O$ (p+1): m/z=414.2294. Found: 414.2313.

By the above method the following compounds are prepared (unless otherwise specified):

| EXAMPLE # | Product (Chemical Name) | Physical Data |
|---|---|---|
| 123 | {3-[6-Methoxy-4-(2-pyridin-2-yl-5,6-dihydro-4H-pyrrolo[1,2-b]pyrazol-3-yl)-quinolin-7-yloxy]-propyl}-dimethyl-amine | TOF MS ES+ exact mass calculated for $C_{26}H_{30}N_5O_2$ (p + 1): m/z = 444.2399 Found: 444.2391 |
| 124 | Cyclopropylmethyl-propyl-{3-[4-(2-pyridin-2-yl-5,6-dihydro-4H-pyrrolo[1,2-b]pyrazol-3-yl)-quinolin-7-yloxy]-propyl}-amine | TOF MS ES+ exact mass calculated for $C_{30}H_{36}N_5O$ (p + 1): m/z = 482.2920 Found: 482.2934 |
| 125 | Diethyl-{3-[4-(2-pyridin-2-yl-5,6-dihydro-4H-pyrrolo[1,2-b]pyrazol-3-yl)-quinolin-7-yloxy]-propyl}-amine | TOF MS ES+ exact mass calculated for $C_{37}H_{32}N_5O$ (p + 1): m/z = 442.2607 Found: 442.2609 |
| 126 | Ethyl-methyl-{3-[4-(2-pyridin-2-yl-5,6-dihydro-4H-pyrrolo[1,2-b]pyrazol-3-yl)-quinolin-7-yloxy]-propyl}-amine | TOF MS ES+ exact mass calculated for $C_{26}H_{30}N_5O$ (p + 1): m/z = 428.2450 Found: 428.2470 |
| 127 | 3-[4-(2-Pyridin-2-yl-5,6-dihydro-4H-pyrrolo[1,2-b]pyrazol-3-yl)-quinolin-7-yloxy]-propylamine | TOF MS ES+ exact mass calculated for $C_{23}H_{24}N_5O$ (p + 1): m/z = 386.1981 Found: 386.1994 |
| 128 | 7-[3-(4-Methyl-piperazin-1-yl)-propoxy]-4-(2-pyridin-2-yl-5,6-dihydro-4H-pyrrolo[1,2-b]pyrazol-3-yl)-quinoline | TOF MS ES+ exact mass calculated for $C_{28}H_{33}N_6O$ (p + 1): m/z = 469.2716 Found: 469.2735 |
| 129 | Benzyl-methyl-{3-[4-(2-pyridin-2-yl-5,6-dihydro-4H-pyrrolo[1,2-b]pyrazol-3-yl)-quinolin-7-yloxy]-propyl}-amine | TOF MS ES+ exact mass calculated for $C_{31}H_{32}N_5O$ (p + 1): m/z = 490.2607 Found: 490.2629 |
| 130 | 7-(3-Piperidin-1-yl-propoxy)-4-(2-pyridin-2-yl-5,6-dihydro-4H-pyrrolo[1,2-b]pyrazol-3- | TOF MS ES+ exact mass calculated for $C_{28}H_{32}N_5O$ |

| EXAMPLE # | Product (Chemical Name) | Physical Data |
|---|---|---|
| | yl)-quinoline | (p + 1)<br>m/z = 454.2607<br>Found: 454.2602 |
| 131 | 4-(2-Pyridin-2-yl-5,6-dihydro-4H-pyrrolo[1,2-b]pyrazol-3-yl)-7-(3-pyrrolidin-1-yl-propoxy)-quinoline | TOF MS ES+ exact mass calculated for $C_{27}H_{30}N_5O$ (p + 1):<br>m/z = 440.2450<br>Found: 440.2468 |
| 132 | 7-(3-Azepan-1-yl-propoxy)-4-(2-pyridin-2-yl-5,6-dihydro-4H-pyrrolo[1,2-b]pyrazol-3-yl)-quinoline | TOF MS ES+ exact mass calculated for $C_{29}H_{34}N_5O$ (p + 1):<br>m/z = 468.2763<br>Found: 468.2762 |
| 133 | 7-(3-Imidazol-1-yl-propoxy)-4-(2-pyridin-2-yl-5,6-dihydro-4H-pyrrolo[1,2-b]pyrazol-3-yl)-quinoline | TOF MS ES+ exact mass calculated for $C_{26}H_{25}N_6O$ (p + 1):<br>m/z = 437.2090<br>Found: 437.2096 |
| 134 | 7-(3-Pyrazol-1-yl-propoxy)-4-(2-pyridin-2-yl-5,6-dihydro-4H-pyrrolo[1,2-b]pyrazol-3-yl)-quinoline | MS ES+ m/e 437 (M + 1) |
| 135 | 1'-{3-[4-(2-Pyridin-2-yl-5,6-dihydro-4H-pyrrolo[1,2-b]pyrazol-3-yl)-quinolin-7-yloxy]-propyl}-[1,4']bipiperidinyl | TOF MS ES+ exact mass calculated for $C_{33}H_{41}N_6O$ (p + 1):<br>m/z = 537.3342<br>Found: 537.3321 |
| 136 | Cyclopropyl-(1-methyl-piperidin-4-yl)-{3-[4-(2-pyridin-2-yl-5,6-dihydro-4H-pyrrolo[1,2-b]pyrazol-3-yl)-quinolin-7-yloxy]-propyl}-amine | MS ES+ m/e 523 (M + 1) |
| 137 | 4-(2-Pyridin-2-yl-5,6-dihydro-4H-pyrrolo[1,2-b]pyrazol-3-yl)-7-(3-[1,2,3]triazol-1-yl-propoxy)-quinoline | MS ES+ m/e 438 (M + 1) |
| 138 | Dimethyl-(3-{4-[2-(6-methyl-pyridin-2-yl)-5,6-dihydro-4H-pyrrolo[1,2-b]pyrazol-3-yl]-quinolin-7-yloxy}-propyl)-amine | TOF MS ES+ exact mass calculated for $C_{26}H_{30}N_5O$ (p + 1):<br>m/z = 428.2450<br>Found: 428.2464 |
| 139 | Diethyl-(3-{4-[2-(6-methyl-pyridin-2-yl)-5,6-dihydro-4H-pyrrolo[1,2-b]pyrazol-3-yl]-quinolin-7-yloxy}-propyl)-amine | TOF MS ES+ exact mass calculated for $C_{28}H_{34}N_5O$ (p + 1):<br>m/z = 456.2763<br>Found: 456.2785 |
| 140 | Cyclopropylmethyl-(3-{4-[2-(6-methyl-pyridin-2-yl)-5,6-dihydro-4H-pyrrolo[1,2-b]pyrazol-3-yl]-quinolin-7-yloxy}-propyl)-propyl-amine | TOF MS ES+ exact mass calculated for $C_{31}H_{38}N_5O$ (p + 1):<br>m/z = 496.3076<br>Found: 496.3094 |
| 141 | Ethyl-methyl-(3-{4-[2-(6-methyl-pyridin-2-yl)-5,6-dihydro-4H-pyrrolo[1,2-b]pyrazol-3-yl]-quinolin-7-yloxy}-propyl)-amine | TOF MS ES+ exact mass calculated for $C_{27}H_{32}N_5O$ (p + 1):<br>m/z = 442.2607<br>Found: 442.2615 |
| 142 | Dimethyl-{2-[4-(2-pyridin-2-yl-5,6-dihydro-4H-pyrrolo[1,2-b]pyrazol-3-yl)-quinolin-7-yloxy]-ethyl}-amine | MS ES+ m/e 400 (M + 1) |
| 143 | Diethyl-{2-[4-(2-pyridin-2-yl-5,6-dihydro-4H-pyrrolo[1,2-b]pyrazol-3-yl)-quinolin-7-yloxy]-ethyl}-amine | MS ES+ m/e 428 (M + 1) |
| 144 | 7-(2-Piperidin-1-yl-ethoxy)-4-(2-pyridin-2-yl-5,6-dihydro-4H-pyrrolo[1,2-b]pyrazol-3-yl)-quinoline | MS ES+ m/e 440 (M + 1) |
| 145 | Ethyl-methyl-{2-[4-(2-pyridin-2-yl-5,6-dihydro-4H-pyrrolo[1,2-b]pyrazol-3-yl)-quinolin-7-yloxy]ethyl}-amine | MS ES+ m/e 414 (M + 1) |
| 146 | 4-(2-Pyridin-2-yl-5,6-dihydro-4H-pyrrolo[1,2-b]pyrazol-3-yl)-7-(2-pyrrolidin-1-yl-ethoxy)-quinoline | MS ES+ m/e 426 (M + 1) |
| 147 | 7-[2-(4-Methyl-piperazin-1-yl)-ethoxy]-4-(2-pyridin-2-yl-5,6-dihydro-4H-pyrrolo[1,2-b]pyrazol-3-yl)-quinoline | MS ES+ m/e 455 (M + 1) |
| 148 | Dimethyl-{3-[1-oxy-4-(2-pyridin-2-yl-5,6-dihydro-4H-pyrrolo[1,2-b]pyrazol-3-yl)-quinolin-7-yloxy]-propyl}-amine | MS ES+ m/e 430 (M + 1) |

-continued

| EXAMPLE # | Product (Chemical Name) | Physical Data |
|---|---|---|
| 149 | 7-Methylsulfanyl-4-(2-pyridin-2-yl-5,6-dihydro-4H-pyrrolo[1,2-b]pyrazol-3-yl)-quinoline | MS ES+ m/e 359.1 (M + 1) |
| 150 | 7-Ethylsulfanyl-4-(2-pyridin-2-yl-5,6-dihydro-4H-pyrrolo[1,2-b]pyrazol-3-yl)-quinoline | MS ES+ m/e 373.2 (M + 1) |
| 151 | 6-Methylsulfanyl-4-(2-pyridin-2-yl-5,6-dihydro-4H-pyrrolo[1,2-b]pyrazol-3-yl)-quinoline | MS ES+ m/e 359.1 (M + 1) |
| 152 | 7-Benzylsulfanyl-4-(2-pyridin-2-yl-5,6-dihydro-4H-pyrrolo[1,2-b]pyrazol-3-yl)-quinoline | MS ES+ m/e 435.4 (M + 1) |
| 153 | 3-[4-(2-Pyridin-2-yl-5,6-dihydro-4H-pyrrolo[1,2-b]pyrazol-3-yl)-quinolin-7-ylsulfanyl]-propan-1-ol | MS ES+ m/e 403.1 (M + 1) |
| 154 | Dimethyl-{2-[4-(2-pyridin-2-yl-5,6-dihydro-4H-pyrrolo[1,2-b]pyrazol-3-yl)-quinolin-7-ylsulfanyl]-ethyl}-amine | MS ES+ m/e 416.2 (M + 1) |
| 155 | Dimethyl[6-(3-quinolin-4-yl-5,6-dihydro-4H-pyrrolo[1,2-b]pyrazol-2-yl)-pyridin-2-yl-methyl]amine | MS ES+ m/e 370 (M + 1) |
| 156 | 7-(2-Propoxy-ethoxy)-4-(2-pyridin-2-yl-5,6-dihydro-4H-pyrrolo[1,2-b]pyrazol-3-yl)-quinoline | MS ES+ m/e 415 (M + 1) |
| 157 | N,N-Dimethyl-N'-[4-(2-pyridin-2-yl-5,6-dihydro-4H-pyrrolo[1,2-b]pyrazol-3-yl)-pyridin-2-yl]-ethane-1,2-diamine | MS APC+ m/e 349 (M + 1) |
| 158 | N,N-Dimethyl-N'-[4-(2-pyridin-2-yl-5,6-dihydro-4H-pyrrolo[1,2-b]pyrazol-3-yl)-pyridin-2-yl]-propane-1,3-diamine | MS CI+ m/e 363 (M + 1) |
| 159 | 3-{3-[4-(2-Pyridin-2-yl-5,6-dihydro-4H-pyrrolo[1,2-b]pyrazol-3-yl)-quinolin-7-yloxy]-propyl}-oxazolidin-2-one | MS APC+ m/e 456 (M + 1) |
| 160 | 1-{3-[4-(2-Pyridin-2-yl-5,6-dihydro-4H-pyrrolo[1,2-b]pyrazol-3-yl)-quinolin-7-yloxy]-propyl}-imidazolidin-2-one | MS APC+ m/e 455 (M + 1) |
| 161 | 3-{3-[4-(2-Pyridin-2-yl-5,6-dihydro-4H-pyrrolo[1,2-b]pyrazol-3-yl)-quinolin-7-yloxy]-propyl}-3H-benzooxazol-2-one | MS APC+ m/e 504 (M + 1) |
| 162 | Dimethyl-(2-{4-[2-(6-methyl-pyridin-2-yl)-5,6-dihydro-4H-pyrrolo[1,2-b]pyrazol-3-yl]-pyridin-2-ylsulfanyl}-ethyl-amine | MS APCI+ m/e 366 (M + 1). |
| 163 | 4-(2-Pyridin-2-yl-5,6-dihydro-4H pyrrolo[1,2-b]pyrazol-3-yl)-2pyrrolidin-1-yl-quinoline | MS APCI+ m/e 382 (M + 1) |
| 164 | 2-Phenylsulfanyl-4-(2-pyridin-2-yl-5,6-dihydro-4H-pyrrolo[1,2-b]pyrazol-3-yl)-quinoline | MS APCI+ m/e 421 (M + 1) |
| 165 | 2-Morpholin-4-yl-4-(2-pyridin-2-yl-5,6-dihydro-4H-pyrrolo[1,2-b]pyrazol-3-yl)-quinoline | MS APCI+ m/e 398 (M + 1) |
| 166 | 2-Ethylsulfanyl-4-(2-pyridin-2-yl-5,6-dihydro-4H-pyrrolo[1,2-b]pyrazol-3-yl)-quinoline | MS APCI+ m/e 373 (M + 1) |
| 167 | Phenyl-[4-(2-pyridin-2-yl-5,6-dihydro-4H-pyrrolo[1,2-b]pyrazol-3-yl)-quinolin-2-yl]-amine | MS APCI+ m/e 404 (M + 1) |
| 168 | 2-Methoxy-4-(2-pyridin-2-yl-5,6-dihydro-4H-pyrrolo[1,2-b]pyrazol-3-yl)-quinoline | MS APCI+ m/e 344 (M + 1) |
| 169 | 2-Ethoxy-4-(2-pyridin-2-yl-5,6-dihydro-4H-pyrrolo[1,2-b]pyrazol-3-yl)-quinoline | MS APCI+ m/e 357 (M + 1) |
| 170 | 4-[2-(6-Phenylsulfanyl-pyridin-2-yl)-5,6-dihydro-4H-pyrrolo[1,2-b]pyrazol-3-yl]-quinoline | MS APCI+ m/e APCI+ m/e 421 (M + 1) |
| 171 | Phenyl-[6-(3-quinolin-4-yl-5,6-dihydro-4H-pyrrolo[1,2-b]pyrazol-2-yl)-pyridin-2-yl]-amine | MS CI+ m/e 404 (M + 1) |
| 172 | 4-{2-[6-(4-Methoxy-phenyl)-pyridin-2-yl]-5,6-dihydro-4H-pyrrolo[1,2-b]pyrazol-3-yl}-quinoline | MS APCI+ m/e 419 (M + 1) |
| 173 | 4-[2-(6-Phenyl-pyridin-2-yl)-5,6-dihydro-4H-pyrrolo[1,2-b]pyrazol-3-yl]-quinoline | MS APCI+ m/e 389 (M + 1) |
| 174 | 4-[2-(6-Morpholin-4-yl-pyridin-2-yl)-5,6-dihydro-4H-pyrrolo[1,2-b]pyrazol-3-yl]-quinoline | MS APCI+ m/e 398 (M + 1) |

-continued

| EXAMPLE # | Product (Chemical Name) | Physical Data |
|---|---|---|
| 175 | 4-[2-(6-Pyrrolidin-1-yl-pyridin-2-yl)-5,6-dihydro-4H-pyrrolo[1,2-b]pyrazol-3-yl]-quinoline | MS APCI$^+$ m/e 382 (M + 1) |
| 176 | 4-[2-(6-Methoxy-pyridin-2-yl)-5,6-dihydro-4H-pyrrolo[1,2-b]pyrazol-3-yl]-quinoline | MS APCI$^+$ m/e 343 (M + 1) |
| 177 | 7-Benzyloxy-4-[2-(6-methyl-pyridin-2-yl)-5,6-dihydro-4H-pyrrolo[1,2-b]pyrazol-3-yl]-quinoline | MS CI$^+$ m/e 433 (M + 1) |

EXAMPLE 178

2-{3-[4-(2-Pyridin-2-yl-5,6-dihydro-4H-pyrrolo[1,2-b]pyrazol-3-yl)-quinolin-7-yloxy]-propyl}-isoindole-1,3-dione

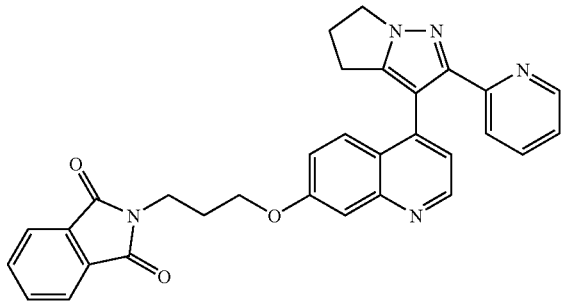

4-(2-Pyridin-2-yl-5,6-dihydro-4H-pyrrolo[1,2-b]pyrazol-3-yl)-quinolin-7-ol (0.100 g, 0.305 mmol), N-(3-bromopropyl)-phthalimide (0.163 g, 0.609 mmol, 2.0 equiv) and cesium carbonate (0.248 g, 0.761 mmol, 2.50 equiv) are combined in N,N-dimethylformamide (1.0 mL) and the reaction is heated at 60° C. for 48 hours. The reaction is diluted with water (1 mL) and the reaction mixture is partitioned between ethyl acetate (6 mL) and water (5 mL). The organic layer is removed and placed on a 10 g SCX resin column. The resin is washed sequentially with dichloromethane (20 mL) and 4:1 dichloromethane/2 N ammonia in methanol (125 mL). The latter fractions are evaporated to dryness and the residue is subjected to chromatography on silica gel (20 g) (9:1 ethyl acetate: methanol (2 N ammonia)) to yield the desired product as a tan solid, 0.117 g (75%).

MS ES$^+$ m/e 516 (M+1).

By the above method the following compounds are prepared (unless otherwise specified:

| EXAMPLE # | Product (Chemical Name) | Physical Data |
|---|---|---|
| 179 | 7-(3-Fluoro-propoxy)-4-(2-pyridin-2-yl-5,6-dihydro-4H-pyrrolo[1,2-b]pyrazol-3-yl)-quinoline | MS ES$^+$ m/e 389 (M + 1) |
| 180 | 7-(3-Chloro-propoxy)-4-(2-pyridin-2-yl-5,6-dihydro-4H-pyrrolo[1,2-b]pyrazol-3-yl)-quinoline | TOF MS ES$^+$ exact mass calculated for $C_{23}H_{22}ClN_4O$ (p + 1): m/z = 405.1482. Found: 405.1483. |
| 181 | 7-(3-Chloro-propoxy)-6-methoxy-4-(2-pyridin-2-yl-5,6-dihydro-4H-pyrrolo[1,2-b]pyrazol-3-yl)-quinoline | TOF MS ES$^+$ exact mass calculated for $C_{24}H_{24}ClN_4O_2$ (p + 1): m/z = 435.1588. Found: 435.1595. |
| 182 | 7-(3-Chloro-propoxy)-4-[2-(6-methyl-pyridin-2-yl)-5,6-dihydro-4H-pyrrolo[1,2-b]pyrazol-3-yl]-quinoline | MS ES$^+$ m/e 419 (M + 1) |
| 183 | (1-{3-[7-(2-Chloro-ethoxy)-quinolin-4-yl]-5,6-dihydro-4H-pyrrolo[1,2-b]pyrazol-2-yl}-propenyl)-methylene-amine | TOF MS ES$^+$ exact mass calculated for $C_{22}H_{20}ClN_4O$ (p + 1): m/z = 391.1325. Found: 391.1339. |
| 184 | N,N-Diethyl-2-[4-(2-pyridin-2-yl-5,6-dihydro-4H-pyrrolo[1,2-b]pyrazol-3-yl)-quinolin-7-yloxy]-acetamide | TOF MS ES$^+$ exact mass calculated for $C_{26}H_{28}N_5O_2$ (p + 1): m/z = 442.2243. Found: 442.2251. |
| 185 | 7-[2-((2R)-1-Methyl-pyrrolidin-2-yl)-ethoxy]-4-(2-pyridin-2-yl-5,6-dihydro-4H-pyrrolo[1,2-b]pyrazol-3-yl)-quinoline | MS APC$^+$ m/e 440 (M + 1) |
| 186 | Dimethyl-{4-[4-(2-pyridin-2-yl-5,6-dihydro-4H-pyrrolo[1,2-b]pyrazol-3-yl)-pyridin-2-yloxy]-butyl}-amine | MS CI$^+$ m/e 378 (M + 1) |

-continued

| EXAMPLE # | Product (Chemical Name) | Physical Data |
|---|---|---|
| 187 | 1-{3-[4-(2-Pyridin-2-yl-5,6-dihydro-4H-pyrrolo[1,2-b]pyrazol-3-yl)-pyridin-2-yloxy]-propyl}-pyrrolidin-2-one | MS APC+ m/e 404 (M + 1) |
| 188 | 7-(1-Methyl-piperidin-3-ylmethoxy)-4-(2-pyridin-2-yl-5,6-dihydro-4H-pyrrolo[1,2-b]pyrazol-3-yl)-quinoline | MS CI+ m/e 440 (M + 1) |
| 189 | 7-(3-N,N-Dimethylamino-2-methyl-propyloxy)-4-(2-pyridin-2-yl-5,6-dihydro-4H-pyrrolo[1,2-b]pyrazol-3-yl)-quinoline | MS APC+ m/e 428 (M + 1) |
| 190 | 4-[2-(6-Methyl-pyridin-2-yl)-5,6-dihydro-4H-pyrrolo[1,2-b]pyrazol-3-yl]-7-propoxy-quinoline | MS APCI+ m/e 385 (M + 1) |
| 191 | 4-[6-Benzyloxymethyl-2-(6-methyl-pyridin-2-yl)-5,6-dihydro-4H-pyrrolo[1,2-b]pyrazol-3-yl]-quinoline | MS CI+ m/e 447 (M + 1). |
| 192 | {4-[2-(6-Methyl-pyridin-2-yl)-5,6-dihydro-4H-pyrrolo[1,2-b]pyrazol-3-yl]-quinolin-7-yloxy}-acetic acid methyl ester | MS APCI+ m/e 415 (M + 1). |
| 193 | 7-Isopropoxy-4-[2-(6-methyl-pyridin-2-yl)-5,6-dihydro-4H-pyrrolo[1,2-b]pyrazol-3-yl]-quinoline | MS APCI+ m/e 385 (M + 1) |
| 194 | 4-[2-(6-Methyl-pyridin-2-yl)-5,6-dihydro-4H-pyrrolo[1,2-b]pyrazol-3-yl]-7-(3-morpholin-4-yl-propoxy)-quinoline | MS APCI+ m/e 470 (M + 1) |
| 195 | 4-(6-Benzyloxymethyl-2-pyridin-2-yl-5,6-dihydro-4H-pyrrolo[1,2-b]pyrazol-6-yl)-quinoline | MS ES+ m/e 433.7 (M + 1) |
| 196 | 7-Benzyloxy-2-Pyridin-2-yl-3-quinolin-4-yl-pyrazolo[1,5-a]piperidine | TOF MS ES+ exact mass calculated for $C_{28}H_{25}N_4O$ (p + 1): m/z = 433.2028 Found: 433.2008 |
| 197 | 2-[4-(2-pyridin-2-yl-5,6-dihydro-4H-pyrrolo[1,2-b]pyrazol-3-yl)-quinolin-7-yloxy]-acetamide | TOF MS ES+ exact mass calculated for $C_{22}H_{20}N_5O_2$ (p + 1): m/z = 444.2399 Found: 444.2391 |
| 198 | 7-(5-Phenyl-[1,2,4]oxadiazol-3-ylmethoxy)-4-(2-pyridin-2-yl-5,6-dihydro-4H-pyrrolo[1,2-b]pyrazol-3-yl)-quinoline | MS APC+ m/e 487 (M + 1) |
| 199 | 7-(2,2-Difluoro-benzo[1,3]dioxol-5-ylmethoxy)-4-(2-pyridin-2-yl-5,6-dihydro-4H-pyrrolo[1,2-b]pyrazol-3-yl)-quinoline | mp: 185–187° C. MS APC+ m/e 410 (M + 1) |
| 200 | 7-[2-((2S)-1-Methyl-pyrrolidin-2-yl)-ethoxy]-4-(2-pyridin-2-yl-5,6-dihydro-4H-pyrrolo[1,2-b]pyrazol-3-yl)-quinoline | MS APC+ m/e 440 (M + 1) |

EXAMPLE 201

5-[4-(2-Pyridin-2-yl-5,6-dihydro-4H-pyrrolo[1,2-b]pyrazol-3-yl)-quinolin-7-yloxymethyl]-pyrrolidin-2-one

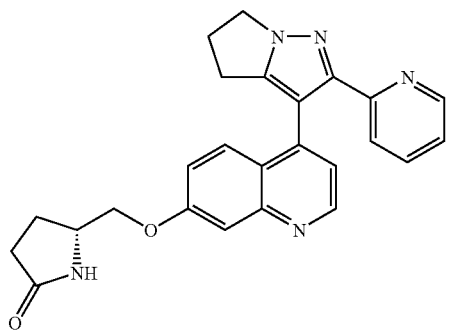

A solution of (R)-(−)-5-(hydroxymethyl)-2-pyrrolidinone (315 mg, 2.74 mmol) in N,N-dimethylformamide (3 mL) is treated with methansulfonyl chloride (320 mg, 2.74 mmol) and heated at 60° C. for 5 h. The reaction mixture is diluted with N,N-dimethylformamide (1 mL) and 4-(2-pyridin-2-yl-5,6-dihydro-4H-pyrrolo[1,2-b]pyrazol-3-yl)-quinolin-7-ol (200 mg, 0.91 mmol) added. The mixture is stirred at 60° C. for additional 16 h, cooled to room temperature, and partitioned between ethyl acetate and water. The organic portion is washed three times with water, once with brine, dried (sodium sulfate), filtered and concentrated in vacuo. The crude residue is chromatographed on $SiO_2$ (89% dichloromethane 10% methanol 1% concentrated ammonium hydroxide) to yield the title compound, 32 mg (8%), as a light red solid.

MS ES+ m/e 426 (M+1).

By the above method the following compounds are prepared (unless otherwise specified):

| EXAMPLE # | Product (Chemical Name) | Physical Data |
|---|---|---|
| 202 | 4-(6-Phenoxymethyl-2-pyridin-2-yl-5,6-dihydro-4H-pyrrolo[1,2-b]pyrazol-3-yl)-quinoline | MS CI$^+$ m/e 419 (M + 1) |
| 203 | 4-(6-Methylene-2-pyridin-2-yl-5,6-dihydro-4H-pyrrolo[1,2-b]pyrazol-3-yl)-quinoline | MS CI+ m/e 325 (M + 1) |
| 204 | 3-(4-Fluoro-phenyl)-6-methylene-2-(6-methyl-pyridin-2-yl)-5,6-dihydro-4H-pyrrolo[1,2-b]pyrazole | MS APCI$^+$ m/e 306 (M + 1) |
| 205 | 7-(1-Methyl-piperidin-2-ylmethoxy)-4-(2-pyridin-2-yl-5,6-dihydro-4H-pyrrolo[1,2-b]pyrazol-3-yl)-quinoline hydrochloride | MS ES$^+$ m/e 441 (M + 1) |
| 206 | 7-[2-(1-Methyl-pyrrolidin-2-yl)-ethoxy]-4-(2-pyridin-2-yl-5,6-dihydro-4H-pyrrolo[1,2-b]pyrazol-3-yl)-quinoline hydrochloride | MS ES$^+$ m/e 441 (M + 1) |

EXAMPLE 207

4-[2-(6-Methyl-1-oxy-pyridin-2-yl)-5,6-dihydro-4H-pyrrolo[1,2-b]pyrazol-3-yl]quinoline 1-oxide

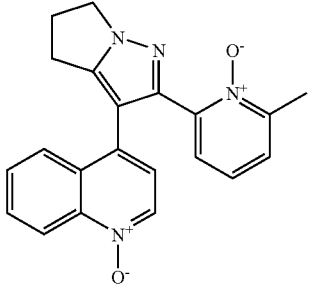

To a solution of 4-[2-(6-methyl-pyridin-2-yl)-5,6-dihydro-4H-pyrrolo[1,2-b]pyrazol-3-yl]-quinoline (133 mg, 0.41 mmol) in dichloromethane is added m-chloroperoxybenzoic acid (248 mg, 1.44 mmol) and the resulting mixture stirred for 3 h. The mixture is diluted with dichloromethane and washed twice with saturated aqueous sodium bicarbonate solution, once with brine, dried (sodium sulfate), filtered and concentrated in vacuo to yield the title compound, 140 mg (96%), as white foam.

TOF MS ES$^+$ exact mass calculated for $C_{21}H_{19}N_4O_2$ (p+1): m/z=359.1508. Found: 359.1516.

By the above method the following compounds are essentially prepared: (unless otherwise specified)

| EXAMPLE # | Product (Chemical Name) | Physical Data |
|---|---|---|
| 208 | 4-[2-(6-Methyl-pyridin-2-yl)-5,6-dihydro-4H-pyrrolo[1,2-b]pyrazol-3-yl]-quinoline 1-oxide | TOF MS ES$^+$ exact mass calculated for $C_{21}H_{19}N_4O$ (p + 1): m/z = 343.1559 Found: 343.1566 |
| 209 | 4-[2-(6-Methyl-1-oxy-pyridin-2-yl)-5,6-dihydro-4H-pyrrolo[1,2-b]pyrazol-3-yl]-quinoline | TOF MS ES$^+$ exact mass calculated for $C_{21}H_{19}N_4O$ (p + 1): m/z = 343.1559 Found: 343.1564 |
| 210 | 7-(3-Chloro-propoxy)-4-(2-pyridin-2-yl-5,6-dihydro-4H-pyrrolo[1,2-b]pyrazol-3-yl)-quinoline 1-oxide | MS ES$^+$ m/e 421 (M + 1) |
| 211 | 7-Methanesulfonyl-4-(2-pyridin-2-yl-5,6-dihydro-4H-pyrrolo[1,2-b]pyrazol-3-yl)-quinoline | MS ES$^+$ m/e 391.1 (M + 1) |
| 212 | 3-(4-Fluoro-phenyl)-2-(6-methyl-1-oxy-pyridin-2-yl)-5,6-dihydro-4H-pyrrolo[1,2-b]pyrazole | MS ES$^+$ m/e 310 (M + 1) |
| 213 | 4-(Quinolin-N-1-oxide-4-yl)-3-(6-methylpyridin-2-yl)-5,6-dihydro-4H-pyrrolo[1,2-b]pyrazole | mp: 235–238° C.; MS ES$^+$ m/e 377 (M + 1) |
| 214 | 6-Methanesulfonyl-4-(2-pyridin-2-yl-5,6-dihydro-4H-pyrrolo[1,2-b]pyrazol-3-yl)-quinoline | MS ES$^+$ m/e 391.1 (M + 1) |

-continued

| EXAMPLE # | Product (Chemical Name) | Physical Data |
|---|---|---|
| 215 | 7-Ethanesulfonyl-4-(2-pyridin-2-yl-5,6-dihydro-4H-pyrrolo[1,2-b]pyrazol-3-yl)-quinoline | MS ES+ m/e 405.4 (M + 1) |
| 216 | 4-(2-Pyridin-2-yl-5,6-dihydro-4H-pyrrolo[1,2-b]pyrazol-3-yl)-7-[3-(pyrimidine-2-sulfonyl)-propoxy]-quinoline | MS ES+ m/e 514 (M + 1) |
| 217 | 7-[3-(1-Methyl-1H-imidazole-2-sulfonyl)-propoxy]-4-(2-pyridin-2-yl-5,6-dihydro-4H-pyrrolo[1,2-b]pyrazol-3-yl)-quinoline | MS ES+ m/e 516 (M + 1) |
| 218 | 7-[3-(4-Chloro-benzenesulfonyl)-propoxy]-4-(2-pyridin-2-yl-5,6-dihydro-4H-pyrrolo[1,2-b]pyrazol-3-yl)-quinoline | MS ES+ m/e 546 (M + 1) |
| 219 | 4-(2-Pyridin-2-yl-5,6-dihydro-4H-pyrrolo[1,2-b]pyrazol-3-yl)-7-[3-(pyridin-2-ylmethanesulfonyl)-propoxy]-quinoline | MS ES+ m/e 527 (M + 1) |
| 220 | 4-(2-Pyridin-2-yl-5,6-dihydro-4H-pyrrolo[1,2-b]pyrazol-3-yl)-7-[3-(pyridin-2-ylmethanesulfinyl)-propoxy]-quinoline | MS ES+ m/e 511 (M + 1) |
| 221 | 4-(Quinolin-1-N-oxide-4-yl)-3-(6-methylpyridin-2-yl-1-N-oxide)-5,6-dihydro-4H-pyrrolo[1,2-b]pyrazole | mp: 240–242° C.; MS ES+ m/e 393 (M + 1) |
| 222 | 4-(2-Pyridin-2-yl-5,6-dihydro-4H-pyrrolo[1,2-b]pyrazol-3-yl)-quinoline 1-oxide | MS ES+ m/e 329 (M + 1) |

EXAMPLE 223

3-{4-[2-(6-Methyl-pyridin-2-yl)-5,6-dihydro-4H-pyrrolo[1,2-b]pyrazol-3-yl]-quinolin-7-yl}-acrylic acid methyl ester

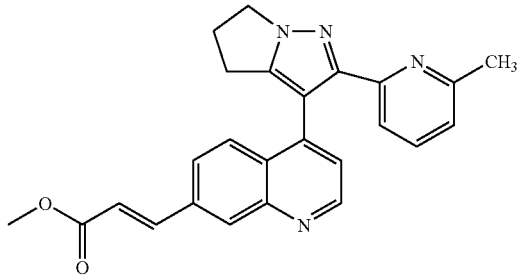

Nitrogen is bubbled through a solution of 7-bromo-4-[2-(6-methyl-pyridin-2-yl)-5,6-dihydro-4H-pyrrolo[1,2-b]pyrazol-3-yl]-quinoline (0.050 g, 0.12 mmol), tributylamine (0.032 mL, 0.17 mmol), methyl acrylate (0.027 mL, 0.24 mmol), and N,N-dimethylformamide (0.5 mL) in toluene (1.0 mL) for 20 min. Pd(OAc)$_2$ (0.002 g, 0.006 mmol) and tri(o-tolyl)phosphine (0.007 g, 0.021 mmol) are added and nitrogen bubbled through the reaction mixture for 10 min. The mixture is heated to 80° C. for 24 h. An additional portion of Pd(OAc)$_2$ (0.002 g, 0.006 mmol) and tri(o-tolyl)phosphine (0.007 g, 0.021 mmol) is added and heating continues for another 24 h. The reaction is cooled and concentrated in vacuo and the residue chromatographed on SiO$_2$ (2% methanol in methylene choloride) to yield the title compound, 0.49 g (97%), as a yellowish solid.

MS APCI+ m/e 411 (M+1).

By the above method the following compounds are prepared (unless otherwise specified):

| EXAMPLE # | Product (Chemical Name) | Physical Data |
|---|---|---|
| 224 | 3-{4-[2-(6-Methylpyrdin-2-yl-5,6-dihydro-4H-pyrrolo[1,2-b]pyrazol-3-yl]quinolin-7-yl}-1-piperidin-1-yl-propenone | MS ES+ m/e 464 (M + 1) |
| 225 | 3-{4-[2-(6-Methyl-pyridin-2-yl)-5,6-dihydro-4H-pyrrolo[1,2-b]pyrazol-3-yl]-quinolin-6-yl}-acrylic acid methyl ester | MS APCI+ m/e 411 (M + 1) |
| 226 | N,N-Dimethyl-3-{4-[2-(6-methyl-pyridin-2-yl)-5,6-dihydro-4H-pyrrolo[1,2-b]pyrazol-3-yl]-quinolin-7-yl}-acrylamide | MS ES+ m/e 424 (M + 1) |

EXAMPLE 227

4-[2-(6-Methyl-pyridin-2-yl)-5,6-dihydro-4H-pyrrolo[1,2-b]pyrazol-3-yl]-7-vinyl-quinoline

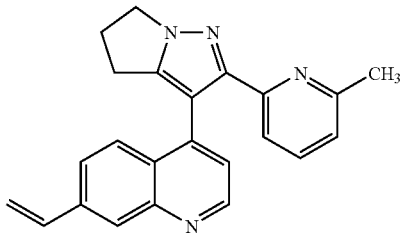

Nitrogen is bubbled through a solution of 7-bromo-4-[2-(6-methyl-pyridin-2-yl)-5,6-dihydro-4H-pyrrolo[1,2-b]pyrazol-3-yl]-quinoline (0.050 g, 0.14 mmol) and tributylvinyltin (0.079 mL, 0.22 mmol) in toluene (2.0 mL) for 20 min. Pd(PPh$_3$)$_2$Cl$_2$ is added and nitrogen bubbled through the reaction mixture for another 10 min. The mixture is heated to 90° C. for 24 h, concentrated in vacuo, and the residue chromatographed on SiO$_2$ (elute with 2% methanol in methylene choloride) to yield the title compound, 0.030 g (61%), as a yellowish solid.

MS APCI$^+$ m/e 353 (M+1).

EXAMPLE 228

4-[2-(6-Benzyl-pyridin-2-yl)-5,6-dihydro-4H-pyrrolo[1,2-b]pyrazol-3-yl]-quinoline

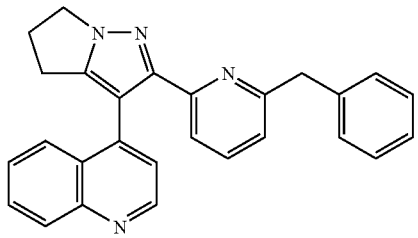

Zinc(II) chloride (0.34 mL, 1.0 M solution, 0.34 mmol) is added, at room temperature with stirring, to a solution of benzyl magnesium chloride (0.15 mL, 2.0 M solution, 0.31 mmol) in tetrahydrofuran (1 mL). After 15 min, Pd(PPh$_3$)$_2$Cl$_2$ (5.4 mg, 0.0076 mmol) is added followed by a solution of 4-[2-(6-bromo-pyridin-2-yl)-5,6-dihydro-4H-pyrrolo[1,2-b]pyrazol-3-yl]-quinoline (60 mg 0.153 mmol) in tetrahydrofuran (1 mL). The reaction mixture is stirred for 18 h at room temperature and quenched with saturated aqueous ammonium chloride (1 mL). The reaction mixture is concentrated in vacuo, filtered, and the residue chromatographed on SiO$_2$ (20–50% acetone/hexanes) to yield the title compound, 33.4 mg (54%), as a white solid.

MS (CI, methane) m/e 403 (M+1).

By the above method, the following compounds are essentially prepared. Unless otherwise specified.

| EXAMPLE # | Product (Chemical Name) | Physical Data |
|---|---|---|
| 229 | 7-Benzyl-4-[2-(6-methyl-pyridin-2-yl)-5,6-dihydro-4H-pyrrolo[1,2-b]pyrazol-3-yl]-quinoline | MS APCI$^+$ m/e 417 (M + 1). |

EXAMPLE 230

4-[2-(6-Methyl-pyridin-2-yl)-5,6-dihydro-4H-pyrrolo[1,2-b]pyrazol-3-yl]-quinoline-7-carboxylic acid

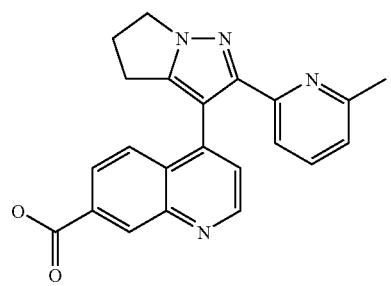

To a solution of 4-[2-(6-methyl-pyridin-2-yl)-5,6-dihydro-4H-pyrrolo[1,2-b]pyrazol-3-yl]-quinoline-7-carboxylic acid ethyl ester (250 mg, 0.6 mmol) in methanol (4 mL) at room temperature is added 1 N lithium hydroxide (1.2 mL, 1.2 mmol). The mixture is heated at 60° C. for 4 h. The mixture is cooled to room temperature and concentrated in vacuo. The mixture is diluted with water and acidified to pH 6 with 1 N hydrochloric acid. The aqueous solution is extracted with dichloromethane 5 times. The combined organic extracts are dried (sodium sulfate), filtered, and concentrated in vacuo to yield the title compound, 150 mg (65%), as an off white solid.

MS ES$^-$ m/e 369 (M−1).

By the above method the following compounds are prepared (unless otherwise specified):

| EXAMPLE # | Product (Chemical Name) | Physical Data |
|---|---|---|
| 231 | 4-[2-(6-Methyl-pyridin-2-yl)-5,6-dihydro-4H-pyrrolo[1,2-b]pyrazol-3-yl]-quinoline-6-carboxylic acid | MS APCI+ m/e 371 (M + 1) |

-continued

| EXAMPLE # | Product (Chemical Name) | Physical Data |
|---|---|---|
| 232 | 3-{4-[2-(6-Methyl-pyridin-2-yl)-5,6-dihydro 4H-pyrrolo[1,2-b]pyrazol-3-yl]-quinolin-7-yl}-acrylic acid | MS APCI+ m/e 397 (M + 1) |
| 233 | 3-{4-[2-(6-Methyl-pyridin-2-yl)-5,6-dihydro-4H-pyrrolo[1,2-b]pyrazol-3-yl]-quinolin-7-yl}-propionic acid | MS APCI+ m/e 399 (M + 1) |
| 234 | 4-[2-(6-Methyl-pyridin-2-yl)-3-quinolin-4-yl-5,6-dihydro-4H-pyrrolo[1,2-b]pyrazol-5-yl]-benzoic acid | MS APCI+ m/e 447 (M + 1) |

EXAMPLE 235

4-(2-Pyridin-2-yl-5,6-dihydro-4H-pyrrolo[1,2-b]pyrazol-3-yl)-quinoline-7-carboxylic acid cyclopentylamide

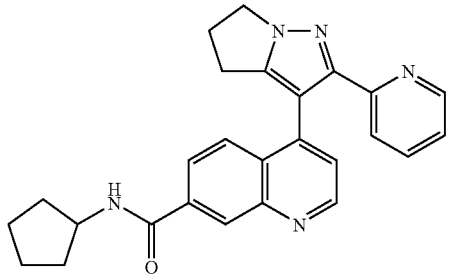

A mixture of 1-(3-dimethylaminopropyl)-3-ethylcarbodiimide hydrochloride, (53 mg, 0.30 mmol), HOBT, (24 mg, 0.28 mmol), cyclopentylamine (0.03 mL, 0.30 mmol), and 4-(2-pyridin-2-yl-5,6-dihydro-4H-pyrrolo[1,2-b]pyrazol-3-yl)-quinoline-7-carboxylic acid (90 mg, 0.25 mmol) in dichloromethane (1 mL) is stirred room temperature for 18 h. The mixture is concentrated in vacuo and the residue chromatographed on $SiO_2$ to yield the title compound, 31 mg (31%,) as a white solid.

MS APC+ m/e 424 (M+1).

By the above method the following compounds are prepared (unless otherwise specified):

| EXAMPLE # | Product (Chemical Name) | Physical Data |
|---|---|---|
| 236 | 4-(2-Pyridin-2-yl-5,6-dihydro-4H-pyrrolo[1,2-b]pyrazol-3-yl)-quinoline-7-carboxylic acid(2-morpholin-4-yl-ethyl)-amide | MS ES+ m/e 469 (M + 1) |
| 237 | 4-(2-Pyridin-2-yl-5,6-dihydro-4H-pyrrolo[1,2-b]pyrazol-3-yl)-quinoline-7-carboxylic acid[2-(1H-imidazol-4-yl)-ethyl]-amide | MS ES+ m/e 450 (M + 1) |
| 238 | 4-(2-Pyridin-2-yl-5,6-dihydro-4H-pyrrolo[1,2-b]pyrazol-3-yl)-quinoline-7-carboxylic acid(2-methylamino-ethyl)-amide | MS ES+ m/e 413 (M + 1) |
| 239 | 4-(2-Pyridin-2-yl-5,6-dihydro-4H-pyrrolo[1,2-b]pyrazol-3-yl)-quinoline-7-carboxylic acid(3-methylamino-propyl)-amide | MS ES+ m/e 427 (M + 1) |
| 240 | 4-(2-Pyridin-2-yl-5,6-dihydro-4H-pyrrolo[1,2-b]pyrazol-3-yl)-quinoline-7-carboxylic acid(2-dimethylamino-ethyl)-amide | MS ES+ m/e 427 (M + 1) |
| 241 | (4-Methyl-piperazin-1-yl)-[4-(2-pyridin-2-yl-5,6-dihydro-4H-pyrrolo[1,2-b]pyrazol-3-yl)-quinolin-7-yl]-methanone | MS ES+ m/e 439 (M + 1) |
| 242 | 4-(2-Pyridin-2-yl-5,6-dihydro-4H-pyrrolo[1,2-b]pyrazol-3-yl)-quinoline-7-carboxylic acid cyclobutylamide | MS APC+ m/e 410 (M + 1) |
| 243 | 4-(2-Pyridin-2-yl-5,6-dihydro-4H-pyrrolo[1,2-b]pyrazol-3-yl)-quinoline-7-carboxylic acid cyclopropylamide | MS APC+ m/e 396 (M + 1) |
| 244 | 4-(2-Pyridin-2-yl-5,6-dihydro-4H-pyrrolo[1,2-b]pyrazol-3-yl)-quinoline-7-carboxylic acid(1-ethyl-propyl)-amide | MS APC+ m/e 426 (M + 1) |
| 245 | 4-(2-Pyridin-2-yl-5,6-dihydro-4H-pyrrolo[1,2-b]pyrazol-3-yl)-quinoline-7-carboxylic acid ethylamide | MS APC+ m/e 384 (M + 1) |
| 246 | 4-(2-Pyridin-2-yl-5,6-dihydro-4H-pyrrolo[1,2-b]pyrazol-3-yl)-quinoline-7-carboxylic acid isobutyl-amide | MS APC+ m/e 412 (M + 1) |
| 247 | 4-(2-Pyridin-2-yl-5,6-dihydro-4H-pyrrolo[1,2-b]pyrazol-3-yl)-quinoline-7-carboxylic acid tert-butylamide | MS APC+ m/e 412 (M + 1) |
| 248 | 4-(2-Pyridin-2-yl-5,6-dihydro-4H-pyrrolo[1,2-b]pyrazol-3-yl)-quinoline-7-carboxylic acid isopropylamide | mp 240–242° C. MS APC+ m/e 398 (M + 1) |

-continued

| EXAMPLE # | Product (Chemical Name) | Physical Data |
|---|---|---|
| 249 | 4-(2-Pyridin-2-yl-5,6-dihydro-4H-pyrrolo[1,2-b]pyrazol-3-yl)-quinoline-7-carboxylic acid propylamide | mp 107–110° C. MS APC+ m/e 398 (M + 1) |
| 250 | 4-(2-Pyridin-2-yl-5,6-dihydro-4H-pyrrolo[1,2-b]pyrazol-3-yl)-quinoline-7-carboxylic acid(2-methyl-butyl)-amide | mp: 126–128° C. MS APC+ m/e 426 (M + 1) |
| 251 | 4-(2-Pyridin-2-yl-5,6-dihydro-4H-pyrrolo[1,2-b]pyrazol-3-yl)-quinoline-7-carboxylic acid((2S)-2-methyl-butyl)-amide | mp: 120–122° C. MS APC+ m/e 426 (M + 1) |
| 252 | 4-(2-Pyridin-2-yl-5,6-dihydro-4H-pyrrolo[1,2-b]pyrazol-3-yl)-quinoline-7-carboxylic acid(2S)-sec-butylamide | mp: 229–231° C. MS APC+ m/e 412 (M + 1) |
| 253 | 4-(2-Pyridin-2-yl-5,6-dihydro-4H-pyrrolo[1,2-b]pyrazol-3-yl)-quinoline-7-carboxylic acid(2R)-sec-butylamide | mp: 229–231° C. MS APC+ m/e 412 (M + 1) |
| 254 | 4-(2-Pyridin-2-yl-5,6-dihydro-4H-pyrrolo[1,2-b]pyrazol-3-yl)-quinoline-7-carboxylic acid((1R)-1,2-dimethyl-propyl)-amide | mp: 115–117 ° C. MS APC+ m/e 426 (M + 1) |
| 255 | 4-(2-Pyridin-2-yl-5,6-dihydro-4H-pyrrolo[1,2-b]pyrazol-3-yl)-quinoline-7-carboxylic acid(pyridin-4-ylmethyl)-amide | MS APC+ m/e 447 (M + 1) |
| 256 | 4-(2-Pyridin-2-yl-5,6-dihydro-4H-pyrrolo[1,2-b]pyrazol-3-yl)-quinoline-7-carboxylic acid(pyridin-3-ylmethyl)-amide | MS APC+ m/e 447 (M + 1) |
| 257 | 4-(2-Pyridin-2-yl-5,6-dihydro-4H-pyrrolo[1,2-b]pyrazol-3-yl)-quinoline-7-carboxylic acid(pyridin-2-ylmethyl)-amide | MS APC+ m/e 447 (M + 1) |
| 258 | 6-(3-Quinolin-4-yl-5,6-dihydro-4H-pyrrolo[1,2-b]pyrazol-2-yl)-pyridine-2-carboxylic acid amide | MS ES+ m/e 356 (M + 1). |

EXAMPLE 259

1-(4-Methyl-piperazin-1-yl)-2-[4-(2-pyridin-2-yl-5,6-dihydro-4H-pyrrolo[1,2-b]pyrazol-3-yl)-quinolin-7-yloxy]-ethanone

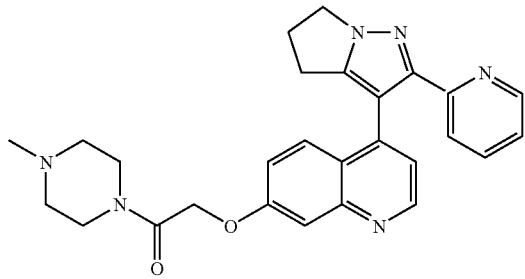

To a solution of [4-(2-pyridin-2-yl-5,6-dihydro-4H-pyrrolo[1,2-b]pyrazol-3-yl)-quinolin-7-yloxy]-acetic acid (150 mg, 0.39 mmol) in dichloromethane (3 mL) is added oxalyl chloride (490 mg, 3.9 mmol) and 1 drop of N,N-dimethylformamide. The mixture is stirred at room temperature for 5 h, concentrated in vacuo, and residual solvents removed by co-evaporation three times with chloroform to yield [4-(2-pyridin-2-yl-5,6-dihydro-4H-pyrrolo[1,2-b]pyrazol-3-yl)-quinolin-7-yloxy]-acetyl chloride as a yellow solid. To a solution of [4-(2-pyridin-2-yl-5,6-dihydro-4H-pyrrolo[1,2-b]pyrazol-3-yl)-quinolin-7-yloxy]-acetyl chloride (50 mg, 0.12 mmol) in dichloromethane at room temperature is added 1-methyl-piperazine (62 mg, 62 mmol) and the mixture stirred for 2.5 h. The mixture is partitioned between dichloromethane and water, the organic portion dried (sodium sulfate), filtered, and concentrated in vacuo. The crude residue is chromatographed on SiO₂ (89% dichloromethane 10% methanol 1% concentrated ammonium hydroxide) to yield the title compound, 28 mg (48%), as a light brown solid.

MS ES+ m/e 469 (M+1).

By the above method the following compounds are essentially prepared: (unless otherwise specified)

| EXAMPLE # | Product (Chemical Name) | Physical Data |
|---|---|---|
| 260 | N-(2-Dimethylamino-ethyl)-2-[4-(2-pyridin-2-yl-5,6-dihydro-4H-pyrrolo[1,2-b]pyrazol-3-yl)-quinolin-7-yloxy]-acetamide | MS ES+ m/e 457 (M + 1) |
| 261 | N-(2-Dimethylamino-ethyl)-N-methyl-2-[4-(2-pyridin-2-yl-5,6-dihydro-4H-pyrrolo[1,2-b]pyrazol-3-yl)-quinolin-7-yloxy]-acetamide | MS ES+ m/e 471 (M + 1) |
| 262 | N,N-Dimethyl-3-[4-(2-pyridin-2-yl-5,6-dihydro-4H-pyrrolo[1,2-b]pyrazol-3-yl)-quinolin-7-yloxy]-benzamide | MS ES+ m/e 475.8 (M + 1) |
| 263 | 4-(2-Pyridin-2-yl-5,6-dihydro-4H-pyrrolo[1,2-b]pyrazol-3-yl)-quinoline-7-carboxylic acid amide | MS ES+ m/e 356 (M + 1) |

-continued

| EXAMPLE # | Product (Chemical Name) | Physical Data |
|---|---|---|
| 264 | 4-(2-Pyridin-2-yl-5,6-dihydro-4H-pyrrolo[1,2-H]pyrazol-3-yl)-quinoline-7-carboxylic acid(2-dimethylamino-ethyl)-methyl-amide | MS ES+ m/e 441 (M + 1) |
| 265 | 4-(2-Pyridin-2-yl-5,6-dihydro-4H-pyrrolo[1,2-H]pyrazol-3-yl)-quinoline-7-carboxylic acid(3-dimethylamino-propyl)-methyl-amide | LCMS ES+ m/e 454 (M+) |
| 266 | 4-(2-Pyridin-2-yl-5,6-dihydro-4H-pyrrolo[1,2-H]pyrazol-3-yl)-quinoline-7-carboxylic acid dimethylamide | LCMS ES+ m/e 383 (M+) |
| 267 | 4-(2-Pyridin-2-yl-5,6-dihydro-4H-pyrrolo[1,2-H]pyrazol-3-yl)-quinoline-7-carboxylic acid methylamide | MS ES+ m/e 370 (M + 1) |
| 268 | 4-(2-Pyridin-2-yl-5,6-dihydro-4H-pyrrolo[1,2-b]pyrazol-3-yl)-quinoline-7-carboxylic acid pyridin-2-ylamide | LCMS ES+ m/e 433 (M+) |
| 269 | N-(2,2-Dimethylamino-ethyl)-N-methyl-3-{4-[2-(6-methyl-pyridin-2-yl)-5,6-dihydro-4H-pyrrolo[1,2-b]pyrazol-3-yl]-quinolin-7-yl}-propionamide | MS CI+ m/e 483 (M + 1) |

EXAMPLE 270

4-[2-(6-Methyl-pyridin-2-yl)-5,6-dihydro-4H-pyrrolo[1,2-b]pyrazol-3-yl]-quinoline-6-carboxylic acid (2-dimethylamino-ethyl)-amide

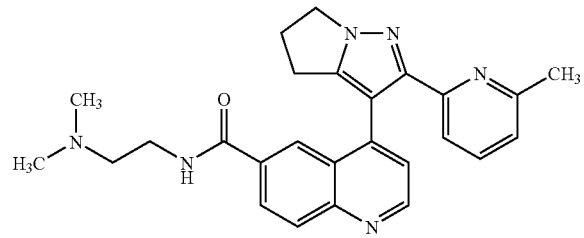

A solution of 4-[2-(6-methyl-pyridin-2-yl)-5,6-dihydro-4H-pyrrolo[1,2-b]pyrazol-3-yl]-quinoline-6-carboxylic acid methyl ester (0.055 g, 0.14 mmol) in 2-N,N-dimethylaminoethylamine (1.5 mL) is heated at 100° C. for 24 h. The mixture is concentrated in vacuo and the residue chromatographed on SiO$_2$ (100% ethyl acetate) to yield the title compound, 0.045 g (74%), as a yellowish solid.

MS APCI+ m/e 441 (M+1).

By the above method the following compounds are essentially prepared: (unless otherwise specified)

| EXAMPLE # | Product (Chemical Name) | Physical Data |
|---|---|---|
| 271 | 4-[2-(6-Methyl-pyridin-2-yl)-5,6-dihydro-4H-pyrrolo[1,2-b]pyrazol-3-yl]-quinoline-6-carboxylic acid(3-dimethylamino-propyl)-amide | MS APCI+ m/e 455 (M + 1). |
| 272 | 4-[2-(6-Methyl-pyridin-2-yl)-5,6-dihydro-4H-pyrrolo[1,2-b]pyrazol-3-yl]-quinoline-6-carboxylic acid(2-morpholin-4-yl-ethyl)-amide | MS APCI+ m/e 483 (M + 1) |
| 273 | 1-[2-(Quinolin-4-yl)-1-(6-methyl-pyridin-2-yl)-5,6-dihydro-4H-pyrrolo[1,2-b]pyrazol-3-yl] quinoline-7-carboxylic acid N,N-dimethylaminoethylamide | mp 148–152° C.; MS ES+ m/e 441 (M + 1). |
| 274 | 4-[2-(6-Methylpyridin-2-yl)-5,6-dihydro4H-pyrrolo[1,2-b]pyrazol-3-yl]quinoline-7-carboxylic acid(2-piperidin-1-yl-ethyl)amide | mp: 173–175° C.; MS ES+ m/e 481 (M + 1) |
| 275 | N-(2-Dimethylamino-ethyl)-3-{4-[2-(6-methyl-pyridin-2-yl)-5,6-dihydro-4H-pyrrolo[1,2-b]pyrazol-3-yl]-quinolin-7-yl}-propionamide | MS APCI+ m/e 469 (M + 1) |
| 276 | 4-[2-(6-Methyl-pyridin-2-yl)-5,6-dihydro-4H-pyrrolo[1,2-b]pyrazol-3-yl]-quinoline-7-carboxylic acid (3-dimethylamino-propyl)-amide | MS APCI+ m/e 455 (M + 1) |
| 277 | 4-[2-(6-Methyl-pyridin-2-yl)-5,6-dihydro-4H-pyrrolo[1,2-b]pyrazol-3-yl]-quinoline-7-carboxylic acid(3-pyrrolidin-1-yl-propyl)-amide | MS APCI+ m/e 481 (M + 1) |
| 278 | 4-[2-(6-Methyl-pyridin-2-yl)-5,6-dihydro-4H-pyrrolo[1,2-b]pyrazol-3-yl]-quinoline-7-carboxylic acid (3-morpholin-4-yl-propyl)-amide | MS APCI+ m/e 497 (M + 1) |
| 279 | 3-{4-[2-(6-Methyl-pyridin-2-yl)-5,6-dihydro-4H-pyrrolo[1,2-b]pyrazol-3-yl]-quinolin-7-yl}-propionamide | MS APCI+ m/e 398 (M + 1) |

| EXAMPLE # | Product (Chemical Name) | Physical Data |
|---|---|---|
| 280 | 4-(2-Pyridin-2-yl-5,6-dihydro-4H-pyrrolo[1,2-b]pyrazol-3-yl)-quinoline-6-carboxylic acid(2-dimethylamino-ethyl)-amide | MS ES+ m/e 427.2 (M + 1) |
| 281 | 4-(2-Pyridin-2-yl-5,6-dihydro-4H-pyrrolo[1,2-b]pyrazol-3-yl)-quinoline-6-carboxylic acid(2-morpholin-4-yl-ethyl)-amide | MS ES+ m/e 469.3 (M + 1) |
| 282 | 4-(2-Pyridin-2-yl-5,6-dihydro-4H-pyrrolo[1,2-b]pyrazol-3-yl)-quinoline-6-carboxylic acid | MS ES+ m/e 357.1 (M + 1) |
| 283 | 4-(2-Pyridin-2-yl-5,6-dihydro-4H-pyrrolo[1,2-b]pyrazol-3-yl)-quinoline-6-carboxylic acid hydrazide | MS ES+ m/e 371.1 (M + 1) |
| 284 | 4-(2-Pyridin-2-yl-5,6-dihydro-4H-pyrrolo[1,2-b]pyrazol-3-yl)-quinoline-6-carboxylic acid amide | MS ES+ m/e 412.3 (M + 1) |
| 285 | 4-(2-Pyridin-2-yl-5,6-dihydro-4H-pyrrolo[1,2-b]pyrazol-3-yl)-quinoline-6-carboxylic acid(3-methylamino-propyl)-amide | MS ES+ m/e 427.3 (M + 1) |
| 286 | 4-(2-Pyridin-2-yl-5,6-dihydro-4H-pyrrolo[1,2-b]pyrazol-3-yl)-quinoline-6-carboxylic acid amide | MS ES+ m/e 356.1 (M + 1) |
| 287 | 4-(2-Pyridin-2-yl-5,6-dihydro-4H-pyrrolo[1,2-b]pyrazol-3-yl)-quinoline-6-carboxylic acid(2-hydroxy-ethyl)-amide | MS ES+ m/e 400.2 (M + 1) |
| 288 | 4-(2-Pyridin-2-yl-5,6-dihydro-4H-pyrrolo[1,2-b]pyrazol-3-yl)-quinoline-7-carboxylic acid hydrazide | MS ES+ m/e 370.8 (M + 1) |
| 289 | 4-(2-Pyridin-2-yl-5,6-dihydro-4H-pyrrolo[1,2-b]pyrazol-3-yl)-quinoline-7-carboxylic acid hydroxyamide | MS ES+ m/e 372.3 (M + 1) |
| 290 | 4-(2-Pyridin-2-yl-5,6-dihydro-4H-pyrrolo[1,2-b]pyrazol-3-yl)-quinoline-7-carboxylic acid(2-amino-ethyl)-amide | MS ES+ m/e 399.0 (M + 1) |
| 291 | 4-(2-Pyridin-2-yl-5,6-dihydro-4H-pyrrolo[1,2-b]pyrazol-3-yl)-quinoline-7-carboxylic acid(2-hydroxy-ethyl)-amide | MS ES+ m/e 399.8 (M + 1). |
| 292 | 4-[2-(6-Methyl-pyridin-2-yl)-5,6-dihydro-4H-pyrrolo[1,2-b]pyrazol-3-yl]-quinoline-7-carboxylic acid amide | MS ES+ m/e 370 (M + 1) |
| 293 | 4-(2-Pyridin-2-yl-5,6-dihydro-4H-pyrrolo[1,2-b]pyrazol-3-yl)-quinoline-7-carboxylic acid(3-dimethylamino-propyl)-amide | MS CI+ m/e 441 (M + 1) |
| 294 | 4-[2-(6-Methyl-pyridin-2-yl)-5,6-dihydro-4H-pyrrolo[1,2-b]pyrazol-3-yl]-quinoline-7-carboxylic acid (2-dimethylamino-ethyl)-methyl-amide | MS ES+ m/e 455 (M + 1) |

EXAMPLE 295

4-(2-Pyridin-2-yl-5,6-dihydro-4H-pyrrolo[1,2-b]pyrazol-3-yl)-quinoline-7-sulfonic acid amide

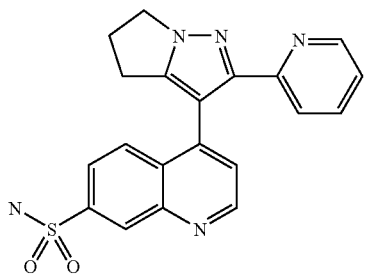

Molecular chlorine is bubbled through a solution of 7-benzylsulfanyl-4-(2-pyridin-2-yl-5,6-dihydro-4H-pyrrolo[1,2-b]pyrazol-3-yl)-quinoline (190.2 mg, 0.44 mmol) in water (0.3 mL) and glacial acetic acid (1.8 mL) for 10 min. The resultant solution is divided into six 4 mL vials and each is concentrated. One vial is treated with 7 M ammonia in methanol for 10 min. The mixture is concentrated in vacuo and the residue chromatographed on SiO$_2$ (dichloromethane, 2%, and 5% methanol/dichloromethane) to yield the desired product, (17 mg), as colorless oil.

MS ES+ m/e 392.3 (M+1).

By the above method the following compounds are essentially prepared. Unless otherwise specified.

| EXAMPLE # | Product (Chemical Name) | Physical Data |
|---|---|---|
| 296 | 4-(2-Pyridin-2-yl-5,6-dihydro-4H-pyrrolo[1,2-b]pyrazol-3-yl)-quinoline-7-sulfonic acid methylamide | MS ES+ m/e 406.3 (M + 1) |
| 297 | 4-(2-Pyridin-2-yl-5,6-dihydro-4H-pyrrolo[1,2-b]pyrazol-3-yl)-quinoline-7-sulfonic acid dimethylamide | MS ES+ m/e 420.4 (M + 1) |

| EXAMPLE # | Product (Chemical Name) | Physical Data |
|---|---|---|
| 298 | 4-(2-Pyridin-2-yl-5,6-dihydro-4H-pyrrolo[1,2-b]pyrazol-3-yl)-quinoline-7-sulfonic acid(3-dimethylamino-propyl)-amide | MS ES+ m/e 476.9 (M + 1) |
| 299 | 4-(2-Pyridin-2-yl-5,6-dihydro-4H-pyrrolo[1,2-b]pyrazol-3-yl)-quinoline-7-sulfonic acid diethylamide | MS ES+ m/e 448.4 (M + 1) |
| 300 | 4-(2-Pyridin-2-yl-5,6-dihydro-4H-pyrrolo[1,2-b]pyrazol-3-yl)-quinoline-7-sulfonic acid(2-piperidin-1-yl-ethyl)-amide | MS ES+ m/e 503.6 (M + 1) |
| 301 | 4-(2-Pyridin-2-yl-5,6-dihydro-4H-pyrrolo[1,2-b]pyrazol-3-yl)-quinoline-7-sulfonic acid(2-hydroxy-ethyl)-amide | MS ES+ m/e 436.4 (M + 1) |

EXAMPLE 302

4-(2-Pyridin-2-yl-5,6-dihydro-4H-pyrrolo[1,2-b]pyrazol-3-yl)-quinolin-7-ylamine

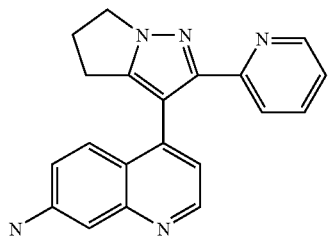

A solution of 7-bromo-4-(2-pyridin-2-yl-5,6-dihydro-4H-pyrrolo[1,2-b]pyrazol-3-yl)-quinoline (135.0 mg, 0.34 mmol), sodium tert-butoxide (64.0 mg, 0.62 mmol), and benzophonone imine (91.0 mg, 0.51 mmol) in toluene (3 mL) is degassed with nitrogen for 20 min. To this solution is added tri(dibenzyldeneacetone)-dipalladium(0) (1.0 mg, 0.0011 mmol) and 2,2'-bis(diphenylphosphine)-1,1'-binaphthyl (1.5 mg, 0.0024 mmol) and the mixture degassed with nitrogen for another 10 min. The mixture is heated at 80° C. for 24 h, cooled to room temperature, quenched with saturated ammonium chloride, and extracted with chloroform. The combined organic portions are washed with water and brine, dried (sodium sulfate), and concentrated in vacuo. The residue is dissolved in 1 M hydrochloric acid (5 mL) and heated at reflux for 2.5 h. The mixture is concentrated in vacuo and the residue neutralized with saturated sodium bicarbonate. The resultant mixture is extract with chloroform and the organic extracts concentrated in vacuo to yield the desired product as a yellow solid, 96.5 mg (85%).

MS ES+ m/e 327.9 (M+1).

EXAMPLE 303

2-Dimethylamino-N-[4-(2-pyridin-2-yl-5,6-dihydro-4H-pyrrolo[1,2-b]pyrazol-3-yl)-quinolin-7-yl]-acetamide

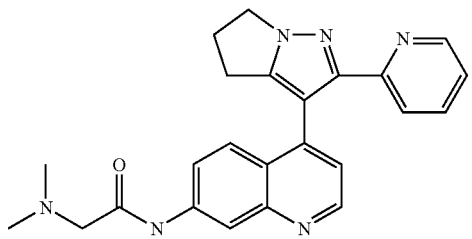

A mixture of dimethylamino-acetyl chloride (620.0 mg, 13.33 mmol), 4-(2-pyridin-2-yl-5,6-dihydro-4H-pyrrolo[1,2-b]pyrazol-3-yl)-quinolin-7-ylamine (75 mg, 0.23 mmol), and 4-N,N-dimethylaminopyridine (10.2 mg, 0.09 mmol) in dry pyridine (1 mL) is refluxed for 72 h. The mixture is treated with saturated sodium bicarbonate solution and extracted with ethyl acetate. The organic layer is washed with brine, dried (sodium sulfate), concentrated in vacuo, and the residue chromatographed on $SiO_2$ ((5% to 20% methanol in dichloromethane) to yield a yellow oil, 62.3 mg (67%).

MS ES+ m/e 413.1 (M+1).

By the above method the following compounds are prepared (unless otherwise specified):

| EXAMPLE # | Product (Chemical Name) | Physical Data |
|---|---|---|
| 304 | 3-Dimethylamino-N-[4-(2-pyridin-2-yl-5,6-dihydro-4H-pyrrolo[1,2-b]pyrazol-3-yl)-quinolin-7-yl]propionamide | MS ES+ m/e 427.1 (M + 1). |
| 305 | N-[4-(2-Pyridin-2-yl-5,6-dihydro-4H-pyrrolo[1,2-b]pyrazol-3-yl)-quinolin-7-yl]-methanesulfonamide | MS ES+ m/e 406.1 (M + 1) |
| 306 | N-[4-(2-Pyridin-2-yl-5,6-dihydro-4H-pyrrolo[1,2-b]pyrazol-3-yl)-quinolin-7-yl]-acetamide | MS ES+ m/e 370.0 (M + 1) |
| 307 | 4-(2-Pyridin-2-yl-5,6-dihydro-4H-pyrrolo[1,2-b]pyrazol-3-yl)-quinoline-7-carboxylic acid(2-acetylamino-ethyl)-amide | MS ES+ m/e 440.9 (M + 1) |

-continued

| EXAMPLE # | Product (Chemical Name) | Physical Data |
|---|---|---|
| 308 | N-{3-[4-(2-Pyridin-2-yl-5,6-dihydro-4H-pyrrolo[1,2-b]pyrazol-3-yl)-quinolin-7-yloxy]-propyl}-methanesulfonamide | TOF MS ES+ exact mass calculated for $C_{24}H_{26}N_5O_3S$ (p + 1): m/z = 464.1756. Found: 464.1766 |
| 309 | 1-Methyl-1H-imidazole-4-sulfonic acid {3-[4-(2-pyridin-2-yl-5,6-dihydro-4H-pyrrolo[1,2-b]pyrazol-3-yl)-quinolin-7-yloxy]-propyl}-amide | TOF MS ES+ exact mass calculated for $C_{27}H_{28}N_7O_3S$ (p + 1): m/z = 530.1974 Found: 530.1992 |
| 310 | 4-[2-(6-Methyl-pyridin-2-yl)-5,6-dihydro-4H-pyrrolo[1,2-b]pyrazol-3-yl]-quinoline-7-carboxylic acid(2-dimethylamino-1-methyl-ethyl)-amide | MS CI+ m/e 455 (M + 1) |

EXAMPLE 311

1-(2-Dimethylamino-ethyl)-3-[4-(2-pyridin-2-yl-5,6-dihydro-4H-pyrrolo[1,2-b]pyrazol-3-yl)-quinolin-7-yl]-urea

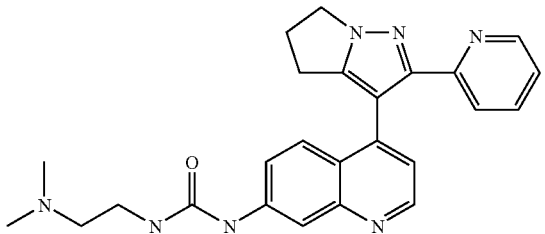

To a mixture of 4-(2-pyridin-2-yl-5,6-dihydro-4H pyrrolo[1,2-b]pyrazol-3-yl)-quinolin-7-ylamine (38.1 mg, 0.11 mmol) and 4-N,N-dimethylaminopyridine (4.2 mg, 0.034 mmol) in dry pyridine (1 mL) is added 20% phosgene in toluene (80 μL, 0.76 mmol). The resulting mixture is stirred at 50° C. for 18 h, treated with N,N-dimethylethylendiame (0.5 mL), and stirred for 4 h. The mixture is concentrated in vacuo and the residue partitioned between ethyl acetate and brine. The organic layer is dried sodium sulfate), filtered, concentrated in vacuo, and the residue chromatographed on $SiO_2$ (10% methanol in dichloromethane to water/methanol/dichloromethane: 0.5:3:7) to yield the desired product 14.2 mg (29%).

MS ES+ m/e 442.1 (M+1).

By the above method, the following compounds are essentially prepared (unless otherwise specified:

| EXAMPLE # | Product (Chemical Name) | Physical Data |
|---|---|---|
| 312 | 1-(3-Dimethylamino-propyl)-3-[4-(2-pyridin-2-yl-5,6-dihydro-4H-pyrrolo[1,2-b]pyrazol-3-yl)-quinolin-7-yl]-urea | MS ES+ m/e 456.2 (M + 1) |
| 313 | 1-(2-Hydroxy-ethyl)-3-[4-(2-pyridin-2-yl-5,6-dihydro-4H-pyrrolo[1,2-b]pyrazol-3-yl)-quinolin-7-yl]-urea | MS ES+ m/e 415.1 (M + 1) |
| 314 | [4-(2-Pyridin-2-yl-5,6-dihydro-4H-pyrrolo[1,2-b]pyrazol-3-yl)-quinolin-7-yl]-carbamic acid methyl ester | MS ES+ m/e 386.0 (M + 1) |
| 315 | [4-(2-Pyridin-2-yl-5,6-dihydro-4H-pyrrolo[1,2-b]pyrazol-3-yl)-quinolin-7-yl]-carbamic acid 2-hydroxy-ethyl ester | MS ES+ m/e 416.4 (M + 1) |
| 316 | [4-(2-Pyridin-2-yl-5,6-dihydro-4H-pyrrolo[1,2-b]pyrazol-3-yl)-quinolin-7-yl]-carbamic acid 2-methoxy-ethyl ester | MS ES+ m/e 430.4 (M + 1) |
| 317 | 1,3-Bis-[4-(2-pyridin-2-yl-5,6-dihydro-4H-pyrrolo[1,2-b]pyrazol-3-yl)-quinolin-7-yl]-urea | MS ES+ m/e 681.1 (M + 1) |
| 318 | Dimethyl-carbamic acid 4-(2-pyridin-2-yl-5,6-dihydro-4H-pyrrolo[1,2-b]pyrazol-3-yl)-quinolin-7-yl ester | MS ES+ m/e 399.9 (M + 1) |

EXAMPLE 319

7-Bromo-2-isopropyl-4-(2-pyridin-2-yl-5,6-dihydro-4H-pyrrolo[1,2-b]pyrazol-3-yl)-quinoline

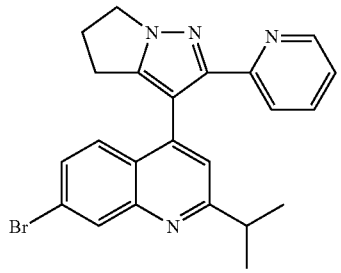

A 2 M solution of isopropyl magnesium chloride in tetrahydrofuran (65 μL, 0.13 mmol) is added to solution of 7-bromo-4-(2-pyridin-2-yl-5,6-dihydro-4H-pyrrolo[1,2-b]pyrazol-3-yl)-quinoline (50.0 mg, 0.13 mmol) in tetrahydrofuran (1 mL) at room, temperature with stirring for 2 h. The mixture is cooled to −78° C. and triethylamine (21.4 μL, 0.154 mmol) and methanesulfonyl chloride (11 μL, 0.14 mmol) added. The mixture is warmed to room temperature and allowed to stand 18 h. The mixture is treated with water, extracted with ethyl acetate, dried (sodium sulfate), filtered, and concentrated in vacuo. The residue is chromatographed on SiO$_2$ (dichloromethane to 75% ethyl acetate/dichloromethane) to yield the title compound as a solid, 4.5 mg (9%).

MS ES$^+$ m/e 433.1 & 435.1 (M+1).

EXAMPLE 320

2-{4-[2-(6-Methyl-pyridin-2-yl)-5,6-dihydro-4H-pyrrolo[1,2-b]pyrazol-3-yl]-quinolin-6-yl}-propan-2-ol

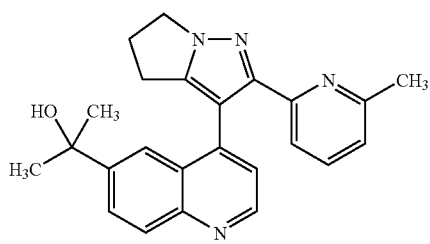

A solution of 4-[2-(6-methyl-pyridin-2-yl)-5,6-dihydro-4H-pyrrolo[1,2-b]pyrazol-3-yl]-quinoline-6-carboxylic acid methyl ester (0.06 g, 0.16 mmol) in tetrahydrofuran (1 mL) is cooled to −78° C. and degassed with nitrogen for 20 min. To this solution is added 3 M methylmagnesium chloride in tetrahydrofuran (0.17 mmol, 0.06 mL) and the resulting mixture stirred at 0° C. for 2 h. The mixture is treated with aqueous saturated ammonium chloride and extracted with ethyl acetate. The combined organic extracts are washed with brine, dried (anhydrous sodium sulfate), filtered, and concentrated, in vacuo. The residue is chromatographed on SiO$_2$ (100% ethyl acetate) to yield the title compound, 17 mg (28%), as an off-white foam.

MS APCI$^+$ m/e 385 (M+1).

EXAMPLE 321

7-(3-Chloro-propylsulfanyl)-4-(2-pyridin-2-yl-5,6-dihydro-4H-pyrrolo[1,2-b]pyrazol-3-yl)-quinoline

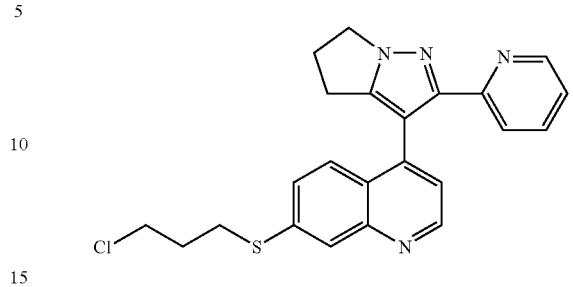

To a solution of Preparation #21, 3-[4-(2-pyridin-2-yl-5,6-dihydro-4H-pyrrolo[1,2-b]pyrazol-3-yl)-quinolin-7-ylsulfanyl]-propan-1-ol (25.0 mg, 0.062 mmol) in dry pyridine (0.1 mL) is added toluene sulfonyl chloride (60.0 mg, 0.31 mmol) and the resulting mixture stirred at room temperature for 72 h. Saturated sodium bicarbonate solution is added and the resulting solution extracted with ethyl acetate. The organic layer is washed with brine, dried (sodium sulfate), filtered, and concentrated in vacuo. Purification of the residue on SiO$_2$ (5% to 10% methanol in dichloromethane) gives the desired product, 11.2 mg (43%).

MS ES$^+$ m/e 421.1 (M+1).

EXAMPLE 322

7-Bromo-4-(4-chloro-2-pyridin-2-yl-5,6-dihydro-4H-pyrrolo[1,2-b]pyrazol-3-yl)-quinoline

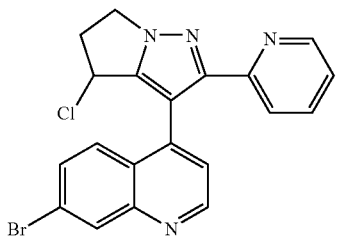

A solution of 1 M sulfuryl chloride in dichloromethane (20 mL, 20 mmol) is added to a solution of 7-bromo-4-(2-pyridin-2-yl-5,6-dihydro-4H-pyrrolo[1,2-b]pyrazol-3-yl)-quinoline (2.2 g, 5.62 mmol) in dry pyridine (50 mL). The mixture is stirred for 18 h and concentrated in vacuo. The residue is partitioned between chloroform and saturated sodium chloride. The organic layer is dried (sodium sulfate), filtered, concentrated in vacuo, and the residue chromatographed on SiO$_2$ (dichloromethane to 20% methanol in dichloromethane) to yield the title compound as a red solid, 1.8 g (75%).

MS ES$^+$ m/e 424.7 & 426.7 (M+1).

By the above method the following compounds are essentially prepared. Unless otherwise specified.

| EXAMPLE # | Product (Chemical Name) | Physical Data |
|---|---|---|
| 323 | 8-Chloro-4-(2-pyridin-2-yl-5,6-dihydro-4H-pyrrolo[1,2-b]pyrazol-3-yl)-quinolin-7-ol | MS ES$^+$ m/e 363.2 (M + 1) |

-continued

| EXAMPLE # | Product (Chemical Name) | Physical Data |
|---|---|---|
| 324 | 8-Bromo-4-(2-pyridin-2-yl-5,6-dihydro-4H-pyrrolo[1,2-b]pyrazol-3-yl)-quinolin-7-ol | MS ES+ m/e 406.8 & 408.8 (M + 1) |

EXAMPLE 325

3-(7-Bromo-quinolin-4-yl)-2-pyridin-2-yl-5,6-dihydro-4H-pyrrolo[1,2-b]pyrazol-4-ol

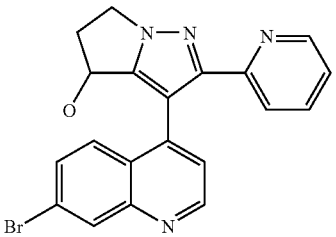

A solution of 7-bromo-4-(4-chloro-2-pyridin-2-yl-5,6-dihydro-4H-pyrrolo[1,2-b]pyrazol-3-yl)-quinoline (765.0 mg, 1.80 mmol) in 15% (v/v) aqueous N-methyl pyrrolidinone (15 mL) is heated at 120° C. for 18 h. The mixture is concentrated in vacuo and the residue chromatographed on SiO$_2$ (dichloromethane to 20% methanol in dichloromethane) to yield a yellow solid, 408.0 mg (60%).

MS ES+ m/e 406.8 and 408.8 (M+1).

By the above method the following compounds are prepared (unless otherwise specified):

| EXAMPLE # | Product (Chemical Name) | Physical Data |
|---|---|---|
| 326 | 7-Bromo-4-(4-methoxy-2-pyridin-2-yl-5,6-dihydro-4H-pyrrolo[1,2-b]pyrazol-3-yl)-quinoline | MS ES+ m/e 421.0 & 423.0 (M + 1) |
| 327 | [3-(7-Bromo-quinolin-4-yl)-2-pyridin-2-yl-5,6-dihydro-4H-pyrrolo[1,2-b]pyrazol-4-yl]-methyl-amine | MS ES+ m/e 420.0 & 422.0 (M + 1) |

EXAMPLE 328

3-(7-Bromo-quinolin-4-yl)-2-pyridin-2-yl-5,6-dihydro-pyrrolo[1,2-b]pyrazol-4-one

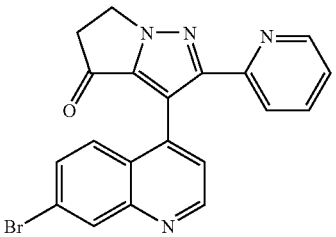

To a solution of 3-(7-bromo-quinolin-4-yl)-2-pyridin-2-yl-5,6-dihydro-4H-pyrrolo[1,2-b]pyrazol-4-ol (89.0 mg, 0.22 mmol) in dry dichloromethane (2 mL) is added Dess-Martin periodinane (301.0 mg, 0.71 mmol) and the resulting mixture stirred for 18 h. The reaction mixture is chromatographed on SiO$_2$ (dichloromethane to 20% methanol in dichloromethane) to yield a yellow solid, 78 mg (88%).

MS ES+ m/e 404.7 and 406.7 (M+1).

EXAMPLE 329

3-[4-(2-Pyridin-2-yl-5,6-dihydro-4H-pyrrolo[1,2-b]pyrazol-3-yl)-quinolin-7-yloxy]-benzonitrile

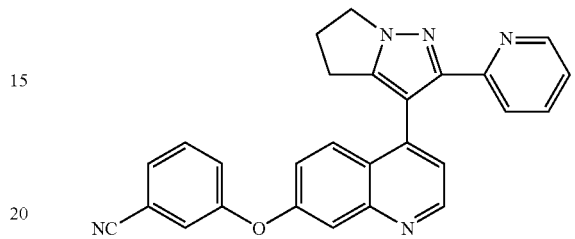

and

3-[4-(2-Pyridin-2-yl-5,6-dihydro-4H-pyrrolo[1,2-b]pyrazol-3-yl)-quinolin-7-yloxy]-benzamide

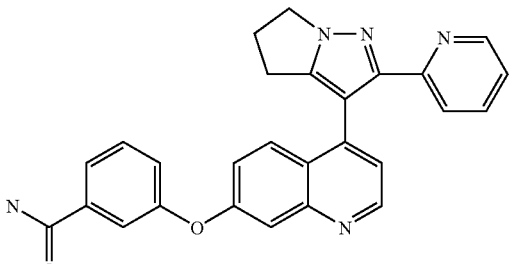

A mixture of 4-(2-pyridin-2-yl-5,6-dihydro-4H-pyrrolo[1,2-b]pyrazol-3-yl)-quinolin-7-ol (1.42 g, 4.30 mmol), 3-fluorobenzonitrile (550.0 mg, 4.5 mmol), 18-crown-6 (80.0 mg, 0.37 mmol), and 37% (w/w) potassium fluoride on alumina (3.5 g) in dimethyl sulfoxide (12 mL) are heated at 140° C. for 18 h. The reaction mixture is cooled to room temperature, filtered, and the solids are washed with chloroform. The organic filtrate is washed with brine, dried (sodium sulfate), filtered, and concentrated in vacuo. The residue is chromatographed on SiO$_2$ (dichloromethane to 20% methanol in dichloromethane) to yield a yellow oil.

3-[4-(2-Pyridin-2-yl-5,6-dihydro-4H-pyrrolo[1,2-b]pyrazol-3-yl)-quinolin-7-yloxy]-benzonitrile;

MS ES+ m/e 430.1 (M+1).

3-[4-(2-Pyridin-2-yl-5,6-dihydro-4H-pyrrolo[1,2-b]pyrazol-3-yl)-quinolin-7-yloxy]-benzamide;

MS ES+ m/e 447.8 (M+1).

By the above method the following compounds are prepared (unless otherwise specified:

| EXAMPLE # | Product (Chemical Name) | Physical Data |
|---|---|---|
| 330 | 7-(6-Methyl-pyridazin-3-yloxy)-4-(2-pyridin-2-yl-5,6-dihydro-4H-pyrrolo[1,2-b]pyrazol-3-yl)-quinoline | ESMS: 420.2 |
| 331 | 4-(2-Pyridin-2-yl-5,6-dihydro-4H-pyrrolo[1,2-b]pyrazol-3-yl)-7-[4-(4-pyrimidin-2-yl-piperazin-1-yl)-butoxy]-quinoline | ESMS: 546.3 |
| 332 | 7-{3-[4-(2-Methoxy-phenyl)-piperazin-1-yl]-propoxy}-4-(2-pyridin-2-yl-5,6-dihydro-4H-pyrrolo[1,2-b]pyrazol-3-yl)-quinoline | ESMS: 560.3 |
| 333 | Pyridin-2-yl-{3-[4-(2-pyridin-2-yl-5,6-dihydro-4H-pyrrolo[1,2-b]pyrazol-3-yl)-quinolin-7-yloxy]-propyl}-amine | ESMS: 462.2 |

EXAMPLE 334

N,N-Dimethyl-3-[4-(2-pyridin-2-yl-5,6-dihydro-4H-pyrrolo[1,2-b]pyrazol-3-yl)-quinolin-7-yloxy]-thiobenzamide

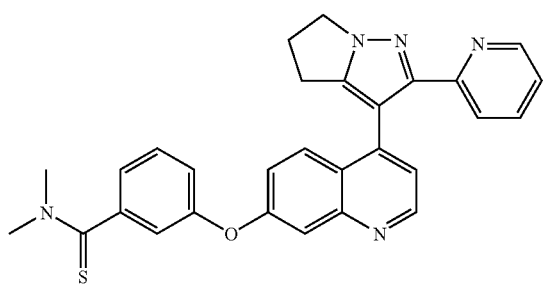

Lawasson's Reagent (1.01 g, 2.49 mmol) is added to a solution of N,N-dimethyl-3-[4-(2-pyridin-2-yl-5,6-dihydro-4H-pyrrolo[1,2-b]pyrazol-3-yl)-quinolin-7-yloxy]-benzamide (0.72 g, 1.51 mmol) in toluene (10 mL). The resulting mixture is heated at 120° C. for 45 min. The mixture is concentrated in vacuo and the residue chromatographed on $SiO_2$ (dichloromethane to 20% methanol in dichloromethane) to yield a red solid, 556 mg (75%).

MS ES$^+$ m/e 491.8 (M+1).

EXAMPLE 335

Dimethyl-{3-[4-(2-pyridin-2-yl-5,6-dihydro-4H-pyrrolo[1,2-b]pyrazol-3-yl)-quinolin-7-yloxy]-benzyl}-amine

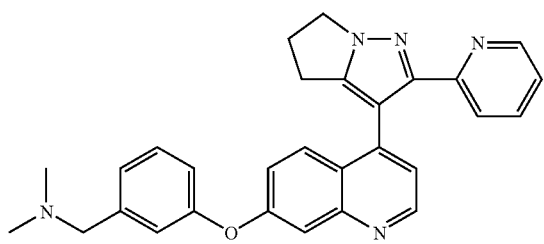

To a refluxing mixture of Raney-nickel and hydrazine-monohydrate (0.5 mL, 10.17 mmol) in methanol (5 mL) is added N,N-dimethyl-3-[4-(2-pyridin-2-yl-5,6-dihydro-4H-pyrrolo[1,2-b]pyrazol-3-yl)-quinolin-7-yloxy]-thiobenzamide (311.0 mg, 0.63 mmol) in methanol (20 mL). The mixture is stirred 10 min and cooled to room temperature, filtered, and concentrated in vacuo. The residue is chromatographed by HPLC ($C_{18}$ column) to yield the title compound, 60.2 mg (20%).

MS ES$^+$ m/e 462.0 (M+1).

EXAMPLE 336

4-[2-(6-Methyl-pyridin-2-yl)-5,6-dihydro-4H-pyrrolo[1,2-b]pyrazol-3-yl]-1H-quinolin-2-one

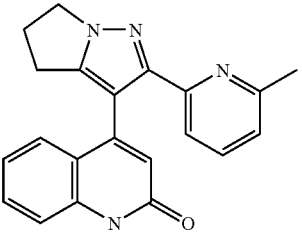

To a solution of 4-[2-(6-methyl-pyridin-2-yl)-5,6-dihydro-4H-pyrrolo[1,2-b]pyrazol-3-yl]-quinoline-1-oxide (103 mg, 0.30 mmol) in N,N-dimethylformamide (3 mL) is added trifluoroacetic anhydride (425 µL, 3.0 mmol). The mixture is stirred for 40 h, poured into water, and the pH adjusted to 8 with saturated aqueous sodium bicarbonate solution. The mixture is extracted three times with ethyl acetate, the combined organic extracts washed three times with water and once with brine, dried (sodium sulfate), filtered, and concentrated in vacuo. The residue is triturated with 10% acetone/90% dichloromethane and filtered. The solid is dried under vacuum to yield the title compound, 11.6 mg (10%), as a yellow solid.

TOF MS ES$^+$ exact mass calculated for $C_{23}H_{22}ClN_4O_2$ (p+1): m/z=343.1559. Found: 343.1550.

EXAMPLE 337

4-(2-Pyridin-2-yl-5,6-dihydro-4H-pyrrolo[1,2-b]pyrazol-3-yl)-quinolin-7-ol

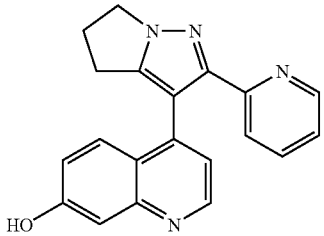

To a solution of 7-methoxy-4-(2-pyridin-2-yl-5,6-dihydro-4H-pyrrolo[1,2-b]pyrazol-3-yl)-quinoline (53 mg, 0.16 mmol) in N,N-dimethylformamide (3 mL) at room temperature is added sodium ethanthiolate (133 mg, 1.6 mmol). The solution is refluxed for 4 h, cooled, and concentrated in vacuo. The residue is dissolved in methanol and loaded onto an SCX column. The column is washed with water, methanol, and 7 N ammonia in methanol. The appropriate fraction is concentrated in vacuo to yield the title compound, 28 mg (56%), as a yellow solid.

TOF MS ES$^+$ exact mass calculated for $C_{20}H_{17}N_4O$ (p+1): m/z=329.1402 Found: 329.1413.

By the above method the following compounds are prepared (unless otherwise specified):

| EXAMPLE # | Product (Chemical Name) | Physical Data |
|---|---|---|
| 338 | 4-[2-(6-Methyl-pyridin-2-yl)-5,6-dihydro-4H-pyrrolo[1,2-b]Pyrazol-3-yl]-quinolin-7-ol | MS APCI+ m/e 343 (M + 1) |

EXAMPLE 339

6-Methoxy-4-(2-pyridin-2-yl-5,6-dihydro-4H-pyrrolo[1,2-b]pyrazol-3-yl)-quinolin-7-ol:

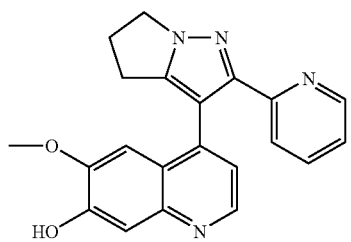

To a mixture of 7-benzyloxy-6-methoxy-4-(2-pyridin-2-yl-5,6-dihydro-4H-pyrrolo[1,2-b]pyrazol-3-yl)-quinoline (17 mg, 0.04 mmol) and 10% palladium on activated carbon (3 mg) in absolute ethanol (2 mL) is added 1,4-cyclohexadiene (100 mg, 1.2 mmol). The mixture is stirred at room temperature for 3 h, treated with methanol (500 μL), and heated at 60° C. for 3 h. The mixture is cooled, filtered, and loaded onto an SCX column. The column is washed with water, methanol, and 7 N ammonia in methanol. The appropriate fraction is concentrated in vacuo to yield the title compound, 10 mg (77%), as a yellow solid.

TOF MS ES$^+$ exact mass calculated for $C_{21}H_{19}N_4O_2$ (p+1): m/z=359.1508 Found: 359.1520.

EXAMPLE 340

3-{4-[2-(6-Methyl-pyridin-2-yl)-5,6-dihydro-4H-pyrrolo[1,2-b]pyrazol-3-yl]-quinolin-7-yl}-propionic acid methyl ester

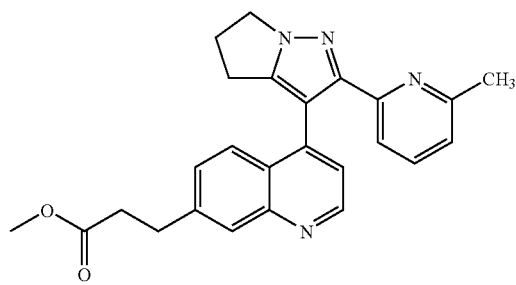

To a solution of 3-{4-[2-(6-methyl-pyridin-2-yl)-5,6-dihydro-4H-pyrrolo[1,2-b]pyrazol-3-yl]-quinolin-7-yl}-acrylic acid methyl ester (0.041 g, 0.1 mmol) in methanol (1 mL) is added 10% Pd/C (0.1 g). The resulting mixture is placed under one atmosphere of hydrogen and: stirred for 18 h. The mixture is filtered and concentrated in vacuo. The residue is chromatographed on SiO$_2$ (2% methanol in dichloromethane) to yield the desired product as a pale yellow solid, 0.035 g (85%).

MS APCI$^+$ m/e 413 (M+1).

By the above method the following compounds are prepared (unless otherwise specified):

| EXAMPLE # | Product (Chemical Name) | Physical Data |
|---|---|---|
| 341 | 4-(6-Methyl-2-pyridin-2-yl-5,6-dihydro-4H-pyrrolo[1,2-b]pyrazol-3-yl)-quinoline | MS APCI$^+$ m/e 327 (M + 1) |
| 342 | 3-{4-[2-(6-Methyl-pyridin-2-yl)-5,6-dihydro-4H-pyrrolo[1,2-b]pyrazol-3-yl]-quinolin-6-yl}-propionic acid methyl ester | MS APCI$^+$ m/e 413 (M + 1) |

EXAMPLE 343

7-Amino-4-[2-(6-methyl-pyridin-2-3,1)-5,6-dihydro-4H-pyrrolo[1,2-b]pyrazol-3-yl]-quinoline

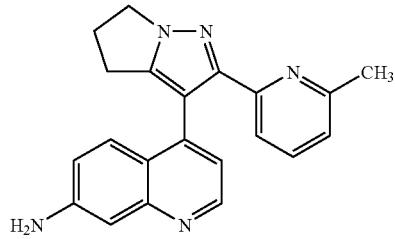

A mixture of 7-bromo-4-[2-(6-methyl-pyridin-2-yl)-5,6-dihydro-4H-pyrrolo[1,2-b]pyrazol-3-yl]-quinoline (1.35 g, 3.34 mmol), sodium t-butoxide (0.64 g, 6.68 mmol), benzophenone imine (0.91 g, 5.01 mmol) in toluene (30 mL) is de-gassed with nitrogen for 20 min. To the mixture is added Pd$_2$(dba)$_3$ (0.008 g, 0.008 mmol) and BINAP (0.012 g, 0.019 mmol), and further de-gassed with nitrogen for 10 min. The mixture is heated at 80° C. for 24 h. Saturated ammonium chloride (30 mL) is added: and the mixture extracted with chloroform. The combined organic portions are washed with water and brine, dried (sodium sulfate), and concentrated in vacuo. The residue is taken up in 1:1 methanol/1 N hydrochloric acid (50 mL) and heated at reflux for 2 h. The mixture is concentrated in vacuo and the residue partitioned between saturated sodium bicarbonate and chloroform. The combined organic layers are washed with water and brine, dried (sodium sulfate), filtered, and concentrated in vacuo. The residue is precipitated from dichloromethane with hexanes (100 mL) and collected by filtration to yield the title compound, 1.10 g (96%), as a yellow solid.

MS APCI$^+$ m/e 342 (M+1).

EXAMPLE 344

N,N-Dimethyl-3-{4-[2-(6-methyl-pyridin-2-yl)-5,6-dihydro-4H-pyrrolo[1,2-b]pyrazol-3-yl]-quinolin-7-yl}-propionamide

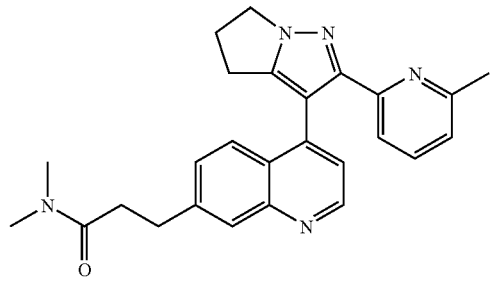

To a solution of 3-{4-[2-(6-methyl-pyridin-2-yl)-5,6-dihydro-4H-pyrrolo[1,2-b]pyrazol-3-yl]-quinolin-7-yl}-propionic acid methyl ester (0.30 g, 0.73 mmol) and 2M dimethylamine in methanol (1.05 mL, 2.1 mmol) in dichloromethane (1 mL) is added 2 M trimethylaluminum in hexane (1.64 mL, 3.25 mmol). The solution is heated at 40° C. for 48 h. The mixture is diluted with dichloromethane (150 mL), treated with saturated potassium sodium tartrate (30 mL), and stirred 18 h. The organic portion is separated and; washed with water and brine, dried (sodium sulfate), filtered, and concentrated in vacuo. The residue is chromatographed on SiO$_2$ (10% methanol in dichloromethane) to yield the title compound, 0.29 g (89%), as a yellow foam.

MS APCI$^+$ m/e 426 (M+1).

EXAMPLE 345

N-{3-[4-(2-Pyridin-2-yl-5,6-dihydro-4H-pyrrolo[1,2-b]pyrazol-3-yl)-quinolin-7-yloxy]-propyl}-acetamide

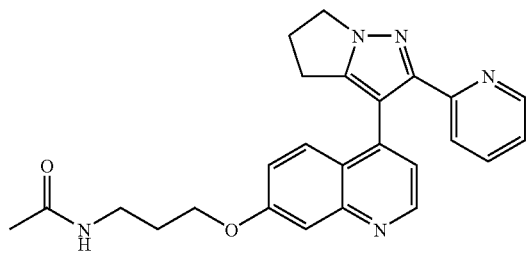

To a solution of 3-[4-(2-pyridin-2-yl-5,6-dihydro-4H-pyrrolo[1,2-b]pyrazol-3-yl)-quinolin-7-yloxy]-propylamine (25 mg, 0.06 mmol) in pyridine (1 mL) at room temperature is added acetic anhydride (500 µL, 5.3 mmol). The mixture is stirred for 2 h, concentrated in vacuo, and the residue chromatographed on SiO$_2$ (89% dichloromethane 10% methanol 1% concentrated ammonium hydroxide) to yield the title compound, 12 mg (47%), as a light brown solid TOF MS ES$^+$ exact mass calculated for C$_{25}$H$_{26}$N$_5$O$_2$ (p+1): m/z=428.2086. Found: 428.2095.

By the above method the following compounds are prepared (unless otherwise specified):

| EXAMPLE # | Product (Chemical Name) | Physical Data |
|---|---|---|
| 346 | N-Acetyl-N-{4-[2-(6-methyl-pyridin-2-yl)-5,6-dihydro-4H-pyrrolo[1,2-b]pyrazol-3-yl]-quinolin-7-yl}-acetamide | MS APCI$^+$ m/e 426 (M + 1) |

EXAMPLE 347

2-Pyridin-2-yl-3-quinolin-4-yl-pyrazolo[1,5-a]piperidin-7-ol

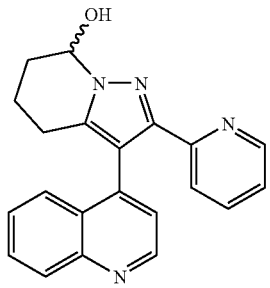

Neat 1-(1-aza-2-pyridin-2-yl-3-quinolin-4-yl-prop-1-enyl)piperidine-2,6-dione (0.64 g, 1.8 mmol) is heated at 180° C. for 2 h. After cooling, the residue is allowed to cool, dissolved in dichloromethane (15 mL), cooled to −70° C., and treated with a 1.0 M solution of DIBAL-H in toluene (1.9 mL, 1.9 mmol) dropwise. The mixture is stirred for 0.5 h, the cold bath removed, and stirred for an additional 18 h. The reaction is diluted with saturated aqueous ammonium chloride solution. The mixture is partitioned between ethyl acetate and water. The organic portion is washed with water and brine, dried (sodium sulfate), filtered, and concentrated in vacuo. The residue is precipitated from ethyl acetate with hexane to yield title compound, 0.58 g (62%), as a white solid.

TOF MS ES+ exact mass calculated for C$_{21}$H$_{18}$N$_4$O (p+1): m/z=343.1559. Found: 343.1570.

EXAMPLE 348

7-Acetoxy-2-pyridin-2-yl-3-quinolin-4-yl-pyrazolo[1,5-a]piperidine

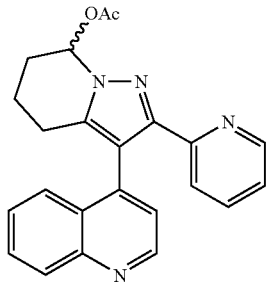

A solution of 2-pyridin-2-yl-3-quinolin-4-yl-pyrazolo[1,5-a]piperidin-7-ol (0.04 g, 0.12 mmol) and acetic anhydride (0.2 mL) in pyridine (2 mL) at room temperature is stirred for 24 h. The mixture is partitioned between ethyl acetate and water. The organic portion is washed with water and brine, dried (sodium sulfate), filtered, and concentrated in vacuo. The residue is chromatographed on SiO$_2$ (5% methanol/dichloromethane) to yield the title compound, 0.41 g (91%), as a white solid.

TOF MS ES+ exact mass calculated for C$_{23}$H$_{21}$N$_4$O$_2$ (p+1): m/z=385.1665. Found: 385.1668.

EXAMPLE 349

Methyl-{3-[4-(2-pyridin-2-yl-5,6-dihydro-4H-pyrrolo[1,2-b]pyrazol-3-yl)-quinolin-7-yloxy]-propyl}-amine

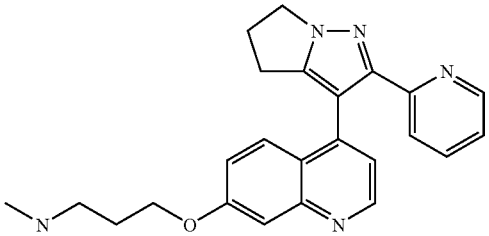

A solution of methyl-{3-[4-(2-pyridin-2-yl-5,6-dihydro-4H-pyrrolo[1,2-b]pyrazol-3-yl)-quinolin-7-yloxy]-propyl}-carbamic acid tert-butyl ester (100 mg, 0.2 mmol) in trifluoroacetic acid (3 mL) is stirred at room temperature for 6 h. The mixture is concentrated in vacuo and traces of trifluoroacetic acid removed by repeated evaporation with chloroform. The residue is placed on an SCX column and washed with water, methanol, and 7 N ammonia in methanol. Concentration of the appropriate fraction yields the title compound, 40 mg (50%), as yellow oil.

MS ES$^+$ m/e 400 (M+1).

By the above method the following compounds are prepared (unless otherwise specified):

| EXAMPLE # | Product (Chemical Name) | Physical Data |
|---|---|---|
| 350 | 7-(Piperidin-4-yloxy)-4-(2-pyridin-2-yl-5,6-dihydro-4H-pyrrolo[1,2-b]pyrazol-3-yl)-quinoline | MS ES+ m/e 412 (M + 1) |
| 351 | 4-[2-(6-Methyl-pyridin-2-yl)-5,6-dihydro-4H-pyrrolo[1,2-b]pyrazol-3-yl]-quinoline-7-carboxylic acid (2-amino-1,1-dimethyl-ethyl)-amide | MS APC$^+$ m/e 469 (M + 1) |

EXAMPLE 352

{6-[3-(4-Fluoro-phenyl)-5,6-dihydro-4H-pyrrolo[1,2-b]pyrazol-2-yl]-pyridin-2-yl}-methanol

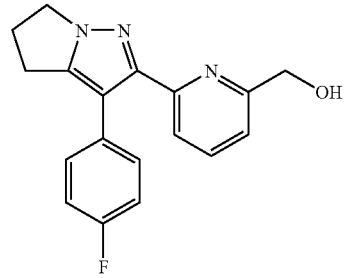

A solution of 3-(4-fluoro-phenyl)-2-(6-methyl-1-oxy-pyridin-2-yl)-5,6-dihydro-4H-pyrrolo[1,2-b]pyrazole (82 mg, 0.27 mmol) in chloroform (2 mL) is treated with excess trifluoroacetic anhydride and warmed at reflux for 2 h then concentrated in vacuo. The residue is treated with excess solid potassium carbonate in methanol at reflux for 30 min. The mixture is concentrated, then partitioned between ethyl acetate and water. The ethyl acetate portion is concentrated and the residue purified on a silica cartridge (10% pyridine ethyl acetate) to yield 24 mg (29%) of the title compound as a yellow foam.

MS, EI$^+$ m/e 310 (M+1).

EXAMPLE 353

[6-(3-Quinolin-4-yl-5,6-dihydro-4H-pyrrolo[1,2-b]pyrazol-2-yl)-pyridin-2-yl]-methanol To a solution of 6-(3-quinolin-4-yl-5,6-dihydro-4H-pyrrolo[1,2-b]pyrazol-2-yl)pyridine-2-carboxylic acid methyl ester (0.550 g, 1.48 mmol) in methanol (20 mL) is added lithium borohydride (35.5 mg, 1.63 mmol). The mixture is stirred 1 h, additional lithium borohydride (35.5 mg, 1.63 mmol) added, and the resulting mixture stirred at room temperature for 16 h. 4 N Hydrochloric acid (3 mL) is added slowly and the resulting mixture concentrated in vacuo. The residue is taken up in methanol (10 mL) and partitioned between ethyl acetate (150 mL) and saturated potassium carbonate (150 mL). The organic portion is washed with brine (150 mL), dried (magnesium sulfate), and a concentrated in vacuo. The residue is precipitated from ethyl acetate with hexanes to yield 296 mg (58%) of the title compound.

MS ES$^+$ m/e 342 (M+1).

EXAMPLE 354

4-[2-(6-Methyl-pyridin-2-yl)-5,6-dihydro-4H-pyrrolo[1,2-b]pyrazol-3-yl]-phenol

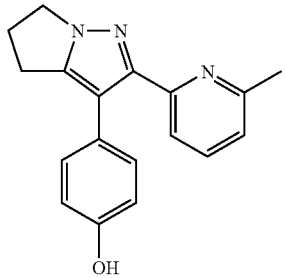

To a solution of 3-(4-methoxy-phenyl)-2-(6-methyl-pyridin-2-yl)-5,6-dihydro-4H-pyrrolo[1,2-b]pyrazole (72 mg, 0.24 mmol) in methylene chloride (1 mL) is added boron tribromide (0.3 mL). The solution is stirred at ambient temperature for 3 h, then quenched with methanol. The mixture is concentrated in vacuo to a reddish solid. The solid is passed through a silica gel cartridge (methylene chloride, ethyl acetate, then acetone). The appropriate methylene chloride fractions are concentrated in vacuo to yield 4 mg (5.8%) of the title compound. The more polar fractions are concentrated in vacuo then treated with aqueous ammonium chloride and methanol. The mixture is concentrated in vacuo and the residue purified on a silica cartridge eluting as above. Appropriate fractions are combined and concentrated in vacuo to yield an additional 49 mg (71%) of the title compound.

MS ES+ m/z 292 (M+1).

EXAMPLE 355

7-(1-Methyl-pyrrolidin-3-ylmethoxy)-4-(2-pyridin-2-yl-5,6-dihydro-4H-pyrrolo[1,2-b]pyrazol-3-yl)-quinoline

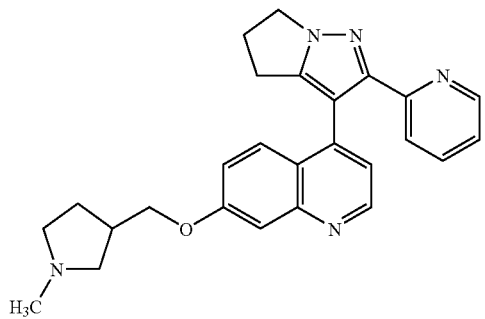

To a 1 M solution of lithium aluminum hydride in tetrahydrofuran (0.60 mL, 0.59 mmol) is added a solution of 3-[4-(2-pyridin-2-yl-5,6-dihydro-4H-pyrrolo[1,2-b]pyrazol-3-yl)-quinolin-7-yloxymethyl]-pyrrolidine-1-carboxylic acid benzyl ester (215 mg, 0.39 mmol) in tetrahydrofuran (2 mL). The mixture is heated at 65° C. for 2 h, cooled to 0° C., and diluted with saturated aqueous sodium potassium tartrate solution. The mixture is extracted with chloroform and the organic portion chromatographed on SiO$_2$ to yield the title compound, 112 mg (67%), as a yellow foam.

MS APC+ m/e 426 (M+1).

By the above method the following compounds are prepared (unless otherwise specified):

| EXAMPLE # | Product (Chemical Name) | Physical Data |
|---|---|---|
| 356 | 7-(1-Methyl-piperidin-4-ylmethoxy)-4-(2-pyridin-2-yl-5,6-dihydro-4H-pyrrolo[1,2-b]pyrazol-3-yl)-quinoline | MS ES+ m/e 440 (M + 1). |

EXAMPLE 357

4-[2-(6-Methyl-pyridin-2-yl)-5,6-dihydro-4H-pyrrolo[1,2-b]pyrazol-3-yl]-quinoline-7-carboxylic acid(2-dimethylamino-1,1-dimethyl-ethyl)-amide

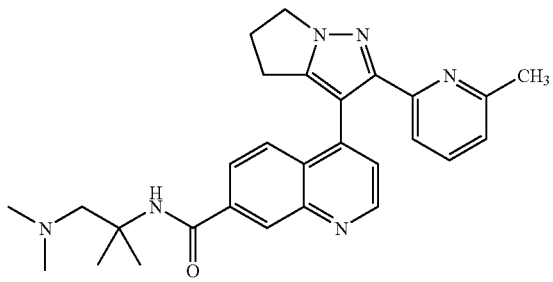

A mixture of 4-[2-(6-methyl-pyridin-2-yl)-5,6-dihydro-4H-pyrrolo[1,2-b]pyrazol-3-yl]-quinoline-7-carboxylic acid (2-amino-1,1-dimethyl-ethyl)-amide (0.12 g, 0.27 mmol), sodium cyanoborohydride (0.038 g, 0.6 mmol), and acetic acid (0.077 mL, 1.3 mmol) in methanol (5 mL) is cooled to 0° C. and stirred for 10 min. A solution of 37% aqueous formaldehyde (0.086 mL, 3.1 mmol) in methanol (2 mL) is added dropwise. The mixture is allowed to warm to room temperature and stirred for 1 h. The reaction is quenched with saturated aqueous potassium carbonate solution and concentrated in vacuo. The residue is taken up in chloroform, washed with water and brine, dried (sodium sulfate) and concentrated in vacuo. The residue is chromatographed on SiO$_2$ (8% methanol/92% dichloromethane) to yield the title compound, 33 mg (27%), as a white foam.

MS APC+ m/e 469 (M+1).

EXAMPLE 358

(S)-[3-(4-Fluoro-phenyl)-2-(6-methyl-pyridin-2-yl)-5,6-dihydro-4H-pyrrolo[1,2-b]pyrazol-6-yl]-methanol

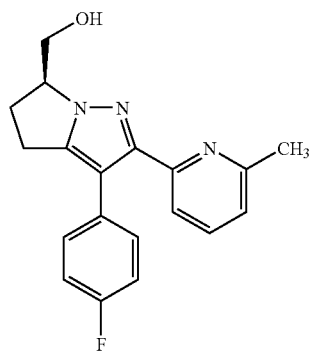

To a solution of (S)-6-benzyloxymethyl-3-(4-fluoro-phenyl)-2-(6-methyl-pyridin-2-yl)-5,6-dihydro-4H-pyrrolo

[1,2-b]pyrazole (0.3 g, 0.73 mmol) in chloroform (1.0 mL) is added trimethylsilyl iodide (0.173 mL, 1.21 mmol). The mixture is stirred 2 h, diluted with methanol (10 mL), stirred 10 min, and concentrated in vacuo. The residue is taken up in ethyl acetate (50 mL), washed with aqueous sodium thiosulfate (2×50 mL), saturated sodium bicarbonate solution, and brine. The resulting solution is dried (magnesium sulfate), filtered, and concentrated in vacuo. The residue is chromatographed on SiO$_2$ (3% methanol/ ethyl acetate) to yield the title compound, 149 mg (64%), as a pale yellow solid.

MS APCI$^+$ m/e 324 (M+1); melting range: 142–144° C.

By the above method the following compounds are essentially prepared. Unless otherwise specified.

| EXAMPLE # | Product (Chemical Name) | Physical Data |
|---|---|---|
| 359 | (R)-[3-(4-Fluoro-phenyl)-2-(6-methyl-pyridin-2-yl)-5,6-dihydro-4H-pyrrolo[1,2-b]pyrazol-6-yl]-methanol | MS APCI$^+$ m/e 324 (M + 1). |

EXAMPLE 360

(S)-[3-(4-Fluoro-phenyl)-2-(6-methyl-pyridin-2-yl)-5,6-dihydro-4H-pyrrolo[1,2-b]pyrazol-6-yl]-acetonitrile

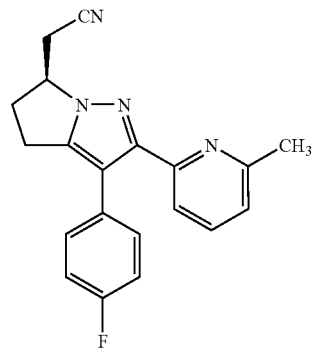

A mixture of potassium cyanide (44 mg, 0.67 mmol), tetrabutylammonium iodide (catalytic), and (S)-methanesulfonic acid 3-(4-fluoro-phenyl)-2-(6-methyl-pyridin-2-yl)-5,6-dihydro-4H-pyrrolo[1,2-b]pyrazol-6-ylmethyl ester (54 mg, 0.135 mmol) in N,N-dimethylformamide (0.35 mL) and water (0.13 mL) is heated at 70° C. for 4 h. The mixture is cooled, taken up in ethyl acetate (20 mL), washed with water and brine, dried (magnesium sulfate), filtered, and concentrated in vacuo. The residue is chromatographed on SiO$_2$ (2% methanol/ chloroform) to yield the title compound, 25 mg (56%).

MS APCI$^+$ m/e 333 (M+1).

By the above method the following compounds are prepared (unless otherwise specified):

| EXAMPLE # | Product (Chemical Name) | Physical Data |
|---|---|---|
| 361 | (R)-[3-(4-Fluoro-phenyl)-2-(6-methyl-pyridin-2-yl)-5,6-dihydro-4H-pyrrolo[1,2-b]pyrazol-6-yl]-acetonitrile | MS APCI$^+$ m/e 333 (M + 1) |

EXAMPLE 362

4-(3-Pyridin-2-yl-5,6-dihydro-4H-pyrrolo[1,2-b]pyrazol-2-yl)-quinoline

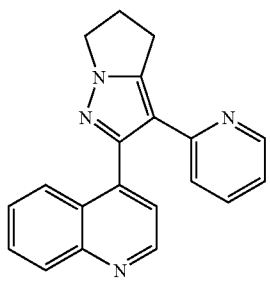

To a solution of (0.230 g, 1 mmol) of 4-(2-(2-pyridyl)ethynyl)quinoline in xylene (2 mL) is added 3a H-pyrrolidino[1,2-C]1,2,3-oxadiazolin-3-one (0.252 g, 2 mmol) and the resulting solution heated in an oil bath at reflux under argon for 48 h, concentrated in vacuo, and the residue chromatographed on SiO$_2$ (0 to 1% methanol in chloroform with 3 drops ammonium hydroxide per 150 mL solvent) to yield 18 mg of title compound as an oil.

MS ES$^+$ m/e 313 (M+1).

EXAMPLE 363

4-(6-Pyridin-2-yl-2,3-dihydro-pyrazolo[5,1-b]oxazol-7-yl)-quinoline dioxylate salt

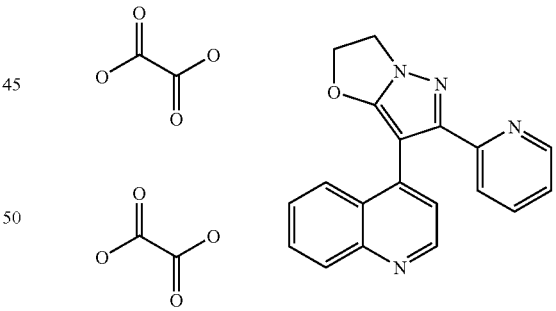

To a solution of 5-pyridin-2-yl-4-quinolin-4-yl 2H-pyrazol-3-ol (50 mg, 0.17 mmol), ethylene glycol (15 mg, 0.24 mmol) and tri-n-butylphosphine (100 mg, 0.50 mmol) in tetrahydrofuran (15 mL) is added 1,1'-(azodicarbonyl)dipiperidine (120 mg, 0.48 mmol). The solution is heated at reflux for 5 h, cooled, and filtered through an SCX cartridge. The residue is chromatographed on SiO$_2$ (15:1 dichloromethane:methanol). The product residue is converted to the disoxylate salt to give the title compound 40 mg (46%).

$^1$H NMR (CDCl$_3$): δ 8.81 (d, J=4 Hz, 1H), 8.42 (m, 1H), 8.11 (d, J=8 Hz, 1H), 7.83 (d, J=8 Hz, 1H), 7.65 (ddd, J=8, 7, 1 Hz, 1H), 7.46 (ddd, J=8, 7, 1 Hz, 1H), 7.38 (ddd, J=8, 7, 1 Hz, 1H) 7.24–7.29 (m, 2H), 7.06–7.10 (m, 1H); MS ES+ m/e 315.0 (M+1). TOF MS ES+ exact mass calculated for C$_{19}$H$_{15}$N$_4$O (p+1): m/z=315.1246. Found: 315.1248.

EXAMPLE 364

3-[4-(2-Pyridin-2-yl-5,6-dihydro-4H-pyrrolo[1,2-b]pyrazol-3-yl)-quinolin-7-yl]-oxazolidin-2-one

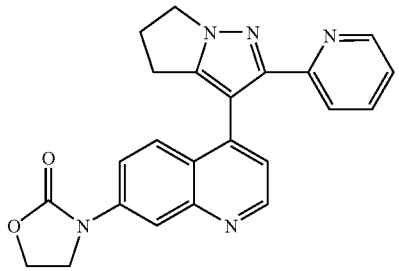

To a solution of [4-(2-pyridin-2-yl-5,6-dihydro-4H-pyrrolo[1,2-b]pyrazol-3-yl)-quinolin-7-yl]-carbamic acid 2-hydroxy-ethyl ester (40.2 mg, 0.097 mmol) and triphenylphosphine (35.0 mg, 0.14 mmol) in tetrahydrofuran (1 mL) at room temperature is added diethyl 40% azodicarboxylate in toluene (50 µL, 0.11 mmol). The mixture is stirred 18 h, filtered, and the filtrate concentrated in vacuo. The residue is chromatographed on SiO$_2$ (2% to 15% methanol in dichloromethane) to yield the desired product, 15.2 mg (40%).

MS ES+ m/e 398.0 (M+1).

By the above method the following compound are prepared (unless otherwise specified):

| EXAMPLE # | Product (Chemical Name) | Physical Data |
|---|---|---|
| 365 | 1-[4-(2-Pyridin-2-yl-5,6-dihydro-4H-pyrrolo[1,2b]pyrazol-3-yl)-quinolin-7-yl]-imidazolidin-2-one | MS ES+ m/e 397.4 (M + 1) |

EXAMPLE 366

4-(2-Pyridin-2-yl-5,6-dihydro-4H-pyrrolo[1,2-b]pyrazol-3-yl)-7-(pyridin-4-ylmethoxy)-quinoline

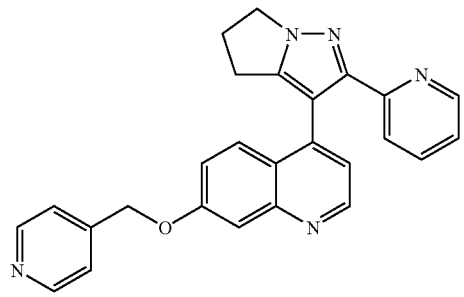

4-(2-Pyridin-2-yl-5,6-dihydro-4H-pyrrolo[1,2-b]pyrazol-3-yl)-quinolin-7-ol (0.100 g, 0.305 mmol), triphenylphosphine (0.080 g, 0.305 mmol), and 4-pyridylcarbinol (0.033 g, 0.305 mmol) are combined in toluene (1.0 mL) and treated with diisopropylazodicarboxylate (0.062 g, 0.305 mmol). The resulting mixture is heated at 75° C. for 18 hours. The mixture is diluted with tetrahydrofuran and heated at 75° C. for 24 h. The mixture is placed on a 10 g SCX resin column which is washed sequentially with dichloromethane (120 mL), methanol (60 mL), and 4:1 dichloromethane/2 N ammonia in methanol (125 mL). The latter fraction is concentrated in vacuo and the residue chromatographed on SiO$_2$ (9:1 ethyl acetate:2N ammonia in methanol) to yield the desired product as a tan solid, 0.035 g (27%).

MS ES+ m/e 420 (M+1).

By the above method the following compound is prepared (unless otherwise specified):

| EXAMPLE # | Product Name | Physical Data |
|---|---|---|
| 367 | 4-(2-Pyridin-2-yl-5,6-dihydro-4H-pyrrolo[1,2-b]pyrazol-3-yl)-7-(3-pyridin-3-yl-propoxy)-quinoline | MS ES+ m/e 448 (M + 1) |

EXAMPLE 368

7-(4,5-Dihydro-1H-imidazol-2-yl)-4-(2-pyridin-2-yl-5,6-dihydro-4H-pyrrolo[1,2-b]pyrazol-3-yl)-quinoline

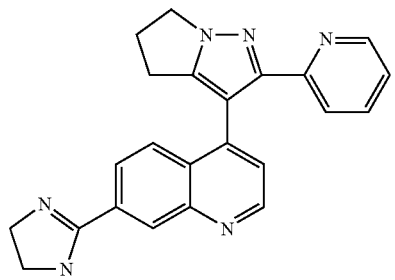

Ethylenediame (45 mL, 0.67 mmol) is added dropwise to a stirred solution of 2.0 M trimethylaluminum in toluene (0.5 mL, 1.0 mmol) and 4-(2-pyridin-2-yl-5,6-dihydro-4H-pyrrolo[1,2-b]pyrazol-3-yl)-quinoline-6-carboxylic acid methyl ester (250.0 mg, 0.675 mmol) at 0° C. The mixture is warmed to room temperature, then refluxed for 3 h. The solution is cooled and diluted with water (0.5 mL) and methanol (1 mL). The mixture is refluxed for 10 min, cooled, filtered, extracted into chloroform, and the organic portion washed with brine. The organic layer is concentrated in vacuo and the residue is chromatographed on SiO$_2$ (10% to 30% methanol in dichloromethane) to yield the title compound, 46 mg (18%), as an yellow oil.

MS ES+ m/e 381.0 (M+1).

EXAMPLE 369

4-[5-(4-Fluoro-phenyl)-2-(6-methyl-pyridin-2-yl)-5,6-dihydro-4H-pyrrolo[1,2-b]pyrazol-3-yl]-quinoline (Enantiomer A)

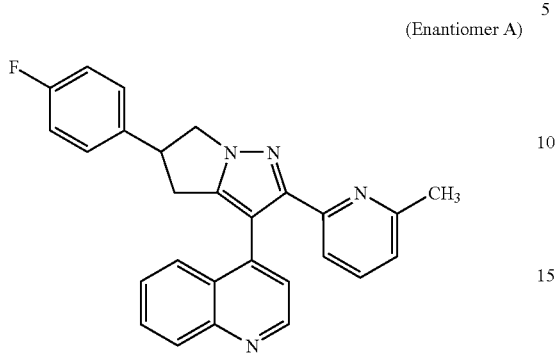

Racemic 4-[5-(4-fluoro-phenyl)-2-(6-methyl-pyridin-2-yl)-5,6-dihydro-4H-pyrrolo[1,2-b]pyrazol-3-yl]-quinoline (110 mg, 0.26 mmol) is separated into pure enantiomers by preparative HPLC with a Chiralcel OD (50×500 mm) column (25:75 isopropanol/heptane and detector at 220 nm). Fractions containing the first eluting compound are combined and concentrated to yield the title compound, 44 mg (40%), as an off-white foam.

$^1$H NMR (CDCl$_3$): δ 8.85 (d, J=4.5 Hz, 1H), 8.10 (d, J=8.4 Hz, 1H), 7.80 (d, J=8.4 Hz, 1H), 7.65 (td, J=1.5, 8 Hz, 1H), 7.35 (td, J=1.5, 8 Hz, 1H), 7.20–7.30 (m, 4H), 6.85–7.10 (m, 4H), 4.80 (dd, J=8.4, 11 Hz, 1H), 4.35 (dd, J=7, 11 Hz, 1H), 4.15–4.25 (m, 1H), 3.30 (dd, J=8.4, 16 Hz, 1H), 2.85 (dd, J=6, 16 Hz, 1H), 2.30 (s, 3H). MS APCI$^+$ m/e 421 (M+1).

EXAMPLE 370

4-[5-(4-Fluoro-phenyl)-2-(6-methyl-pyridin-2-yl)-5,6-dihydro-4H-pyrrolo[1,2-b]pyrazol-3-yl]-quinoline (Enantiomer B)

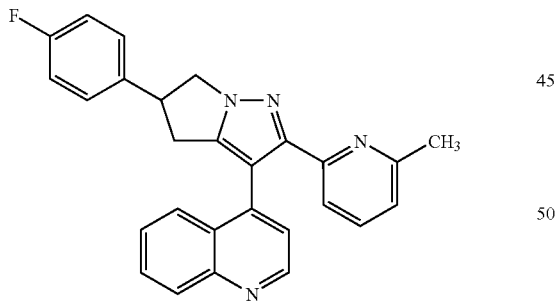

Racemic 4-[5-(4-fluoro-phenyl)-2-(6-methyl-pyridin-2-yl)-5,6-dihydro-4H-pyrrolo[1,2-b]pyrazol-3-yl]-quinoline (110 mg, 0.26 mmol) is separated into pure enantiomers by preparative HPLC with a Chiralcel OD (50×500 mm) column (25:75 isopropanol/heptane and detector at 220 nm). Fractions containing the second eluting compound are combined and concentrated to give the title compound, 59 mg (54%), as an off-white foam.

$^1$H NMR (CDCl$_3$): δ 8.85 (d, J=4.5 Hz, 1H), 8.10 (d, J=8.4 Hz, 1H), 7.80 (d, J=8.4 Hz, 1H), 7.65 (td, J=1.5, 8 Hz, 1H), 7.35 (td, J=1.5, 8 Hz, 1H), 7.20–7.30 (m, 4H), 6.85–7.10 (m, 4H), 4.80 (dd, J=8.4, 11 Hz, 1H), 4.35 (dd, J=7, 11 Hz, 1H), 4.15–4.25 (m, 1H), 3.30 (dd, J=8.4, 16 Hz, 1H), 2.85 (dd, J=6, 16 Hz, 1H), 2.30 (s, 3H). MS APCI$^+$ m/e 421 (M+1).

EXAMPLE 371

4-[2-(6-Vinyl-pyridin-2-yl)-5,6-dihydro-4H-pyrrolo[1,2-b]pyrazol-3-yl]-quinoline

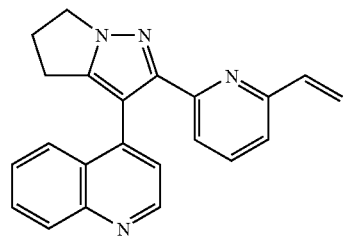

Add tributylvinyltin (0.059 mL, 0.19 mmol) to a solution of 4-[2-(6-chloro-pyridin-2-yl)-5,6-dihydro-4H-pyrrolo[1,2-b]pyrazol-3-yl]-quinoline, EXAMPLE 101, (59 mg, 0.17 mmol) in toluene (0.7 mL) at RT. Bubble nitrogen into the reaction mixture for 5 min and add tetrakis-(triphenylphosphine) palladium (0) (10 mg, 0.0085 mmol). Bubble nitrogen into the solution for an additional 2 min and heat the reaction to 110° C. for 18 h. Concentrate the reaction in vacuo and purify by flash column chromatography (SiO2, 20–40% acetone/hexanes) to provide the title compound (35 mg, 62%) as a white solid.

MS Calcd. 338; MS (APCI) (M+1) 339.

EXAMPLE 372

3-{4-[2-(6-Methyl-pyridin-2-yl)-5,6-dihydro-4H-pyrrolo[1,2-b]pyrazol-3-yl]-quinolin-6-yl}-acrylic acid

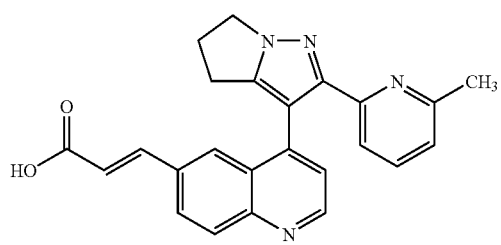

Dissolve 3-{4-[2-(6-methyl-pyridin-2-yl)-5,6-dihydro-4H-pyrrolo[1,2-b]pyrazol-3-yl]-quinolin-6-yl}-acrylic acid methyl ester (0.040 g, 0.1 mmol) in methanol/water (3:1, 2 mL). Add lithium hydroxide (0.010 g, 0.25 mmol) and stir the mixture 18 h. Remove the solvent then load the residue on a SCX resin column with methanol. Elute the column with methanol (50 mL) then with 2 N ammonia/methanol to give the desired product as a pale yellow solid 0.036 g (92%) MS APCI+ m/e 397 (M+1).

The compounds disclosed herein were tested by the following protocols for TGF-β inhibition, as described below in the protocol description. The data collected thereby is shown below.

TGF-β Receptor I and II Purification and in vitro Kinase Reactions

For TGF-β Type I (RIT204D) and Type II (RII WT) Receptors: The 6×-HIS tagged cytoplasmic kinase domain of each receptor was expressed and purified from Sf9 insect cell lysates as briefly described below:

Cell pellets after 48–72 hrs of infection were lysed in lysis buffer (LB: 50 mM Tris pH 7.5, 150 mM NaCl, 50 mM NaF, 0.5% NP40 with freshly added 20 mM, β-mercaptoethanol, 10 mM imidazole, 1 mM PMSF, 1×EDTA-free Complete Protease Inhibitor (Boehringer Mannheim).

Cell lysates were clarified: by centrifugation and 0.45 uM filtered prior to purification by Ni/NTA affinity chromatography (Qiagen).

Chromatography Protocol:

Equilibrate with 10 CV of LB, load sample, wash with 10 CV RIPA buffer (50 mM Tris pH 7.5, 150 mM NaCl, 1% NP40, 1 mM EDTA, 0.25% sodium deoxycholate, added fresh 20 mM β-mercaptoethanol, 1 mM PMSF), wash with 10 CV LB, wash with 10 CV 1×KB (50 mM Tris pH 7.5, 150 mM NaCl, 4 mM $MgCl_2$, 1 mM NaF, 2 mM β-mercaptoethanol), elute with a linear gradient of 1×KB containing 200 mM Imidazole.

Both enzymes were approximately 90% pure and had autophosphorylation activity.

Reactions: 170–200 nM enzyme in 1×KB, compound dilution series in 1×KB/16% DMSO (20 uM to 1 nM final concentration with 4% DMSO final concentration), reactions started by adding ATP mix (4 uM ATP/1 uCi $^{33}$P-□-ATP final concentrations) in 1×KB.

Reactions were incubated at 30° C. for 1 hr RIT204D or 40 min for RII WT. Reactions were stopped and quantitated using standard TCA/BSA precipitation onto Millipore FB glass fiber filter plates and by liquid scintillation counting on a MicroBeta JET.

Representative data for compounds of the current invention with the RIT204D IC50<20.00 (uM) are given in Table I.

TGF-β Receptor I

Table I:

TABLE 1

| COMPOUND NAME |
| --- |
| 7-Methanesulfonyl-4-(2-pyridin-2-yl-5,6-dihydro-4H-pyrrolo[1,2-b]pyrazol-3-yl)-quinoline |
| 4-(2-Thiophen-2-yl-5,6-dihydro-4H-pyrrolo[1,2-b]pyrazol-3-yl)quinoline |
| 4-[2-(6-Benzyl-pyridin-2-yl)-5,6-dihydro-4H-pyrrolo[1,2-b]pyrazol-3-yl]-quinoline |
| 2-(6-methyl-pyridin-2-yl)-3-pyridin-3-yl-5,6-dihydro-4H-pyrrolo[1,2-b]pyrazole |
| N,N-Dimethyl-3-[4-(2-pyridin-2-yl-5,6-dihydro-4H-pyrrolo[1,2-b]pyrazol-3-yl)-quinolin-7-yloxy]-benzamide |
| 4-[2-(3-Chloro-phemyl)-4,5,6,7-tetrahydro-pyrazolo[1,5-alpyridin-3-y]-quinoline |
| N,N-Dimethyl-N'-[4-(2-pyridin-2-yl-5,6-dihydro-4H-pyrrolo[1,2-b]pyrazol-3-yl)-pyridin-2-yl]-propane-1,3-diamine |
| Dimethyl-{4-[4-(2-pyridin-2-yl-5,6-dihydro-4H-pyrrolo[1,2-b]pyrazol-3-yl)-pyridin-2-yloxy]-butyl}-amine |
| 4-(2-Pyridin-2-yl-5,6-dihydro-4H-pyrrolo[1,2-H]pyrazol-3-yl)-quinoline-7-carboxylic acid(3-dimethylamino-propyl)-methyl-amide |
| 4-[2-(3-Trifluoromethoxy-phenyl)-5,6-dihydro-4H-pyrrolo[1,2-b]pyrazol-3-yl]-quinoline |
| 3-(4-Fluorophenyl)-2-(6-methylpyridin-2-yl)-5,6-dihydro-4H-pyrrolo[1,2-b]pyrazole |
| 3-{4-[2-(6-Methyl-pyridin-2-yl)-5,6-dihydro-4H-pyrrolo[1,2-b]pyrazol-3-yl]-quinolin-7-yl}-acrylic acid methyl ester |
| 3-(4-Methoxyphenyl)-2-(6-methylpyridin-2-yl)-5,6-dihydro-4H-pyrrolo[1,2-b]pyrazole |
| 4-(2-Pyridin-2-yl-5,6-dihydro-4H-pyrrolo[1,2-H]pyrazol-3-yl)-quinoline-7-carboxylic acid methylamide |
| N-{3-[4-(2-Pyridin-2-yl-5,6-dihydro-4H-pyrrolo[1,2-b]pyrazol-3-yl)-quinolin-7-yloxy]-propyl}-acetamide |
| 4-(2-Pyridin-2-yl-5,6-dihydro-4H-pyrrolo[1,2-b]pyrazol-3-yl)-quinoline-7-carboxylic acid propylamide |
| Dimethyl-{3-[4-(2-pyridin-2-yl-5,6-dihydro-4H-pyrrolo[1,2-b]pyrazol-3-yl)-quinolin-7-yloxy]-propyl}-amine |
| N-(2-dimethylamino-ethyl)-2-[4-(2-pyridin-2-yl-5,6-dihydro-4H-pyrrolo[1,2-b]pyrazol-3-yl)-quinolin-7-yloxy]-acetamide |
| Dimethyl-{2-[4-(2-pyridin-2-yl-5,6-dihydro-4H-pyrrolo[1,2-b]pyrazol-3-yl)-quinolin-7-yloxy]-ethyl}-amine |

Representative data for compounds of the current invention with the RII WT IC50<20.00 (uM) are given in Table II.

TGF-β Receptor II
Table II:

TABLE II

| COMPOUND NAME |
|---|
| Dimethyl-{3-[4-(2-pyridin-2-yl-5,6-dihydro-4H-pyrrolo[1,2-b]pyrazol-3-yl)-quinolin-7-yloxy]-propyl}-amine |
| N-(2-Dimethylamino-ethyl)-2-[4-(2-pyridin-2-yl-5,6-dihydro-4H-pyrrolo[1,2-b]pyrazol-3-yl)-quinolin-7-yloxy]-acetamide |
| Dimethyl-{2-[4-(2-pyridin-2-yl-5,6-dihydro-4H-pyrrolo[1,2-b]pyrazol-3-yl)-quinolin-7-yloxy]-ethyl}-amine |
| 7-Bromo-2-isopropyl-4-(2-pyridin-2-yl-5,6-dihydro-4H-pyrrolo[1,2-b]pyrazol-3-yl)-quinoline |
| 4-[2-(3-Trifluoromethylphenyl)-5,6-dihydro-4H-pyrrolo[1,2-b]pyrazol-3-yl]-quinoline |
| 4-[2-(6-Methyl-pyridin-2-yl)-5,6-dihydro-4H-pyrrolo[1,2-b]pyrazol-3-yl]-6-phenyl-quinoline |
| 4-(Quinolin-4-yl)-3-(5-fluoropyridin-2-yl)-5,6-dihydro-4H-pyrrolo[1,2-b]pyrazole |
| 4-(2-Pyridin-2-yl-5,6-dihydro-4H-pyrrolo[1,2-b]pyrazol-3-yl)-quinoline-7-carboxylic acid(2-methyl-butyl)-amide |
| 4-(2-Pyridin-2-yl-5,6-dihydro-4H-pyrrolo[1,2-b]pyrazol-3-yl)-quinoline-7-carboxylic acid pyridin-2-ylamide |
| 4-[5-(3-Methoxy-phenyl)-2-pyridin-2-yl-5,6-dihydro-4H-pyrrolo[1,2-b]pyrazol-3-yl]-quinoline. |
| [3-(7-Bromo-quinolin-4-yl)-2-(6-methyl-pyridin-2-yl)-5,6-dihydro-4H-pyrrolo[1,2-b]pyrazol-6-yl]3-methanol |
| 7-(3-Chloro-propoxy)-4-(2-pyridin-2-yl-5,6-dihydro-4H-pyrrolo[1,2-b]pyrazol-3-yl)-quinoline |
| 2-Pyridin-2-yl-3-quinolin-4-yl-pyrazolo[1,5-a]piperidin-7-ol |
| 4-(2-Pyridin-2-yl-5,6-dihydro-4H-pyrrolo[1,2-b]pyrazol-3-yl)-quinoline-7-carboxylic acid cyclopropylamide |
| 4-(2-Pyridin-2-yl-5,6-dihydro-4H-pyrrolo[1,2-b]pyrazol-3-yl]-quinolin-7-ylamine |
| 3-{4-[2-(6-Methyl-pyridin-2-yl)-5,6-dihydro-4H-pyrrolo[1,2-b]pyrazol-3-yl]-quinolin-7-yl}-acrylic acid |
| 3-[4-(2-Pyridin-2-yl-5,6-dihydro-4H-pyrrolo[1,2-b]pyrazol-3-yl)-quinolin-7-yl]-oxazolidin-2-one |
| 3-[4-(2-Pyridin-2-yl-5,6-dihydro-4H-pyrrolo[1,2-b]pyrazol-3-yl)-quinolin-7-ylsulfanyl]-propan-1-ol |
| 4-(2-Pyridin-2-yl-5,6-dihydro-4H-pyrrolo[1,2-H]pyrazol-3-yl)-quinoline-7-carboxylic acid methylamide |
| Ethyl-methyl-{3-[4-(2-pyridin-2-yl-5,6-dihydro-4H-pyrrolo[1,2-b]pyrazol-3-yl)-quinolin-7-yloxy]-propyl}-amine |

MV1LU p3TP-Lux Assay

A stable Mv1Lu clone (C1) containing the p3TP-Lux reporter was created by standard transfection and puromycin selection protocols. This stable clone was used to screen the example compounds for their ability to inhibit TGF-β dependent luciferase production as briefly described below:

1. Plated Mv1Lu C1 cells in Wallac™ Black Isoplates
2. Allowed cells to adhere overnight.
3. Removed media and replaced with 0.5% FBS DMEM media
4. Added the compound dilution series in 0.5% FBS/DMEM containing 1% DMSO such that the final compound concentration ranged from 20 uM to 0.1 nM and the final DMSO concentration was 0.2%.
5. Incubated at 37° C./5% $CO_2$ for 2 hrs.
6. Added 0.5% FBS/DMEM as control or TGF-β1 diluted in 0.5% FBS/DMEM (final concentration of 10 pM) to the −/+ TGF-β wells respectively
7. Incubated for 16–20 hrs. at 37° C./5% $CO_2$
8. Removed media and rinsed 1× with PBS.
9. Removed PBS and lysed the cells with 1× Passive Lysis Buffer (Promega) at room temperature.
10. Counted relative luciferase activity on the MicroBeta JET by injecting Luciferase Assay Reagent II (PROMEGA).

The use of the above assay in measuring TGF-β responsive activity is described in Wrana, et al. *Cell* 71: 1003–1014 (1992).

Representative data for compounds of the current invention with the p3TP-LUX IC50<20.00 (uM) are given in Table III.

MV1LU p3TP-Lux/Assay

Table III:

TABLE III

| COMPOUND NAME |
| --- |
| 4-[5-(4-Fluoro-phenyl)-2-(6-methyl-pyridin-2-yl)-5,6-dihydro-4H-pyrrolo[1,2-b]pyrazol-3-yl]-quinoline(Enantiomer B) |
| 3-(2-Chloro-pyridin-4-yl)-2-pyridin-2-yl-5,6-dihydro-4H-pyrrolo[1,2-b]pyrazole |
| 4-(2-Pyridin-2-yl-5,6-dihydro-4H-pyrrolo[1,2-b]pyrazol-3-yl)-quinoline-6-carboxylic acid hydrazide |
| 2-(6-methyl-pyridin-2-yl)-3-naphthalen-1-yl-5,6-dihydro-4H-pyrrolo[1,2-b]pyrazole |
| 2-{4-[2-(6-Methyl-pyridin-2-yl)-5,6-dihydro-4H-pyrrolo[1,2-b]pyrazol-3-yl]-quinolin-6-yl}-propan-2-ol |
| 6-Benzo[1,3]dioxol-5-yl-4-[2-(6-methyl-pyridin-2-yl)-5,6-dihydro-4H-pyrrolo[1,2-b]pyrazol-3-yl]-quinoline |
| 8-Fluoro-4-[2-(6-methyl-pyridin-2-yl)-5,6-dihydro-4H-pyrrolo[1,2-b]pyrazol-3-yl]-quinoline |
| 5-(4-Chloro-phenyl)-3-(4-fluoro-phenyl)-2-(6-methyl-pyridin-2-yl)-5,6-dihydro-4H-pyrrolo[1,2-b]pyrazole |
| 4-(6-Hydroxymethyl-2-pyridin-2-yl-5,6-dihydro-4H-pyrrolo[1,2-b]pyrazol-3yl)-quinoline |
| 4-[2-(6-Methyl-pyridin-2-yl)-5,6-dihydro-4H-pyrrolo[1,2-b]pyrazol-3-yl]-quinoline-6-carboxylic acid methyl ester |
| N,N-Dimethyl-3-{4-[2-(6-methyl-pyridin-2-yl)-5,6-dihydro-4H-pyrrolo[1,2-b]pyrazol-3-yl]-quinolin-7-yl}-propionamide |
| 4-[2-(6-Methylpyridin-2-yl)-5,6-dihydro4H-pyrrolo[1,2-b]pyrazol-3-yl]quinoline-7-carbox-ylic acid(2-piperidin-1-yl-ethyl)amide |
| 7-(3-chloro-propoxy)-4-[2-(6-methyl-pyridin-2-yl)-5,6-dihydro-4H-pyrrolo[1,2-b]pyrazol-3-yl]-quinoline |
| 7-(3-azepan-1-yl-propoxy)-4-(2-pyridin-2-yl-5,6-dihydro-4H-pyrrolo[1,2-b]pyrazol-3-yl)-quinoline |
| [6-(3-Quinolin-4-yl-5,6-dihydro-4H-pyrrolo[1,2-b]pyrazol-2-yl)-pyridin-2-yl]-methanol |
| 4-(2-Pyridin-2-yl-5,6-dihydro-4H-pyrrolo[1,2-H]pyrazol-3-yl)-quinoline-7-carboxylic acid(2-dimethylamino-ethyl)-methyl-amide | p38α in vitro Kinase Assay

Active p38α/SAPK2α was purchased from Upstate Biotechnology (cat#14-251). A known p38α substrate from EGFR was used in the assay (Young, et al. (1997) JBC 272: 12116–12121).

Reactions were performed in 1× kinase buffer (25 mM Tris-HCl pH 7.5, 5 mM β-glycerophosphate, 2 mM DTT, 0.1 mM $Na_3VO_4$, 10 mM $MgCl_2$, 1 uM Microcystin) with 5 nM p38α, 62.5 uM substrate, 40 uM to 0.2 nM compound dilution series in 1×KB/16% DMSO (final 4% DMSO concentration). Reactions were started by addition of 100 uM ATP (final concentration) with 1 uCi $^{33}$P-γ-ATP in 1×KB and incubated at 30° C. for 40 min. Reactions were stopped with $H_3PO_4$ and quantitated on Millipore PH phosphocellulose filter plates by liquid scintillation counting on a MicroBeta JET.

Representative data for compounds of the current invention with the p38α IC50<20.00 (uM) are given in Table IV.

p38α/SAPK2α

Table IV:

TABLE IV

| COUMPOUND NAME |
| --- |
| 3-Benzo[1,3]dioxol-5-yl-2-(6-methyl-pyridin-2-yl)-5,6-dihydro-4H-pyrrolo[1,2-b]pyrazole |
| 4-(2-Pyridin-2-yl-5,6-dihydro-4H-pyrrolo[1,2-H]pyrazol-3-yl)-quinoline-7-carboxylic acid methylamide |
| 3-Naphthalen-2-yl-2-pyridin-2-yl-5,6-dihydro-4H-pyrrolo[1,2-b]pyrazole |
| 3-[4-(2-Pyridin-2-yl-5,6-dihydro-4H-pyrrolo[1,2-b]pyrazol-3-yl)-quinolin-7-ylsulfanyl]-propan-1-ol |
| 6-(4-Fluoro-phenyl)-4-[2-(6-methyl-pyridin-2-yl)-5,6-dihydro-4H-pyrrolo[1,2-b]pyrazol-3-yl]-quinoline |
| 7-[3-(4-Methyl-piperazin-1-yl)-propoxy]-4-(2-pyridin-2-yl-5,6-dihydro-4H-pyrrolo[1,2-b]pyrazol-3-yl)-quinoline |
| 7-Methoxy-4-(2-pyridin-2-yl-5,6-dihydro-4H-pyrrolo[1,2-b]pyrazol-3-yl)-quinoline |
| 7-(3-Imidazol-1-yl-propoxy)-4-(2-pyridin-2-yl-5,6-dihydro-4H-pyrrolo[1,2-b]pyrazol-3-yl)-quinoline |
| 4-[2-(4-Fluoro-phenyl)-5,6-dihydro-4H-pyrrolo[1,2-b]pyrazol-3-yl]-quinoline |
| 7-Amino-4-[2-(6-Methyl-pyridin-2-yl)-5,6-dihydro-4H-pyrrolo[1,2-b]pyrazol-3-yl]-quinoline |
| 6-Methylsulfanyl-4-(2-pyridin-2-yl-5,6-dihydro-4H-pyrrolo[1,2-b]pyrazol-3-yl)-quinoline |
| 4-[2-Pyridin-2-yl-5,6-dihydro-4H-pyrrolo[1,2-b]pyrazol-3-yl]-quinoline-7-carboxylic acid methyl ester |
| 4-(2-Pyridin-2-yl-5,6-dihydro-4H-pyrrolo[1,2-b]pyrazol-3-yl)-quinoline-7-carboxylic acid [2-(1H-imidazol-4-yl)-ethyl]-amide |
| (R)-[3-(4-Fluoro-phenyl)-2-(6-methyl-pyridin-2-yl)-5,6-dihydro-4H-pyrrolo[1,2-b]pyrazol-6-yl]-acetonitrile |
| 2-Dimethylamino-N-[4-(2-pyridin-2-yl-5,6-dihydro-4H-pyrrolo[1,2-b]pyrazol-3-yl)-quinolin-7-yl]-acetamide |
| 4-[2-(6-Methyl-pyridin-2-yl)-5,6-dihydro-4H-pyrrolo[1,2-b]pyrazol-3-yl]-quinoline-6-carboxylic acid |

KDR (VEGFR2) Purification and in vitro Kinase Assay

The 6×-HIS tagged cytoplasmic kinase domain of KDR was expressed and purified from Sf9 insect cell lysates as described above with the following modification:

1× kinase buffer for chromatography washes and elution was changed to 100 mM HEPES pH 7.5, 10 mM $MnCl_2$ and 5 mM β-mercaptoethanol. The resulting material was approximately 40% pure and had tyrosine autophosphorylation activity.

Reactions: 1 ug enzyme in 1×KB, compound dilution series in 1×KB/16% DMSO (20 uM to 1 nM final concentration with 4% DMSO final concentration), reactions were started by adding ATP mix (1 uM ATP/1 uCi $^{33}$P-□-ATP final concentrations) in 1×KB.

Reactions were incubated at 30° C. for 20 min. The reactions were stopped and quantitated using standard TCA/BSA precipitation onto Millipore FC glass fiber filter plates and by liquid scintillation counting on a MicroBeta JET.

Representative data for compounds of the current invention with the KDR IC50<20.00 (uM) are given in Table V.

KDR (VEGFR2)
Table V:

TABLE V

COMPOUND NAME 4-(2-Pyridin-2-yl-5,6-dihydro-4H-pyrrolo[1,2-b]pyrazol-3-yl)-quinolin-7-ol
4-(2-Pyridin-2-yl-5,6-dihydro-4H-pyrrolo[1,2-b]pyrazol-3-yl)-7-(3-[1,2,3]triazol-1-yl-propoxy)-quinoline
Benzyl-methyl-{3-[4-(2-pyridin-2-yl-5,6-dihydro-4H-pyrrolo[1,2-b]pyrazol-3-yl)-quinolin-7-yloxy]-propyl}-amine
4-[2-(6-Methyl-pyridin-2-yl)-5,6-dihydro-4H-pyrrolo[1,2-b]pyrazol-3-yl]-7-(3-morpholin-4-yl-propoxy)-quinoline
4-[2-(6-Methyl-pyridin-2-yl)-5,6-dihydro-4H-pyrrolo[1,2-b]pyrazol-3-yl]-quinoline-7-carboxylic acid (3-dimethylamino-propyl)-amide
4-(2-Pyridin-2-yl-5,6-dihydro-4H-pyrrolo[1,2-b]pyrazol-3-yl)-7-(3-pyrrolidin-1-yl-propoxy)-quinoline
N,N-Dimethyl-3-[4-(2-pyridin-2-yl-5,6-dihydro-4H-pyrrolo[1,2-b]pyrazol-3-yl)-quinolin-7-yloxy]-benzamide
4-(2-Pyridin-2-yl-5,6-dihydro-4H-pyrrolo[1,2-b]pyrazol-3-yl)-quinoline-7-carboxylic acid (2-acetylamino-ethyl)-amide
4-[2-Pyridin-2-yl-5,6-dihydro-4H-pyrrolo[1,2-b]pyrazol-3-yl]-quinoline-7-carboxylic acid methyl ester
3-[4-(2-pyridin-2-yl-5,6-dihydro-4H-pyrrolo[1,2-b]pyrazol-3-yl)-quinolin-7-yloxy]-propylamine
4-(6-Pyridin-2-yl-2,3-dihydro-pyrazolo[5,1-b]oxazol-7-yl)-quinoline
(1-{3-[7-(2-Chloro-ethoxy)-quinolin-4-yl]-5,6-dihydro-4H-pyrrolo[1,2-b]pyrazol-2-yl}-propenyl)-methylene-amine
4-[2-(6-Methyl-pyridin-2-yl)-5,6-dihydro-4H-pyrrolo[1,2-b]pyrazol-3-yl]-quinoline-7-carboxylic acid methyl ester
Diethyl-(3-{4-[2-(6-methyl-pyridin-2-yl)-5,6-dihydro-4H-pyrrolo[1,2-b]pyrazol-3-yl]-quinolin-7-yloxy}-propyl)-amine
4-(7-Ethoxyquinolin-4-yl)-3-(6-methylpyridin-2-yl)-5,6-dihydro-4H-pyrrolo[1,2-b]pyrazole Conditions "characterized by enhanced TGF-β activity" include those wherein TGF-β synthesis is stimulated so that TGF-β is present at increased levels or wherein TGF-β latent protein is undesirably activated or converted to active TGF-β protein or wherein TGF-β receptors are upregulated or wherein the TGF-β protein shows enhanced binding to cells or extracellular matrix in the location of the disease. Thus, in either case "enhanced activity" refers to any condition wherein the biological activity of TGF-β is undesirably high, regardless of the cause.

A number of diseases have been associated with TGF-β1 over production. Inhibitors of TGF-β intracellular signaling pathway are useful treatments for fibroproliferative diseases. Specifically, fibroproliferative diseases include kidney disorders associated with unregulated TGF-β activity and excessive fibrosis including glomerulonephritis (GN), such as mesangial proliferative GN, immune GN, and crescentic GN. Other renal conditions include diabetic nephropathy, renal interstitial fibrosis, renal fibrosis in transplant patients receiving cyclosporin, and HIV-associated nephropathy. Collagen vascular disorders include progressive systemic sclerosis, polymyositis, scleroderma, dermatomyositis, eosinophilic fascitis, morphea, or those associated with the occurrence of Raynaud's syndrome. Lung fibroses resulting from excessive TGF-β activity include adult respiratory distress syndrome, idiopathic pulmonary fibrosis, and interstitial pulmonary fibrosis often associated with autoimmune disorders, such as systemic lupus erythematosus and scleroderma, chemical contact, or allergies. Another autoimmune disorder associated with fibroproliferative characteristics is rheumatoid arthritis.

Eye diseases associated with a fibroproliferative condition include retinal reattachment surgery accompanying proliferative vitreoretinopathy, cataract extraction with intraocular lens implantation, and post glaucoma drainage surgery are associated with TGF-β1 overproduction.

Fibrotic diseases associated with TGF-β1 overproduction can be divided into chronic conditions such as fibrosis of the kidney, lung and liver and more acute conditions such as dermal scarring and restenosis (Chamberlain, J. Cardiovascular Drug Reviews, 19(4):329–344). Synthesis and secretion of TGF-β1 by tumor cells can also lead to immune suppression such as seen in patients with aggressive brain or breast tumors (Arteaga, et al. (1993) J. Clin. Invest. 92:2569–2576). The course of Leishmanial infection in mice is drastically altered by TGF-β1 (Barral-Netto, et al. (1992) Science 257:545–547). TGF-β1 exacerbated the disease, whereas TGF-β1 antibodies halted the progression of the disease in genetically susceptible mice. Genetically resistant mice became susceptible to Leishmanial infection upon administration of TGF-β1.

The profound effects of TGF-β1 on extracellular matrix deposition have been reviewed (Rocco and Ziyadeh (1991) in Contemporary Issues in Nephrology v.23, Hormones, autocoids and the kidney. ed. Jay Stein, Churchill Livingston, New York pp.391–410; Roberts, et al. (1988) Rec. Prog. Hormone Res. 44:157–197) and include the stimulation of the synthesis and the inhibition of degradation of extracellular matrix components. Since the structure and filtration properties of the glomerulus are largely determined by the extracellular matrix composition of the mesangium and glomerular membrane, it is not surprising that TGF-β1 has profound effects on the kidney. The accumulation of mesangial matrix in proliferative glomerulonephritis (Border, et al. (1990) Kidney Int. 37:689–695) and diabetic nephropathy (Mauer, et al. (1984) J. Clin. Invest. 74:1143–1155) are clear and dominant pathological features of the diseases. TGF-β1 levels are elevated in human diabetic glomerulosclerosis (advanced neuropathy) (Yamamoto, et al. (1993) Proc. Natl. Acad. Sci. 90:1814–1818). TGF-β1 is an important mediator in the genesis of renal fibrosis in a number of animal models (Phan, et al. (1990) Kidney Int. 37:426; Okuda, et al. (1990) J. Clin. Invest. 86:453). Suppression of experimentally induced glomerulonephritis in rats has been demonstrated by antiserum against TGF-β1 (Border, et al. (1990) Nature 346:371) and by an extracellular matrix protein, decorin, which can bind TGF-β1 (Border, et al. (1992) Nature 360:361–363).

Too much TGF-β1 leads to dermal scar-tissue formation. Neutralizing TGF-β1 antibodies injected into the margins of healing wounds in rats have been shown to inhibit scarring without interfering with the rate of wound healing or the tensile strength of the wound (Shah, et al. (1992) Lancet 339:213–214). At the same time there was reduced angiogenesis, reduced number of macrophages and monocytes in the wound, and a reduced amount of disorganized collagen fiber deposition in the scar tissue.

TGF-β1 may be a factor in the progressive thickening of the arterial wall which results from the proliferation of smooth muscle cells and deposition of extracellular matrix in the artery after balloon angioplasty. The diameter of the restenosed artery may be reduced 90% by this thickening, and since most of the reduction in diameter is due to extracellular matrix rather than smooth muscle cell bodies, it may be possible to open these vessels to 50% simply by reducing extensive extracellular matrix deposition. In uninjured pig arteries transfected in vivo with a TGF-β1 gene, TGF-β1 gene expression was associated with both extracellular matrix synthesis and hyperplasia (Nabel, et al. (1993) Proc. Natl. Acad. Sci. USA 90:10759–10763). The TGF-β1 induced hyperplasia was not as extensive as that induced with PDGF-BB, but the extracellular matrix was more extensive with TGF-β1 transfectants. No extracellular matrix deposition was associated with FGF-1 (a secreted form of FGF) induced hyperplasia in this gene transfer pig model (Nabel (1993) Nature 362:844–846).

There are several types of cancer where TGF-β1 produced by the tumor may be deleterious. MATLyLu rat prostate cancer cells (Steiner and Barrack (1992) Mol. Endocrinol 6:15–25) and MCF-7 human breast cancer cells (Arteaga, et al. (1993) Cell Growth and Differ. 4:193–201) became more tumorigenic and metastatic after transfection with a vector expressing the mouse TGF-β1. TGF-β1 has been associated with angiogenesis, metastasis and poor prognosis in human prostate and advanced gastric cancer (Wikstrom, P., et al. (1998) Prostate 37: 19–29; Saito, H. et al. (1999) Cancer 86: 1455–1462). In breast cancer, poor prognosis is associated with elevated TGF-β (Dickson, et al. (1987) Proc. Natl. Acad. Sci. USA 84:837–841; Kasid, et al. (1987) Cancer Res. 47:5733–5738; Daly, et al. (1990) J. Cell Biochem. 43:199–211; Barrett-Lee, et al. (1990) Br. J. Cancer 61:612–617; King, et al. (1989) J. Steroid Biochem. 34:133–138; Welch, et al. (1990) Proc. Natl. Acad. Sci. USA 87:7678–7682; Walker, et al. (1992) Eur. J. Cancer 238:641–644) and induction of TGF-β1 by tamoxifen treatment (Butta, et al. (1992) Cancer Res. 52:4261–4264) has been associated with failure of tamoxifen treatment for breast cancer (Thompson, et al. (1991) Br. J. Cancer 63:609–614). Anti TGF-β1 antibodies inhibit the growth of MDA-231 human breast cancer cells in athymic mice (Arteaga, et al. (1993) J. Clin. Invest. 92:2569–2576), a treatment which is correlated with an increase in spleen natural killer cell activity. CHO cells transfected with latent TGF-β1 also showed decreased NK activity and increased tumor growth in nude mice (Wallick, et al. (1990) J. Exp. Med. 172:1777–1784). Thus, TGF-β secreted by breast tumors may cause an endocrine immune suppression. High plasma concentrations of TGF-β1 have been shown to indicate poor prognosis for advanced breast cancer patients (Anscher, et al. (1993) N. Engl. J. Med. 328:1592–1598). Patients with high circulating TGF-β before high dose chemotherapy and autologous bone marrow transplantation are at high risk for hepatic veno-occlusive disease (15–50% of all patients with a mortality rate up to 50%) and idiopathic interstitial pneumonitis (40–60% of all patients). The implication of these findings is 1) that elevated plasma levels of TGF-β1 can be used to identify at risk patients and 2) that reduction of TGF-β1 could decrease the morbidity and mortality of these common treatments for breast cancer patients.

Many malignant cells secrete transforming growth factor-β (TGF-β), a potent immunosuppressant, suggesting that TGF-β production may represent a significant tumor escape mechanism from host immunosurveillance. Establishment of a leukocyte sub-population with disrupted TGF-β signaling in the tumor-bearing host offers a potential means for immunotherapy of cancer. A transgenic animal model with disrupted TGF-β signaling in T cells is capable of eradicating a normally lethal TGF-β overexpressing lymphoma tumor, EL4 (Gorelik and Flavell, (2001) Nature Medicine 7(10): 1118–1122). Down regulation of TGF-β secretion in tumor cells results in restoration of immunogenicity in the host, while T-cell insensitivity to TGF-β results in accelerated differentiation and autoimmunity, elements of which may be required in order to combat self-antigen-expressing tumors in a tolerized host. The immunosuppressive effects of TGF-β have also been implicated in a subpopulation of HIV patients with lower than predicted immune response based on their CD4/CD8 T cell counts (Garba, et al. J. Immunology (2002) 168: 2247–2254). A TGF-β neutralizing antibody was capable of reversing the effect in culture, indicating that TGF-β signaling inhibitors may have utility in reversing the immune suppression present in this subset of HIV patients.

During the earliest stages of carcinogenesis, TGF-β1 can act as a potent tumor suppressor and may mediate the actions of some chemopreventive agents. However, at some point during the development and progression of malignant neoplasms, tumor cells appear to escape from TGF-β-dependent growth inhibition in parallel with the appearance of bioactive TGF-β in the microenvironment. The dual tumor suppression/tumor promotion roles of TGF-β have been most clearly elucidated in a transgenic system overexpressing TGF-β in keratinocytes. While the transgenics were more resistant to formation of benign skin lesions, the rate of metastatic conversion in the transgenics was dramatically increased (Cui, et al (1996) Cell 86(4):531–42). The production of TGF-β1 by malignant cells in primary tumors appears to increase with advancing stages of tumor progression. Studies in many of the major epithelial cancers suggest that the increased production of TGF-β by human cancers occurs as a relatively late event during tumor progression. Further, this tumor-associated TGF-β provides the tumor cells with a selective advantage and promotes tumor progression. The effects of TGF-β on cell/cell and cell/stroma interactions result in a greater propensity for invasion and metastasis. Tumor-associated TGF-β may allow tumor cells to escape from immune surveillance since it is a potent inhibitor of the clonal expansion of activated lymphocytes. TGF-β has also been shown to inhibit the production of angiostatin. Cancer therapeutic modalities such as radiation therapy and chemotherapy induce the production of activated TGF-β in the tumor, thereby selecting outgrowth of malignant cells that are resistant to TGF-β growth inhibitory effects. Thus, these anticancer treatments increase the risk and hasten the development of tumors with enhanced growth and invasiveness. In this situation, agents targeting TGF-β-mediated signal transduction might be a very effective therapeutic strategy. The resistance of tumor cells to TGF-β has been shown to negate much of the cytotoxic effects of radiation therapy and chemotherapy and the treatment-dependent activation of TGF-β in the stroma may even be detrimental as it can make the microenvironment more conducive to tumor progression and contributes to tissue damage leading to fibrosis. The development of a TGF-β signal transduction inhibitors is likely to benefit the treatment of progressed cancer alone and in combination with other therapies.

The compounds are useful for the treatment of cancer and other disease states influenced by TGF-β by inhibiting TGF-β in a patient in need thereof by administering said compound(s) to said patient. TGF-β would also be useful against atherosclerosis (T. A. McCaffrey: TGF-βs and TGF-β Receptors in Atherosclerosis: Cytokine and Growth Factor Reviews 2000, 11, 103–114) and Alzeheimer's (Masliah, E.; Ho, G.; Wyss-Coray, T.: Functional Role of TGF-β in Alzheimer's Disease Microvascular Injury: Lessons from Trangenic Mice: Neurochemistry International 2001, 39, 393–400) diseases.

Pharmaceutical Compositions

The compositions of the present invention are therapeutically effective amounts of the TGF-β antagonists, noted above. The composition may be formulated with common excipients, diluents or carriers, and compressed into tablets, or formulated elixirs or solutions for convenient oral administration or administered by intramuscular intravenous routes. The compounds can be administered transdermally and maybe formulated as sustained release dosage forms and the like.

The method of treating a human patient according to the present invention includes administration of the TGF-β antagonists. The TGF-β antagonists are formulated into formulations which may be administered by the oral and rectal routes, topically, parenterally, e.g., by injection and by continuous or discontinuous intra-arterial infusion, in the form of, for example, tablets, lozenges, sublingual tablets, sachets, cachets, elixirs, gels, suspensions, aerosols, ointments, for example, containing from 1 to 10% by weight of the active compound in a suitable base, soft and hard gelatin capsules, suppositories, injectable solutions and suspensions in physiologically acceptable media, and sterile packaged powders adsorbed onto a support material for making injectable solutions. Advantageously for this purpose, compositions may be provided in dosage unit form, preferably each dosage unit containing from about 5 to about 500 mg (from about 5 to 50 mg in the case of parenteral or inhalation administration, and from about 25 to 500 mg in the case of oral or rectal administration) the compounds. Dosages from about 0.5 to about 300 mg/kg per day, preferably 0.5 to 20 mg/kg, of active ingredient may be administered although it will, of course, readily be understood that the amount of the compound actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The formulations useful for separate administration of the TGF-β antagonists will normally consist of at least one compound selected from the compounds specified herein mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semi-solid or liquid material which serves as a vehicle, excipient or medium for the active therapeutic substance. Some examples of the diluents or carrier which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup, methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tableting machine. For such purpose there may be employed for instance aluminum, magnesium or calcium stearates, talc or mineral oil.

Preferred pharmaceutical forms of the present invention are capsules, tablets, suppositories, injectable solutions, creams and ointments. Especially preferred are formulations for inhalation application, such as an aerosol, for injection, and for oral ingestion.

We claim:

1. A compound of the structure

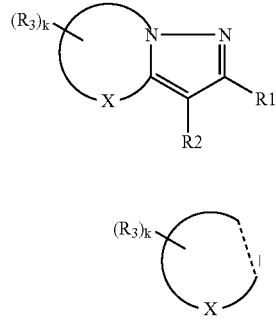

Formula (I)

wherein is a four, five, or six membered saturated ring and X is C, O or S with the proviso that the ring is a fully saturated carbon ring wherein X in the ring may be a single substitution of either C, O or S, except X cannot be O when it would be adjacent to carbon of the pyrazolo ring and R1 is pyridine and R2 is a sulfonyl substituted phenyl or thienyl;

R1 is unsubstituted or substituted phenyl; unsubstituted or substituted pyridine; unsubstituted or substituted pyridine N-oxide; unsubstituted or substituted quinoline; unsubstituted or substituted quinoline N-oxide; unsubstituted or substituted naphthyridine; unsubstituted or substituted pyrazine; furyl; unsubstituted or substituted thiazolyl; unsubstituted or substituted imidazolyl; unsubstituted or substituted pyrazolyl; or unsubstituted or substituted thiophenyl; wherein the substitution may be one or more of the following: $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_{2-6})$alkynyloxy, $(C_1-C_6)$alkylthio, $(C_1C_6)$alkylsulphinyl, $(C_1-C_6)$ alkylsulphonyl, $(C_1-C_6)$alkylamino, di-[$(C_1-C_6)$alkyl]amino, $(C_1-C_6)$alkoxycarbonyl, N—$(C_1-C_6)$alkylcarbamoyl, N,N-di-[$(C_1-C_6)$alkyl]carbamoyl, $(C_2-C_6)$alkanoyl, $(C_2-C_6)$alkanoyloxy, $(C_2-C_6)$alkanoylamino, N—$(C_1-C_6)$alkyl-$(C_2-C_6)$alkanoylamino, $(C_3-C_6)$alkenoylamino, N—$(C_1-C_6)$alkyl-$(C_3-C_6)$alkenoylamino, $(C_3-C_6)$alkynoylamino, N—$(C_1-C_6)$ alkyl-$(C_3-C_6)$alkynoylamino, N—$(C_1-C_6)$alkylsulphamoyl, N,N-di-[$(C_1-C_6)$alkyl]sulphamoyl, $(C_1-C_6)$alkanesulphonylamino, N—$(C_1-C_6)$alkyl-$(C_1-C_6)$alkanesulphonylamino, carboxamide, thiophenyl, aminophenyl, trifluoromethyl, halo, trifluoromethoxy, hydroxymethyl, N-pyrrolidino, N-morpholino, phenylthio, $(C_1-C_4)$dialkylaminomethyl, methoxyphenyl, amino, hydroxy, carboxyl, phenyl, arylalky;

R2 is unsubstituted or substituted quinoline; unsubstituted or substituted quinoline N-oxide; unsubstituted or substituted phenyl; unsubstituted or substituted naphthalene; unsubstituted or substituted pyridine; unsubstituted or substituted pyridine N-oxide; unsubstituted or substituted quinazoline; unsubstituted or substituted cinnoline; unsubstituted or substituted benzodioxole; unsubstituted or substituted benzodioxane; unsubstituted or substituted benzothiophene; or unsubstituted or substituted phenanthroline; wherein the substitution may independently be one or more of the following: hydrogen, $(C_1-C_6)$alkyl, $(C_2-C_6)$alkenyl, $(C_2-C_6)$alkynyl, $(C_1-C_6)$alkylhalide, $(C_1-C_6)$alkoxy, $(C_2-C_6)$alkenyloxy, $(C_2-C_6)$alkynyloxy, $(C_1-C_6)$alkylthio, $(C_1-C_6)$alkylsulphinyl, $(C_1-C_6)$alkylsulphonyl, $(C_1-C_6)$alkylamino, di-[$(C_1-C_6)$alkyl]amino, $(C_1-C_6)$alkoxycarbonyl, N—$(C_1-C_6)$alkylcarbamoyl, N,N-di-[$(C_1-C_6)$alkyl]carbamoyl, aminooxy, N—$(C_1-C_6)$alkyl aminooxy, N,N-di-[$(C_1-C_6)$alkyl]aminooxy, $(C_2-C_6)$alkanoyl, $(C_2-C_6)$alkanoyloxy, $(C_2-C_6)$alkanoylamino, N—$(C_1-C_6)$alkyl-$(C_2-C_6)$alkanoylamino, $(C_3-C_6)$alkenoylamino, N—$(C_1-C_6)$alkyl-$(C_3-C_6)$alkenoylamino, $(C_3-C_6)$alkynoylamino, N—$(C_1-C_6)$alkyl-$(C_3-C_6)$alkynoylamino, sulphamoyl, N—$(C_1-C_6)$alkylsulphamoyl, N,N-di-[$(C_1-C_6)$alkyl] sulphamoyl, $(C_1-C_6)$alkanesulphonylamino, N—$(C_1-C_6)$alkyl-$(C_1-C_6)$alkanesulphonylamino, carboxamide, phenyl, thiophenyl, aminophenyl, phenylthio, halo, cyano, pyridinyl, arylalkyl, hydroxy, N-pyrrolidino, N-morpholino, carboxyl, [5-phenyl-1,2,4-oxadiazole-3-yl]methoxy, 6-methyl-pyridazin-3-yloxy, (5-oxo-2-pyrrolidinyl)methoxy, 2-(4,5-dihydro-1H-imidazolyl), N,N-dialkylcarbamoyloxy, 1-hydroxy-1-methylethyl, 4-fluorophenyl, 3,4-methylenedioxyphenyl, trifluoromethyl, trifluoromethoxy, or a group of the formula

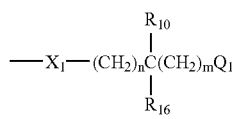

wherein: $X_1$ is O, N, S, $SO_2$, $NR_{13}$, C(O), or bond; $Q_1$ is hydrogen, phenyl, 5-(2,2-difluoro-1,3-benzodioxolyl), C(O)$Q_5$, or pyridyl when, m and n are independently 0–2, except when one is 0 the other cannot be 0; $Q_1$, is OR, $NR^{11}R^{12}$, halo, N-morpholino, N-piperazino-N'$R_{13}$, N-imidazolyl, N-pyrazolyl, N-triazolyl, N-(4-piperidinylpiperidine), $SO_2R_{14}$, $SOR_{14}$, $NHSO_2R_{15}$, acetamido, N-phthalimido, N-oxazolidino, N-imidazolino, N-benzoxazolidino, N-pyrolidinonyl, N(N'-methylbenzimidazolino), N,N-di$(C_1-C_4)$alkylamino$(C_1-C_4)$alkoxy, N-benzimidazolino; when m and n are independently 0–2, but one or the other of m or n is not 0; $Q_5$ is hydroxy, methoxy, amino, diethylamino, dimethylamino; $R_{10}$ is hydrogen, halo, $(C_1-C_6)$alkyl; $R_{11}$ and $R_{12}$ are independently hydrogen, $(C_1-C_6)$alkyl, $(C_1-C_6)$alkoxy, arylalkyl, $(C_3-C_8)$cycloalkyl, $(C_3-C_8)$cycloalkylmethyl, 4-(N-methylpiperidinyl), pyridyl, or $R_{11}$ and $R_{10}$ can be taken together to form a 4, 5, 6, or 7 membered ring, or $R_{11}$ and $R_{12}$ can be taken together to form a 3, 4, 5, 6, or 7 membered ring; $R_{13}$ is hydrogen, $(C_1-C_6)$alkyl, 2-methoxyphenyl, 2-pyridimidinyl; $R_{14}$ is 2-pyrimidinyl, N-methyl-2-imidazolyl, 4-chlorophenyl, 2-pyridylmethyl; $R_{15}$ is $(C_1-C_6)$alkyl, N-methyl-4-imidazolyl; $R_{16}$ is hydrogen, halo, arylalkyl, aryl, or a group of the formula

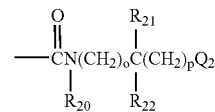

wherein: $Q_2$ is hydrogen, 4-imidazolyl, or C(O)$NR_{24}R_{25}$ when o and p are independently 0–2; $Q_2$ is $OR_{23}$, $NR_{24}R_{25}$, or N-morpholino, when o and p are independently 0–2, but one or the other of o or p is not 0; $R_{20}$ is hydrogen, or $(C_1-C_6)$alkyl; $R_{21}$ is hydrogen, $(C_1-C_6)$alkyl, or $R_{21}$ and $R_{20}$ can be taken together to form a 4, 5, 6, or 7 membered ring; $R_{22}$ is hydrogen, $(C_1-C_6)$alkyl, arylalkyl, aryl, or $R_{21}$ and $R_{22}$ can be taken together to be a 3, 4, 5, 6, 7 membered ring; $R_{23}$ is hydrogen or $(C_1-C_6)$alkyl; $R_{24}$ is hydrogen, $(C_1-C_6)$alkyl, or $R_{24}$ and $R_{25}$ can be taken together to form a 3, 4, 5, 6, or 7 membered ring, or $R_{24}$ and $R_{20}$ can be taken together to form a 6 or 7 membered ring; $R_{25}$ is hydrogen, $(C_1-C_6)$alkyl, or acetyl, or a group of the formula

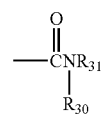

wherein: $R_{30}$ is hydrogen, or $(C_1-C_6)$alkyl; $R_{31}$ is hydrogen, $(C_1-C_6)$alkyl, 2-pyridyl, pyridylmethyl, amino, or hydroxy, or a group of the formula

wherein: $R_{32}$ and $R_{33}$ are each independently hydrogen, $(C_1-C_6)$alkyl, acetyl, $(C_1-C_4)$alkylsulphonyl, or $R_{32}$ and $R_{33}$ can be taken together to form a 4, 5, 6, or 7 membered ring, or a group of the formula

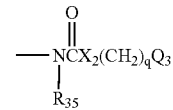

wherein: $X_2$ is $CH_2$, O, or N; q is 0–3; $Q_3$ is $NR_{36}R_{37}$, or $OR^{38}$, and $R^{35}$ is hydrogen, or $R^{35}$ and $Q_3$ can be taken together to form a 5 membered ring; $R_{36}$, $R_{37}$, and $R_{38}$ are each independently hydrogen, or $(C_1-C_6)$alkyl, or a group of the formula

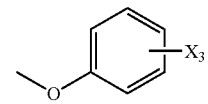

wherein: $X_3$ is cyano, carboxamide, N,N-dimethylcarboxamide, N,N-dimethylthiocarboxamide, N,N-dimethylaminomethyl, 4-methylpiperazin-1-yl-methyl or carboxylate, or a group of the formula

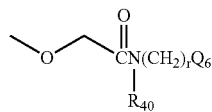

wherein: $Q_6$ is $NR_{41}R_{42}$; r is 2–3; $R_{40}$ is hydrogen, or $(C_1-C_6)$alkyl; $R_{41}$ and $R_{42}$ are hydrogen, $(C_1-C_6)$alkyl, or $R_{41}$ and $R_{40}$ can be taken together to form a 6 or 7 membered ring,
or a group of the formula

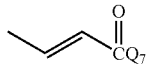

wherein: $Q_7$ is hydroxy, methoxy, dimethylamino, or N-piperidinyl; with the proviso that when one of $R_1$ or $R_2$ is unsubstituted or substituted phenyl, then the other cannot be unsubstituted or substituted phenyl or thiophen-2-yl; and with the proviso that when $R_2$ is quinolin-4-yl, substitution at the quinoline 7-position cannot include an aryl, heteroaryl, fused aryl, or fused heteroaryl;

k is 1–8; $R_3$ is one or more of the following: hydrogen; $(C_1-C_4)$alkyl; $(C_1-C_4)$ alkylhydroxy; hydroxy; N,N-di $(C_1-C_4$alkylamino$(C_1-C_4)$alkoxy; benzyl oxymethyl; phenyloxymethyl; oxo; carboxyl; $(C_1-C_4)$alkylaryl; benzyloxy; acetoxy; amino$(C_1-C_4)$alkyl; $(C_2-C_4)$ alkenyl; halo; —O—$(C_1-C_4)$alkyl; chlorophenethyl; acetonitrile; unsubstituted or substituted phenyl; wherein the substitution may be one or more of the following: $(C_1-C_6)$alkoxy, halo, carboxy, or $(C_1-C_6)$ alkoxycarbonyl; and the pharmaceutically acceptable salts, esters and prodrugs thereof.

2. A compound according to claim 1 of the structure

Formula (II)

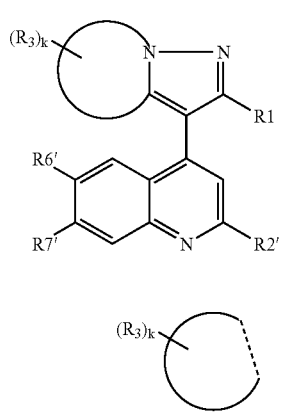

wherein is a five or six membered saturated ring with the proviso that the ring is a fully saturated carbon ring;
R1 is defined as in claim 1;
R2 is hydrogen; $(C_1-C_6)$alkyl; $(C_1-C_6)$alkylthio; $(C_1-C_6)$ alkoxy; halo; thiophenyl; aminophenyl; N-pyrrolidino; N-morpholino;
R6' and R7' are independently one or more of the following: hydrogen, $(C_1-C_6)$ alkyl, $(C_2-C_6)$alkenyl, $(C_2-C_6)$ alkynyl, $(C_1-C_6)$ alkylhalide, $(C_1-C_6)$alkoxy, $(C_2-C_6)$ alkenyloxy, $(C_2-C_6)$alkynyloxy, $(C_1-C_6)$alkylthio, $(C_1-C_6)$alkylsulphinyl, $(C_1-C_6)$ alkylsulphonyl, $(C_1-C_6)$alkylamino, di-[$(C_1-C_6)$alkyl]amino, $(C_1-C_6)$ alkoxycarbonyl, N—$(C_1-C_6)$alkylcarbamoyl, N,N-di-[$(C_1-C_6)$alkyl]carbamoyl, aminooxy, N—$(C_1-C_6)$alkyl aminooxy, N,N-di-[$(C_1-C_6)$alkyl]aminooxy, $(C_2-C_6)$ alkanoyl, $(C_2-C_6)$alkanoyloxy, $(C_2-C_6)$alkanoylamino, N—$(C_1-C_6)$alkyl-$(C_2-C_6)$alkanoylamino, $(C_3-C_6)$ alkenoylamino, N—$(C_1-C_6)$ alkyl-$(C_3-C_6)$ alkenoylamino, $(C_3-C_6)$alkynoylamino, N—$(C_1-C_6)$ alkyl-$(C_3-C_6)$alkynoylamino, sulphamoyl, N—$(C_1-C_6)$alkylsulphamoyl, N,N-di-[$(C_1-C_6)$ alkyl] sulphamoyl, $(C_1-C_6)$alkanesulphonylamino, N—$(C_1-C_6)$alkyl-$(C_1-C_6)$ alkanesulphonylamino, carboxamide, phenyl, thiophenyl, aminophenyl, phenylthio, halo, cyano, pyridinyl, arylalkyl, hydroxy, N-pyrrolidino, N-morpholino, carboxyl, [5-phenyl-1,2, 4-oxadiazole-3-yl]methoxy, 6-methyl-pyridazin-3-yloxy, (5-oxo-2-pyrrolidinyl)methoxy, 2-(4,5-dihydro-1H-imidazolyl), N,N-dialkylcarbamoyloxy, 1-hydroxy-1-methylethyl, 4-fluorophenyl, 3,4-methylenedioxyphenyl, trifluoromethyl, trifluoromethoxy,
or a group of the formula

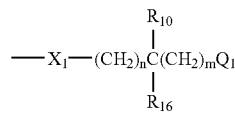

wherein: $X_1$ is O, N, S, $SO_2$, $NR_{13}$, C(O), or bond; $Q_1$ is hydrogen, phenyl, 5-(2,2-difluoro-1,3-benzodioxolyl), C(O) $Q_5$, or pyridyl when m and n are independently 0–2, except when one is 0 the other cannot be 0; $Q_1$ is $OR_{11}$, $NR_{11}R_{12}$, halo, N-morpholino, N-piperazino-$N'R_{13}$, N-imidazolyl, N-pyrazolyl, N-triazolyl, N-(4-piperidinylpiperidine), $SO_2R_{14}$, $SOR_4$, $NHSO_2R_{15}$, acetamido, N-phthalimido, N-oxazolidino, N-imidazolino, N-benzoxazolidino, N-pyrolidinonyl, N(N'-methylbenzimidazolino), N,N-di $(C_1-C_4)$alkylamino$(C_1-C_4)$alkoxy, N-benzimidazolino; when m and n are independently 0–2, but one or the other of m or n is not 0; $Q_5$ is hydroxy, methoxy, amino, diethylamino, dimethylamino; $R_{10}$ is hydrogen, halo, $(C_1-C_6)$alkyl; $R_{11}$ and $R_{12}$ are independently hydrogen, $(C_1-C_6)$alkyl, $(C_1-C_6)$alkoxy, arylalkyl, cycloalkyl, cycloalkylmethyl, 4-(N-methylpiperidinyl), pyridyl, or $R_{11}$ and $R_{10}$ can be taken together to form a 4, 5, 6, or 7 membered ring, or $R_{11}$ and $R_{12}$ can be taken together to form a 3, 4, 5, 6, or 7 membered ring; $R_{13}$ is hydrogen, $(C_1-C_6)$ alkyl, 2-methoxyphenyl; $R_{14}$ is 2-pyrimidinyl, N-methyl-2-imidazolyl, 4-chlorophenyl, 2-pyridylmethyl; $R_{15}$ is $(C_1-C_6)$ alkyl, N-methyl-4-imidazolyl; $R_{16}$ is hydrogen, halo, arylalkyl, aryl,
or a group of the formula

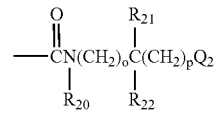

wherein: $Q_2$ is hydrogen, 4-imidazolyl, or $C(O)NR_{24}R_{25}$ when o and p are independently 0–2; $Q_2$ is $OR_{23}$, $NR_{24}R_{25}$, or N-morpholino, when o and p are independently 0–2, but one or the other of o or p is not 0; $R_{20}$ is hydrogen, or $(C_1-C_6)$alkyl; $R_{21}$ is hydrogen, $(C_1-C_6)$alkyl, or $R_{21}$ and $R_{20}$ can be taken together to form a 4, 5, 6, or 7 membered ring; $R_{22}$ is hydrogen, $(C_1-C_6)$alkyl, arylalkyl, aryl, or $R_{21}$ and $R_{22}$ can be taken together to be a 3, 4, 5, 6, 7 membered ring;

$R_{23}$ is hydrogen or $(C_1-C_6)$alkyl; $R_{24}$ is hydrogen, $(C_1-C_6)$alkyl, or $R_{24}$ and $R_{25}$ can be taken together to form a 3, 4, 5, 6, or 7 membered ring, or $R_{24}$ and $R_{20}$ can be taken together to form a 6 or 7 membered ring; $R_{25}$ is hydrogen, $(C_1-C_6)$alkyl, or acetyl,
or a group of the formula

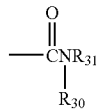

wherein: $R_{30}$ is hydrogen, or $(C_1-C_6)$alkyl; $R_3$ is hydrogen, $(C_1-C_6)$alkyl, 2-pyridyl, pyridylmethyl, amino, or hydroxy, or a group of the formula

wherein: $R_{32}$ and $R_{33}$ are each independently hydrogen, $(C_1-C_6)$alkyl, acetyl, alkylsulphonyl, or $R_{32}$ and $R_{33}$ can be taken together to form a 4, 5, 6, or 7 membered ring,
or a group of the formula

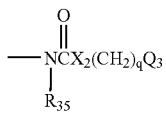

wherein: $X_2$ is $CH_2$, O, or N; q is 0–3; $Q_3$ is $NR_{36}R_{37}$, or $OR_{38}$; $R_{35}$ is hydrogen, or $R_{35}$ and $Q_3$ (when $Q_3$ is a bond) can be taken together to form a 5 membered ring; $R_{36}$, $R_{37}$, and $R_{38}$ are each independently hydrogen, or $(C_1-C_6)$alkyl, or a group of the formula

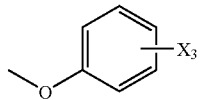

wherein: $X_3$ is cyano, carboxamide, N,N-dimethylcarboxamide, N,N-dimethylthiocarboxamide, N,N-dimethylaminomethyl, 4-methylpiperazin-1-yl-methyl or carboxylate,
or a group of the formula

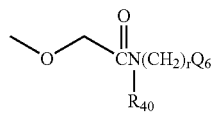

wherein: $Q_6$ is $NR_{41}R_{42}$; r is 2–3; $R_{40}$ is hydrogen, or $(C_1-C_6)$alkyl; $R_{41}$ and $R_{42}$ are hydrogen, $(C_1-C_6)$alkyl, or $R_{41}$ and $R_{40}$ can be taken together to form a 6 or 7 membered ring,
or a group of the formula

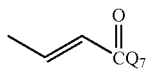

wherein: $Q_7$ is hydroxy, methoxy, or N-piperidinyl;
k is 1–8; $R_3$ is one or more of the following: hydrogen; $(C_1-C_4)$ alkyl; $(C_1-C_4)$ alkylhydroxy; hydroxy; N,N-di$(C_1-C_4)$alkylamino$(C_1-C_4)$alkoxy; benzyl oxymethyl; phenyloxymethyl; oxo; carboxyl; $(C_1-C_4)$ alkylaryl; benzyloxy; acetoxy; amino$(C_1-C_4)$alkyl; $(C_2-C_4)$alkenyl; halo; —O—$(C_1-C_4)$alkyl; chlorophenethyl; acetonitrile; phenyl; or an optionally substituted phenyl; wherein the substitution may be one or more of the following:
$(C_1-C_6)$alkoxy, halo, carboxy, or $(C_1-C_6)$alkoxycarbonyl; with the proviso that $R_7$ cannot be aryl; heteroaryl; fused aryl; or fused heteroaryl, and the pharmaceutically acceptable salts, esters and prodrugs thereof.

3. A compound according to claim 1 of the structure

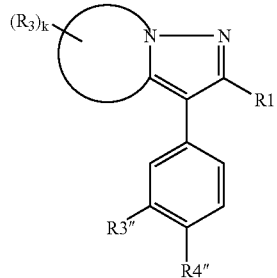

Formula (III)

wherein

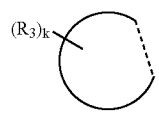

is a five or six membered saturated ring, with the proviso that the ring is a fully saturated carbon ring;
R1 is defined as in claim 1;
R3" is hydrogen; halo; trifluoromethyl;
R4" is hydrogen; halo; $(C_1-C_6)$alkyl; $(C_1-C_6)$alkoxy; hydroxy; $(C_1-C_6)$alkylsulphonyl;
k and R3 are defined as in claim 1;
and the pharmaceutically acceptable salts, esters and prodrugs thereof.

4. A compound according to claim 1 of the structure

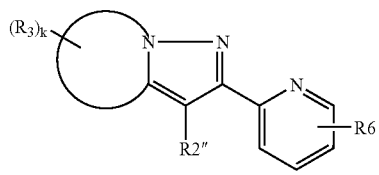

wherein

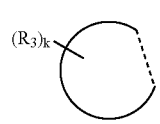

is a five or six membered saturated ring, with the proviso that the ring is a fully saturated carbon ring;
R6 may be one or more of the following: hydrogen, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $(C_1-C_6)$alkylthio, $(C_1-C_6)$alkylsulphinyl, $(C_1-C_6)$alkylsulphonyl, $(C_1-C_6)$alkylamino, di-[$(C_1-C_6)$alkyl]amino, $(C_1-C_6)$alkoxycarbonyl, N—$(C_1-C_6)$alkylcarbamoyl, N,N-di-[$(C_1-C_6)$alkyl]carbamoyl, $(C_2-C_6)$alkanoyl, $(C_2-C_6)$alkanoyloxy, $(C_2-C_6)$alkanoylamino, N—$(C_1-C_6)$alkyl -$(C_2-C_6)$alkanoylamino, $(C_3-C_6)$alkenoylamino, N—$(C_1-C_6)$ alkyl-$(C_3-C_6)$alkenoylamino, $(C_3-C_6)$alkynoylamino, N—$(C_1-C_6)$alkyl-$(C_3-C_6)$alkynoylamino, N—$(C_1-C_6)$alkylsulphamoyl, N,N-di-[$(C_1-C_6)$alkyl] sulphamoyl, $(C_1-C_6)$alkanesulphonylamino, N—$(C_1-C_6)$alkyl-$(C_1-C_6)$ alkanesulphonylamino, carboxamide, thiophenyl, aminophenyl, trifluoromethyl, halo, trifluoromethoxy, hydroxymethyl, N-pyrrolidino, N-morpholino, phenylthio, dialkylaminomethyl, methoxyphenyl, amino, hydroxy, carboxyl, phenyl, arylalky;

R2" is unsubstituted or substituted quinoline-8-yl; unsubstituted or substituted quinoline-6-yl; unsubstituted or substituted 1-naphthyl; unsubstituted or substituted 2-naphthyl; unsubstituted or substituted 3,4-methylenedioxyphenyl; unsubstituted or substituted 3,4-ethylenedioxyphenyl; unsubstituted or substituted benzothiophen-2-yl; wherein the substitution may independently be one or more of the following: $(C_1-C_6)$ alkyl, $(C_2-C_6)$alkenyl, $(C_2-C_6)$alkynyl, $(C_1-C_6)$ alkylhalide, $(C_1-C_6)$alkoxy, $(C_2-C_6)$alkenyloxy, $(C_2-C_6)$alkynyloxy, $(C_1-C_6)$alkylthio, $(C_1-C_6)$ alkylsulphinyl, $(C_1-C_6)$alkylsulphonyl, $(C_1-C_6)$ alkylamino, di-[$(C_1-C_6)$alkyl]amino, $(C_1-C_6)$ alkoxycarbonyl, N—$(C_1-C_6)$alkylcarbamoyl, N,N-di-[$(C_1-C_6)$alkyl]carbamoyl, aminooxy, N—$(C_1-C_6)$alkyl aminooxy, N,N-di-[$(C_1-C_6)$alkyl]aminooxy, $(C_2-C_6)$ alkanoyl, $(C_2-C_6)$alkanoyloxy, $(C_2-C_6)$alkanoylamino, N—$(C_1-C_6)$alkyl-$(C_2-C_6)$alkanoylamino, $(C_3-C_6)$ alkenoylamino, N—$(C_1-C_6)$alkyl-$(C_3-C_6)$ alkenoylamino, $(C_3-C_6)$alkynoylamino, N—$(C_1-C_6)$ alkyl-$(C_3-C_6)$alkynoylamino, sulphamoyl, N—$(C_1-C_6)$alkylsulphamoyl, N,N-di-[$(C_1-C_6)$alkyl] sulphamoyl, $(C_1-C_6)$ alkanesulphonylamino, N—$(C_1-C_6)$alkyl-$(C_1-C_6)$alkanesulphonylamino, carboxamide, ethylene, phenyl, thiophenyl, aminophenyl, phenylthio, halo, cyano, pyridinyl, arylalkyl, hydroxy, N-pyrrolidino, N-morpholino, carboxyl, [5-phenyl-1,2,4-oxadiazole-3-yl]methoxy, 6-methyl-pyridazin-3-yloxy, (5-oxo-2-pyrrolidinyl) methoxy, 2-(4,5-dihydro-1-H-imidazolyl), N,N-dialkylcarbamoyloxy, 1-hydroxy-1-methylethyl, 4-fluorophenyl, 3,4-methylenedioxyphenyl, trifluoromethyl, trifluoromethoxy, or a group of the formula

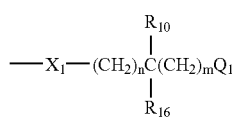

wherein: $X_1$ is O, N, S, $SO_2$, $NR_{13}$, C(O), or bond; $Q_1$ is hydrogen, phenyl, 5-(2,2-difluoro-1,3-benzodioxolyl), C(O)$Q_5$, or pyridyl when m and n are independently 0–2, except when one is 0 the other cannot be 0; $Q_1$ is $OR_1$, $NR_{11}R_{12}$, halo, N-morpholino, N-piperazino-N'$R_{13}$, N-imidazolyl, N-pyrazolyl, N-triazolyl, N-(4-piperidinylpiperidine), $SO_2R_{14}$, $SOR_{14}$, $NHSO_2R_{15}$, acetamido, N-phthalimido, N-oxazolidino, N-imidazolino, N-benzoxazolidino, N-pyrolidinonyl, N(N'-methylbenzimidazolino), N,N-di $(C_1-C_4)$alkylamino$(C_1-C_4)$alkoxy, N-benzimidazolino; when m and n are independently 0–2, but one or the other of m or n is not 0; $Q_5$ is hydroxy, methoxy, amino, diethylamino, dimethylamino; $R_{10}$ is hydrogen, halo, $(C_1-C_6)$alkyl; $R_{11}$ and $R_{12}$ are independently hydrogen, $(C_1-C_6)$alkyl, $(C_1-C_6)$alkoxy, arylalkyl, cycloalkyl, cycloalkylmethyl, 4-(N-methylpiperidinyl), pyridyl, or $R_{11}$ and $R_{10}$ can be taken together to form a 4, 5, 6, or 7 membered ring, or $R_{11}$ and $R_{12}$ can be taken together to form a 3, 4, 5, 6, or 7 membered ring; $R_{13}$ is hydrogen, $(C_1-C_6)$ alkyl, 2-methoxyphenyl; $R_{14}$ is 2-pyrimidinyl, N-methyl-2-imidazolyl, 4-chlorophenyl, 2-pyridylmethyl; $R_{15}$ is $(C_1-C_6)$alkyl, N-methyl-4-imidazolyl; $R_{16}$ is hydrogen, halo, arylalkyl, aryl, or a group of the formula

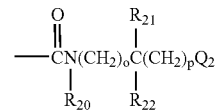

wherein: $Q_2$ is hydrogen, 4-imidazolyl, or C(O)$NR_{24}R_{25}$ when o and p are independently 0–2; $Q_2$ is $OR_{23}$, $NR_{24}R_{25}$, or N-morpholino, when o and p are independently 0–2, but one or the other of o or p is not 0; $R_{20}$ is hydrogen, or $(C_1-C_6)$alkyl; $R_{21}$ is hydrogen, $(C_1-C_6)$alkyl, or $R_{21}$ and $R_{20}$ can be taken together to form a 4, 5, 6, or 7 membered ring; $R_{22}$ is hydrogen, $(C_1-C_6)$alkyl, arylalkyl, aryl, or $R_{21}$ and $R_{22}$ can be taken together to be a 3, 4, 5, 6, 7 membered ring; $R_{23}$ is hydrogen or $(C_1-C_6)$alkyl; $R_{24}$ is hydrogen, $(C_1-C_6)$ alkyl, or $R_{24}$ and $R_{25}$ can be taken together to form a 3, 4, 5, 6, or 7 membered ring, or $R_{24}$ and $R_{20}$ can be taken together to form a 6 or 7 membered ring; $R_{25}$ is hydrogen, $(C_1-C_6)$alkyl, or acetyl, or a group of the formula

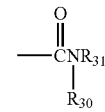

wherein: $R_{30}$ is hydrogen, or $(C_1-C_6)$alkyl; $R_{31}$ is hydrogen, $(C_1-C_6)$alkyl, 2-pyridyl, pyridylmethyl, amino, or hydroxy, or a group of the formula

wherein: $R_{32}$ and $R_{33}$ are each independently hydrogen, $(C_1-C_6)$alkyl, acetyl, alkylsulphonyl, or $R_{32}$ and $R_{33}$ can be taken together to form a 4, 5, 6, or 7 membered ring, or a group of the formula

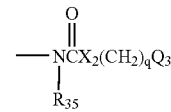

wherein: $X_2$ is $CH_2$, O, or N; q is 0–3; $Q_3$ is $NR_{36}R_{37}$ or $OR_{38}$; $R_{35}$ is hydrogen, or $R_{35}$ and $Q_3$ (when $Q_3$ is a bond) can be taken together to form a 5 membered ring; $R_{36}$, $R_{37}$, and $R_{38}$ are each independently hydrogen, or $(C_1-C_6)$alkyl, or a group of the formula

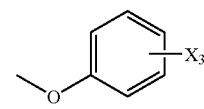

wherein: $X_3$ is cyano, carboxamide, N,N-dimethylcarboxamide, N,N dimethylthiocarboxamide, N,N-dimethylaminomethyl, 4-methylpiperazin-1 yl-methyl or carboxylate,
or a group of the formula

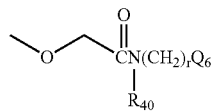

wherein: $Q_6$ is $NR_{41}R_{42}$; r is 2–3; $R_{40}$ is hydrogen, or $(C_1-C_6)$alkyl; $R_{41}$ and $R_{42}$ are hydrogen, $(C_1-C_6)$alkyl, or $R_{41}$ and $R_{40}$ can be taken together to form a 6 or 7 membered ring,
or a group of the formula

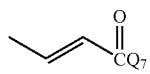

wherein: $Q_7$ is hydroxy, methoxy, dimethylamino, or N-piperidinyl;

k is 1–8; $R_3$ is hydrogen; and the pharmaceutically acceptable salts thereof.

5. A pharmaceutical formulation comprising a compound according to claim 1 or a pharmaceutically acceptable salt, ester or prodrug thereof together with a pharmaceutically acceptable diluent or carrier.

6. A method of treating cancer which comprises administering to a patient in need thereof a therapeutically effective amount of a compound according to claim 1 or a pharmaceutically acceptable salt, ester or prodrug thereof.

7. A method of treating cancer which comprises administering to a patient in need thereof a therapeutically effective amount of a compound according to claim 1 or a pharmaceutically acceptable salt, ester or prodrug thereof in combination with any other anti-cancer agent.

* * * * *

UNITED STATES PATENT AND TRADEMARK OFFICE
CERTIFICATE OF CORRECTION

PATENT NO.        : 7,087,626 B2  
APPLICATION NO. : 10/477111  
DATED             : August 8, 2006  
INVENTOR(S)       : Jason Scott Sawyer Page 1 of 1

It is certified that error appears in the above-identified patent and that said Letters Patent is hereby corrected as shown below:

Title Page, Item (75) Inventors: The following Inventors should be included:

Paola Ciapetti  
David Kent Herron  
Junkai Jao  
Nicholas Anthony Mort

Signed and Sealed this

Twenty-third Day of December, 2008

JON W. DUDAS  
*Director of the United States Patent and Trademark Office*